US011591295B2

(12) United States Patent
Kelner

(10) Patent No.: US 11,591,295 B2
(45) Date of Patent: Feb. 28, 2023

(54) AFFINITY ILLUDOFULVENE CONJUGATES

(71) Applicant: AF Chemicals, LLC, San Diego, CA (US)

(72) Inventor: Michael Kelner, San Diego, CA (US)

(73) Assignee: AF CHEMICALS LLC, San Diego, CA (US)

( * ) Notice: Subject to any disclaimer, the term of this patent is extended or adjusted under 35 U.S.C. 154(b) by 0 days.

(21) Appl. No.: 17/103,780

(22) Filed: Nov. 24, 2020

(65) Prior Publication Data

US 2021/0155583 A1 May 27, 2021

Related U.S. Application Data

(60) Provisional application No. 63/116,772, filed on Nov. 20, 2020, provisional application No. 62/940,096, filed on Nov. 25, 2019.

(30) Foreign Application Priority Data

Nov. 24, 2020 (EP) .................................... 20209541

(51) Int. Cl.

| | |
|---|---|
| ***C07C 317/44*** | (2006.01) |
| ***C07C 271/34*** | (2006.01) |
| ***C07C 309/72*** | (2006.01) |
| ***C07C 311/16*** | (2006.01) |
| ***C07D 207/444*** | (2006.01) |
| ***A61K 31/27*** | (2006.01) |
| ***C07K 5/083*** | (2006.01) |
| ***C07K 5/062*** | (2006.01) |
| ***C07C 225/14*** | (2006.01) |
| ***A61K 31/215*** | (2006.01) |
| ***A61K 31/265*** | (2006.01) |
| ***A61K 31/255*** | (2006.01) |
| ***A61K 38/06*** | (2006.01) |
| ***A61K 38/05*** | (2006.01) |
| ***A61K 31/4015*** | (2006.01) |
| ***A61K 47/54*** | (2017.01) |
| ***C07C 205/42*** | (2006.01) |

(52) U.S. Cl.

CPC .......... *C07C 317/44* (2013.01); *A61K 31/215* (2013.01); *A61K 31/255* (2013.01); *A61K 31/265* (2013.01); *A61K 31/27* (2013.01); *A61K 31/4015* (2013.01); *A61K 38/05* (2013.01); *A61K 38/06* (2013.01); *A61K 47/554* (2017.08); *C07C 205/42* (2013.01); *C07C 225/14* (2013.01); *C07C 271/34* (2013.01); *C07C 309/72* (2013.01); *C07C 311/16* (2013.01); *C07D 207/444* (2013.01); *C07K 5/06026* (2013.01); *C07K 5/06052* (2013.01); *C07K 5/0806* (2013.01); *C07C 2603/94* (2017.05)

(58) Field of Classification Search

None

See application file for complete search history.

(56) References Cited

U.S. PATENT DOCUMENTS

| | | | |
|---|---|---|---|
| 3,230,201 | A | 1/1966 | Hart |
| 5,439,936 | A | 8/1995 | Kelner |
| 5,439,942 | A | 8/1995 | Kelner |
| 5,523,490 | A | 6/1996 | Kelner |
| 5,563,176 | A | 10/1996 | Kelner |
| 5,723,632 | A | 3/1998 | McMorris |
| 5,932,553 | A | 8/1999 | McMorris |
| 6,025,328 | A | 2/2000 | McMorris |
| 6,069,283 | A | 5/2000 | McMorris |
| 6,160,184 | A | 12/2000 | McMorris |
| 6,252,093 | B1 | 6/2001 | McMorris |
| 6,323,181 | B1 | 11/2001 | McMorris |
| 6,380,403 | B1 | 4/2002 | McMorris |
| 6,469,184 | B2 | 10/2002 | McMorris |
| 6,548,679 | B1 | 4/2003 | McMorris |
| 6,639,105 | B2 | 10/2003 | McMorris |
| 6,717,017 | B2 | 4/2004 | McMorris |
| 6,855,696 | B2 | 2/2005 | McMorris |
| 6,908,918 | B2 | 6/2005 | McMorris |
| 6,987,193 | B2 | 1/2006 | McMorris |
| 7,141,603 | B2 | 11/2006 | McMorris |

(Continued)

FOREIGN PATENT DOCUMENTS

| | | |
|---|---|---|
| WO | PCT/US2005/017804 | 12/2005 |
| WO | PCT/US2015/025208 | 10/2015 |

OTHER PUBLICATIONS

A. Annamalai et al., Reaction of the Adenine Nucleotide Analogue W-p-Fluorosulfonylbenzoyl Adenosine at Distinct Tyrosine and Cysteine Residues of Rabbit Muscle Pyruvate Kinase, J. Biol. Chem., 256, 10276-10283, 1981.

(Continued)

*Primary Examiner* — Bethany P Barham
*Assistant Examiner* — Peter Anthopolos
(74) *Attorney, Agent, or Firm* — Sci-Law Strategies PC

(57) ABSTRACT

In an embodiment of the invention, a composition for treating a cell population comprises a medicant. The medicant moiety can be an illudofulvene analog. In an embodiment of the invention, a composition for treating a cell population comprises an Affinity Medicant Conjugate (AMC). The affinity moiety can be an antibody, an antibody fragment, a receptor protein, a peptidic growth factor, an anti-angiogenic protein, a specific binding peptide, protease cleavable peptide, a glycopeptide, a peptide, a peptidic toxin, a protein toxin and an oligonucleotide. The affinity moiety can be covalently bound to the medicant via a linker.

20 Claims, 8 Drawing Sheets

Specification includes a Sequence Listing.

(56) References Cited

U.S. PATENT DOCUMENTS

| | | | | |
|---|---|---|---|---|
| 7,329,759 | B2 | 2/2008 | McMorris | |
| 7,629,380 | B2 | 12/2009 | McMorris | |
| 7,655,695 | B2 | 2/2010 | McMorris | |
| 7,713,939 | B2 | 5/2010 | McMorris | |
| 7,855,275 | B2 | 12/2010 | Eigenbrot | |
| 8,937,161 | B2 | 1/2015 | Mao | |
| 9,381,178 | B2 | 7/2016 | Kelner | |
| 9,725,769 | B1 | 8/2017 | Knudsen | |
| 9,980,926 | B1 | 5/2018 | Kelner | |
| 10,285,955 | B2 | 5/2019 | Kelner | |
| 10,806,708 | B2 | 10/2020 | Kelner | |
| 2005/0250675 | A1 | 11/2005 | McMorris | |
| 2007/0072790 | A1 | 3/2007 | McMorris | |
| 2007/0092940 | A1 | 4/2007 | Eigenbrot | |
| 2008/0306147 | A1 | 12/2008 | McMorris | |
| 2011/0033378 | A1 | 2/2011 | Dimasi | |
| 2016/0015658 | A1 * | 1/2016 | Kelner | A61K 47/6803 424/450 |
| 2018/0100197 | A1 | 4/2018 | Knudsen | |
| 2019/0231795 | A1 | 8/2019 | Knudsen | |
| 2020/0340067 | A1 | 10/2020 | Knudsen | |

OTHER PUBLICATIONS

E. Brandsteterova, M.J. Kelner, T.C. McMorris, W. Wang, and R. Bagnell. HPLC analysis of novel anticancer agents Illudins and analogs. *J. Liquid Chromatography*. 16:115-126, 1993.

E. Brandsteterova, M.J. Kelner, T.C. McMorris, L. Estes, R. Bagnell, and M. Montoya.HPLC determination of a new anticancer agent (acylfulvene).in serum. *Neoplasma* 39:369-373, 1992.

R.F. Colman, Affinity Labelling of Purine Nucleotide Sites in proteins, 52, 67-91, 1983.

SR Demeade et al., Prostate-Specific Antigen-Activated Thapsigargin Prodrug as Targeted Therapy for Prostate Cancer, JNCI 95, 990, 2003.

R.P.M. Dings, et al., Chapter 18: Non-peptidic mimietics as cancer-sensitizing agents. In: Sensitization of cancer cells for Chemo/Immuno/Radiotherapy, 305-325.Editor Benjamin Bonavida, Human Press, 2008.

R.P. M. Dings, et al., Inhibiting Tumor Growth by Targeting Tumor Vasculature with Galectin-1 Antagonist Anginex Conjugated to the Cytotoxic Acylfulvene, 6-Hydroxylpropylacylfulvene. Bioconjugate Chemistry 21:20-27, 2010.

R.P. M. Dings, et al., Ovarian tumor growth regression using a combination of vascular targeting agents anginex or topomimetic 0118 and the chemotherapeutic irofulven. Cancer Letters 265: 270-280, 2008.

K.E. Dombrowski, et al., 5 -p-(Fluorosulfonyl)benzoyl-8-azidoadenosine: A New Bifunctional Affinity Label for Nucleotide Binding Sites in Proteins, Arch. Biochem. Biophys. 275, 302-308, 1989.

F.S. Esch et al., A procedure for the synthesis of p-Fluorosulfonyl[14C]benzoyl-5'-Adenosine with [14C] in the benzoyl moiety, Anal Biochem., 84, 642-645, 1978.

F.S. Esch et al., Identification of a tyrosine residue at a nucleotide binding site in the B subunit of the mitochondrial ATPase with p-Fluorosulfonyl[14C]benzoyl-5'-Adenosine, J. Biol. Chem., 253, 6100-6106, 1978.

VM Garsky, The Synthesis of a Prodrug of Doxorubicin Designed to Provide Reduced Systemic Toxicity and Greater Target Efficacy, J. Med. Chem. 44, 4216-4224, 2001.

M. Jaffe et al., Use of 5'-[p-Fluorosulfonylbenzoyl] guanosine as an affinity probe for the Guanine Nucleotide Binding Site of Transducin, The Prot. Journal, 26, 125-133, 2007.

N.G.J. Jaspers, et al., Anti-tumor compounds illudin S and Irofulven induce DNA lesions ignored by global repair and exclusively processed by transcription- and replication-coupled repair pathways. *DNA Repair* 1:1027-1038, 2002.

M.J. Kelner, et al., Preclinical evaluations of Illudins as anticancer agents. *Cancer Res.* 47:3186-9, 1987.

M.J. Kelner, et al., Preclinical evaluation of Illudins as anti-cancer agents. Basis for selective cytotoxicity. *J. Natl. Cancer Inst.* 82:1562-1565, 1990.

M.J. Kelner, et al., Characterization of Illudin S sensitivity of DNA repair-deficient Chinese Hamster cells: unusually high sensitivity of ERCC2 and ERCC3 DNA-helicase deficient mutants in comparison to other chemotherapeutic agents. *Biochem. Pharmacol.* 48:403-409, 1994.

M.J. Kelner, et al., Nonresponsiveness of the metastatic human lung carcinoma MV522 xenograft to conventional anticancer agents. *Anticancer Res.* 15:867-872, 1995.

M.J. Kelner, et al., In vitro and In vivo studies on the anticancer activity of dehydroilludin M. *Anticancer Res.* 15:873-878, 1995.

M.J. Kelner, et al., Efficacy of Acylfulvene Illudin analogs against a metastatic lung carcinoma MV522 xenograft nonresponsive to traditional anticancer agents retention of activity against various mdr phenotypes and unusual cytotoxicity against ERCC2 and ERCC3 DNA helicase-deficient cells. *Cancer Res.* 55:4936-4940, 1995.

M.J. Kelner, et al., Efficacy of HMAF (MGI-114) in the MV522 metastatic lung carcinoma xenograft model nonresponsive to traditional anticancer agents. *Invest. New Drugs* 14:161-167, 1996.

M.J. Kelner, et al., Characterization of cellular accumulation and toxicity of Illudin S in sensitive and non-sensitive tumor cells. *Cancer Chemother. Pharmacol.* 40:65-71, 1997.

M.J. Kelner, et al., Characterization of Acylfulvene histiospecific toxicity in human tumor cell lines. *Cancer Chemother. Pharmacol.* 41:237-242, 1998.

M.J. Kelner, et al., Efficacy of MGI 114 (6-hydroxymethylacylfulvene, HMAF) against the mdr1/gp170 Metastatic MV522 lung carcinoma xenograft. *Eur. J. Cancer*. 34:908-913, 1998.

M.J. Kelner, et al., Characterization of MGI 114 (HMAF): Histiospecific toxicity in human tumor cell lines. *Cancer Chemother. Pharmacol.* 44:235-240, 1999.

M.J. Kelner, et al., Anti-leukemic action of the novel agent MGI 114 (HMAF) and synergistic action with Topotecan. *Leukemia* 14:136-141, 2000.

M.J. Kelner, et al., Efficacy of MGI 114 against the MRP-positive metastatic MV522 lung carcinoma Xenograft. *Anti-Cancer Drugs* 11: 217-224, 2000.

M.J. Kelner, et al., Enhanced antitumor activity of irofulven in combination with thiotepa or mitomycin C. *Cancer Chemother. Pharmacol.* 49:412-8, 2002.

M.J. Kelner, et al., Enhanced antitumor activity of Irofulven in combination with antimitotic agents. *Invest New Drugs* 20:271-279, 2002.

M.J. Kelner, et al., Synergy of Irofulven in combination with other DNA damaging Agents: synergistic interaction with altretamine, alkylating, and platinum-derived agents in the MV522 lung tumor model. *Cancer Chemotherap Pharmacol.* 63:19-26, 2008.

M.J. Kelner, et al., Synergy of Irofulven in combination with various anti-metabolites, enzyme inhibitors, and miscellaneous agents in MV522 lung carcinoma cells: marked interaction with gemcitabine and 5-fluorouracil. *Invest. New Drugs.* 26:407-415, 2008.

J.J. Likos et al., Affinity labelling of the active site of yeast Pyruvate Kinase by 5'-p-Fluorosulfonyl benzoyl Adenosine, J. Biol. Chem., 255, 9388-9398, 1980.

J.R. MacDonald, et al., Preclinical antitumor activity of 6-Hydroxymethylacylfulvene, a semisynthetic derivative of the mushroom toxin Illudin S. *Cancer Res.* 57:279-283, 1997.

T.C. McMorris, et al., Structure and reactivity of Illudins. *Tetrahedron* 45:5433-5440, 1989.

T.C. McMorris, et al., On the mechanism of toxicity of Illudins. The role of glutathione. *Chem. Res. Toxicol.* 3:574-579, 1990.

T.C. McMorris, et al., Structure activity-relationships of Illudins Analogs with improved therapeutic index. *J. Org. Chem.* 57:6876-6883, 1992.

T.C. McMorris, et al., Acylfulvenes, a new class of potent antitumor agents. *Experientia* 52:75-80, 1996.

T.C. McMorris, et al., (Hydroxymethyl)acylfulvene: an Illudin derivative with superior antitumor properties. *J. Natural Products* 59:896-899, 1996.

(56) References Cited

OTHER PUBLICATIONS

T.C. McMorris, et al., Total synthesis of Hydroxymethylacylfulvene; an antitumor derivative of Illudin S. *Chem. Commun.* 3:315-316, 1997.
T.C. McMorris, et al., An Acetal derivative of Illudin S with improved tumor activity. *Tetrahedron Lett.* 38:1697-1698, 1997.
T.C. McMorris, et al., The design and total synthesis of antitumor acylfulvenes. *J. Organic Chem.* 62:3015-3018, 1997.
T.C. McMorris, et al., Reaction of antitumor hydroxymethylacylfulvene (HMAF) with thiols. *Tetrahedron*.53: 14579-90, 1997.
T.C. McMorris, et al., Synthesis of [$^3$H]-Illudin S, [$^3$H]-Acylfulvene, [$^3$H] & [$^{14}$C]-Hydroxymethylacylfulvene (MGI 114). *J. Labelled Cpd. Radiopharm.* XLI: 279-285, 1998.
T.C. McMorris, et al., Metabolism of antitumor Acylfulvene by rat liver cytosol. *Biochem. Pharmacol.* 57:83-88, 1999.
T.C. McMorris, et al., Metabolism of antitumor hydroxymethylacylfulvene by rat liver cytosol. *Drug Metab. Dispos.* 27:983-985, 1999.
T.C. McMorris, et al., Preparation and biological activity of amino acid and peptide conjugates of antitumor hydroxymethylacylfulvene. *J. Med. Chem.* 43: 3577-3580, 2000.
T.C. McMorris, et al., Sequiterpenes from the Basidiomycete *Omphalotus illudens. J. Nat. Prod.* 63:1557-1559, 2000.
T.C. McMorris, et al., Structure-activity studies of antitumor agent irofulven (hydroxymethylacylfulvene) and related analogues. *J. Org. Chem.* 66:6158-6163, 2001.
T.C. McMorris, et al., Sesquiterpenes from Omphalotus illudens. *Phytochemistry* 61:395-398, 2002.
T.C. McMorris, et al., Reaction of Irofulven with Zinc and Acid. *J Nat Products*. 66:310-312, 2003.
T.C. McMorris, et al., Structure-activity relationship studies of Illudins: Analogues possessing a spiro-cyclobutane ring. *J. Org. Chem.* 68:9648-53, 2003.
T.C. McMorris, et al., Synthesis and biological activity of enantiomers of antitumor Irofulven. *J. Org. Chem* 69:619-623, 2004.
T.C. McMorris, et al., Synthesis and Antitumor Activity of Amine Analogs of Irofulven *Bioorganic & Medicinal Chemistry Letters*. 17: 6770-72, 2007.
T.C. McMorris, et al., Structure-Activity Studies of Urea, Carbamate and Sulfonamide Derivatives of Acylfulvene. *J. Med. Chem.* 53: 1109-16, 2010.
Narayanan, A. and Jones, L.H. Sulfonyl fluorides as privileged warheads in chemical biology, *Chem Sci*., 6, 2650, 2015.
P.K. Pal et al., Affinity Labeling of a Regulatory Site of Bovine Liver Glutamate Dehydrogenase, Biochem., 14, 707-714, 1975.
P.K. Pal et al., Affinity Labeling of a inhibitory DPNH Site of Bovine Liver Glutamate Dehydrogenase by 5'-Fluorosulfonylbenzoyl Adenosine, J.Biol. Chem. 250, 8140-8147, 1975.
T.L. Poulos, The involvement of serine and carboxyl groups in the activity of Bovine Pancreatic Deoxyribonuclease A, J. Biol. Chem. 249, 1453-1457, 1974.
S. Roy et al., Affinity Labeling of a Lysine Residue in the Coenzyme Binding Site of Pig Heart Mitochondrial Malate Dehydrogenase, Biochemistry, 18, 4683-4690, 1979.
K.V. Saradambal ey al., Lysine and Tyrosine in the NADH Inhibitory Site of Bovine Liver Glutamate Dehydrogenase, J. Biol. Chem. 256, 11866-11872, 1981.
R. Schobert, et al., Conjugates of the fungal cytotoxin illudin M with improved tumour specificity. Biorg Med Chem 16:8592-97, 2008.
R. Schobert, et al., Cancer selective metallocenedicarboxylates of the fungal cytotoxin Illudin M. J Med Chem. 54: 6177-82, 2011.
R. Schobert, et al., Anticancer Active Illudins: Recent developments of a potent alkylating compound class. Current Medicinal Chemistry 18:790-807, 2011.
M.D. Staake , et al., Hydroxyurea derivatives of irofulven with improved antitumor efficacy. *Bioorg. Med. Chem. Lett*. 26: 2836-38, 2016.2010.
M. Tanasova, S.J. Sturla. “Chemistry and Biology of Acylfulvenes: Sesquiterpene-derived antitumor agents” (2012) Chemical Reviews. 112, 3578-3610.
C.T. Togashi et al., 5'-p-Fluorosulfonylbenzoyladenosine: Inactivvatio of myosine subfragment I and a model reaction with Cysteine (1981) J Biol. Chem. 257, 10112-10118.
J.M. Tomich et al., Modification of two essential cysteines in rabbit muscle pyruvate kinase by the guanosine nucleotide analogue 5'-[p-(Fluorosulfonyl)benzoyl] guanosine, 1981 Biochem, 20, 6711-6720.
PCT/US2015/025208, ISR dated Oct. 23, 2015, 26 pages.
A. Narayanan et al., Sulfonyl fluorides as privileged warheads in chemical biology, Chem Sci, 2650, 6 (2015).
A Paci et al., “Pharmacokinetics, Metabolism, and Routes of Excretion of Intravenous Irofulven in Patients with Advanced Solid Tumors”, Drug Metabolism and Disposition, vol. 34, No. 11, Aug. 16, 2006.
J. Gong et al., “Depurinating Acylfulvene-DNA Adducts: Characterizing Cellular Chemical Reactions of a Selective Antitumor Agent”, Journal ofthe American Chemical Society, vol. 129, No. 7, Feb. 1, 2007, pp. 2101-2111.
Partial Supplementary eSR 15776253.5 PCT/US2015/025208, dated Feb. 5, 2018 (stamped by foreign associate as incoming on Jan. 31, 2018), 18 pages.
A. Stornetta, “DNA Adducts from Anticancer Drugs as Candidate Predictive Markers for Precision Medicine”, (2017) Chemical Research in Toxicology, 30, 388-409.
A. Intra, “Regioselective Enzymatic Acylation of Polyhydroxylated Sesquiterpenoids” (2004) J. Molecular Catalysis B: Enzymatic 29, 95-98.
C. Nord, “Cytotoxic Illudane Sesquiterpenes from the Fungus Granulobasidium vellereum (Ellis and Cragin) Jülich”, J. of Natural Products (2015) 78, 2559-2564.
T. Horn et al., “High-Order Drug Combinations Are Required to Effectively Kill Colorectal Cancer Cells”, (2016) Cancer Res. 76, 6950-6963.
K. Mouw, “Improving Methods to Detect and Target Nucleotide Excision Repair (NER) Deficiency in Bladder Cancer” (2020) IBCN, https://www.urotoday.com/conference-highlights/iben-2020/125289-iben-2020-improving-methods-to-detect-and-target-nucleotide-excision-repair-deficiency-in-bladder-cancer.html, last visited Feb. 25, 2021.
European Search Report, Application 3667323, dated Feb. 11, 2020, 4 pages.
C. McCann et al., “Molecular Targets and Cancer Therapeutics” (2015) Poster Abstract, htpps://www.aacr.org/Documents/Targets15_AbstractsPosterC.pdf.
K. E. Pietsch et al., “Quantification of Acylfulvene- and Illudin S-DNA Adducts in Cells with Variable Bioactivation Capacities” (2013) Chemical Res. in Toxicology, 26 146-155.
W. Yang et al., “Genomics of Drug Sensitivity in Cancer (GDSC): a resource for therapeutic biomarker discovery in cancer cells” (2013) Nucleic Acids Res. 41 D955-D961.
EP 20209541.0, eESR dated Jun. 15, 2022, 9 pages.
Le Philllipe et al., A Chemical Proteomic Analysis of Illudin-Interacting Proteins, 25 (2019) 12644-12651.

* cited by examiner

FIG. 1A
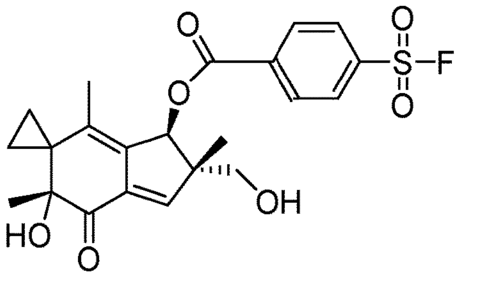
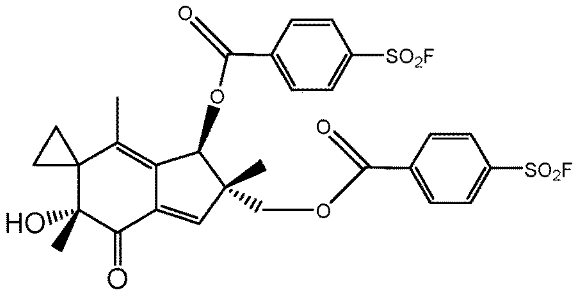
FIG. 1B
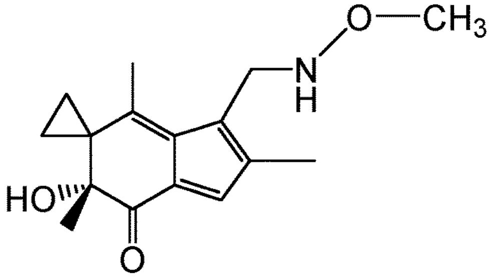
FIG. 1C
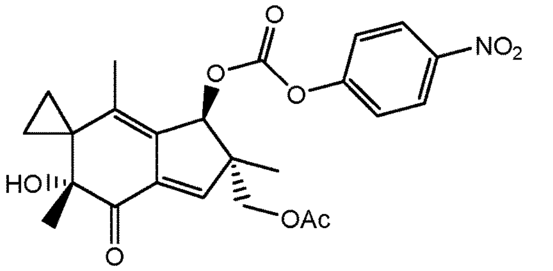
FIG. 1D
FIG. 1E
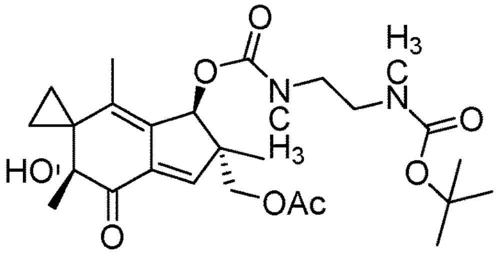
FIG. 1F
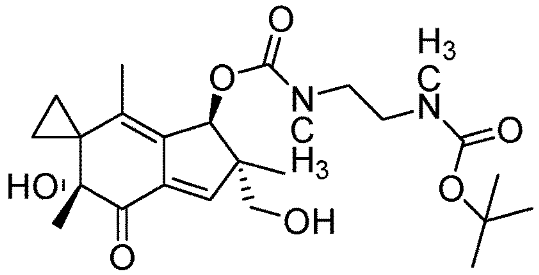
FIG. 1G
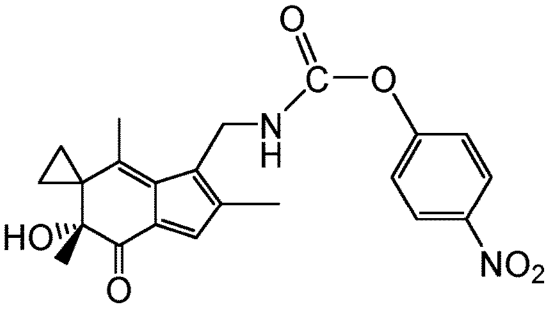
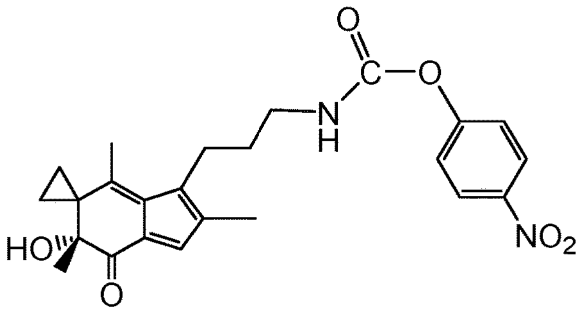
FIG. 1H

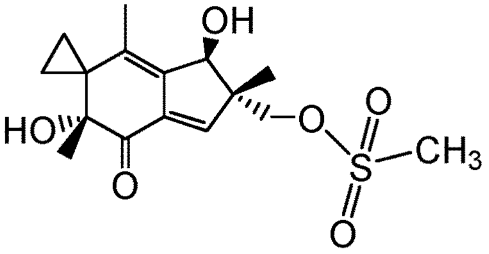
FIG. 1U
FIG. 1V
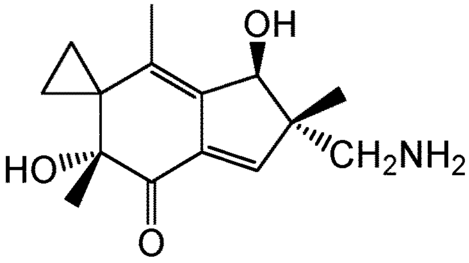
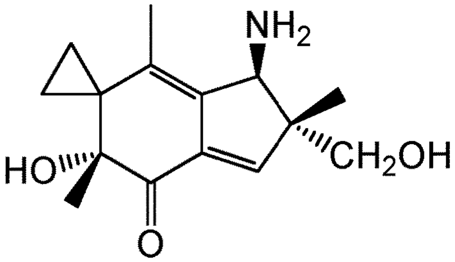
FIG. 1W
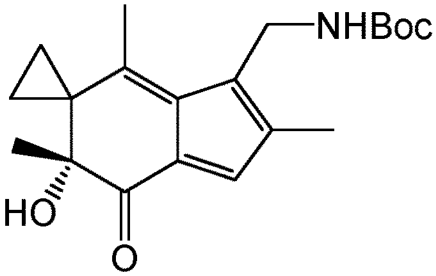
FIG. 1X
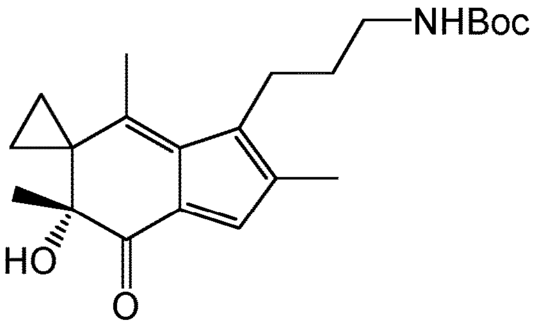
FIG. 1Y
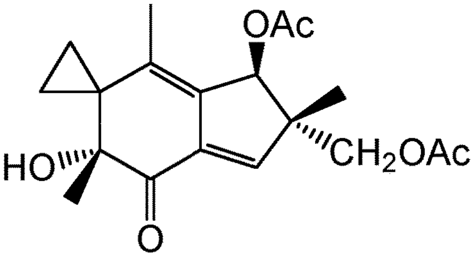
FIG. 1Z
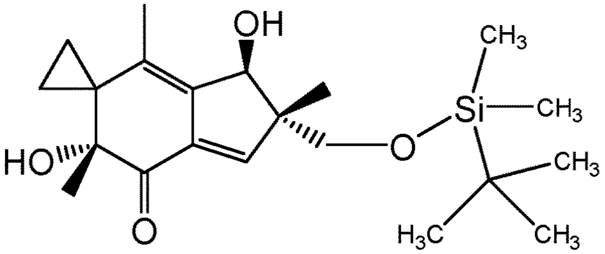
FIG. 2A
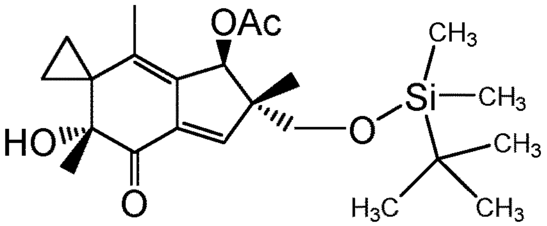
FIG. 2B

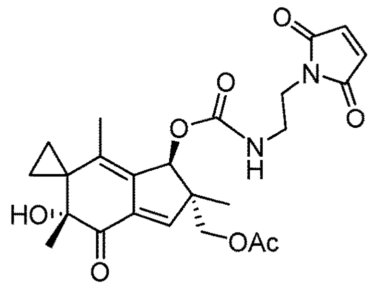
FIG. 2Q
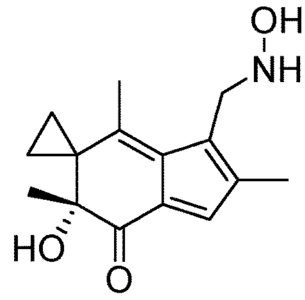
FIG. 2R
FIG. 2S
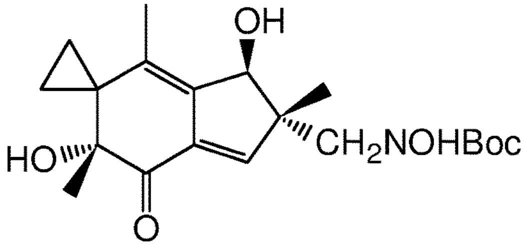
FIG. 2T
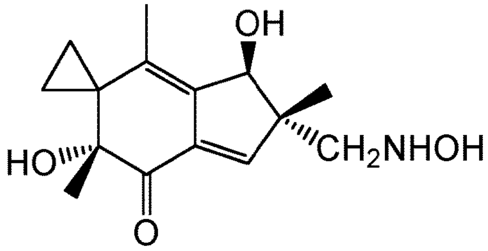
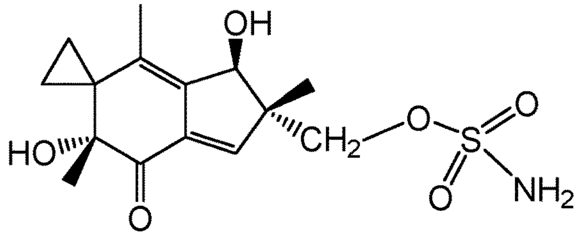
FIG. 2U
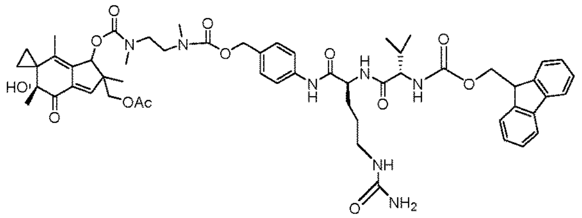
FIG. 2V
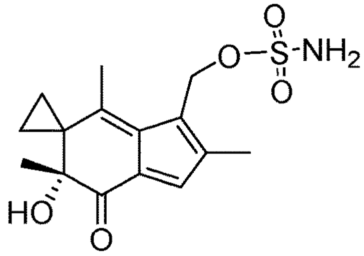
FIG. 2W
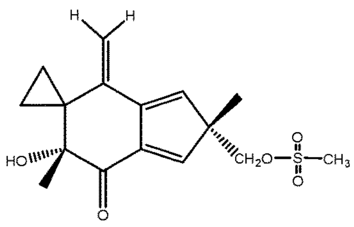
FIG. 2X

AFFINITY ILLUDOFULVENE CONJUGATES

PRIORITY CLAIM

This application claims priority to (i) U.S. Provisional Application No. 62/940,096 entitled "AFFINITY ILLUDOFULVENE CONJUGATES", inventor: Michael Kelner et al. filed Nov. 25, 2019, (ii) U.S. Provisional Application No. 63/116,772 entitled "AFFINITY ILLUDOFULVENE CONJUGATES", inventor: Michael Kelner et al. filed Nov. 20, 2020, and (ii) EP Patent Application No. 20209541.0 entitled "AFFINITY ILLUDOFULVENE CONJUGATES", inventor: Michael Kelner et al. filed Nov. 24, 2020 which applications (i)-(iii) are herein expressly incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file MKEL-01049US2_ST25.TXT, created Feb. 21, 2021, 846,409 bytes, machine format IBM-PC, MS-Windows operating system, is hereby incorporated by reference.

TECHNICAL FIELD

The present invention relates to compositions and methods for treating target molecules including cell populations with either a medicant or an affinity medicant conjugate including an antibody drug conjugate or a small molecule medicant conjugate.

BACKGROUND ART

The present invention is directed to a medicant or an Affinity Medicant Conjugate (AMC) including illudofulvene based medicants, illudofulvene based Affinity Medicant Linker Conjugates (AMLC), illudofulvene based antibody-drug conjugates (ADC) and illudofulvene based medicant-linker (ML) compounds, as well as to compositions of the same, and to methods for their use in treating cancer, an autoimmune to methods of using illudofulvene based Ligand Linker Medicant (LLM) conjugates and illudofulvene based ML compounds in vitro, in situ, and in vivo for the detection, diagnosis or treatment of cells and associated pathological conditions.

SUMMARY OF INVENTION

There exists a continuing need for chemotherapeutic agents for treating cancer. In particular there is a need for chemotherapeutic agents that have activity against cancers with resistant phenotypes and which can inhibit tumor growth and which have an adequate therapeutic index to be effective for in vivo treatment. In an embodiment of the invention, the chemotherapeutic agents can be delivered to tumors as a stand alone treatment. In an alternative embodiment of the invention, the chemotherapeutic agents can be delivered to a specific patient population having a specific tumors as a stand alone treatment. In another embodiment of the invention, the chemotherapeutic agents can be conjugated with an antibody to form an effective treatment. In another embodiment of the invention, the chemotherapeutic agents can be conjugated with an antibody, an antibody fragment, a receptor protein, a peptidic growth factor, an anti-angiogenic protein, a specific binding peptide, protease cleavable peptide, a glycopeptide, a peptide, a peptidic toxin, a protein toxin and an oligonucleotide and delivered to a specific patient population having a specific tumors to form an effective treatment. In various embodiments of the invention, the therapeutic treatment can be delivered in humans as well as in animals. For example, such therapeutic applications can include: cancer, adenocarcinoma, carcinoma, breast cancer, prostate cancer, ovarian cancer, endometrial cancer, neuroendocrine tumors, infertility, polycystic ovary syndrome, endometriosis, and precocious puberty. For example, veterinary and agricultural applications can include treatment of cancer, adenocarcinoma, carcinoma, ovarian cancer, endometrial cancer, neuroendocrine tumors, and endometriosis in farmyard and/or companion animals.

BRIEF DESCRIPTION OF THE DRAWINGS

This invention is described with respect to specific embodiments thereof. Additional features can be appreciated from the FIG.s in which:

FIG. 1A shows analog 317; FIG. 1B shows analog 318; FIG. 1C shows analog 332; FIG. 1D shows analog 333; FIG. 1E shows analog 334; FIG. 1F shows analog 335; FIG. 1G shows analog 337; FIG. 1H shows analog 338; FIG. 1U shows analog 362; FIG. 1V shows analog 363; FIG. 1W shows analog 364; FIG. 1X shows analog 366; FIG. 1Y shows analog 367; FIG. 1Z shows analog 368; FIG. 2A shows analog 369; FIG. 2B shows analog 370; FIG. 2Q shows analog 393; FIG. 2R shows analog 394; FIG. 2S shows analog 397; FIG. 2T shows analog 398; FIG. 2U shows analog 399; FIG. 2V shows analog 401; FIG. 2W shows analog 402; FIG. 2X shows analog 403.

DETAILED DESCRIPTION OF THE INVENTION

Figure 1I:
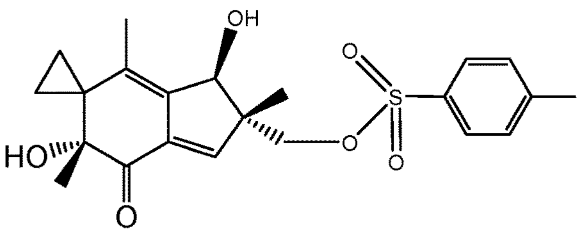
FIG. 1I shows analog 339.

Definitions. As used herein, the term "receptor for a biologically active polypeptide" means a receptor which can bind a biologically active peptide conjugate.

As used herein, the term "cell population" is used to describe a set or subset of cells expressing a molecule such as a receptor.

The phrase 'Other Drugs' means docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

'Acylfulvene' means an Illudofulvene subgroup with the following structural molecular formula:

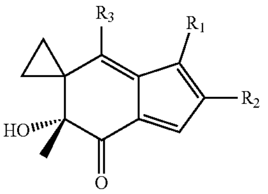

where $R_1$, $R_2$, $R_3$, $R_8$, $R_9$, $R_{10}$, $R_{11}$, are as set forth in Formula P1, as given herein.

'Formula P1' means $R_1$ represents —H, —$CR_9R_8OH$, —$CHR_9CHR_8OH$, —$CHR_{10}CHR_9CHR_8OH$, —$CH_2CHR_{10}CHR_9CHR_8OH$, —$CR_9R_8OH$, —$CHR_9CHR_8OH$, —$CHR_{10}CHR_9CHR_8OH$, —$CH_2CHR_{10}CHR_9CHR_8OH$, —$C(=O)H$, —$CH_2(C=O)H$, —$CH_2CH_2(C=O)H$, —$CH_2CH_2CH_2(C=O)H$, —$CH_2CH_2CH_2CH_2(C=O)H$, —$CR_9R_8(C=O)H$, —$CHR_9CHR_8(C=O)H$, —$CH_2CHR_9CHR_8(C=O)H$, —$CR_9R_8(C=O)R_{10}$, —$CHR_9CHR_8(C=O)R_{10}$, —$CH_2CHR_9CHR_8(C=O)R_{10}$, —$CH_2CH_2CHR_9CHR_8(C=O)R_{10}$, —$CO_2H$, —$CHR_9CO_2H$, —$CHR_8CHR_9CO_2H$, —$CHR_{10}CHR_8CHR_9CO_2H$, —$CO_2R_{10}$, —$CHR_9CO_2R_{10}$, —$CHR_8CHR_9CO_2R_{10}$, —$CH_2CHR_8CHR_9CO_2R_{10}$, —$CHR_9CH_2CH_2CHR_8CO_2H$, —$CHR_9CH_2CH_2CHR_8CO_2R_{10}$, —$CR_8=CH_2$, —$CHR_8CH=CH_2$, —$CH_2CHR_8CH=CH_2$, —$CH_2CH_2CHR_8CH=CH_2$, —$CR_8=CHR_9$, —$CHR_8CR_9=CH_2$, —$CH_2CHR_8CR_9=CH_2$, —$CH_2CH_2CHR_8CR_9=CH_2$, —$CR_8=CR_9R_{10}$, —$CHR_8CH=CR_9R_{10}$, —$CH_2CHR_8CH=CHR_9R_{10}$, —$CH_2CH_2CHR_8CH=CHR_9R_{10}$, —Cl, —Br, —I, —F, —$NO_2$, —$NR_8R_9$, —$CH_2Cl$, —$CH_2Br$, —$CH_2I$, —$CH_2F$, —$CR_8Cl_2$, —$CR_8Br_2$, —$CR_8I_2$, —$CR_8F_2$, —$CCl_3$, —$CBr_3$, —$CI_3$, —$CF_3$, —$CHR_8Cl$, —$CR_8R_9Cl$, —$CHR_8CHR_9Cl$, —$CHR_{10}CHR_8CHR_9Cl$, —$CH_2CHR_{10}CHR_8CHR_9Cl$, —$CHR_8Br$, —$CR_8R_9Br$, —$CHR_8CHR_9Br$, —$CHR_{10}CHR_8CHR_9Br$, —$CH_2CHR_{10}CHR_8CHR_9Br$, —$CHR_8I$, —$CR_8R_9I$, —$CHR_8CHR_9Br$, —$CHR_{10}CHR_8CHR_9I$, —$CH_2CHR_{10}CHR_8CHR_9I$, —$CR_8R_9NH_2$, —$CHR_8CHR_9NH_2$, —$CHR_{10}CHR_8CHR_9NH_2$, —$CH_2CHR_{10}CHR_8CHR_9NH_2$, —$CR_9R_{10}NHR_8$, —$CHR_9CHR_{10}NHR_8$, —$CH_2CHR_9CHR_{10}NHR_8$, —$CH_2CH_2CHR_9CHR_{10}NHR_8$, —$CHR_9NHR_8R_{10}$, —$CHR_9CH_2NHR_8R_{10}$, —$CH_2CH_2CHR_9NR_{10}R_8$, —$CH_2CH_2CH_2CH_2NHR_8$, —$CR_9R_8OR_{10}$, —$CH_2CR_8R_9OR_{10}$, —$CH_2CH_2CR_8R_9OR_{10}$, —$CH_2CH_2CH_2R_8R_9OR_{10}$, —$CH_2CH_2CH_2CH_2R_8R_9OR_{10}$, —$CHR_8OC(=O)CHR_9R_{10}$, —$CHR_8OC(=O)CHR_9R_{10}$, —$CH_2CH_2OC(=O)CHR_9R_{10}$, —$CH_2CH_2CHR_8OC(=O)CHR_9R_{10}$, —$CH_2CH_2CH_2CH_2OC(=O)CHR_9R_{10}$, —$CHR_8(=O)OCHR_9R_{10}$, —$CHR_8(=O)OCHR_9R_{10}$, —$CH_2CHR_8(=O)OCHR_9R_{10}$, —$CH_2CH_2CHR_8(=O)OCHR_9R_{10}$, —$CH_2CH_2CH_2CHR_8(=O)OCHR_9R_{10}$, —$R_{12}C=CR_9CH_2OH$, —$R_{12}C=CR_9C(=O)H$, —$R_{12}C=CR_9CH_2OR_{10}$, —$R_{12}C=CR_9C(=O)R_{10}$, —$CH_3$, —$CH_2CH_2$, —$CHR_8CH_2$, —$CHR_8CH_2CH_2$, —$CHR_8CHR_9CH_3$, —$OCH_3$, —$OCR_8R_9R_{10}$, —$OCH_2CR_8R_9R_{10}$, —$OCR_9R_8CHR_{10}$, —$OCHR_8CH_2CH_3$, —$OCHR_8CHR_9CH_3$, —$NR_8CH_3$, —$NR_8CH_2CH_3$, —$NR_9CHR_8CH_3$, —$NR_9CHR_8CH_2CH_3$, —$NR_{10}CHR_8CHR_9CH_3$, —$OCH_2OR_8$, —$OCHR_8OR_9$, —$OCHR_8CH_2OR_9$, —$OCHR_8CHR_9OR_{10}$, —$OC(=O)OR_8$, —$OCH_2C(=O)OR_8$, —$OCHR_9C(=O)OR_8$, —$CR_8(=N)H$, —$CH_2CR_8(=N)H$, —$CH_2CR_8(=N)H$, —$CH_2CH_2CR_8$ $(=N)H$, —$CH_2CH_2CH_2CR_8(=N)H$, —$CH_2CH_2CH_2CH_2CR_8(=N)H$, —$CR_8(=N)OH$, —$CH_2CR_8(=N)OH$, —$CH_2CR_8(=N)OH$, —$CH_2CH_2CR_8(=N)OH$, —$CH_2CH_2CH_2CR_8(=N)OH$, —$CH_2CH_2CH_2CH_2CR_8$ $(=N)OH$, —$CR_8(=N)R_9$, —$CH_2CR_8(=N)$ $R_9$, —$CH_2CR_8(=N)$ $R_9$, —$CH_2CH_2CR_8(=N)$ $R_9$, —$CH_2CH_2CH_2CR_8(=N)R_9$, —$CH_2CH_2CH_2CH_2CR_8(=N)R_9$, —$CR_8(=N)OR_9$, —$CH_2CR(=N)OR_9$, —$CH_2CR(=N)OR_9$, —$CH_2CH_2CR_8$ $(=N)OR_9$, —$CH_2CH_2CH_2CR_8(=N)OR_9$, —$CH_2CH_2CH_2CH_2CR_8(=N)OR_9$, —$CR_8(=N)NR_9$, —$CH_2CR_8(=N)NR_9$, —$CH_2CR_8(=N)NR_9$, —$CH_2CH_2CR_8$ $(=N)NR_9$, —$CH_2CH_2CH_2$—$CR_8(=N)NR_9$, —$CH_2CH_2CH_2CH_2CR_8(=N)NR_9$, —$CR_8(=N)NR_9S(=O)_2R_{10}$, —$CH_2C(R_8)(=N)NR_9S(=O)_2R_{10}$, —$CH_2CH_2C(R_8)(=N)NR_9S(=O)_2R_{10}$, —$CH_2CH_2CH_2C(R_8)(=N)NR_9S(=O)_2R_{10}$, —$CH_2CH_2CH_2CH_2$, —$C(R_8)(=N)NR_9S(=O)_2R_{10}$, —$R_{12}N(R_8)C(=O)NR_9R_{10}$, —$R_{12}N(R_8)C(=S)NR_9R_{10}$, —$R_{12}N(OR_8)C(=O)NR_9R_{10}$, —$R_{12}N(OR_8)C(=S)NR_9R_{10}$, —$R_{12}OS(O_2)NH_2$, —$R_{12}NHS(O_2)NH_2$, —$R_{12}OS(O_2)NR_8R_9$, —$R_{12}NHS(O_2)NR_8R_9$, —$CH_2N(R_8)S(O_2)NR_9R_{10}$, —$CH_2CH_2N(R_8)S(O_2)NR_9R_{10}$, —$CH_2CH_2CH_2N(R_8)S(O_2)NR_9R_{10}$, —$CH_2N(R_8)S(O_2)CR_9R_{10}R_{11}$, —$CH_2CH_2N(R_8)S(O_2)CR_9R_{10}R_{11}$, —$CH_2CH_2CH_2N(R_8)S(O_2)CR_9R_{10}R_{11}$, —$N(R_8)C(=O)R_9$, —$CH_2N(R_8)C(=O)R_9$, —$CH_2CH_2N(R_8)C(=O)R_9$, —$CH_2CH_2CH_2N(R_8)C(=O)R_9$, —$CH_2N(R_8)(C=O)NR_9R_{10}$, —$CH_2CH_2N(R_8)(C=O)NR_9R_{10}$, —$CH_2CH_2N(R_8)(C=O)NR_9R_{10}$, —$CH_2N(R_8)(C=O)CR_9R_{10}R_{11}$, —$CH_2CH_2N(R_8)(C=O)$ $CR_9R_{10}R_{11}$, —$CH_2CH_2N(R_8)(C=O)$ $CR_9R_{10}R_{11}$, —$R_{12}N(OH)C(=O)NHOH$, —$R_{12}N(OH)C(=S)NHOH$, —$R_{12}N(OR_8)C(=O)NHOR_9$, —$R_{12}N(OR_8)C(=S)NHOR_9$, —$R_{12}OS(O_2)NHOH$, —$R_{12}NHS(O_2)NHOH$, —$R_{12}OS(O_2)NHOR_9$, —$R_{12}OS(O_2)N(R_8)OR_9$, —$R_{12}NR_8S(O_2)NHOR_9$, —$CR_9(=N)OR_8$, —$NH(OR_8)$, —$C(C=O)NHR_8$, —$C(C=O)NR_9R_8$, —$NR_{10}(OR_8)C(=O)R_9$, —$N(OR_8)C(=O)NR_9$, —$NR_8(R_9)SR_{10}$, —$N(R_8)S(=O)R_9$, —$NR(R_8)S(=O)_2R_9$, —$OC(=O)NR_8$, —$N(OR_8)C(=O)OR_9$, —$N(R_8)C(=S)R_9$, —$O(S(=O)_2R_8$, —$R_{12}O(S(=O)_2R_8$, —$O(S(=O)_2NR_8$, —$R_{12}O(S(=O)_2NR_8$, —$S(=O)R_8$, —$R_{12}S(=O)R_8$, —$S(=O)_2R_8$, —$R_{12}S(=O)_2R_8$, —$NR_{10}(R_9)S(=O)_2NHR_8$, —$NR_9(C=O)R_8$, —$NR_9(C=O)OR_8$, —$NR_9O(C=O)OR_8$, —$NR_9(C=O)NR_8R_{10}$, —$R_{12}N(R_9)S(=O)_2NHR_8$, —$R_{12}N(R_9)(C=O)R_8$, —$R_{12}N(R_9)(C=O)OR_8$, —$R_{12}N(R_9)(C=O)NR_8$, —$N(=NR_{10})R_8$, —$R_9$—$N(=NR_{10})R_8$, —$C(R_{10})(=N—N=)CR_8R_9$; —$N_3$, —$CH_2N_3$, —$CH_2CH_2N_3$, —$CH_2CH_2CH_2N_3$, —$CH_2CH_2CH_2CH_2N_3$, —$CHR_8N_3$, —$CR_9R_8N_3$, —$CHR_9CHR_8N_3$, —$CH_2CHR_9CHR_8N_3$, —$CH_2CH_2CH_2CHR_8N_3$, —$C(R_8)=N—R_9$, —$CH_2C(R_8)=N—R_9$, —$CH_2CH_2C(R_8)=N—R_9$, —$CH_2CH_2CH_2C(R_8)=N—R_9$, —$N_3$, —$CH_2CH_2N_3$, —$CH_2CH_2CH_2N_3$, —$CH_2CH_2CH_2CH_2N_3$; —$CH_2NHC(=O)OC(CH_3)_3$, —$CH_2NOHC(=O)OC(CH_3)_3$, —$CH_2CH_2NHC(=O)OC(CH_3)_3$, —$CH_2CH_2NOHC(=O)OC(CH_3)_3$, —$CH_2CH_2CH_2NHC(=O)OC(CH_3)_3$, —$CH_2CH_2CH_2NOHC(=O)OC(CH_3)_3$, —$CH_2NHFmoc$; —$CH_2NOHFmoc$; —$CH_2CH_2NHFmoc$; —$CH_2CH_2NOHFmoc$. —$CH_2CH_2CH_2NH$—Fmoc; —$CH_2CH_2CH_2NOH$—Fmoc, and R2 and R3 each independently represent —H, —OH, —$CH_3$, —$OCH_3$, —$C(=O)CH_3$, —$OC(=O)CH_3$, —$C(=O)OCH_3$, —$C(=O)CH_2CH_3$, —$OC(=O)CH_2CH_3$, —$C(=O)OCH_2CH_3$, —$CH_2CH_3$, —$CH(CH_3)_2$, —$C(CH_3)_3$, —$CH_2CH_2CH_3$, —$CH_2CH(CH_3)_2$, —$CHC(CH_3)_3$, —$CH_2OH$, —$NH_2$, —NHOH, —$CH_2NH_2$, —$CH_2NHOH$, —$N_3$, and $(C_1\text{-}C_4)$alkyl; where $R_8$, $R_9$, $R_{10}$, $R_{11}$ each independently represent —H, —OH, —$CH_3$, —$CH_2CH_3$, —$CH_2=CH_2$, —$CH_2CH_2=CH_2$, —$CH_2CH_2CH_2=CH_2$, —C(H)=O, —$CH_2C(H)=O$, —$CH_2CH_2C(H)=O$, —$CH(CH_3)CH_3$, —$CH_2CH_2CH_3$, —$CH_2CH(CH_3)CH_3$, —$CHC(CH_3)_2CH_3$, —$C(=O)CH_3$, —$C(=O)CH_2CH_3$, —$C(=O)NH_2$, —$CH_2OH$, —$CH_2CH_2OH$, —$C(H)(OH)C(H_2)(OH)$, —$OCH_3$, —$OC(CH_3)_3$, —$OCH_2CH_3$, —$OCH(CH_3)_2$, —$CO_2H$, —$C(=O)OCH_3$, —$C(=O)OCH_2CH_3$, —$OC(=O)CH_3$, —$OC(=O)CH_2CH_3$, —$OC(=O)OCH_3$, —$OC(=O)OCH_2CH_3$, —$C(CH_3)_3$, —$CH_2CH_2(CH_3)_2$, —$CHC(CH_3)_3$, —$CH_2CH_2OH$, $CH_2CH_2CH_2OH$, —Cl, —Br, —I, —F, —$CH_2Cl$, —$CH_2Br$, —$CH_2I$, —$CH_2F$, —$CHCl_2$, —$CHBr_2$, —$CHI_2$, —$CHF_2$, —$CCl_3$, —$CBr_3$, —$CI_3$, —$CF_3$, —$NH_2$, —$CH_2NH_2$, —NH(OH), —$CH_2N(OH)$, —$NH(OCH_3)$, —$N(OCH_2CH_3)$, —$CH_2NH(OCH_3)$, —$CH_2N(OCH_2CH_3)$, —$N_3$, —$CH_2N_3$, —$CH_2CH_2N_3$, —CH=NH, —CH=NOH, —$CH=NOCH_3$, —SH, —$SCH_3$, —$SCH_2CH_3$, —$NO_2$, —CN, cyclopropane ring, saturated or unsaturated cyclobutane ring, saturated or unsaturated cyclopentane ring, saturated or unsaturated cyclohexane ring, benzene ring, phenolic ring, xylene ring, an amino acid(s), and $(C_1\text{-}C_4)$alkyl, and R12 represents —$CH_2$—, —$CH_2CH_2$—, —$CH(CH_3)CH_2$—, —$C(CH_3)CH_2$—, —CH=CH—, —O—, —S—, —O(C=O)—, —(C=O)O—, —NH—, —$N(R_8)$—, —N(OH)—, —CH2-O—, —O—$CH_2$—, —$CH_2CH_2$—O—, —O—$CH_2CH_2$—, —S(=O)—, —$(S=O)_2$—, —$NH(S=O)_2$—, —$N(OH)S(=O)_2$—, —$S(=O)_2NH$—, —$S(=O)_2N(OH)$—, —$NHS(=O)_2$—, —$N(OH)S(=O)_2$—, —$CH_2NH$—, —$CH_2N(R_8)$—, —$CH_2N(OH)$—, —$NHCH_2$—, —$N(R_8)CH_2$—, —$N(OH)CH_2$—, —OC(C=O)O—, —$OC(=O)NR_8$—, —NRC(=O)O—.

'Illudin' means an Illudofulvene subgroup with the following structural molecular formula:

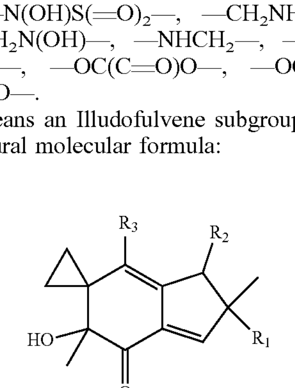

where $R_1$, $R_2$, $R_3$, are as set forth in Formula P2, as given herein.

'Formula P2' means where $R_1$, $R_2$, and $R_3$ each independently represent —H, —OH, —$CH_3$, —$OCH_3$, —$C(=O)CH_3$, —$OC(=O)CH_3$, —$C(=O)OCH_3$, —$C(=O)CH_2CH_3$, —$OC(=O)CH_2CH_3$, —$C(=O)OCH_2CH_3$,—$CH_2CH_3$, —$CH(CH_3)_2$, —$C(CH_3)_3$, —$CH_2CH_2CH_3$, —$CH_2CH(CH_3)_2$, —$CHC(CH_3)_3$, —$CH_2OH$, —$NH_2$, —$CH_2NH_2$, —$N_3$, —$CH_2NHOH$, —NHOH, —$CH_2NHC(=O)OC(CH_3)_3$, —$CH_2NOHC(=O)OC(CH_3)_3$, —C(=O)H, —C(=O)OH, —$CH_2OSi(CH_3)_2C(CH_3)_3$, —$OS(=O)_2CH_3$,—$CH_2OS(=O)_2(C_4H_6)CH_3$, —$OC(=O)O(C_6H_4)NO_2$, —$OC(=O)N(CH_3)CH_2CH_2N(CH_3)C(=O)OC(CH_3)_3$, —$OC(C=O)N(CH_3)CH_2CH_2N(CH_3)H$, —$OC(=O)NHCH_2CH_2NH_2$, —NH(FMOC), —NOH(FMOC), —$CH_2NH(FMOC)$, —$CH_2NOH(FMOC)$, —$OSi(CH_2CH_2CH_2CH_3)_3$, —$OSi(CH_3)_2C(CH_3)_3$, and $(C_1\text{-}C_4)$alkyl.

Figure 1J:
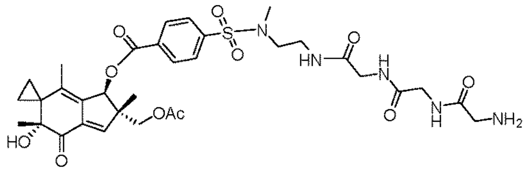
FIG. 1J shows analog 345.
Figure 1K:
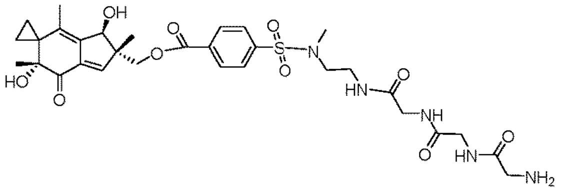
FIG. 1K shows analog 346.
Figure 1L:
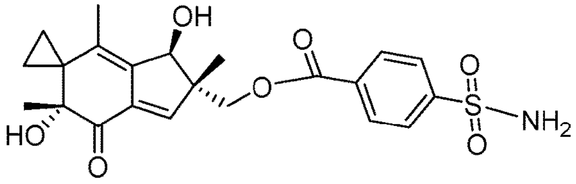
FIG. 1L shows analog 347.
Figure 1M:
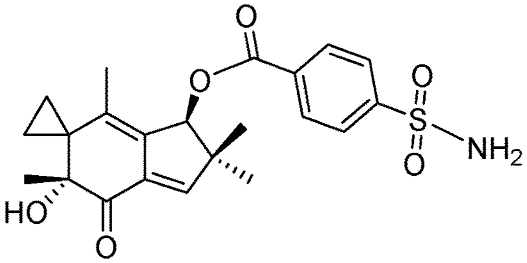
FIG. 1M shows analog 348.
Figure 1N:
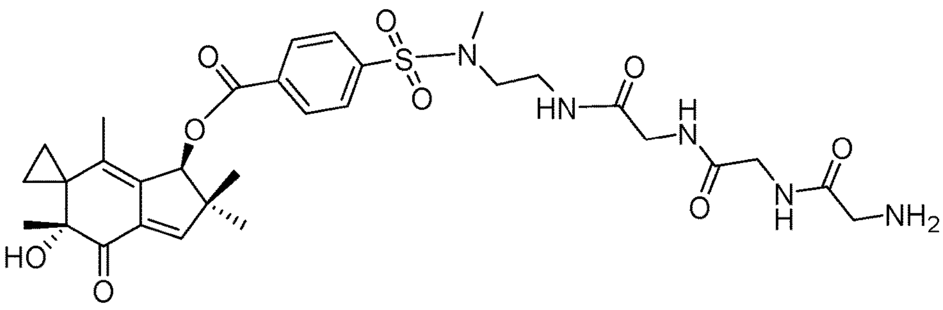
FIG. 1N shows analog 351.
Figure 1O:
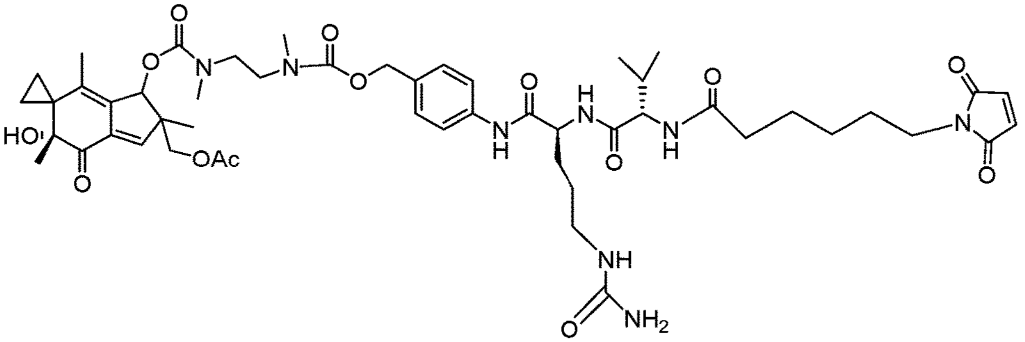
FIG. 1O shows analog 353.
Figure 1P:
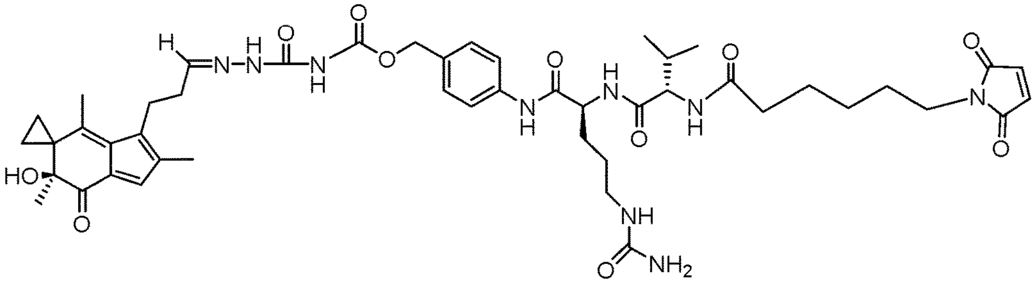
FIG. 1P shows analog 354.
Figure 1Q:
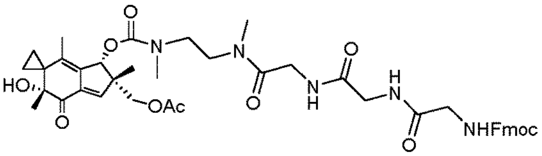
FIG. 1Q shows analog 356.
Figure 1R:
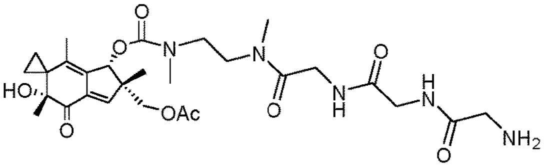
FIG. 1R shows analog 357.
Figure 1S:
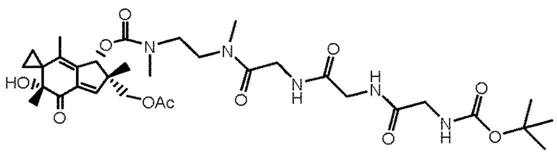
FIG. 1S shows analog 359.
Figure 1T:
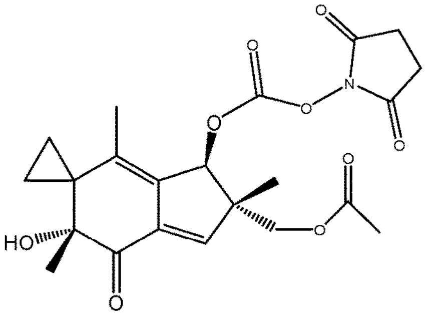
FIG. 1T shows analog 361.
Figure 2C:
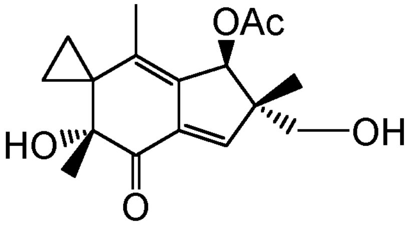
FIG. 2C shows analog 371.
Figure 2D:
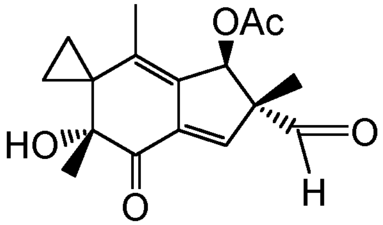
FIG. 2D shows analog 372.
Figure 2E:
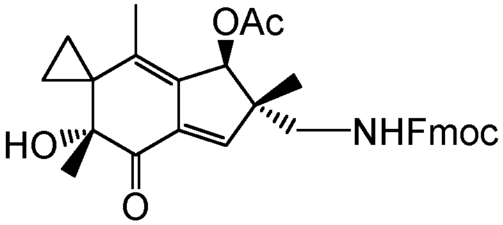
FIG. 2E shows analog 373.
Figure 2F:
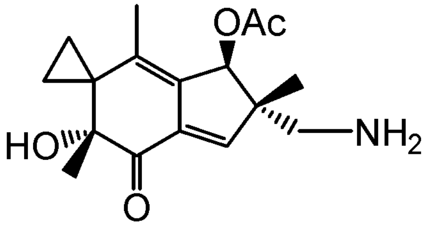
FIG. 2F shows analog 374.
Figure 2G:
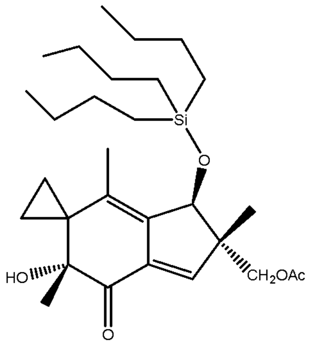
FIG. 2G shows analog 377.
Figure 2H:
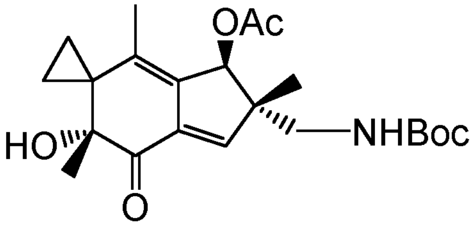
FIG. 2H shows analog 378.
Figure 2I:
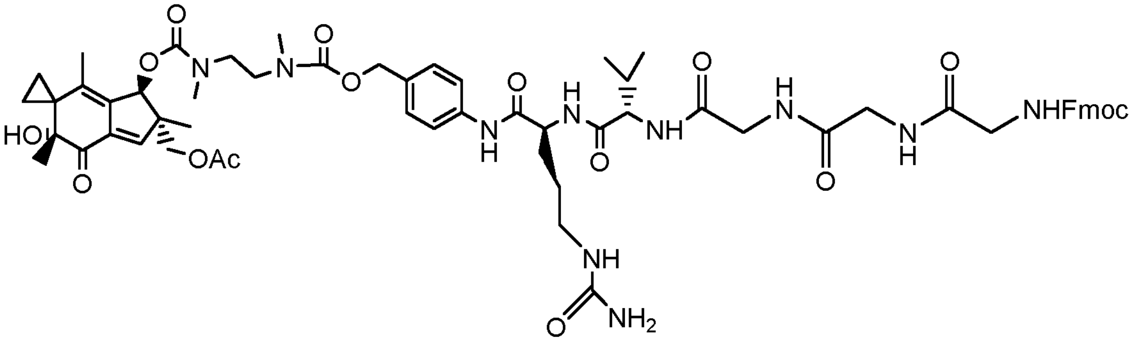
FIG. 2I shows analog 379.
Figure 2J:
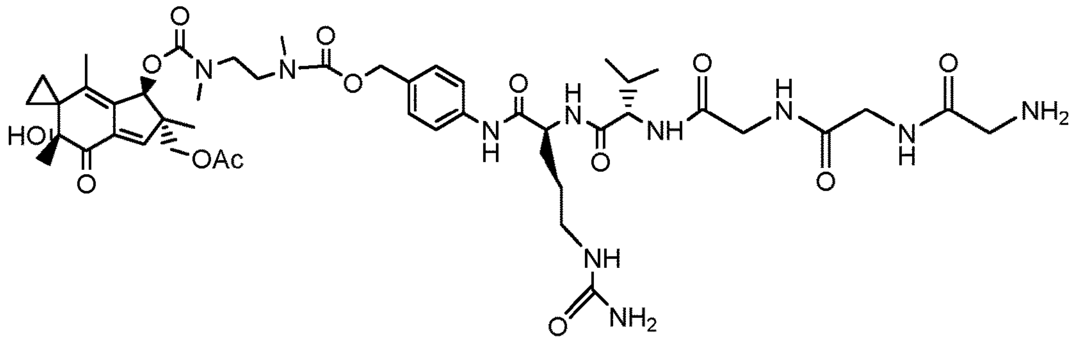
FIG. 2J shows analog 380.
Figure 2K:
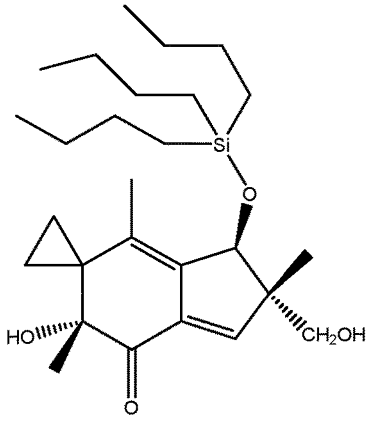
FIG. 2K shows analog 381.
Figure 2L:
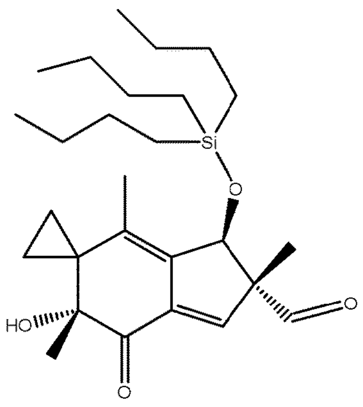
FIG. 2L shows analog 382.
Figure 2M:
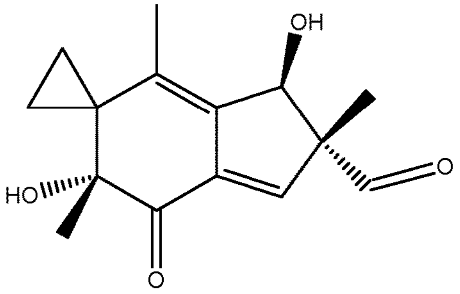
FIG. 2M shows analog 383.
Figure 2N:
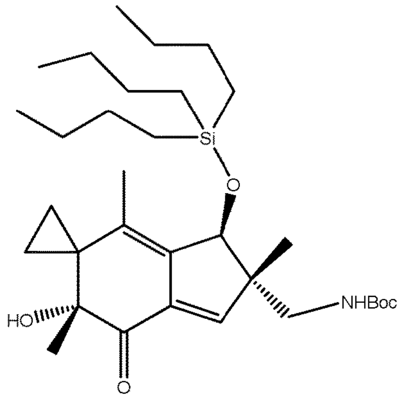
FIG. 2N shows analog 384.
Figure 2O:
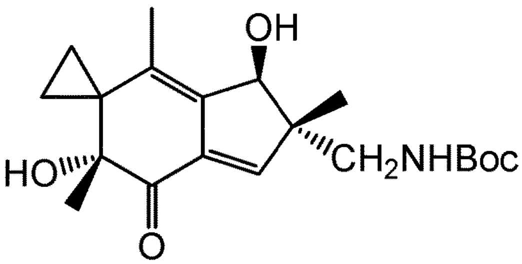
FIG. 2O shows analog 389.
Figure 2P:
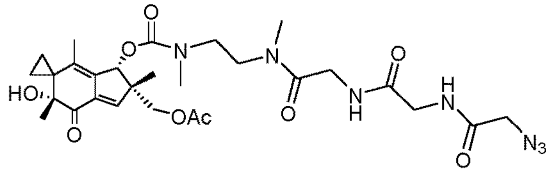
FIG. 2P shows analog 392.
Figure 2Y:
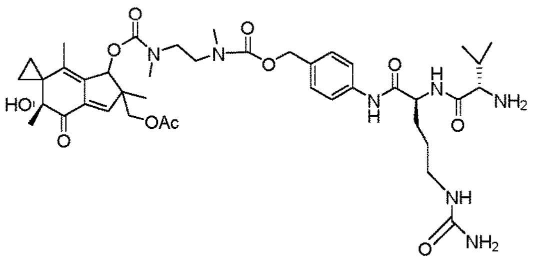
FIG. 2Y shows analog 404.
Figure 3A:
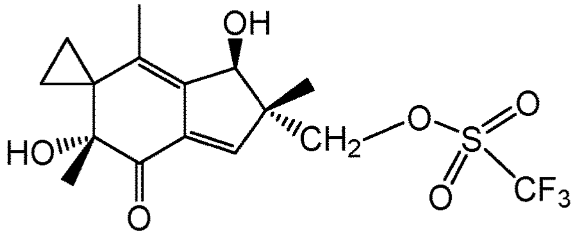
FIG. 3A shows analog 407.
Figure 2Z:
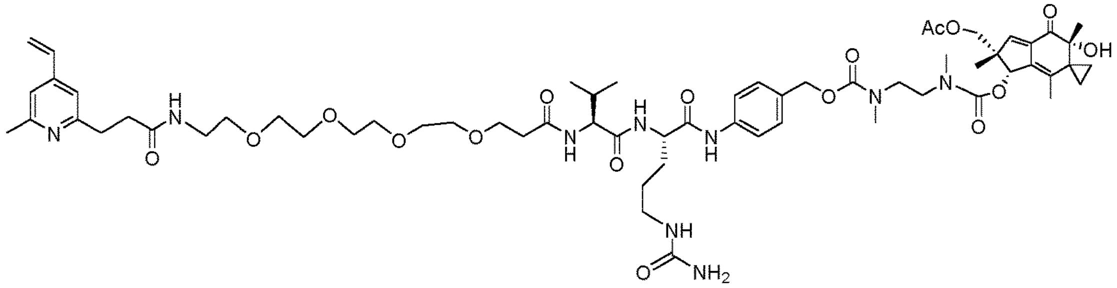
FIG. 2Z shows analog 405.
Figure 3B:
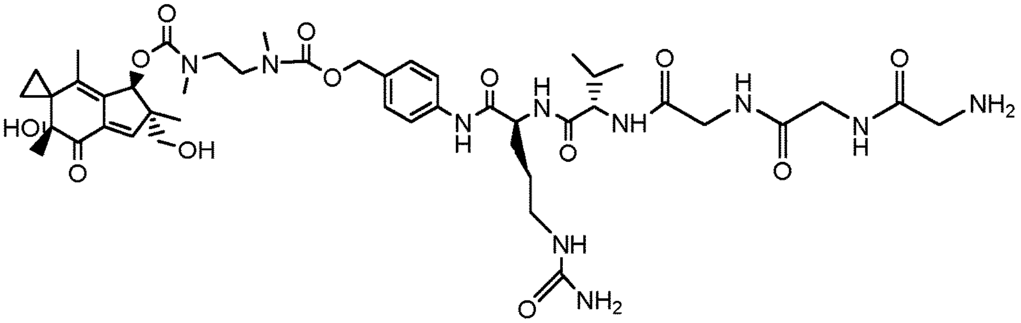
FIG. 3B shows analog 408.
Figure 3C:
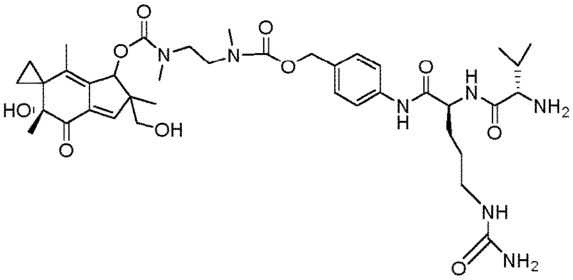
FIG. 3C shows analog 409 and FIG. 3D shows analog 410, according to various embodiments of the invention.
Figure 3D:
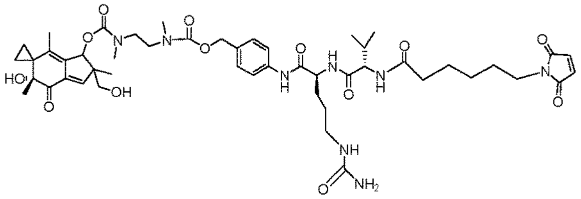

Table V is a listing of IUPAC names of the Illudofulvene Analog according to various embodiments of the present invention. FIGS. 1A-3D show the structure of analogs 317, 318, 332, 333, 334, 335, 337, 338, 339, 345, 346, 347, 348, 351, 353, 354, 356, 357, 359, 361, 362, 363, 364, 366, 367, 368, 369, 370, 371, 372, 373, 374, 377, 378, 379, 380, 381, 382, 383, 384, 389, 392, 393, 394, 397, 398, 399, 401, 402, 403, 404, 405, 407, 408, 409, and 410 respectively.

As used herein, the terms "analog", "medicant" and "medicant moiety" are used interchangeably and comprise synthetic and naturally occurring drugs, toxins, nutraceuticals and other cytoactive, anti-inflammatory and bioactive molecules including Doxorubicin (Immunomedics), auristatins E (Seattle Genetics), auristatins F (Celdex), monomethyl auristatin E (MMAE) (Amgen), monomethyl auristatin F (MMAF) (Astelles), maytanasines (Immunogen), DM1 (Biotest), DM4 (Amgen), calicheamicin (CellTech), irinotecan, folate, SN38 (Immunomedics), Pyrrolobenzodiazepines (Seattle Genetics), MGBA a duocarmycin derivative (Medarex), thalidomides, taxanes, penicillins, Trastuzumab emtansine (Genentech for Breast cancer uses maytanasine derive DM-1). Some of the above analogs are stand alone drugs, but can be used as a medicant moiety in an affinity drug conjugate according to various embodiments of the invention.

As used herein, the phrase "peptide receptor" includes peptide hormone receptors, protein hormone receptors, chemotactic receptors and chemokine receptors.

As used herein, the term "receptor" includes growth factor receptors, peptide hormone receptors, peptide receptors, steroid hormone receptors, steroid receptors and lipid receptors.

As used herein, phrase "affinity medicant conjugate" is an Affinity Moiety covalently bound to a medicant moiety, and includes antibody medicant conjugates, where the antibody is directed to a specific receptor. As used herein the phrase 'Affinity Moiety' includes antibodies, antibody fragments, peptides, proteins, growth factors, steroids, and lipids, where the antibodies, antibody fragments, peptides, proteins, growth factors, steroids, folate or lipids have an affinity for a specific receptor, receptors, is processed by an enzyme to produce a ligand that has an affinity for a specific receptor or otherwise directs the Affinity Moiety to a specific subset of cells. A 'medicant moiety' includes a group bound to an Affinity Moiety, which when released acts as a medicant.

As used herein, the term "Affinity Moiety" (AM) is used to describe a chemical group or molecule that can bind a receptor or proteins. An AM is understood to have a minimum binding affinity greater than approximately $1\times10^{-3}$ M affinity. As used herein, the term AM includes "ligands", "ligand moieties", "affinity unit" and an AM modified to include a linker. As used herein, the phrase "an affinity moiety directed to a peptide receptor" is used to describe a molecule or a portion of a molecule which has a binding affinity to the peptide receptor greater than approximately $1\times10^{-10}$ M. In this range approximately means $1\times10^{-9}$ M to $1\times10^{-11}$ M. In an embodiment of the invention, an AM directed to a peptide receptor has a binding affinity to the peptide receptor greater than approximately $1\times10^{-12}$ M. In this range approximately means $1\times10^{-11}$ M to $1\times10^{-13}$ M.

As used herein, the term "cytoactive" (which is abbreviated as "CA") is used to describe a small molecule that disrupts a cellular process, modulates a cellular process or otherwise affects the normal function of the cell. As used herein, the term "toxin" or "toxic" is used to describe a small molecule which interferes with RNA or DNA synthesis, causes RNA or DNA strand scission, blocks cell cycling, division, replication or is otherwise cytotoxic to the cell. As used herein, the term "toxin moiety" is used to describe a toxin modified to include a linker. As used herein, the phrase "a moiety possessing cell cytotoxicity" is used to describe a toxin moiety which when given in the concentration range of approximately $1\times10^{-3}$ M to approximately $1\times10^{-9}$ M results in inhibition of DNA synthesis or proliferation in an appropriate cultured cell line and/or when administered intravenously to an animal in the dosage approximately $1\times10^{-4}$ g to approximately $1\times10^{-9}$ g of the compound per kilogram of body weight of the animal results in in vivo cell death. As used herein, the term "ablated" is used to describe a reduction in the cell population of between approximately 50% and approximately 95%. In this range approximately means plus or minus five (5) percent. In an embodiment of the invention, a toxin moiety ablating a cell population reduces the cell population by approximately 100 percent. As used herein, the term "impaired" is used to describe a reduction in the cell population of between approximately 30% and approximately 50%. In this range approximately means plus or minus ten (10) percent.

As used herein, the term "linker" is used to describe one or more covalently bonded groups of atoms that are covalently bonded to a medicant moiety and an AM. For example a linker can be covalently bound to both an illudofulvene moiety and to an antibody or other ligand moiety with an affinity for a receptor.

As used herein, the term "non releasable linker" is used to describe a linker covalently bound to an AM and a medicant moiety in which the AM and the medicant moiety remain covalently bound to the linker after internalization and exposure to both reducing and acidic environments of vesicles within the cell. As used herein, the term "membrane permeability" is used to describe a compound comprising a linker covalently bound to an AM and an illudofulvene moiety, where the compound can diffuse across membranes within the cell.

As used herein, the term "transmembrane receptor" means a protein that spans the plasma membrane of a cell with the extracellular domain of the protein having the ability to bind an AM and the intracellular domain having an activity such as activation of G protein signaling which is induced upon the AM binding.

As used herein, the term "seven transmembrane receptor" is a transmembrane receptor including a transmembrane domain where the protein spans the cell membrane in seven (7) regions.

As used herein, the term "G-protein coupled receptor" means a seven transmembrane domain receptor which transduces a biological signal via G-protein coupling.

As used herein, the term "conjugated" or "conjugate" means a chemical compound that is formed by joining two or more compounds with one or more chemical bonds or linkers. In an embodiment of the invention, an antibody and a medicant form a conjugate.

As used herein, the term "antibody" herein is used in the broadest sense and specifically covers intact antibodies, monoclonal antibodies, polyclonal antibodies, mono-specific antibodies, multi-specific antibodies (e.g., bi-specific antibodies), and antibody fragments that exhibit the desired biological activity, including those antibodies directed against Alk, Alk fusion proteins, CD 2 (SEQ. ID. 001), CD3epsilon (SEQ. ID. 002), CD5 (SEQ. ID. 003), CD7 (SEQ. ID. 004), CD19 (SEQ. ID. 005), CD20 (SEQ. ID. 006), CD22 (SEQ. ID. 007), CD25 (SEQ. ID. 008), CD30 (SEQ. ID. 009), CD33 (SEQ. ID. 010), CD37 (SEQ. ID. 011), CD44 (SEQ. ID. 012), CD44v6 (SEQ. ID. 013), CD56 (SEQ. ID. 014), CD70 (SEQ. ID. 015), CD74 (SEQ. ID. 016), CD79 (SEQ. ID. 017), CD79b (SEQ. ID. 018), CD 80 (SEQ. ID. 019), CD 86 (SEQ. ID. 020), CD138 (syndecan 1) (SEQ. ID. 021), CAIX (SEQ. ID. 022), Integrin alphaV-beta 3 (SEQ. ID. 023), EphA2 (SEQ. ID. 024), Cryptol (SEQ. ID. 025), CanAg (SEQ. ID. 026), ENPP3 (SEQ. ID. 027), Nectin-4 (SEQ. ID. 028), Mesothelin (SEQ. ID. 029), Lewis Y (SEQ. ID. 030), EGFRvIII (SEQ. ID. 031), SLC44A4 (SEQ. ID. 032), EBTR (endothelin) (SEQ. ID. 033), erbB2/neu/HER2 (SEQ. ID. 034), Transferrin receptor (SEQ. ID. 035), 55 kDa breast cancer antigen, 72 kDa TAA, GPNMB (osteoactivin) (SEQ. ID. 038), CA-IX (SEQ. ID. 039), CEA (CD66e) (SEQ. ID. 040), CEACAM5 (SEQ. ID. 041), PSMA (SEQ. ID. 042), CA125 (MUC16) (SEQ. ID. 043), Muc (CA6) (SEQ. ID. 044), Melanoma glycoprotein NMB (SEQ. ID. 045), IL-2R (SEQ. ID. 166 and 046), IL13R (SEQ. ID. 047), TACSTD2 (TROP2 or EGP1) (SEQ. ID. 048), Folate receptor 1 (SEQ. ID. 049), Mucin 16 (SEQ. ID. 050), Endothelin receptor ETB (SEQ. ID. 051), STEAPI (SEQ. ID. 052), SLC44A4 (AGS-5) (SEQ. ID. 053), AGS-16 (SEQ. ID. 054), and Guanylyl cyclase C (SEQ. ID. 055). An intact antibody has primarily two regions: a variable region and a constant region. The variable region binds to and interacts with a target antigen. The variable region includes a complementary determing region (CDR) that recognizes and binds to a specific binding site on a particular antigen. The constant region may be recognized by and interact with the immune system. An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

As used herein, the terms "specifically binds" and "specific binding" refer to antibody binding to a predetermined antigen. Typically, the antibody binds with an affinity of at least about $1\times10^{7}$ M, and binds to the predetermined antigen with an affinity that is at least two-fold greater than its affinity for binding to a non-specific antigen (e.g., Bovine Serum Albumin, casein) other than the predetermined antigen or a closely-related antigen.

As used herein, the term "monoclonal antibody" as used herein refers to an antibody obtained from a population of substantially homogeneous antibodies, i.e., the individual antibodies comprising the population are identical except for possible naturally-occurring mutations that may be present in minor amounts and includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

As used herein, an "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

As used herein, the term an "intact antibody" may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (AMCC) and antibody-dependent cell-mediated phagocytosis.

As used herein, the term an "antibody fragment" comprises a portion of an intact antibody, preferably comprising the antigen-binding or variable region thereof. Examples of antibody fragments include Fab, Fab', $F(ab')_2$, and Fv fragments, di-abodies, tri-abodies, tetrabodies, linear antibodies, single-chain antibody molecules, scFv, scFv-Fc, multi-specific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

As used herein, the term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the Framework Regions (FRs). The variable domains of native heavy and light chains each comprise four FRs connected by three hypervariable regions.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

As used herein, an "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

As used herein, the term "therapeutically effective amount" refers to an amount of a medicant effective to treat a disease or disorder in a mammal. In the case of cancer, the therapeutically effective amount of the medicant may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the medicant may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

As used herein, the term "substantial amount" refers to a majority, i.e. greater than approximately fifty percent (50%) of a population, of a mixture or a sample. In this range approximately means plus or minus ten percent (10%).

As used herein, the term "intracellular metabolite" refers to a compound resulting from a metabolic process or reaction inside a cell on an Affinity Medicant Linker conjugate (e.g., an Antibody Drug Conjugate (AMC)). The metabolic process or reaction may be an enzymatic process such as proteolytic cleavage of a peptide linker of the AMC. Intracellular metabolites include, but are not limited to, antibodies and free medicant which have undergone intracellular cleavage after entry, diffusion, uptake or transport into a cell.

As used herein, the terms "intracellularly cleaved" and "intracellular cleavage" refer to a metabolic process or reaction inside a cell on an Affinity Medicant Linker conjugate (e.g., an Antibody Medicant conjugate (AMC) or the like), whereby the covalent attachment, e.g., the linker, between the Medicant moiety (M) and the Affinity unit (e.g., an antibody (Ab)) is broken, resulting in the free Medicant, or other metabolite of the conjugate dissociated from the antibody inside the cell. The cleaved moieties of the Affinity Medicant Linker conjugate are thus intracellular metabolites.

As used herein, the term "bioavailability" refers to the systemic availability (i.e., blood/plasma levels) of a given amount of a medicant administered to a patient. Bioavailability is an absolute term that indicates measurement of both the time (rate) and total amount (extent) of medicant that reaches the general circulation from an administered dosage form.

As used herein, the term "cytotoxic activity" refers to a cell-killing, a cytostatic or an anti-proliferative effect of an Affinity Medicant Linker conjugate or an intracellular metabolite of an Affinity Medicant Linker conjugate. Cytotoxic activity may be expressed as the $IC_{50}$ value, which is the concentration (molar or mass) per unit volume at which half the cells survive.

As used herein, the term "cytotoxic agent" as used herein refers to a substance that inhibits or inhibits the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term does not include a radioactive isotope(s).

As used herein, a "disorder" is any condition that would benefit from treatment with an Affinity Medicant Linker Conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

As used herein, the terms "cancer" and "cancerous" refer to or describe the physiological condition or disorder in mammals that is typically characterized by unregulated cell growth. A "tumor" comprises one or more cancerous cells.

As used herein, an "autoimmune disease" herein is a disease or disorder arising from and directed against an individual's own tissues or a co-segregate or manifestation thereof or resulting condition therefrom.

As used herein, an example of a "patient" includes, but is not limited to, a human, rat, mouse, guinea pig, monkey, pig, goat, cow, horse, dog, cat, bird and fowl. In an exemplary embodiment, the patient is a human.

As used herein, the terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

As used herein, in the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

As used herein, in the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

As used herein, in the context of an infectious disease, the term "treating" includes any or all of: inhibiting the growth, multiplication or replication of the pathogen that causes the infectious disease and ameliorating one or more symptoms of an infectious disease.

As used herein, the term "package insert" is used to refer to instructions customarily included in commercial packages of therapeutic products, that contain information about the indication(s), usage, dosage, administration, contraindications and/or warnings concerning the use of such therapeutic products.

As used herein, a "native sequence" polypeptide is one which has the same amino acid sequence as a polypeptide, e.g., a tumor-associated antigen receptor, derived from nature. Such native sequence polypeptides can be isolated from nature or can be produced by recombinant or synthetic means. Thus, a native sequence polypeptide can have the amino acid sequence of a naturally-occurring human polypeptide, a murine polypeptide, or a polypeptide from any other mammalian species.

As used herein, an "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid where, for example, the nucleic acid molecule is in a chromosomal location different from that of natural cells.

As used herein, the expression "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, a nucleic acid is "operably linked" when it is placed into a functional relationship with another nucleic acid sequence. For example, DNA for a pre-sequence or secretory leader is operably linked to DNA encoding a polypeptide if it is expressed as a pre-protein that participates in the secretion of the polypeptide; a promoter or enhancer is operably linked to a coding sequence, for example, if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, the synthetic oligonucleotide adaptors or linkers can be used in accordance with conventional practice.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein, "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH═CHO—CH_3$, $—Si(CH_3)_3$, $—CH_2—CH═N—OCH_3$, $—CH═CH—N(CH_3)—CH_3$, $—O—CH_3$, $—O—CH_2—CH_3$, and —CN. Up to two heteroatoms may be consecutive, such as, for example, $—CH_2—NH—OCH_3$.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, and 3-bromopropyl.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfoxide" as used herein, means a moiety having the formula R—S(O)—R', where R and R' are alkyl groups as defined above. R and R' may have a specified number of carbons (e.g., "$C_1$-$C_4$ alkylsulfoxide").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR'", —S(O)R', —S$(O)_2$R', —S$(O)_2$NR'R", —NR$SO_2$R', —OS$(O)_2$NR'R", —NRS$(O)_2$NR'R", —CN, and —$NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR'", —S(O)R', —S$(O)_2$R', —S$(O)_2$NR'R", —NR$SO_2$R', —OS$(O)_2$NR'R", —NRS$(O)_2$NR'R", —CN, —$NO_2$, —R', —$N_3$, —CH$(Ph)_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S$(O)_2$—, —S$(O)_2$NR'—, —OS$(O)_2$NR'—, —NRS$(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''')_d$—, where s and d are independently integers of from 0 to 3, and X' is —O—, —NR'—, —S—, —S(O)—, —$S(O)_2$—, —$OS(O)_2NR'$—, —$NRS(O)_2NR'$—, or —$S(O)_2NR'$—. The substituents R, R', R'', and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate, and salts of organic acids like glucuronic or galacturonic acids. Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), carbon-13 ($^{13}C$), or carbon-14 ($^{14}C$). All isotopic variations of the compounds of the present invention, whether radioactive or not, are encompassed within the scope of the present invention.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, an amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs$_1$ of an amino acid with substituted linkages, as well as other modifications known in the art.

As used herein, a "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

As used herein, a "protecting group" refers to a moiety that when attached to a reactive group in a molecule masks, reduces or prevents that reactivity. Representative hydroxy protecting groups include acyl groups, benzyl and trityl ethers, tetrahydropyranyl ethers, trialkylsilyl ethers and allyl ethers. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

As used herein, a "leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound (e.g., a Medicant Linker compound, or an Affinity Medicant Linker conjugate). The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used herein, a "pharmaceutically acceptable solvate" or "solvate" refer to an association of one or more solvent molecules and a compound of the invention, e.g., an Affinity Medicant Linker conjugate or a Medicant Linker compound. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: Boc is N-(t-butoxycarbonyl), cit is citrulline, dap is dolaproine, DCM is dichloromethane, DIEA is N,N-diisopropylethylamine, dil is dolaisoleuine, DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, Fmoc is N-(9-fluorenylmethoxycarbonyl), gly is glycine, HATU is O-(7-azabenzotriazol-1-yl)-N,N,N',N'-tetramethyluronium hexafluorophosphate, HBTU is 2-[1H-benzotriazole-1-yl]-1,1,3,3-tetramethylaminium hexafluorophosphate; HOBt is 1-hydroxybenzotriazole, HIPLC is high pressure liquid chromatography, ile is isoleucine, lys is lysine, MeOH is methanol, MeVal is N-methyl-valine, PAB is p-aminobenzyl, PBS is phosphate-buffered saline (pH 7.4), Ph is phenyl, phe is L-phenylalanine, PyBrop is bromo tris-pyrrolidino phosphonium hexafluorophosphate, TFA is trifluoroacetic acid, UV is ultraviolet, and val is valine.

The following LU abbreviations are used herein and have the indicated definitions: Val Cit or vc is a valine-citrulline dipeptide site in protease cleavable linker; PABC is p-aminobenzylcarbamoyl; (Me)vc is N-methyl-valine citrulline, where the linker peptide bond has been modified to prevent its cleavage by cathepsin B; and $MC(PEG)_6$-OH is maleimidocaproyl-polyethylene glycol.

As used herein, a "pegylated compound" refers to a compound conjugated with two or more polyethylene glycol moieties or two or more polypropylene glycol moieties or a combination thereof.

As used herein, a "pro-peptide" includes pro-peptide, pre-peptide, pro-protein and pre-protein amino acid sequences including those amino acid sequences cleaved by enzymes disclosed in Table III.

Malignant neoplasia is the second most common cause of death in the United States behind cardiovascular disease.

Chemotherapy has exerted a predominant role in increasing life spans for patients with a variety of tumors including Burkitt's lymphoma, acute lymphocytic leukemia and Hodgkin's disease. Further, new cancer chemotherapeutic agents and methods of care combined with early detection and treatment have resulted in decreases in the overall incidence of cancer and decreases in the death rates from all cancers combined. Responsive tumors represent only a small fraction of the various types of cancer. Further, agents such as cyclophosphamide, adriamycin, 5-fluorouracil and hexamethylmelamine, which are highly active against clinical solid tumors, are limited. Thus, patients with many types of malignancies remain at significant risk for relapse and mortality. After relapse, some patients can be re-induced into remission with their initial treatment regimen. However, higher doses of the initial chemotherapeutic agent or the use of additional agents are frequently required, indicating the development of at least partial medicant resistance. Evidence indicates medicant resistance can develop simultaneously to several agents, including medicant resistance to treatments to which the patient was not exposed. The development of multiple-medicant resistant tumors may be a function of tumor mass and constitutes a major cause of treatment failure. To overcome this medicant resistance, high-dose chemotherapy with or without radiation and allogenic or autologous bone marrow transplantation can be employed. The high-dose chemotherapy may employ the original medicant(s) or be altered to include additional agents. As a result, there remain many cancer patients for whom no or minimally effective therapy exists. Accordingly, there is a need for the development of novel chemotherapeutics with greater efficacy or safety, either as monotherapy or in combination with other chemotherapeutic agents, and such agents with the potential to overcome medicant resistance in cancer cells.

Illudins are toxic natural products produced by mushrooms of the genus *Omphalotus*. Syn-Illudins are semi-synthetic derivatives of Illudins. Acylfulvenes are also semi-synthetic derivatives of Illudins. Syn-Illudins and Acylfulvenes have each been chemically modified at select sites to allow their use as medicants. The modifications in the Syn-Illudins do not alter any of the cyclic rings (cyclopropane, cyclopentane, cyclohexane) of the basic Illudin chemical structure. The modifications of Acylfulvenes differ from Syn-Illudins in that an additional double bond (an unsaturated bond) has been created in the 5 membered (cyclopentane) ring.

Illudins function as alkylating agents that damage DNA and thereby block transcription. The blockage can be repaired through nucleotide excision. The toxicity of the illudins has prevented any applications in human tumor therapy. Acylfulvenes have been developed which exhibit promising antitumor activity with a better safety profile, as described in U.S. Pat. Nos. 5,439,936; 5,523,490 and 6,380,403 which are each herein expressly incorporated by reference in their entireties. (6'R)-6'-hydroxy-3'-(hydroxymethyl)-2',4',6'-trimethylspiro[cyclopropane-1,5'-inden]-7'(6'H)-one (analog 002, Table V) is an illudofulvene analog of illudin S which has demonstrated clinical activity with an acceptable safety profile in hormone-refractory prostate cancer. Most relevant to clinical applications, irofulven activity is independent of common resistance mechanisms such as the multi-medicant resistance phenotype, anti-apoptotic B-cell lymphoma 2 (Bcl-2) (SEQ. ID. 056) over expression, as well as tumor protein 53 (p53) (SEQ. ID. 057) and cyclin dependent kinase inhibitor 1 (p21/WAF1) (SEQ. ID. 058) mutations.

Growth factors, including peptides and proteins are critical mediators of a wide range of cell-cell communication. They are important endocrine, paracrine and autocrine messengers. Growth factors function as neurotransmitters and neuromodulators, regulate chemotaxis, immune function, development, cell growth, and can influence tumor cells. The receptors that recognize growth factors are highly selective and define specific cell populations. As a result, growth factor receptors are a large and important class of medicant (including drug) targets. In addition to physiologic noncancerous cell populations, these receptors can also be expressed in various cancer cell populations.

A polypeptide is a long, continuous, and unbranched chain of amino acids. A glycol-peptide is a peptide that contains one or more carbohydrate moieties covalently attached to the side chains of specific amino acids. A pro-peptide, is an inactive peptide that can be turned into an active form through a post translational modification that enzymatically cleaves the pro-peptide. Examples include pro-insulin (SEQ. ID. 059) and pro-opiomelanocortin (SEQ. ID. 060). Enzymatically cleaving the pro-peptide, allows for the peptide to be available on short notice and/or in large quantities. Some pro-peptides are secreted from the cell. Many of these are synthesized with an N-terminal signal peptide that targets the pro-peptide for secretion.

Cytokines are small proteins (approximately 5 to 20 kDa) that affect the behavior of other cells, and sometimes the releasing cell itself and are thereby important in cell signaling. Many specific cytokines can be released by a variety of different kinds of cells, e.g., macrophages, B lymphocytes, T lymphocytes, mast cells, endothelial cells, fibroblasts, and various stromal cells. Cytokines act through specific receptors, and are important in the humoral and cell-based immune responses. Cytokines also regulate the maturation, growth, and responsiveness of specific cell populations. Cytokines circulate in much higher concentrations than hormones and in contrast with hormones are made by a variety of different kinds of cells. Cytokines are important in host responses to infection, immune responses, inflammation, trauma, sepsis, cancer, and reproduction. As a result, cytokine receptors are upregulated in many forms of cancers.

A steroid is an organic compound that contains four cycloalkane rings joined to each other. Examples of steroids include the dietary lipid cholesterol and the sex hormones estradiol and testosterone. The core of a steroid molecule is composed of seventeen carbon atoms bonded together that take the form of four fused rings: three six-carbon atom rings and one five-carbon atom ring. A variety of functional groups can be attached to the four-ring core. Steroids can also vary depending on the oxidation state of the rings. A steroid hormone is a steroid that acts as a hormone. Steroid hormones can be grouped into five groups (glucocorticoids, mineralocorticoids, androgens, estrogens, and progesterones) based on the receptors to which they bind. Steroid hormones, particularly androgens, are essential not only for growth and development but also in the progression of many forms of cancer. As a result, steroid hormone receptors are upregulated in many forms of cancers.

The retinoic acid receptor (RAR) is a nuclear receptor which can also act as a transcription factor. The RAR can be activated by either all-trans retinoic acid or 9-cis retinoic acid. There are three RAR isoforms (alpha (SEQ. ID. 061), beta (SEQ. ID. 062), and gamma (SEQ. ID. 063)), each encoded by separate genes, where splice variants generate still further diversity in the expressed receptor. The retinoid X receptor (RXR) is a nuclear receptor activated by 9-cis retinoic acid. There are also three RXR isoforms (alpha (SEQ. ID. 064), beta (SEQ. ID. 065), and gamma (SEQ. ID. 066)), each encoded by separate genes. RXR hetero-dimerizes with subfamily 1 nuclear receptors including RAR. In the absence of ligand, the RAR/RXR dimer binds to retinoic acid response elements complexes with a co-repressor protein. Binding of agonist ligands to RAR results in dissociation of the co-repressor and recruitment of a co-activator protein that, in turn, promotes transcription of the downstream target gene into mRNA and thereby protein or other RNA signaling mechanisms.

Lipid metabolism is altered in many forms of cancer, including upregulation of de novo lipid synthesis. Cancer cells can also use alternative enzymes and pathways to facilitate the production of fatty acids. These newly synthesized lipids may support a number of cellular processes to promote cancer cell proliferation and survival. Elaidic acid or (E)-octadec-9-enoic acid is the trans isomer of oleic acid and is found in small quantities in caprine milk, bovine milk and some meats. It increases Cholesteryl Ester Transfer Protein (CETP) (SEQ. ID. 067) activity, which in turn raises levels of very low density lipoprotein and lowers levels of high density lipoprotein (HDL) cholesterol. CETP is found in plasma, where it is involved in the transfer of cholesteryl ester from HDL to other lipoproteins. Defects in the CETP gene are a cause of hyperalphalipoproteinemia 1.

An antibody is a protein made up of four peptide chains disulfide linked together to form a "Y"-shape. Antibodies are produced by plasma cells and are used by the immune system to identify and neutralize foreign antigens such as bacteria and viruses. The antibody recognizes a unique part of the antigen using each FAB portion of the protein (i.e., the tip of the "Y" portion of the antibody), allowing a specific high affinity binding interaction to occur. The binding interaction of different antibodies can target specific antigen epitopes. An antibody fragment containing one or both FAB portions can also target specific antigen epitopes.

The ability of the Illudofulvene analogs to inhibit tumor cell growth is shown in Table VII and Table VIII. Table VII shows the ability of Illudofulvene analogs to inhibit tumor cell growth. Table VIII shows screening data with the National Cancer Institute (NCI) Developmental Therapeutics Program (DTP) NCI 60 cell line screen assay comparing conventional anti cancer drugs Epothilone A, MMA, DM1 with the previously reported illudofulvene analogs (analog 002, analog 142, analog 159, analog 176) and with the illudofulvene analogs (analog 334 (FIG. 1AE), analog 362 (FIG. 1AU), analog 371 (FIG. 1BC), analog 383 (FIG. 1BM), and analog 394 (FIG. 1AE)). In Table VIII, 'Cytotoxicity' is defined as the ability to actually kill tumor cells was detected versus only inhibiting growth of tumor cells, while 'MDR activity' is the ability to equally kill a drug resistant daughter cell as compared to the non-drug resistant parent cell. The conventional anticancer drugs, Epothilone A, MMA and DM1 were able to inhibit the growth of cells in the NCI 60 cell line screen but were not able to actually kill timor cells. That is they were not cytotoxic. Further, they were not MDR active. All of the illudofulvene analogs in Table VIII (analog 334, analog 362, analog 371, analog 383 and analog 394) were cytotoxic in the NCI 60 cell line assay. The illudofulvene analog 371 is the most potent compound at lysing the NCI 60 tumor cell line. The MV522 cell line is a lung-derived adenocarcinoma cell line. In various embodiments of the invention, the MV522 cell line represents a "target" cell line. That is an illudofulvene analog that exhibits toxicity against this solid tumor cell line shows a desirable result. The 8392B cell line represents a hematopoietic (non-solid) cell line. In various embodiments of the invention, the 8392B cell line is considered a "nontarget" cell line. The two hour toxicity data represents the concentration of a given analog for which a two hour exposure will inhibit 50% of the DNA synthesis activity in a given cell line. The 48 hour exposure data represents the concentration at which a given analog with a 48 hour exposure will inhibit the growth or viability in a given cell line as defined by the standard Trypan Blue Exclusion assay. As an example, analog 002 will inhibit the target MV522 cell line at 110 nM with only a2 hour exposure but has no inhibitory effect on the nontarget 8392B cell line at 26,000 nM (26 μM). Analog 002 with a prolonged exposure period (e.g. 48 hours) can eventually inhibit the nontarget cell line. In contrast, Analog 201 will inhibit the target MV522 cell line with only a 2 hour exposure (IC50=360 nM) but has minimal effect on the 8392B cell nontarget line with even a 48 hour exposure (IC50=26,000 nM) indicating superior anticancer activity as a monotherapeutic agent In contrast to these two analogs, analog 224 displayed minimal toxicity as well as no differential toxicity between the target and nontarget cell line indicating it would have minimal properties as a monotherapeutic anticancer agent.

As used herein, a "growth factor" or an "anti-angiogenic protein" includes Adrenomedullin (SEQ. ID. 068), Angiopoietin (Ang) (SEQ. ID. 069, 106, 111, and 145), Autocrine motility factor (SEQ. ID. 070), Bone morphogenetic proteins (BMPs) (SEQ. ID. 071), Brain-derived neurotrophic factor (BDNF) (SEQ. ID. 072), Endostatin (SEQ. ID. 073), Endostar (SEQ. ID. 074), Epidermal growth factor (EGF) (SEQ. ID. 075), Erythropoietin (EPO) (SEQ. ID. 076), Fibroblast growth factor (FGF) (SEQ. ID. 077), Glial cell line-derived neurotrophic factor (GDNF) (SEQ. ID. 078), Granulocyte colony-stimulating factor (G-CSF) (SEQ. ID. 079), Granulocyte macrophage colony-stimulating factor (GM-CSF) (SEQ. ID. 080), Growth differentiation factor-9 (GDF9) (SEQ. ID. 081), Hepatocyte growth factor (HGF) (SEQ. ID. 082), Hepatoma-derived growth factor (HDGF) (SEQ. ID. 083), Insulin-like growth factor (IGF) (SEQ. ID. 084), Migration-stimulating factor (SEQ. ID. 085), Myostatin (GDF-8) (SEQ. ID. 086), Nerve growth factor (NGF) (SEQ. ID. 087) and other neurotrophins (SEQ. ID. 144), Platelet-derived growth factor (PDGF A) (SEQ. ID. 088), PDGF B (SEQ. ID 168), PDGF C (SEQ. ID. 036), PDGF D (SEQ. ID. 037), Thrombopoietin (TPO) (SEQ. ID. 089), Transforming growth factor alpha (TGF-α) (SEQ. ID. 090), Transforming growth factor beta (TGF-β) (SEQ. ID. 091), Tumor necrosis factor-alpha (TNF-α) (SEQ. ID. 092), Vascular endothelial growth factor (VEGF) (SEQ. ID. 093), and placental growth factor (PlGF) (SEQ. ID. 094).

As used herein, a "protein toxin" includes ricin A chain (SEQ. ID. 095), ricin B chain (SEQ. ID. 096), diphtheria toxin (SEQ. ID. 097), *Pseudomonas aeurginosa* exotoxin A (SEQ. ID. 098), r-gelonin (SEQ. ID. 099), saporin (SEQ. ID. 100), glycosylated protein toxins, deglcosylated protein toxins and protein toxin fragments which includes deglycosylated ricin A, deglycosylated ricin B, *Pseudomonas aeurginosa* exotoxin A PE40 fragment (SEQ. ID. 101) and *Pseudomonas aeurginosa* exotoxin A PE38 fragment (SEQ. ID. 102).

As used herein, a "steroid" includes cholesterol (5-cholesten-3beta-ol), pregnenolone (3beta-hydroxy-5-pregnen-20-one), 17-hydroxyprenenolone (3-beta,17-dihydroxy-5-pregnen-20-one), progesterone (4-pregnene-3,20-dione), 17-hydroxyprogesterone (17-hydroxy-4-pregnene-3,20-dione), androstenedione (4-androstene-3,17-dione), 4-hydroxyandrostenedione (4-hydroxy-4-androstene-3,17-dione), 11-beta-hydroxyandostenedione (11beta-4-androstene-3,17-dione), androstanediol (3-beta,17-beta-Androstanediol), androsterone (3-alpha-hydroxy-5alpha-androstan-17-one), epiandrosterone (3-beta-hydroxy-5alpha-androstan-17-one), adrenosterone (4-androstene-3,11,17-trione), dehydroepiandrosterone (3beta-hydroxy-5-androsten-17-one), dehydroepiandrosterone sulfate (3-beta-sulfooxy-5-androsten-17-one), testosterone (17beta-hydroxy-4-androsten-3-one), epitestosterone (17-alpha-hydroxy-4-androsten-3-one), 5-alpha-dihydrotesterone (17-beta-hydroxy-5alpha-androstan-3-one), 5-beta-dihydrotestosterone (17-beta-hydroxy-5beta-androstan-3-one), 11-beta-hydroxytesosterone (11-beta,17beta-dihydroxy-4-androsten-3-one), 11-ketotesosterone (17-beta-hydroxy-4-androsten-3,17-dione), estrogen (including: estrone (3-hydroxy-1,3,5(10)-estratrien-17-one), estradiol (1,3,5(10)-estratriene-3,17beta-diol), and estriol (1,3,5(10)-estratriene-3,16alpha,17beta-triol)), corticosterone (11-beta,21-dihydroxy-4-pregnene-3,20-dione), deoxycorticosterone (21-hydroxy-4-pregnene-3,20-dione), cortisol (11-beta,17,21-trihydroxy-4-pregnene-3,20-dione), 11-deoxycortisol (17,21-dihydroxy-4-pregnene-3,20-dione), cortisone (17,21-dihydroxy-4-pregnene-3,11,20-trione), 18-hydroxycorticosterone (11-beta,18,21-trihydroxy-4-pregnene-3,20-dione), 1-alpha-hydroxycorticosterone (1-alpha,11-beta,21-trihydroxy-4-pregnene-3,20-dione), and aldosterone (18,11-hemiacetal of 11beta,21-dihydroxy-3,20-dioxo-4-pregnen-18-al).

As used herein, a "Specific Binding Peptide" includes an "anti-angiogenic peptide" (SEQ. ID. 146) and an "integrin binding peptide" (SEQ. ID. 147). A "Specific Binding Peptide" includes integrin binding peptide RGD4C=CDCRGDFC (SEQ. ID. 147), integrin binding peptide RGD10 (SEQ. ID. 148), c(RGDyK) (SEQ. ID. 149), integrin binding peptide c(RGDfK) (SEQ. ID. 150), integrin binding peptide [c(RGDyK)]2 (SEQ. ID. 151), integrin binding peptide CAGKNFFWKTFTSC (SEQ. ID. 152), cilengitide (cyclic RGD pentapeptide) (SEQ. ID. 153), ATN-161 (peptide antagonist of integrin alpha5beta1) (SEQ. ID. 154), ATN-454 (Ac-PHSCN—$NH_2$) (peptide antagonist of integrin alpha5beta1) (SEQ. ID. 155), tumstatin T7 peptide TMPFLFCNVNDVCNFASRNDYSYWL (SEQ. ID. 156), tumstatin sequence 1 YSNS (SEQ. ID. 157), tumstatin sequence 2 YSNSG (SEQ. ID. 158), endostatin motif FLSSRLQDLYSIVRRADRAA (SEQ. ID. 159), endostatin motif IVRRADRAAVP (SEQ. ID. 160), laminin peptide A13 (RQVFQVAYIIIKA) (SEQ. ID. 161), laminin peptide C16 (KAFDITYVRLKF) (SEQ. ID. 162), laminin peptide C16S (DFKLFAVTIKYR) (SEQ. ID. 163), and VEGFR1 peptide (CPQPRPLC) (SEQ. ID. 164).

As used herein, a traditional linker includes linkers that can be formed from those reagents disclosed in Tables IA-ID, IIA-IID, IIIA-IIIC, IVA-IVC, VA-VB, and VIA-VID of U.S. Pat. No. 9,381,178.

As used herein, a "FSB linker" includes those linkers selected from the group consisting of 4-fluorosulfonyl benzoyl, 3-fluorosulfonyl benzoyl and 2-fluorosulfonyl benzoyl as depicted in FIG. 15 of U.S. Pat. No. 9,381,178.

As used herein, a "Mall" linker includes a malonic linker and a maleimide linker covalently attached to an illudofulvene analog.

As used herein, a "protease" includes those enzymes disclosed in Table III.

As used herein, a "cytokine" includes chemokines, interferons, interleukins, lymphokines, tumor necrosis factor, neutrophil activating protein-2, monocyte chemotactic protein-1 and the like.

Despite recent advances in therapy, many patients with cancer invariably relapse and require additional treatments. Most of these patient's cancers become refractory to standard chemotherapy and/or radiation treatment regimens. The prognosis for these patients is poor and long term survival rates for metastatic solid tumor cancers remain very low. Thus, there is a need for the development of novel agents and treatment regimens that specifically target these recurring tumor cells and also produce less systemic toxicity. Target therapies, such as monoclonal antibodies, now provide a promising alternative to the conventional cytotoxic chemotherapy approach.

Monoclonal antibody based therapy has recently achieved considerable success in oncology and there are currently nine monoclonal antibodies (without a medicant attached) approved by the FDA as cancer therapeutics. As an example, HERCEPTIN® and RITUXAN® (both produced by Genentech, South San Francisco, Calif.), are used to successfully treat breast cancer and non-Hodgkin's lymphoma, respectively. HERCEPTIN® is a recombinant DNA-derived humanized monoclonal antibody selectively binding to the extracellular domain of the Human Epidermal growth factor Receptor 2 (HER2) proto-oncogene whereas RITUXAN® is a genetically engineered chimeric murine/human monoclonal antibody directed against the CD20 antigen overexpressed on the surface of normal and malignant B lymphocytes.

Recent clinical evidence indicates that while the monoclonal antibody based therapies are effective at inducing remission, they do not always produce a complete cure, and relapses eventually occur in most patients. There is now a tremendous interest in the use of antibody medicant conjugates as a class of therapeutics that utilize the antigen-selectivity of monoclonal antibodies to deliver potent cytotoxic medicants to specific tumor cells. Antibody medicant conjugates are produced by attaching a cytotoxic agent to an antibody that binds specifically to a tumor-associated antigen.

In theory, antibody medicant conjugates can confer an increased therapeutic index to highly potent medicants by improving therapeutic efficacy and reducing systemic toxicity (by minimizing damage to normal tissues), although this goal has been elusive in achieving. The basis for the efficacy of antibody medicant conjugates is that they target tumor cells that preferentially express an antigen that is recognized by the associated antibody. In contrast, non-tumor cells either fail to express this antigen, or express the antigen at a very low level. In theory, only the tumor cells expressing the associated antibody are recognized and destroyed by the AMC, and other cells are left untouched and undamaged.

While different medicant classes have been tried for delivery via antibodies, only a few have proved efficacious for use as antibody medicant conjugates. The two main medicant classes used to date to produce antibody medicant conjugates are the auristatins (MMAE/N-methylvaline-valine-dolaisoleuine-dolaproine-norephedrine or MMAF/N-methylvaline-valine-dolaisoleuine-dolaproine-phenylalanine) and the maytansines (DM1 or DM4). Currently only two antibody medicant conjugates are approved by the U.S.F.D.A. and marketed; brentuximab vedotin (auristatin based) and ado-trastuzumab emtansine (maytansine based).

Illudofulvenes have several unique properties over agents traditional used to make medicants and/or antibody drug conjugates (ADCs). Firstly, these are the only agents known to function by inhibition of the DNA transcription-coupled repair pathway, see e.g., U.S. Pat. No. 10,285,955 entitled AFFINITY MEDICANT CONJUGATES, issued May 14, 2019, which is herein incorporated by reference inits entirety and for all purposes. No other toxin, drug or medicant inhibits this pathway. The result is that illudofulvenes are true cytotoxic agents whereas other agents traditionally used to produce ADCs (pyrrolobenzodiazepines, maytansines, fumagillols, dolstatins, auristatins, enadiynes, halichondrins, and tubulysins) are only cytostatic. In the NCI-DTP 60 cell line panel these other agents were capable of inhibiting tumor cell growth ($IC_{50}$ value), had some ability to block tumor cell growth (TGI value) but none were capable of actually causing tumor cell death or cytotoxicity (Table VI). The illudin derivatives, however, are capable of killing tumor cells at nanomolar concentrations (Table VI). This means that while ADCs developed using other toxins can stall tumor cell growth, they cannot actually kill the tumor cell. Once the effect of the drug has worn off the tumor cells will again grow and kill the patient. In contrast, the illudofulvenes actually kill the tumor cell with as little as a 2 hour exposure. Secondly, whereas tumor cells will undergo apoptosis or cell death with hours once the DNA transcription-coupled repair pathway is blocked, normal diploid non-tumor cells can survive for hours. This translates into a wide therapeutic window for ADCs developed with illudofulvenes. The two ADC agents currently FDA approved for administration deliver a dose of the associated toxin that is 300% higher than a lethal dose which is why these agents have severe systemic toxicity. In contrast, the comparable ADC developed with illudofulvenes will deliver a dose of the associated toxin that is 40% of a known non-toxic dose (estimated at 28% of a toxic dose and only 12% of a lethal dose). Thus, ADCs developed with illudofulvenes will have minimal systemic toxicity as compared to current agents. Thirdly, these agents are stable down to a pH of 2.0. An ADC is engulfed by a tumor cell, transported to the endosomes (pH<6.0) and then into the lysozomes (pH<4). Many agents used for ADCs will degrade in these low pH environment, whereas illudofulvenes are stable. 4). Cancer cells can become resistant to various toxins and drugs through the development of what is termed multi-drug resistance. This process is known to occur through several different mechanisms. Whereas other toxins and drugs are substrates for the most common MDR mechanisms (MDR1/gp170 and MRP/gp180), and cancer cells can become resistant to these agents, the illudofulvenes remain active against all MDR phenotypes regardless of the mechanism (see Table IV). Hence, if tumor cells have already developed multi-drug resistance prior to ADC with a conventional toxin, or during the administration of a course of the ADC, the ADC will have no efficacy. In contrast, ADCs developed with illudofulvenes will continue to kill cancer cells. Illudofulvenes as stand alone treatments or in ADCs can be coupled with a screen to select a patient population that will respond to the illudofulvenes, see e.g., U.S. patent application Ser. No. 16/708,005 entitled METHODS, COMPOSITIONS AND DEVICES FOR TREATING CANCER WITH ILLUDOFULVENES, filed Dec. 9, 2020, which is herein incorporated by reference inits entirety and for all purposes The present invention is based on the discovery that illudofulvene are active as medicant delivery agents in vitro and in vivo and can be conjugated directly to a linker, via a variety of peptide or non-peptide bonds, and are active as medicant delivery agents in vitro and in vivo. Similar to other medicant classes used to produce antibody medicant conjugates, the illudofulvenes can be conjugated to a linker that allows subsequent coupling to a monoclonal antibody. Unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), many of the illudofulvenes compounds do not require a linker and can be directly attached to a monoclonal antibody or fragment thereof by a variety of simple chemical reactions. In this sense, the lack of requirement for a linker or a spacer, the illudofulvenes compounds are unique. They will directly form covalent bonds with reactive groups on an AM such as a monoclonal antibody. In addition, because of their very small size and extreme cytotoxicity the illudofulvenes can be coupled directly to very small molecular weight entities (or affinity moieties) that allow tumor specific cytotoxicity without the concomitant requirement of use of a monoclonal antibody. Examples include the ability to link illudofulvenes directly to steroids which allow the medicant-affinity complex to kill cells overexpressing a specific steroid receptor (such as estrogen- or progesterone-positive breast cancer cells) or even to be chemically coupled to various lipids. The small size and extreme cytotoxicity illudofulvenes allows direct coupling to peptides which can preferentially bind to tumor cells (integrin binding peptides) or display anti-angiogenic properties to hinder tumor invasion. The illudofulvenes can also be coupled to specific peptides which actually renders the medicant-affinity complex non-toxic until the peptide is cleaved by a protease secreted by tumor cells. An example includes PSA (prostate specific antigen) secreted by prostate adenocarcinoma cells. Again, unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), the illudofulvenes compounds do not require a linker and can be directly attached to a steroid or a peptide that will subsequently function as an AM and direct the associated complex to specific tumor cells. In an embodiment of the invention, an illudofulvenes is attached to either a Specific Binding Peptide or a peptide which when cleaved by a specific protease (see Table III) such as PSA generates an entity which is cytotoxic (see Table II).

Trastuzumab emtansine (Genentech for Breast cancer) uses maytanasine derive DM-1, a stable non-cleavable linker. Brentuximab vedotin (Seattle Genetics/Takeda for Hodgkin's Lymphoma) uses auristatin MMAE to anti-CD30, an enzyme sensitive cleavable linker.

The malonic linker, maleimide linker and SMCC [succinimidyl 4-(N-maleimidomethyl)-cyclohexane-1-carboxylate] linker can form active intermediates that react with sulfhydryl groups on an antibody. SMCC has been used to bind maytansine derivative DM1 to the monoclonal antibody Herceptin. The AMC was internalized where the Herceptin was degraded by proteases and DM1 was released into the cytosol. Further, Sulfo-SMCC [sulfosuccinimidyloxycarbonyl-α-methyl-α-(2-pyridyldithio)toluene] forms an active intermediate that reacts with sulfhydryl groups on an antibody. The resulting Sulfo-SMCC AMC is more water soluble than the SMCC AMC.

Compounds and Conjugates. The present invention is drawn to a series of compounds and conjugates containing a Medicant moiety (M) linked via its C terminus to a LU (LU). The LU can operate to provide a suitable release of M.

In one group of embodiments, the invention provides Medicant Linker compounds having Formula I: LU-M (I) or a pharmaceutically acceptable salt or solvate thereof where the medicant loading is represented by p, the average number of medicant molecules per affinity (e.g., an antibody) (e.g. of Formula II, IIa, IIa'). Medicant loading may range from 1 to 20 Medicant units (M) per Affinity unit (e.g., Ab or in Ab). Compositions of Formula IIa and Formula IIa' include mixtures of antibodies conjugated with a range of medicants, from 1 to 20.

In some embodiments, p is from about 1 to about 8 Medicant units per Affinity unit. In some embodiments, p is 1. In some embodiments, p is from about 2 to about 8 Medicant units per Affinity unit. In some embodiments, p is from about 2 to about 6, 2 to about 5, or 2 to about 4 Medicant units per LU. In some embodiments, p is about 2, about 4, about 6 or about 8 Medicant units per Affinity unit.

The average number of Medicants units per Affinity unit in a preparation from a conjugation reaction may be characterized by conventional means such as mass spectroscopy, ELISA assay, and HPLC. The quantitative distribution of Affinity Medicant Linker conjugates in terms of p may also be determined. In some instances, separation, purification, and characterization of homogeneous Affinity Medicant Linker conjugates, where p is a certain value from Affinity Medicant Linker conjugates with other medicant loadings may be achieved by means such as reverse phase HPLC or electrophoresis.

Returning to Formula IIa', the conjugates comprise an antibody covalently attached to one or more Medicant units (moieties) via a LU: A, a, W and w are as described above. The antibody medicant conjugate include pharmaceutically acceptable salts or solvates thereof.

The medicant loading is represented by p, the average number of Medicant units per antibody in a molecule of Formula II. Medicant loading may range from 1 to 20 medicants (M) per Ab or mAb. Compositions of the AMC of Formula IIa' include mixtures of antibodies conjugated with a range of medicants, from 1 to 20. In some embodiments, p is from about 1 to about 8 Medicant units per antibody. In some embodiments, p is 1. In some embodiments, p is from about 2 to about 8 Medicant units per antibody. In some embodiments, p is from about 2 to about 6, 2 to about 5, or 2 to about 4 Medicant units per antibody. In some embodiments, p is about 2, about 4, about 6 or about 8 Medicant units per antibody.

The average number of medicants per antibody in preparations of AMCs from conjugation reactions may be characterized by conventional means such as UV/visible spectroscopy, mass spectrometry, ELISA assay, and HPLC. The quantitative distribution of AMCs in terms of p may also be determined. In some instances, separation, purification, and characterization of homogeneous AMCs where p is a certain value from AMC with other medicant loadings may be achieved by means such as reverse phase HPLC or electrophoresis.

For some antibody medicant conjugates, p may be limited by the number of attachment sites on the antibody. For example, where the attachment is a cysteine thiol, an antibody may have only one or several cysteine thiol groups, or may have only one or several sufficiently reactive thiol groups through which a LU may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond.

Typically, less than the theoretical maximums of medicant moieties are conjugated to an antibody during a conjugation reaction. An antibody may contain, for example, many lysine residues that do not react with the Medicant Linker compound intermediate or LU reagent. Only the most reactive lysine groups may react with an amine-reactive LU reagent. Generally, antibodies do not contain many, if any, free and reactive cysteine thiol groups which may be linked to a Medicant moiety via a LU. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (medicant/antibody ratio) of an AMC may be controlled in several different manners, including: (i) limiting the molar excess of Medicant Linker compound intermediate or LU reagent relative to antibody, (ii) limiting the conjugation reaction time or temperature, and (iii) partial or limiting reductive conditions for cysteine thiol modification.

Where more than one nucleophilic group reacts with a Medicant Linker compound intermediate, or LU reagent followed by Medicant moiety reagent, then the resulting product is a mixture of Affinity Medicant Linker Conjugates (e.g., AMCs) with a distribution of one or more Medicant moieties per Affinity unit (e.g., an antibody). The average number of medicants per Affinity unit (e.g., antibody) may be calculated from the mixture by, for example, dual enzyme linked immune serum assay (ELISA) antibody assay, specific for antibody and specific for the medicant. Individual Affinity Medicant Linker Conjugate molecules may be identified in the mixture by mass spectroscopy, and separated by high performance liquid chromatography (HPLC), e.g., hydrophobic interaction chromatography. Thus, a homogeneous conjugate with a single loading value may be isolated from the conjugation mixture by electrophoresis or chromatography.

A "Linker Unit" (LU) is a bifunctional compound which can be used to link a Medicant unit and/or an Affinity unit to form an Affinity Medicant Linker conjugate. Such conjugates are useful, for example, in the formation of immuno conjugates directed against tumor associated antigens. Such conjugates allow the selective delivery of cytotoxic drugs to tumor cells. A LU includes a traditional linker, a 4-fluorosulfonyl benzoyl (4-FSB) linker, a 3-fluorosulfonyl benzoyl (3-FSB) linker a 2-fluorosulfonyl benzoyl (2-FSB) linker, a maleimide (Mall) linker, an azlactone linker and a bridging amino acid.

A traditional linker is as defined in U.S. Pat. No. 9,381,178. A Stretcher Unit includes two or more Linker Units.

A bridging amino acid means —NH—C(R')H—CO— or —N(R")—C(R')H—CO— including glycine, L-alanine, L-serine, L-threonine, L-cysteine, L-valine, L-leucine, L-isoleucine, L-methionine, L-proline, L-phenylalanine, L-tyrosine, L-tryptophan, L-aspartic acid, L-glutamic acid, L-asparagine, L-glutamine, L-histidine, L-lysine, L-arginine, L-homocysteine, L-selenocysteine, L-pyrrolysine, L-carnitine, L-hypusine, 2-aminoisobutyric acid, dehydroalanine, L-gamma-aminobutyric acid, L-ornithine, L-citrulline, L-α-Amino-n-butyric acid, L-Norvaline, L-Norleucine, L-Pipecolic acid, L-Alloisoleucine, L-α,β-diaminopropionic acid, L-α,γ-diaminobutyric acid, L-Allothreonine, L-α-Amino-n-heptanoic acid, L-Homoserine, β-Amino-n-butyric acid, β-Aminoisobutyric acid, γ-Aminobutyric acid, L-isovaline, L-Sarcosine, N-ethyl glycine, N-propyl glycine, N-isopropyl glycine, L-N-methyl alanine, L-N-ethyl alanine, N-methyl β-alanine, N-ethyl β-alanine, Isoserine, L-α-hydroxy-γ-aminobutyric acid, L-diaminopimelic acid, cystathione, L-aminoisobutyric acid, dehydroalanine, delta-aminolevulinic acid, 4-aminobenzoic acid, L-Hydroxyproline, Formylmethioinine, L-lanthionine, djenkolic acid, L-Pyroglutamic acid, Hypusine, L-carboxyglutamic acid, penicillamine, L-thialysine, quisqualic acid, L-canavine, L-azetidine-2-carboxylic acid, D-alanine, D-serine, D-threonine, D-cysteine, D-valine, D-leucine, D-isoleucine, D-methionine, D-proline, D-phenylalanine, D-tyrosine, D-tryptophan, D-aspartic acid, D-glutamic acid, D-asparagine, D-glutamine, D-histidine, D-lysine, D-arginine, D-homocysteine, D-selenocysteine, D-pyrrolysine, D-carnitine, D-hypusine, D-gamma-aminobutyric acid, D-ornithine, D-citrulline, D-α-Amino-n-butyric acid, D-Norvaline, D-Norleucine, D-Pipecolic acid, D-Alloisoleucine, D-α,β-diaminopropionic acid, D-α,γ-diaminobutyric acid, D-Allothreonine, D-α-Amino-n-heptanoic acid, D-Homoserine, D-isovaline, D-Sarcosine, D-N-methyl alanine, D-N-ethyl alanine, D-α-hydroxy-γ-aminobutyric acid, D-diaminopimelic acid, D-aminoisobutyric acid, D-Hydroxyproline, D-lanthionine, D-Pyroglutamic acid, D-carboxyglutamic acid, D-thialysine, quisqualic acid, D-canavine, D-azetidine-2-carboxylic acid. A 'modified bridging amino acid' means a bridging amino acid with R' including a hydroxyl group that has been esterified, a bridging amino acid with R' including a sulphur atom where the sulphur atom has been reacted with an alkyl or other organic group and/or a bridging amino acid with R' including a primary amino group that has been converted into a secondary or tertiary amino group.

In one embodiment, the LU of the Medicant Linker compound and Affinity Medicant Linker conjugate has the formula: —$W_w$-$A_a$ wherein -A- is a Stretcher Unit; a is 1 or 2; each —W— is independently an Amino Acid unit; w is independently an integer ranging from 1 to 20. In the Affinity Medicant Linker conjugate, the LU serves to attach the Medicant moiety and the AM.

The Affinity Moiety (AM) includes within its scope an Affinity Unit (AU) that specifically binds or reactively associates or complexes with a receptor, antigen or other receptive moiety associated with a given target-cell population. An AU is a molecule that binds to, complexes with, or reacts with a receptor, antigen or other receptive moiety of a cell population sought to be therapeutically or otherwise biologically modified. In one aspect, the AM acts to deliver the Medicant unit to the particular target cell population with which the AM interacts. Such AM's include, but are not limited to, proteins, polypeptides and peptides and include, antibodies, binding proteins, smaller molecular weight proteins, polypeptides, peptides, lectins, glycoproteins, non-peptides, vitamins, nutrient-transport molecules (such as, but not limited to, transferrin), or any other cell binding molecule or substance.

In an embodiment of the invention, an AM can form a bond to a Stretcher Unit. In an alternative embodiment of the invention, an AM can form a bond to the Stretcher Unit of the LU via a heteroatom of the AM. Heteroatoms that may be present on an AM include sulfur (in one embodiment, from a sulfhydryl group of an AM), oxygen (in one embodiment, from a carbonyl, carboxyl or hydroxyl group of an AM) and nitrogen (in one embodiment, from a primary or secondary amino group of an AM). These hetero atoms can be present on the AM in the AM's natural state, for example a naturally-occurring antibody, or can be introduced into the AM via chemical modification.

In one embodiment, an AM unit has a sulfhydryl group and the AM bonds to the LU via the sulfhydryl group's sulfur atom. In another embodiment, the AM has lysine residues that can react with activated esters (such esters include, but are not limited to, N-hydroxysuccinimide, pentafluorophenyl, and p-nitrophenyl esters) of the Stretcher Unit of the AM and thus form an amide bond consisting of the primary nitrogen atom of the AM and the carboxyl group of the AM. In yet another aspect, the AM has one or more lysine residues that can be chemically modified to introduce one or more sulfhydryl groups. The AM bonds to the LU via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the AM can have one or more carbohydrate groups that can be chemically modified to have one or more sulfhydryl groups. The AM bonds to the LU (or a Stretcher Unit) via the sulfhydryl group's sulfur atom. In yet another embodiment, the AM can have one or more carbohydrate groups that can be oxidized to provide an aldehyde (—CHO) group. The corresponding aldehyde can form a bond with a reactive site on a Stretcher Unit. Reactive sites on a Stretcher Unit that can react with a carbonyl group on an AM include, but are not limited to, hydrazine and hydroxylamine.

Useful non-immunoreactive protein, polypeptide, or peptide affinity moieties include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-.alpha. and TGF-.beta., vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art.

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay).

Other useful antibodies include fragments of antibodies such as, but not limited to, $F(ab')_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. Humanized antibodies are antibody molecules from non-human species having one or more complementarity determining regions (CDRs) from the non-human species and a framework region from a human immunoglobulin molecule. Such chimeric and humanized monoclonal antibodies can be produced by recombinant DNA techniques known in the art.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. Human antibodies can also be produced using various techniques known in the art, including phage display libraries.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor.

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, N.C.) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART MI95 (Protein Design Labs, Inc., CA) and SGN-33 (Seattle Genetics, Inc., WA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEACIDE (Immunomedics, N.J.) which is a humanized anti-CEA antibody for the treatment of colorectal cancer.

Other antibodies useful in the treatment of cancer include, but are not limited to, antibodies against the following antigens (where exemplary cancers that can be treated with the antibody are in parentheses): Alk (adrenocarcinomas) (SEQ. ID. 103), CA125 (ovarian) (SEQ. ID. 104), CA15-3 (carcinomas) (SEQ. ID. 105), CA19-9 (carcinomas), L6 (carcinomas) (SEQ. ID. 107), Lewis Y (carcinomas) (SEQ. ID. 108), Lewis X (carcinomas) (SEQ. ID. 109), alpha fetoprotein (carcinomas) (SEQ. ID. 110), CA 242 (colorectal), placental alkaline phosphatase (carcinomas) (SEQ. ID.

112), prostate specific antigen (prostate) (SEQ. ID. 113), prostate specific membrane antigen (prostate) (SEQ. ID. 114), prostatic acid phosphatase (prostate) (SEQ. ID. 115), epidermal growth factor (carcinomas), MAGE-1 (carcinomas) (SEQ. ID. 117), MAGE-2 (carcinomas) (SEQ. ID. 118), MAGE-3 (carcinomas) (SEQ. ID. 119), MAGE-4 (carcinomas) (SEQ. ID. 120), anti-transferrin receptor (carcinomas) (SEQ. ID. 121), p97 (melanoma) (SEQ. ID. 122), MUC1 (breast cancer) (SEQ. ID. 123), CEA (colorectal) (SEQ. ID. 124), gp100 (melanoma) (SEQ. ID. 125), MART-1 (melanoma) (SEQ. ID. 126), IL-2 receptor (T-cell leukemia and lymphomas), CD2 (buccal mucosa) (SEQ. ID. 128), CD20 (non-Hodgkin's lymphoma) (SEQ. ID. 129), CD52 (leukemia) (SEQ. ID. 130), CD33 (leukemia), CD22 (lymphoma), beta human chorionic gonadotropin (carcinoma) (SEQ. ID. 133), CD38 (multiple myeloma) (SEQ. ID. 134), CD40 (lymphoma) (SEQ. ID. 135), CD80 (colorectal), CD86 (colorectal), mucin (carcinomas), P21 (carcinomas), MPG (melanoma) (SEQ. ID. 140), Neu oncogene product (carcinomas) and STEAP-1 (prostate).

Compositions and Methods of Administration. In other embodiments, described is a pharmaceutical composition including an effective amount of an Affinity Medicant Linker conjugate and/or a Medicant Linker compound and a pharmaceutically acceptable carrier or vehicle. The compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow an Affinity Medicant Linker conjugate and/or a Medicant Linker compound to be bioavailable upon administration of the composition to a patient. Compositions can take the form of one or more dosage units, where for example, a tablet can be a single dosage unit, and a container of an Affinity Medicant Linker conjugate and/or a Medicant Linker compound in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Affinity Medicant Linker conjugate and/or a Medicant Linker compound, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Affinity Medicant Linker conjugate and/or a Medicant Linker compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of an Affinity Medicant Linker conjugate and/or a Medicant Linker compound such that a suitable dosage will be obtained. Typically, this amount is at least about 0.01% of an Affinity Medicant Linker conjugate and/or a Medicant Linker compound by weight of the composition. In an exemplary embodiment, pharmaceutical compositions are prepared so that a parenteral dosage unit contains from about 0.01% to about 2% by weight of the Affinity Medicant Linker conjugate and/or a Medicant Linker compound.

For intravenous administration, the composition can comprise from about 0.01 to about 100 mg of an Affinity Medicant Linker conjugate and/or a Medicant Linker compound per kg of the patient's body weight. In one aspect, the composition can include from about 1 to about 100 mg of an Affinity Medicant Linker conjugate and/or a Medicant Linker compound per kg of the patient's body weight. In another aspect, the amount administered will be in the range from about 0.1 to about 25 mg/kg of body weight of the Affinity Medicant Linker conjugate and/or a Medicant Linker compound.

Prior art ADC's such as Kadcyla or Adcetris deliver a dose of the associated toxin (auristatins MMAE or emtansine DM-1) that is three or more times the lethal dose (for that toxin) which results in severe systemic (or non-target) toxicity. In contrast, illudofulvenes ADC's (such as analog 189, analog 190, analog 217, analog 218, analog 219, analog 222, or analog 316 deliver less than one third (i.e., <⅓) of a lethal dose, minimizing the risk and severity of systemic toxicity. Illudofulvenes are true cytotoxic agents whereas other toxic agents used in prior art ADC's (e.g., pyrrolobenzodiazepines, maytansines, fumagillols, dolstatins, auristatins, enadiynes, halichondrins, and tubulysins) are only cytostatic. See Table VI (based on the NCI-DTP 60 cell line). Hence, other payloads, such as those used in Herceptin, Adcetris or Rituxin only stall tumor cell growth and do not actually kill the tumor cells. Other payloads (e.g., pyrrolobenzodiazepines, maytansines, fumagillols, dolstatins, auristatins, enadiynes, halichondrins, and tubulysins) are not active against multidrug phenotypes, notably the MDR1/GP170 and MRP/GP180 transport mechanisms (see Table IV). Illudofulvenes show the excellent effect of remaining active against all MDR phenotypes known regardless of the mechanism of resistance (see Table IV). Hence, if tumor cells have already developed multi-drug resistance to a prior art ADC with a prior art toxin, or develop multi-drug resistance during the administration of a course of the prior art ADC with a prior art toxin, then the ADC will have no efficacy. In contrast, ADCs developed with illudofulvenes have the advantageous effect that they will continue to kill cancer cells.

Generally, the dosage of an Affinity Medicant Linker conjugate and/or a Medicant Linker compound administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The Affinity Medicant Linker conjugate and/or a Medicant Linker compound can be administered by any convenient route, for example by infusion or bolus injection. Administration can be systemic or local. Various delivery systems are known, e.g., encapsulation in liposomes, microparticles, microcapsules, capsules, etc., and can be used to administer an Affinity Medicant Linker conjugate and/or a Medicant Linker compound. In certain embodiments, more than one Affinity Medicant Linker conjugate and/or a Medicant Linker compound is administered to a patient.

In specific embodiments, it can be desirable to administer one or more Affinity Medicant Linker conjugates and/or a Medicant Linker compound locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the Affinity Medicant Linker conjugate and/or a Medicant Linker compound can be delivered in a controlled release system, such as but not limited to, a pump or various polymeric materials can be used. In yet another embodiment, a controlled-release system can be placed in proximity of the target of the Linker Affinity conjugate and/or a Medicant Linker compound, e.g., the liver, thus requiring only a fraction of the systemic dose.

The term "carrier" refers to a diluent, adjuvant or excipient, with which an Affinity Medicant Linker conjugate and/or a Medicant Linker compound is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the Affinity Medicant Linker conjugate and/or the Medicant Linker compound and pharmaceutically acceptable carriers are sterile. Water is an exemplary carrier when the Affinity Medicant Linker conjugate and/or a Medicant Linker compound are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use.

In an embodiment, the Affinity Medicant Linker conjugates and/or Medicant Linker compounds are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where an Affinity Medicant Linker conjugate and/or Medicant Linker compound is to be administered by infusion, it can be dispensed, for example, with an infusion bottle containing sterile pharmaceutical grade water or saline. Where the Affinity Medicant Linker conjugate and/or Medicant Linker compound is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer, an autoimmune disease or an infectious disease.

Treatment of Cancer. The Affinity Medicant Linker conjugates and Medicant Linker compounds are useful for inhibiting the multiplication of a tumor cell or cancer cell, causing apoptosis in a tumor or cancer cell, or for treating cancer in a patient. The Affinity Medicant Linker conjugates and/or Medicant Linker compounds can be used accordingly in a variety of settings for the treatment of animal cancers. The Affinity Medicant Linker Conjugates can be used to deliver a Medicant or Medicant unit to a tumor cell or cancer cell. Without being bound by theory, in one embodiment, the AM of an Affinity Medicant Linker conjugate binds to or associates with a cancer-cell or a tumor-cell-associated antigen, and the Affinity Medicant Linker conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, one or more specific peptide sequences within or at the Medicant unit's proximal end of the LU are hydrolytically cleaved by one or more tumor cell or cancer cell-associated proteases, resulting in release of the Medicant unit. The released Medicant unit is then free to migrate within the cell and induce cytotoxic or cytostatic activities. The Affinity Medicant Linker conjugate also can be cleaved by an intracellular protease to release the Medicant moiety. In an alternative embodiment, the Medicant or Medicant unit is cleaved from the Affinity Medicant Linker conjugate outside the tumor cell or cancer cell, and the Medicant or Medicant unit subsequently penetrates the cell.

The Affinity Medicant Linker conjugates provide conjugation-specific tumor or cancer medicant targeting, thus reducing general toxicity of the Medicant. The LUs stabilize the Affinity Medicant Conjugates in blood, yet are cleavable by tumor-specific proteases within the cell, liberating a Medicant unit.

In one embodiment, the AM binds to the tumor cell or cancer cell. In another embodiment, the AM binds to a tumor cell or cancer cell antigen which is on the surface of the tumor cell or cancer cell. In another embodiment, the AM binds to a tumor cell or cancer cell antigen which is an extracellular matrix protein associated with the tumor cell or cancer cell.

The specificity of the AM for a particular tumor cell or cancer cell can be important for determining those tumors or cancers that are most effectively treated. For example, an Affinity Medicant Linker conjugate and/or Medicant Linker compound having a BR96 AM can be useful for treating antigen positive carcinomas including those of the lung, breast, colon, ovaries, and pancreas. Affinity Medicant Linker conjugates having an anti-CD30 or an anti-CD70 binding affinity moiety can be useful for treating hematologic malignancies.

Other particular types of cancers that can be treated with an Affinity Medicant Linker conjugate and/or a Medicant Linker compound include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma blood-borne cancers, including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma acute and chronic leukemias: lymphoblastic, myelogenous, lymphocytic, myelocytic leukemias Lymphomas: Hodgkin's disease, non-Hodgkin's Lymphoma, Multiple myeloma, Waldenstrom's macroglobulinemia, Heavy chain disease, Polycythemia vera.

Multi-Modality Therapy for Cancer. Cancers, including, but not limited to, a tumor, metastasis, or other disease or disorder characterized by uncontrolled cell growth, can be treated or inhibited by administration of an Affinity Medicant Linker conjugate or Medicant Linker compound.

In other embodiments, methods for treating cancer are provided, including administering to a patient in need thereof an effective amount of an Affinity Medicant Linker conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Affinity Medicant Linker conjugates can be administered to a patient that has also undergone surgery as treatment for the cancer.

In some embodiments, the patient also receives an additional treatment, such as radiation therapy. In a specific embodiment, the Affinity Medicant Linker conjugate is administered concurrently with the chemotherapeutic agent or with radiation therapy. In another specific embodiment, the chemotherapeutic agent or radiation therapy is administered prior or subsequent to administration of an Affinity Medicant Linker conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with an Affinity Medicant Linker conjugate and/or a Medicant Linker compound are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Example 1. Synthesis of Medicant 113. The Wittig reaction was performed on analog 010. First 65 mg $CH_3PPh_3Br$ (0.185 mmol) in anhydrous THF was cooled to −75° C. and stirred for 1 hour. Then 200 μL of n-butyl lithium (0.183 mmol) was added very slowly to the flask while maintaining temperature at −75° C., and a yellow precipitate formed. It was stirred for another 1.5 hours then analog 010 (50 mg, 0.183 mmol) was slowly added while maintaining temperature at −75° C., followed by stirring for 2.0 hours. The reaction was quenched with ammonium chloride, extracted with $CH_2Cl_2$, washed with water, $NaHCO_3$, and saline. Dried over $Na_2SO_4$ and concentrated. The residue was eluted through a column (10% ethyl acetate in hexane) to give analog 113 as a solid.

Example 2. Synthesis of Medicant-Estrone 107. Analog 106 (see Example 13) (139 mg 0.384 mmol, 1 equiv.), DMAP (4 mg, 0.03 mmol, 0.08 equiv.) and estrone (104.4 mg, 0.384 mmol, 1 equiv.) were dissolved in $CH_2Cl_2$ (14 mL) at 0° C. To this solution was added $CH_2Cl_2$ solution of DCC (460 μL, 1 M, 0.46 mmol, 1.2 equiv.) through a syringe. After 0.5 hours the solution was raised to RT. After 2 hours the mixture was filtered and the filtrate was washed with dilute HCl (1.5%), saturated $NaHCO_3$ and brine in sequence. The organic phase was then dried and evaporated. The residue was eluted through a column ($CH_2Cl_2$/Methanol, 10:0.25) to give analog 107 (100 mg, 42%) as semisolid. Analog 107 can be subsequently linked to estrone.

Example 3. Preparation of Medicant-Estradiol 108. Analog 038 (58.5 mg, 0.2035 mmol), beta-estradiol (58.0 mg, 0.2150 mmol) and DMAP (5 mg. 0.048 mmol) were dissolved in $CH_2Cl_2$ (5.6 mL) at 0° C. To this solution was added $CH_2Cl_2$ solution of DCC (250 μL, 1 M, 0.244 mmol), stirred for 30 minutes, allowed to warm to RT then stirred for 1.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 108 (45 mg) as a solid.

Table I shows the cytotoxic data $IC_{50}$ values (micromolar, 2 hour exposure, N=3, mean±SD) for 108. MCF7 over express estrogen alpha-receptors. MCF7 cells are preferentially killed by 110 the acylfulvene-estrone analog and to a lesser extent 108 the acylfulvene-estradiol analog because estrone preferentially binds to alpha-receptor.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$(5 mL) at 0° C. To this solution was added $CH_2Cl_2$ solution of DCC (165 μL, 1 M, 0.165 mmol, 1.1 equiv.). The mixture was raised to RT after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to RT then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 110 (40 mg) as a solid.

Table I shows the cytotoxic data $IC_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table I demonstrates that analog 108 and analog 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in $CH_2Cl_2$ (8.0 mL) at 0° C. To this solution was added $CH_2Cl_2$ solution of DCC (250 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in $CH_2Cl_2$(5.0 mL) at 0° C. To this solution was added $CH_2Cl_2$ solution of DCC (150 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (2:3 ethyl acetate: hexane) to give analog 112 (15 mg) as a solid.

In an embodiment of the present invention, an illudin2 moiety 1302 linked via a traditional linker 1240 to a steroid 1140 bind to receptors for the steroid and directs the illudin2 moiety 1302 to cell populations expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tissues containing cells expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tumors containing cells over-expressing the receptor compared to non tumor cells.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$(5 mL) at 0° C. To this solution was added $CH_2Cl_2$ solution of DCC (165 μL, 1 M, 0.165 mmol, 1.1 equiv.). The mixture was raised to RT after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to RT then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 110 (40 mg) as a solid.

Table I shows the cytotoxic data $IC_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table I demonstrates that compounds 108 and 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in $CH_2Cl_2$ (8.0 mL) at 0° C. To this solution was added $CH_2Cl_2$ solution of DCC (250 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in $CH_2Cl_2$(5.0 mL) at 0° C. To this solution was added $CH_2Cl_2$ solution of DCC (150 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (2:3 ethyl acetate: hexane) to give analog 112 (15 mg) as a solid.

Example 13. Synthesis of Medicant 106. Illudin M (450 mg, 1.845 mmol, 1 equiv.), glutaric anhydride (2.10 g, 18.45 mmol, 10 equiv.) and DMAP (171 mg, 1.4 mmol, 0.76 equiv.) were dissolved in $CH_2Cl_2$ (5 mL) at RT. After 3.5 hours the mixture was taken up by $CH_2Cl_2$, which was washed with water, and brine in sequence. It was then dried and evaporated. The residue was eluted through a column (Hexane/EtOAc 4:1) to give analog 106 (365 mg, 55%) as a liquid. UV ($CHCl_3$) λ nm (ε): 309 (3387).

Analog 106 was generated from illudin M as outlined in Example 13. The carboxylic acid derivative was activated using DCC/DMAP to synthesize steroid AFC's 107 and 109. In addition, Irofulven carboxylic acid derivative, analog 038 was activated using DCC/DMAP to produce analogs 108, 110, 111, and 112. In general, carboxylate group containing compounds can be activated using a carbodiimide in the presence of an amino acid to form an azlactone. The azlactone formed will react spontaneously with primary amine groups on an amino acid, a peptide, an antibody, a protein, or another drug, and undergo ring opening with the formation of an amide bond. For proteins, antibodies and peptides the amino acids capable of reacting with the azlactone derivative includes arginine and lysine.

To form an Illudin derived azlactone active drug-linker moiety, either analog 106 or analog 038 can be activated by DCC/DMAP in the presence of a small amino acid such as glycine to form the azlactone. DCC cannot be added without the presence of an amine containing target (such as the glycine) or the activated carboxylate reacts with another carboxylate to form a symmetrical anhydride. The azlactone formed will react spontaneously with primary amine groups on a peptide, an antibody, a protein, or a medicant.

Example 14. Activation of analog 038 by DCC to form medicant-azlactone. Part A: Production of Azlactone from carboxylate Acylfulvene analog: Analog 038 (58.5 mg, 0.2035 mmol), and DMAP (5 mg. 0.048 mmol) were dissolved in $CH_2Cl_2$ (5.6 mL) at 0° C. The desired amino acid (such as glycine) was added in an equimolar amount. Note that amino acids having substitutions on the C4 carbon (such as alpha-methyl glycine or 2-dimethylglycine) are preferred over conventional amino acids as substitution cannot occur at the C4 position after ring-opening and all nucleophilic coupling reactions must occur at the C5 position, resulting only in the desired amide-bond formation with the amine-containing molecule. To this solution was added $CH_2Cl_2$ solution of DCC (250 μL, 1 M, 0.244 mmol), stirred for 30 minutes, allowed to warm to RT then stirred for 1.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give the desired azlactone analog as a solid. Part B: Coupling of Azlactone to the protein component (reacting with primary amines on amino acids such as the one on lysine): The typical protein coupling reaction consists of the Azlactone suspended in buffer [25 mM sodium phosphate, 150 mM NaCl (pH 7.5)] and the desired amount of protein (20 g to 5.0 mg) was added. The mixture was gently rocked for 60 minutes, then the reaction terminated by the addition of the blocking reagent, 1.0 ml of 1.0 M ethanolamine in 25 mM sodium pyrophosphate (titrated to pH 9.0 with HCl) Sample rocked gently for 5 minutes then the residual ethanolamine removed by dialysis or chromatography using pH 7.5 phosphate-NaCl buffer.

Example 15. Reaction of the medicant-azlactone product with an antibody. The azlactone derivative generated in Example 14 (note that other amino acids can be used in place of glycine) was then reacted with the desired peptide or protein or other compound containing a primary amino group at a 1:1 ratio in buffer (25 mM sodium phosphate, 150 mM sodium chloride, pH 7.5) with gentle rocking at RT for 60 minutes. The reaction was terminated by the addition of 1.0 mL of 25 mM ethanolamine (titrated to pH 9.00) with rocking for 5 minutes at RT). The drug-azlactone-ligand product can be purified by column chromatography or dialysis to remove the ethanolamine by-product.

Example 16. Synthesis of Medicant 114. $(CH_3)_3S(O)I$ (110 mg, 0.4 mmol) and tBuOK (50 mg, 0.4 mmol) were dissolved in anhydrous DMSO (1 mL) and stirred at RT for 40 minutes at RT. Then analog 010 (50 mg, 0.2 mmol) in 1.0 mL of DMSO was added via syringe, and stirred for 3 hours. Reaction quenched with saturated $NH_4Cl$ (1 mL), extracted with $CH_2Cl_2$, dried over $Na_2SO_4$, concentrated then chromatographed (2:3 hexane:ethyl acetate) to yield analog 114 (20 mg., 50% yield).

Example 17. Synthesis of Medicant 115. Analog 010 (40 mg) and $NAHCO_3$ (50 mg) are dissolved in 10 mL of 1:1 Ethanol and water mixture, then hydroxylamine hydrochloride (20 mg) was added, stirred for 30 minutes at RT. Water and ethyl acetate (1:1 mixture) was added, stirred, the organic layer was recovered, washed with saturated $NaHCO_3$ and then brine, dried over $Na_2SO_4$, concentrated then chromatographed (2:3 ethyl acetate: hexane) to yield analog 115.

Example 18. Synthesis of Medicant 116. $SeO_2$ (45 mg) and 500 mg SiO2 transferred into a dried RB flask, 5 mL of $CH_2Cl_2$ added, and stirred for 1 hour under nitrogen. Then 250 μL of $tBuO_2H$ added and stirred for 15 minutes. Then 100 mg of Irofulven in 1 mL $CH_2Cl_2$ was added, and stirred for 3 hours at RT under a nitrogen atmosphere. Product was filtered, wash twice with water (25 mL), twice with brine (25 mL), dried over $Na_2SO_4$ and concentrated then chromatographed (4:1 hexane: ethyl acetate) to yield analog 116.

Example 19. Synthesis of Medicant 116. Analog 117: Illudin S (100 mg, 0.378 mmol) and glutaric anhydride (215.46 mg, 1.89 mmol) are dissolved in 5 mL of $CH_2Cl_2$, and DMAP added (92.23 mg, 0.756 mmol), and stirred for 2 hours at RT. The $CH_2Cl_2$ was evaporated, 5 mL of water was added, and stirred for 1 hour. The solution was extracted with 10 mL of $CH_2Cl_2$, washed with water, dried over $Na_2SO_4$ and concentrated to yield analog 117 (120 mg).

Example 20. Synthesis of Analog 118: Analog 302 (75 mg), glutaric anhydride (20 mg) are dissolved in 5 mL of $CH_2Cl_2$, and DMAP added (42 mg), and stirred for 2 hours at RT. The $CH_2Cl_2$ was evaporated, 5 mL of water added, and stirred for 1 hour. Solution was extracted with 10 mL of $CH_2Cl_2$, washed with water, dried over $Na_2SO_4$ and concentrated to yield analog 118 (120 mg).

Example 21. Synthesis of Analog 119: Analog 114 (10 mg) was dissolved in 1.5 mL of acetone with 1.0 mL of 4N $H_2SO_4$, and contents stirred for 1.5 hours at RT. Then 10 mL of $CH_2Cl_2$ and 10 mL of water are added, extracted, and the organic layer recovered which was then washed with saturated $NaHCO_3$ and saline, dried over $Na_2SO_4$ and concentrated, and analog 119 recovered (analog 128 was a byproduct).

Example 22. Synthesis of Analog 120: Analog 010 (50 mg), $NaHCO_3$ are dissolved in 10 mL of 1:1 mixture of water and ethanol, then $NH_2NH_2$ (0.5 mL added with stirring at RT for one hour. The solution was extracted with $CH_2Cl_2$ twice, the organic layer recovered, washed with water, then $NaHCO_3$ solution, dried over $Na_2SO_4$, and evaporated to yield analog 120 (30 mg).

Example 23. Synthesis of Analog 121: Analog 010 (50 mg) and $NaCO_2CH_3$ (75 mg) are dissolved in 10 mL of 1:1 mixture of water and ethanol 1:1, then semicarbazide hydrochloride salt ($H_2NNHCONH_2$.HCl, 50 mg) added, and stirred for 2 hours at RT. The solution was extracted with $CH_2Cl_2$ twice, the organic layer recovered, washed with water, then $NaHCO_3$ solution, dried over $Na_2SO_4$, and evaporated then chromatographed (5% methanol in ethyl acetate) to yield analog 121.

Example 24. Synthesis of Analog 122: Analog 010 (50 mg) and $NaCO_2CH_3$ (75 mg) are dissolved in 5 mL of ethanol, then phenylhydrazide (50 mg) was added, stirred for 1 hour at RT. Then 5 mL of water was added, followed by extraction with ethyl acetate, washed with water, dried over $Na_2SO_4$ and concentrated and chromatographed (5% methanol in ethyl acetate) to yield analog 122.

Example 25. Synthesis of Analog 123: Analog 010 (50 mg) and $NaCO_2CH_3$ (75 mg) are dissolved in 10 mL of 1:1 water and ethanol, then $H_2NNHTS(H_2NNHS(=O)_2$(phenyl)methyl, 50 mg) was added, stirred for 2 hour at RT. Then 5 mL of water was added, followed by extraction with ethyl acetate, washed with water, dried over $Na_2SO_4$ and concentrated and chromatographed (5% methanol in ethyl acetate) to yield analog 123.

Example 26. Synthesis of Analog 124: Analog 115 (15 mg) and NaOAc (15 mg) are dissolved in acetic anhydride (1 mL) and stirred for 2 hours, then sodium acetate (300 mg) was added with stirring for 1 hour. Then the mixture was chromatographed (10% ethyl acetate in hexane) to give analog 124.

Example 27. Synthesis of Analog 125: Analog 010 (50 mg) and $NaCO_2CH_3$ (75 mg) are dissolved in 5 mL of ethanol, then the dinitrophenylhydrazide (50 mg) was added, stirred for 1 hour at RT. Then 5 mL of water was added, followed by extraction with ethyl acetate, washed with water, dried over $Na_2SO_4$ and concentrated and chromatographed (5% methanol in ethyl acetate) to yield analog 125.

Example 28. Synthesis of Analog 126: Analog 011 (40 mg), hydroxylamine (20 mg), $NaHCO_3$ (50 mg) are dissolved in 10 mL of ethanol and water (1:1) then stirred at RT for 90 minutes. Then the mixture was extracted with water (10 mL) and ethyl acetate (20 mL), the organic layer washed with saturated $NaHCO_3$ then brine, dried over $Na_2SO_4$ and concentrated, then chromatographed (2:3 ethyl acetate: hexane) to give analog 126.

Example 29. Synthesis of Analog 127: Analog 010 (100 mg) and $NH_4Cl$ (1.5 equivalent) are dissolved in 1,4-dioxane (5 mL) and water (0.2 mL), then NaCN added (1.3 equivalents), stirred for 1 hour at RT. Then ethyl ether (20 mL) was added, the organic layer recovered, washed with water, washed with brine, then dried over $Na_2SO_4$, then chromatographed (2:3 ethyl acetate: hexane) to yield analog 127.

Example 30. Synthesis of Analog 128: Analog 114 (10 mg) was dissolved in 1.5 mL of acetone with 1.0 mL of 4N $H_2SO_4$, and contents stirred for 1.5 hours at RT. Then 10 mL of $CH_2Cl_2$ and 10 mL of water are added, extracted, and the organic layer recovered which was then washed with saturated $NaHCO_3$ and saline, dried over $Na_2SO_4$ and concentrated, and analog 128 recovered (analog 119 was a byproduct).

Example 31. Synthesis of Analog 129: Analog 001 (200 mg) was dissolved in anhydrous THF (10 mL) at RT then $NaBH_4$ (100 mg) was added slowly for 30 minutes. Reaction was quenched with 1 mL of water then extracted with ethyl acetate (10 mL), washed with saturated $NaHCO_3$, and dried over $Na_2SO_4$, then concentrated to yield analog 129. If need be the compound can be purified by chromatography (1:1 ethyl acetate: hexane).

Example 32. Analog 141: Analog 129 (200 mg) was dissolved in $CH_2Cl_2$ at RT, then 1,4-dimethyl but-2-ynedioate (1.1 equivalent) was added slowly and mixture allowed to react for one hour, then evaporated to yield analog 141. If need be the compound can be purified by chromatography (1:1 ethyl acetate: hexane).

Example 33. Synthesis of Analog 142: Analog 141 (100 mg) was dissolved in $CH_2Cl_2$ at RT then Dess-Martin Periodinane reagent (200 mg) added with stirring for 1 hour to yield analog 142. If need be the compound can be purified by chromatography (1:1 ethyl acetate: hexane).

Example 34. Synthesis of Analog 146: Analog 127 (35 mg, 0.117 mmol), DMAP (5 mg), and diimidazole (22 mg, 1.2 eq) were dissolved in anhydrous $CH_2Cl_2$ under an argon atmosphere, and stirred for 30 minutes. The solution was cooled to 20° C. then tributyl tin hydride ($Bu_3SnH$, 0.6 mL) and azobis isobutylnitrite (4 mg) were added with stirring for 30 minutes. The mixture was filtered then chromatographed (1:10 ethyl acetate: hexane) to remove impurities and starting materials, then chromatographed (2:3 ethyl acetate: hexane) to yield analog 146.

Example 35. Synthesis of Analog 147: Irofulven (10 mg) was dissolved in 3 mL of acetone and 1 M $H_2S04$ solution (1:1) with stirring at RT and 2-Mercaptobenzothiazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 147.

Example 36. Synthesis of Analog 148: Irofulven (10 mg) was dissolved in 3 mL of acetone and 1 M $H_2S04$ solution (1:1) with stirring at RT and 2-Mercaptobenzoxazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 Ethyl acetate: hexane) to give analog 148.

Example 37. Synthesis of Analog 149: Irofulven (10 mg) was dissolved in 4 mL of acetone and 1 M $H_2SO_4$ solution (1:1) with stirring at RT and thiol-imidazole (1 equivalent) was added, stirred for 24 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 149.

Example 38. Synthesis of Analog 150: Irofulven (10 mg) was dissolved in 4 mL of acetone and 1 M $H_2SO_4$ solution (1:1) with stirring at RT and 2-mercapto-5-methylbenzimidazole (1 equivalent) was added, stirred for 12 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 150.

Example 39. Synthesis of Analog 151: Irofulven (10 mg) was dissolved in 3 mL of acetone and 1 M $H_2SO_4$ solution (1:1) with stirring at RT and 1-phenyl-1,2,3,4-tetraazole-5-thiol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 151.

Example 40. Synthesis of Analog 152: Irofulven (10 mg) was dissolved in 3 mL of acetone and 1 M $H_2SO_4$ solution (1:1) with stirring at RT and 2-mercapto-5-nitro benzimidazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 152.

Example 41. Synthesis of Analog 153: Irofulven (10 mg) was dissolved in 3 mL of acetone and 1 M $H_2SO_4$ solution (1:1) with stirring at RT and 1, 2, 4-Triazole-3-thiol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 153.

Example 42. Synthesis of Analog 154: Irofulven (10 mg) was dissolved in 3 mL of acetone and 1 M $H_2SO_4$ solution (1:1) with stirring at RT and 2-sulfanylpteridin-4-ol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 154.

Example 43. Synthesis of Analog 155: Irofulven (10 mg) was dissolved in 3 mL of acetone and 1 M $H_2SO_4$ solution (1:1) with stirring at RT and 4-(5-sulfanyl-H-1,2,3,4-tetrazol-1-yl)phenol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 155.

Example 44. Synthesis of Analog 156: Irofulven (10 mg) was dissolved in 3 mL of acetone and 1 M $H_2SO_4$ solution (1:1) with stirring at RT and 4-(5-sulfanyl-1-1,2,3,4-tetrazol-1-yl)benzoic acid (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 156.

Example 45. Synthesis of Analog 159: Illudin S (300 mg) was dissolved acetic anhydride (6 mL) and stirred for 15 minutes, then sodium acetate (300 mg) was added with stirring for 1 hour. Water (6 mL) was added, ethyl acetate extraction performed, washed with sodium bicarbonate solution, dried over $Na_2SO_4$, concentrated then chromatographed (2:3 ethyl acetate:hexane) to give analog 159.

Example 46. Synthesis of Analog 160: Analog 159 (60 mg) was dissolved in dry $CH_2Cl_2$ (6 mL) under nitrogen at RT and glutaric anhydride (100 mg) with DMAP (20 mg) was added with stirring for 30 minutes. The solvent was removed, water added, extracted with $CH_2Cl_2$, washed with water, dried over $Na_2SO_4$, concentrated then chromatographed (2:3 ethyl acetate: hexane) to give analog 160.

Example 47. Synthesis of Analog 161: Dehydroilludin S (300 mg) was dissolved acetic anhydride (6 mL) and stirred for 15 minutes, then sodium acetate (300 mg) was added with stirring for 1 hour. Water (6 mL) was added, ethyl acetate extraction performed, washed with sodium bicarbonate solution, dried over $Na_2SO_4$, concentrated then chromatographed (2:3 ethyl acetate:hexane) to give analog 161.

Example 48. Synthesis of Analog 162: Dehydroilludin S (60 mg) was dissolved in dry $CH_2Cl_2$ (6 mL) under nitrogen at RT and glutaric anhydride (150 mg) with DMAP (50 mg) was added with stirring for 30 minutes. The solvent was removed, water added, extracted with $CH_2Cl_2$, washed with water, dried over $Na_2SO_4$, concentrated then chromatographed (2:3 ethyl acetate:hexane) to give analog 162.

Example 49. Synthesis of Analog 163: Analog 159 (20.25 mg), DMAP (20 mg) are dissolved in dry $CH_2Cl_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 1 5 minutes. Then water (6 mL) was added, mixed, and then extracted with $CH_2Cl_2$. The organic layer was washed with saturated $NaHCO_3$ followed by a saline wash, dried over $Na_2SO_4$ then chromatographed (2:3 ethyl acetate: hexane) to yield analog 163 (60% yield).

Example 50. Synthesis of Analog 164: Irofulven (50 mg), DMAP (40 mg) are dissolved in dry $CH_2Cl_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 15 minutes. Then water (6 mL) was added, mixed, and then extracted with $CH_2Cl_2$. The organic layer was washed with saturated $NaHCO_3$ followed by a saline wash, dried over $Na_2SO_4$ then chromatographed (2:3 ethyl acetate: hexane) to yield analog 164 (60% yield).

Example 51. Synthesis of Analog 165: Analog 164 (40 mg) was dissolved in dry $CH_2Cl_2$ (6 mL) at RT under nitrogen atmosphere and stirred for 10 minutes. Then 1 mL of morpholine was added drop wise, with stirring for 30 minutes. The reaction was diluted with water (6 mL), extracted with $CH_2Cl_2$ (12 mL). The organic layer was washed with saturated $NaHCO_3$ then washed with saline, dried over $Na_2SO_4$ and chromatographed (2:3 ethyl acetate: hexane) to yield 165 (35% yield).

Example 52. Synthesis of Analog 166 and analog 167 (prepared together): Analog 160 (30 mg) was dissolved in methanol (4 mL) at 0° C., and 1N $H_2SO_4$ (1 mL) was added with stirring for 1 hour. Water (6 mL) was added, extracted with ethyl acetate, washed with $NaHCO_3$ then a brine solution, dried over $MgSO_4$, concentrated and then chromatographed (1:1 ethyl acetate:hexane) to yield analogs 166 and 167 in equal amounts.

Example 53. Synthesis of Analog 168: Analog 162 (20 mg) was dissolved in methanol (5 mL) at 0° C. and stirred for 10 minutes, then 1 mL of 1N $H_2SO_4$ in methanol was slowly added, followed by stirring for 30 minutes. Water was added, followed by an ethyl acetate extraction, washed with $NaHCO_3$ then a brine solution, dried over $Na_2SO_4$, concentrated then chromatographed (1:1 ethyl acetate: hexane) to yield analog 168.

Example 54. Synthesis of Analog 169: Dehydroilludin S (20 mg), DMAP (20 mg) are dissolved in dry $CH_2Cl_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 15 minutes. Then water (6 mL) was added, mixed, then extracted with $CH_2Cl_2$. The organic layer was washed with saturated $NaHCO_3$ followed by a saline wash, dried over $Na_2SO_4$ then chromatographed (2:3 ethyl acetate: hexane) to yield analog 169 (60% yield).

Example 55. Synthesis of Analog 176: To a solution of analog 009 (266 umol), Boc protected leucine amino acid (300 umol) and DMAP (dimethylaminopyridine, 110 umol) in $CH_2Cl_2$ (2.5 mL) at 0° C. was added DCC (dicyclohexylcarbodiimide; 1.0M in $CH_2Cl_2$, 300 umol). The mixture was stirred for 35 minutes then 5 μL of water added to quench the reaction. The mixture was diluted with hexane and precipitate filtered off, solvent evaporated off and crude product chromatographed (2:1 hexanes-ethyl acetate) to give the desired Boc-protected derivative of 176 at 80% yield. The Boc group was removed by dissolving the Boc-protected derivative in a 1:1 mixture (2.0 mL) of 1,4-dioxane and 2M $H_2SO_4$, stirred for 18 hours, then partitioned between ethyl acetate and water. Aqueous layer was extracted with ethyl acetate and extracts discarded. Aqueous layer was neutralized with saturated $NaHCO_3$ and extracted again with ethyl acetate. Organic layer was washed with brine, dried with $MgSO_3$, solvent evaporated to yield the analog 009 amino acid derivative. As the amine derivative was unstable over prolonged periods of time it can be converted to the very stable trifluoroacetate salt by dissolving in $CH_2Cl_2$ adding the equal molar amount of trifluoroacetic acid and concentrating to dryness.

Example 56. Synthesis of Analog 178: Analog 009 (15 mg) was dissolved in $CH_2Cl_2$ (2.0 mL) under a nitrogen atmosphere at RT, succinic anhydride (1 equivalent) was added, followed by DMAP (10 mg) and stirring for 30 minutes. Solvent was removed and product recrystallized to give analog 178.

Example 57. Synthesis of Analog 179: To a solution of Analog 009 (266 μmol), Boc protected glycine amino acid (300 umol) and DMAP (dimethylaminopyridine, 110 umol) in $CH_2Cl_2$ (2.5 mL) at 0° C. was added DCC (dicyclohexylcarbodiimide; 1.0M in $CH_2Cl_2$, 300 umol). The mixture was stirred for 35 minutes then 5 μL of water added to quench the reaction. The mixture was diluted with hexane and precipitate filtered off, solvent evaporated off and crude product chromatographed (2:1 hexanes-ethyl acetate) to give the desired Boc-protected derivative of 179 at 80% yield. The Boc group was removed by dissolving the Boc-protected derivative in a 1:1 mixture (2.0 mL) of 1,4-dioxane and 2M $H_2SO_4$, stirred for 18 hours, then partitioned between ethyl acetate and water. Aqueous layer was extracted with ethyl acetate and extracts discarded. Aqueous layer was neutralized with saturated $NaHCO_3$ and extracted again with ethyl acetate. Organic layer was washed with brine, dried with $MgSO_3$, solvent evaporated to yield the analog 009 amino acid derivative. As the amine derivative was unstable over prolonged periods of time it can be converted to the very stable trifluoroacetate salt by dissolving in $CH_2Cl_2$ adding the equal molar amount of trifluoroacetic acid and concentrating to dryness.

Example 58. Synthesis of Analog 180: Illudin M (50 mg) was dissolved in dry benzene (10 mL) under a nitrogen atmosphere, and vanadyl acetylacetonate ($VO(acac)_2$, 1.2 mg) was added. Then t-butyl hydroperoxide (t-$BuO_2H$, 0.5 mL) in benzene was added drop wise with stirring for 30 minutes. A saturated solution of $Na_2S_2O_3$ was added (10 mL), then extraction with ethyl acetate, and the organic layer was dried over $Na_2SO_4$, concentrated then chromatographed) (1:1 ethyl acetate:hexane) to give analog 180.

Example 59. Synthesis of Analog 181: Analog 159 (40 mg) was dissolved in dry benzene (8 mL) under a nitrogen atmosphere, and vanadyl acetylacetonate ($VO(acac)_2$, 2 mg) was added. Then t-butyl hydroperoxide (t-$BuO_2H$, 0.5 mL) in benzene was added drop wise with stirring for 30 minutes. A saturated solution of $Na_2S_2O_3$ was added (10 mL), then extraction with ethyl acetate, followed by a brine wash, and the organic layer was then dried over $Na_2SO_4$, concentrated then chromatographed) (1:1 ethyl acetate:hexane) to give analog 181.

Example 60. Synthesis of Analog 189: To a solution of Irofulven (1.00 equivalent), maleimide (1.71 equivalent), triphenylphosphine ($PPh_3$, 1.71 equivalent) in 1.5 mL of THF at −40° C., was added DEAD (diethylazodicarboxylate; 1.68 equivalent). The mixture was stirred for 30 minutes then water (20 μL) added to quench the reaction. The mixture was concentrated on a rotary evaporator and crude product was chromatographed on a silica column (10:3 hexanes: ethyl acetate) to yield an orange compound (20% yield).

Example 61. Synthesis of Analog 190: To a solution of analog 009 (6-hydroxy-n-propylacylfulvene—structure below, 1.00 equivalent), maleimide (1.23 equivalent), triphenylphosphine ($PPh_3$, 1.13 equivalent) in 2.5 mL of THF at −40° C., was added DIAD (diisopropylcarbodiimide; 1.44 equivalent). The mixture was stirred for 1 hour then water (10 μL) added to quench the reaction. The mixture was concentrated on a rotary evaporator and crude product was chromatographed on a silica column (5:1→10:3 hexanes: ethyl acetate) to yield an orange compound (15% yield).

Example 62. Synthesis of Analog 196: To a solution of analog 009 (266 umol), Boc protected proline amino acid (300 umol) and DMAP (dimethylaminopyridine, 110 umol) in $CH_2Cl_2$ (2.5 mL) at 0° C. was added DCC (dicyclohexylcarbodiimide; 1.0M in $CH_2Cl_2$, 300 umol). The mixture was stirred for 35 minutes then 5 μL of water added to quench the reaction. The mixture was diluted with hexane and precipitate filtered off, solvent evaporated off and crude product chromatographed (2:1 hexanes-ethyl acetate) to give the desired Boc-protected derivative of 196 at 80% yield. The Boc group was removed by dissolving the Boc-protected derivative in a 1:1 mixture (2.0 mL) of 1,4-dioxane and 2M $H_2SO_4$, stirred for 18 hours, then partitioned between ethyl acetate and water. Aqueous layer was extracted with ethyl acetate and extracts discarded. Aqueous layer was neutralized with saturated $NaHCO_3$ and extracted again with ethyl acetate. Organic layer was washed with brine, dried with $MgSO_3$, solvent evaporated to yield the analog 009 amino acid derivative. As the amine derivative was unstable over prolonged periods of time it can be converted to the very stable trifluoroacetate salt by dissolving in $CH_2Cl_2$ adding the equal molar amount of trifluoroacetic acid and concentrating to dryness.

Example 63. Synthesis of Analog 198: Irofulven (26.3 mg, 107 umol), p-nitrophenol (16.2 mg, 116 umol) and PPh3 (30.8 mg, 117 umol) were dissolved in anhydrous THF (1.5 mL) at −40° C., the DEAD (25 μL, 160 umol) was added, followed by stirring for 30 minutes, then diluted with hexane. The precipitate was filtered off, solvent evaporated, and crude product chromatographed (6:1→2:1 hexane: ethyl acetate) to give analog 198 as a yellow product (18.5 mg, 47%).

Example 64. Analogs 199 and 200 (prepared together): Irofulven (25.2 mg, 102 umol), phenol (11.5 mg, 122 umol) and $PPh_3$ (29.1 mg, 117 μmol) were dissolved in anhydrous THF (1.0 mL) at −40° C., the DEAD (25 μL, 192 μmol) was added, followed by stirring for 30 minutes, then diluted with hexane. The precipitate was filtered off, solvent evaporated, and crude product chromatographed (6:1→3:1 hexane: ethyl acetate) to give analog 199 (8.2 mg, 25%) and analog 200 (14.6 mg, 44%) as a yellow products.

Example 65. Synthesis of Analog 201 [6-(acetamidopropyl)acylfulvene]: To a solution of analog 195 (49.1 umol)

and water (20 μL in THF (0.5 ml) was added a solution of O-acetyl-2-(diphenylphosphino)phenol (39.0 umol) in THF (0.5 mL). The mixture was stirred for 3 days at RT then concentrated. The crude product was chromatographed (100% ethyl acetate) to yield 8.2 mg of analog 201.

Example 66. Synthesis of Analog 202 (i.e., analog 211 linked to proline): Prepared via Staudinger ligation. To a solution of analog 195 (94 umol) in THF (1.2 mL), water (40 μL) was added, the was added N-Boc-proline, 2-(diphenylphosphino)phenyl ester (101 μmol) in THF (0.8 mL). The mixture was stirred for 3 days at RT then concentrated. The crude product was chromatographed (5:1→1:2 hexanes-ethyl acetate) to yield 31.4 mg (66.7 umol) of analog 202-Boc (71%). The analog 202-Boc was dissolved (66.7 umol) in dioxane (2.0 mL) and 2.0 mL of 2M $H_2SO_4$ was added, and the mixture was stirred overnight. Water and ethyl acetate was added, orange color appeared in the aqueous. The aqueous was extracted again with ethyl acetate and organic layer discarded. Sodium bicarbonate was added to aqueous until basic, re-extracted with ethyl acetate. The solution was dried with magnesium sulphate, concentrated to dryness, dissolved in $CH_2Cl_2$ and 8 mg of TFA added (1 drop). Analog 202 was obtained in an amount of 22.2 mg (69%).

Example 67. Synthesis of Analog 203: Analog 208 (9.2 mg, 16.5 umol) was dissolved in $CH_2Cl_2$ (1.5 mL), 1 drop of anisole added, then 0.5 mL of trifluoro acetic acid for 15 minutes. The mixture was concentrated, dissolved in water, then re-extracted with $CH_2Cl_2$, and the orange color remains in the aqueous phase, which was concentrated to give analog 203 as the orange colored TFA salt (10.0 mg).

Example 68. Synthesis of Analog 204: Although the Fmoc-Pro-OH would preferentially react with the primary hydroxyl group on Illudin S, the resulting ester linkage was not stable, as illudin S was recovered after storage in $CDCl_3$ for several days at RT. The secondary hydroxy group of illudin S was therefore used for coupling with peptides. The primary hydroxy group of illudin S first protected with a TBS group (TBSCl, Imidazole, and DMF, 92%) to produce analog 204.

Example 69. Synthesis of Analog 205: Analog 309 (20 mg, 0.050 mmol, 1 equiv.), triphenylphosphine (40 mg, 0.1525 mmol, 3 equiv.) was dissolved in THF (1 mL) at RT. After 20 hours a few drops of water was added and the mixture was heated up at 70° C. After 5 hours the solution was cooled down and evaporated. The residue was chromatographed (hexane/EtOAc/$Et_3N$ 4:1:0.1) to give analog 205 (5.3 mg, 29%) as an oil.

Example 70. Synthesis of Analog 206: Analog 205 (14 mg, 0.037 mmol, 1 equiv.) was dissolved in $CH_3CN$ (0.5 mL) and pyridine (0.1 mL) at 0° C. To this solution was added HF-Pyridine (7 μL, 0.245 mmol, 35 M, 6.6 equiv.). After 10 min $K_2CO_3$ (0.5 mL, 0.5 M) was added and this mixture was chromatographed ($CH_2Cl_2$/Methanol/$Et_3N$ 5:0.5:0.1) to give analog 206 (10 mg, 68%) as an oil.

Example 71. Synthesis of Analog 207 (211-leucine): Prepared via Staudinger ligation. To a solution of analog 195 (101 umol) in THF (1.0 mL), water (40 μL) was added, then was added N-Boc-leucine, 2-(diphenylphosphino)phenyl ester (95.9 μmol) in THF (1.2 mL). The mixture was stirred for 6 days at RT then concentrated. The crude product was chromatographed (1:1 hexanes-ethyl acetate) to yield 27.3 mg of analog 207-Boc. The analog 207-Boc was dissolved (16 μmol) in $CH_2Cl_2$ with 3 drops of anisole, TFA was added (0.3 mL), and the mixture was stirred for 15 minutes then concentrated. The crude material was dissolved in water then extracted with $CH_2Cl_2$. The aqueous layer was recovered and concentrated to yield 17.4 mg of the analog 207 TFA salt (87%).

Example 72. Analog 208: The TFA salt of analog 196 (13.7 mg, 28.2 μmol) was dissolved in anhydrous DMF (2.5 mL), Boc-Serine-OH (9.6 mg, 47 umol) was added, ODHBT (13.0 mg, 79.4 umol), cooled to 0° C. under a nitrogen atmosphere. Next EDC (15.1 mg) was added followed by NMM (10 μL) to adjust pH, and the mixture stirred at 0° C. for 3 hours. The reaction was added to ethyl acetate/water mixture, and the orange product appeared in the organic layer. The aqueous layer was re-extracted with ethyl acetate, organic layers combined, washed with dilute $NaHSO_4$, water, saturated $NaHCO_3$, brine, then dried with $MgSO_4$. The organic layer was concentrated then chromatographed (1:3 hexane: ethyl acetate) to yield analog 208 as an orange residue (63% yield).

Example 73. Synthesis of Analog 209: The TFA salt of analog 196 (12.5 mg, 25.7 μmol) was dissolved in anhydrous DMF (2.5 mL), Boc-Serine-Ser OH (88.6 umol) was added, ODHBT (33.9 mg, 205 umol), cooled to 0° C. under a nitrogen atmosphere. Next EDC (142 umol) was added followed by NMM (10 μL) to adjust pH, and the mixture stirred at 0° C. but allowed to gradually warm as the ice melts. The mixture was stirred a total of 16 hour then 1 mL water added followed by stirring for 50 minutes. The reaction was added to ethyl acetate/water mixture, and the orange product appeared in the organic layer. The aqueous layer was re-extracted with ethyl acetate, organic layers combined, washed with dilute $NaHSO_4$, water, saturated $NaHCO_3$, brine, and then dried with $MgSO_4$. The organic layer was concentrated then chromatographed (10:1 ethyl acetate: methanol) to give analog 209 as an orange residue (5.9 mg, 36% yield).

Example 74. Synthesis of Analog 210 (Ac-Hyp-Ser-Ser-Chg-Gln-Ser-Ser-Pro-O—$(CH_2)_3$-acylfulvene): To a mixture of Analog 196 TFA salt (21.6 umol), the peptide Ac-Hyp-Ser-Ser-Chg-Gln-Ser-Ser-OH (30.3 umol), ODHBt (3,4,-dihydroxy-4-oxo-1,2,3-benzo-triazine-3-yl ester, 71.7 μmol) and NMM (N-methylmorpholine; 7.5 ul) in DMF (2.0 ml) at RT was added EDC (1-(3-dimethylaminopropyl)-3-ethylcarbodiimide hydrochloride, 68 μmol), the mixture stirred for 2 hours at RT, then diluted with 10 mL of water. Solution was directly chromatographed on a reverse phase C18 column (4:1→2:1, water/acetonitrile gradient) to yield 69% of analog 210.

Example 75. Synthesis of Analog 212 (Illudin M-proline) Illudin M (20 mg, 0.081 mmol, 1 equivalent), DMAP (1 mg, 0.008 mmol, 0.1 equiv.) and Fmoc-Pro-OH (33 mg, 0.097 mmol, 1.2 equiv.) were dissolved in $CH_2Cl_2$ (1 mL) at 0° C., to which was added a $CH_2Cl_2$ solution of DCC (100 μL, 0.1 mmol, 1 M, 1.2 equiv.). The temperature of the mixture gradually rose to 5° C. in 1.5 hours and then the mixture was filtered through a pad of Celite. The filtrate was concentrated and the residue was chromatographed ($CH_2Cl_2$/EtOAc 5:0.1-5:0.4) to give Illudin-M-proline-Fmoc protected analog (36 mg, 79%) as oil. The proton spectra of this oil showed that it was a mixture of two isomers (rotamers). And then this oil was dissolved in $CH_2Cl_2$ (4 mL) and treated with piperidine (1 mL) at 0° C. After 0.5 hours the solution was concentrated and the concentrate was chromatographed ($CH_2Cl_2$/Methanol 5:0.4) to give analog 212 (15 mg, 54%) as oil.

Example 76. Synthesis of Analog 213: Analog 204 was coupled with Fmoc-Pro-H (DMAP, $CH_2Cl_2$, DCC, 0° C., 85%), followed by deprotection of Fmoc group with 20% piperidine in $CH_2Cl_2$ to produce analog 213 in 78% yield.

Example 77. Synthesis of Analog 214 (Illudin S-Pro-Ser-Ser-HHOAc): The Fmoc protected peptide of H-Ser-Ser-OH was prepared by taking H-Ser-Ser-OH (50 mg, 0.26 mmol, 1 equiv.) and $K_2CO_3$ (89.7 mg, 0.65 mmol, 2.5 equiv.), dissolving in a mixture of water (4 mL) and dioxane (3 mL) at 0° C. To this solution Fmoc (67.3 mg, 0.26 mmol, 1 equiv.) was added in several portions. After 18 hours the mixture was acidified by $KHSO_4$ and the pH raised to 2.5. Then this mixture was taken up by ethyl acetate, which was washed with brine, dried, filtered and evaporated. The residue was chromatographed ($CH_2Cl_2$/Methanol/HOAc 5:1:0.1) to give 3.27 (75 mg, 70%) as a white solid. The analog 212 (Illudin S tosylate-Pro) (42.8 mg 0.09 mmol, 0.9 equiv.), and the Fmoc protected H-Ser-Ser-OH peptide (41.2 mg, 0.1 mmol, 1 equiv.) were dissolved in DMF (1.5 mL) at 0° C. To this solution was added NMM (22 μL, 0.2 mmol, 2 equiv.), ODHBt (29.4 mg, 0.18 mmol, 1.8 equiv.), and EDC (31.1 mg, 0.16 mmol, 1.6 equiv.). The solution temperature was then raised to RT and kept for 3 hours before it was taken up by ethyl acetate. The mixture was then washed with saturated sodium bicarbonate and brine. It was then dried, filtered and evaporated. The residue was chromatographed ($CH_2Cl_2$/Methanol 5:0.3) to give analog 214 (50.5 mg, 67%) as an oil.

Example 78. Synthesis of Analog 215: (Illudin S-Pro-Ser-Ser-Gln-Chg-Ser-Ser-Hyp-Ac) Analog 204 was coupled with Fmoc-Pro-H (DMAP, $CH_2Cl_2$, DCC, 0° C., 85%), followed by deprotection of Fmoc group with 20% piperidine in $CH_2Cl_2$ to produce analog 213 in 78% yield. Peptide conjugate, analog 215 was obtained from further coupling with hepta-peptide Ac-Hyp-Ser-Ser-Chg-Gln-Ser-Ser-OH (ODHBt, NMM, DMF, 0° C., 47%).

Example 79. Synthesis of Analog 216: (Illudin M-Pro-Ser-Ser-Gln-Chg-Ser-Ser-Hyp-Ac). Analog 212 was further coupled with the commercially available hepta-peptide Ac-Hyp-Ser-Ser-Chg-Gln-Ser-Ser-OH (ODHBt, NMM, DMF, EDC, 0° C.) to yield analog 216 at 33%. The low yield resulted from repeated chromatographic purification as the purity of the final raw product was estimated by HPLC to be only 70%.

Example 80. Synthesis of Analog 217: To a solution of Irofulven (1.00 equivalent), epsilon-maleimidocaproic acid (1.27 equivalent), DMAP (0.15 equivalent) in 1.0 mL of methylene chloride ($CH_2Cl_2$) at 0° C., was added DCC (dicyclohexylcarbodiimide; 1.27 equivalent) in methylene chloride ($CH_2Cl_2$). The mixture was stirred for 1.25 hours, diluted with hexane and precipitated was filtered. Residual solvent was evaporated off, and oil residue was chromatographed on a silica column (2:1 hexanes:ethyl acetate) to yield analog 217, an orange compound (77% yield).

Example 81. Synthesis of Analog 218: To a solution of Illudin M (1.00 equivalent), epsilon-maleimidocaproic acid (1.33 equivalent), DMAP (0.18 equivalent) in 1.0 mL of methylene chloride ($CH_2Cl_2$) at 0° C., was added DCC (dicyclohexylcarbodiimide; 1.33 equivalent) in methylene chloride ($CH_2Cl_2$). The mixture was stirred for 2.25 hours, diluted with hexane and precipitated was filtered. Residual solvent was evaporated off, and oil residue was chromatographed on a silica column (2:1 hexane: ethyl acetate) to yield analog 218, an orange compound (83% yield).

Example 82. Synthesis of Analog 219: Analog 204 (33.4 mg) was dissolved in 1.0 mL of anhydrous pyridine under a nitrogen atmosphere, then DMAP (5.1 mg) was added, followed by 4-fluorosulfonyl-benzoyl chloride (86.1 mg). The mixture was stirred for 90 minutes at RT The mixture was diluted with ethyl acetate, washed once with saturated copper sulfate solution, washed twice with water, then dried over $MgSO_4$, concentrated then chromatographed (20% ethyl acetate: hexane) to give analog 219.

Example 83. Synthesis of Analog 221: Prepared from Analog 207 by coupling with Mu-His-Ser-Ser-Lys(Fmoc)-Leu-Gln-OH in DIC/HOBt for 5 minutes, then 5% piperidine/DMF for 1 minute. Followed by TFA quenching to yield analog 221 at 21% yield.

Example 84. Synthesis of Analog 222: Illudin M (63 mg) was dissolved in 1.0 mL of anhydrous pyridine under a nitrogen atmosphere, then DMAP (6.4 mg) was added, followed by 4-fluorosulfonyl-benzoyl chloride (86 mg). The mixture was stirred for 35 minutes at RT then chromatographed (20% ethyl acetate: hexane) to give analog 222 (70.9 mg).

Example 85. Synthesis of Analog 223: The disulfhydryl peptide CNGRC was first converted to a cyclic disulfide peptide by dissolving 355 mg in 3.0 mL DMSO, adding 9 mL of water, allowing to sit overnight at RT, followed by water removal on a rotoevaporator then DMSO removal under high vacuum. The TFA salt of analog 179 (14.5 mg) was dissolved in DMF (2.0 mL) and the CNGRC disulfide peptide added (19.0 mg), 60 μL of DIPEA was added, followed by gradual addition of a solution of Py-BOP (19.6 mg) and HOBt (8.9 mg) in DMF (2.0 mL) over 150 minutes at RT. The reaction was stopped by adding two drops of TFA and water. The mixture was applied to a reverse phase column and analog 223 was eluted with acetonitrile: water (1:4).

Example 86. Synthesis of Analog 224: Analog 001 (116 mg) was dissolved in ethanol (4.0 mL) with stirring, hydroxylamine hydrochloride (84.2 mg) added, Sodium acetate (233 mg) added, then refluxed for 70 minutes at 85° C. The ethanol was removed, then ethyl acetate (10 mL) added to dissolve crude product, then water (10 mL) added, the organic layer was washed with brine, dried over $Na_2SO_4$, concentrated then chromatographed (20% ethyl acetate: hexane) to give analog 224 (63.7 mg, 54% yield).

Example 87. Synthesis of Analog 225: Illudin S (439 mg) was dissolved in ethanol (15 mL) with stirring, hydroxylamine hydrochloride (233 mg) added, sodium acetate (933 mg) added, then refluxed for 130 minutes at 85° C. The solution was cooled to RT, filtered, ethanol was removed, then ethyl acetate (30 mL) added to dissolve crude product, then water (30 mL) added, the organic layer was washed with brine, dried over $Na_2SO_4$, concentrated then chromatographed (30%→50%, acetone: hexane) to give analog 225 (372 mg, 80% yield).

Example 88. Synthesis of Analog 226: Irofulven (37.6 mg) was dissolved with stirring in $CH_2Cl_2$, elaidic acid (180 mg. 1.3 equivalents) added, DMAP (15 mg) added, cooled to 0° C., then DCC (180 μL) in $CH_2Cl_2$ (640 μL) added. Reaction mixture stirred at 0° C. for 1 hour, then additional DCC (120 μL) added, and stirred for 2 more hours. Mixture chromatographed (20% ethyl acetate: hexane) to give analog 226 as a yellow oil (50.5 mg, 48% yield).

Example 89. Synthesis of Analog 227: Analog 009 (87 mg) was dissolved with stirring in $CH_2Cl_2$, elaidic acid (108 mg) added, DMAP (15.4 mg) added, cooled to 0° C., then DCC (0.5 mL) in $CH_2Cl_2$ (1.5 mL) added. Reaction mixture stirred at 0° C. for 3 hours, then the mixture directly chromatographed (20% ethyl acetate: hexane) to give analog 227 as a yellow oil (105 mg, 61% yield).

Example 90. Synthesis of Analog 228: Illudin S (86 mg) was dissolved with stirring in $CH_2Cl_2$, elaidic acid (202 mg) added, DMAP (15.4 mg) added, cooled to 0° C., then DCC (1.0 mL) in $CH_2Cl_2$ (3.0 mL) added. Reaction mixture stirred at 0° C. for 3 hours, then the mixture directly chromatographed (20% ethyl acetate: hexane) to give analog 228 as a yellow oil (198 mg, 77% yield).

Example 91. Synthesis of Analog 229: The elaidic ester of 0-diphenylphosphine phenol was first prepared by dissolving with stirring in 3.0 mL of $CH_2Cl_2$ the O-diphenylphosphine phenol (91.3 mg), elaidic acid (94.5 mg, 1 equivalent), DMAP (9.4 mg). The solution was cooled to 0° C. then DDC (0.44 mL, 1.0 M in $CH_2Cl_2$) was added with stirring for 3.5 hours. The precipitate was filtered off and discarded. The elaidic ester was chromatographed and concentrated to dryness then dissolved in THF (1.0 mL). Analog 195 (26.1 mg) was dissolved in THF (1.0 mL) and water (80 μL) added. The elaidic ester solution was slowly added to the analog 195 solution with stirring, and reacted for 22 hours at RT. The mixture was directly chromatographed (30% acetone: hexane) to give analog 229 (22.2 mg, 47% yield).

Example 92. Synthesis of Analog 230: Analog 308 (22 mg) was dissolved in anhydrous $CH_2Cl_2$ (1.5 mL), diisopropylethylamine (20 μL) added, and the mixture cooled to 0° C., then methylsulfonyl chloride added (15 μL), mixture stirred at 0° C. for 1 hour, and allowed to warm to RT while being stirred for an additional hour. The mixture was chromatographed (30% ethyl acetate in hexane) to yield analog 230 (35% yield).

Example 93. Synthesis of Analog 231: Analog 308 (16 mg) was dissolved in anhydrous $CH_2Cl_2$ (1.5 mL), diisopropylethylamine (20 μL) added, and the mixture cooled to 0° C., then tosyl chloride added (18.4 mg), mixture stirred at 0° C. for 1 hour, and allowed to warm to RT while being stirred for an additional 3 hours. The mixture was chromatographed (30% ethyl acetate in hexane) to yield analog 231 (8.6 mg).

Example 94. Synthesis of Analog 240: Analog 232 (25.1 mg) was dissolved in anhydrous $CH_2Cl_2$ (2.0 mL), 15 μL of acetic anhydride added, and the mixture cooled to RT, then DMAP added (5 mg), and stirred for 25 minutes. The mixture was partially concentrated then chromatographed (30% ethyl acetate in hexane) to yield analog 240 (26.6 mg, 93% yield).

Example 95. Synthesis of Analog 254: Analog 009 (51.4 mg), 4-carboxybenzene sulfonamide (59.4 mg), and DCC (39.6 mg) were dissolved in anhydrous DMF (1.0 mL) at RT, stirred, then DMAP (15 mg) added. The mixture was stirred for 2 hours at RT then solid material was filtered off. The mixture was then chromatographed (1:1 ethyl acetate: hexane) to give analog 254 (38.6 mg, 45% yield).

Example 96. Synthesis of Analog 255: Analog 009 (244.3 mg) and sulfamoyl chloride (157 mg) were dissolved in anhydrous DMAP (2.0 mL) at RT, and stirred for 3.5 hours. The mixture was concentrated under high vacuum then chromatographed (30% ethyl acetate in hexane) to give analog 255.

Example 97. Synthesis of Analog 259: Analog 255 (64.7 mg), (diacetoxyiodo)benzene (64.7 mg), dirhodiumtetraacetate or $Rh_2(OAc)_4$ and magnesium (16.8) dissolved in 5.0 mL of $CH_2Cl_2$ are heated to 70° C. and stirred for 7 hours. The mixture was filtered, concentrated, then chromatographed (1:1 ethyl acetate: hexane) to give analog 259.

Example 98. Synthesis of Analog 262 and 263 (prepared together): Analog 025 (44.7 mg) was dissolved in methanol (1.0 mL), Oxone® reagent (246 mg, 3 equivalents) was dissolved in water (1.0 mL). The oxone solution was slowly added to the methanol solution with stirring at RT for 3.5 hours, then an additional amount of Oxone reagent added followed by stirring for 1.5 hours. Then 2 mL of saturated sodium sulfite solution was added, followed by ethyl acetate extraction, dried over $Na_2SO_4$, concentrated then chromatographed (1:1 Ethyl acetate:hexane) to yield first analog 263 (21.4 mg) and then analog 262 (14.3 mg).

Example 99. Synthesis of Analog 284 and 289 (prepared together): Analog 034 (174 mg) and uracil (227 mg) are dissolved in $CH_2Cl_2$ with stirring and the mixture cooled to 0° C. Then $SnCL_4$ (148.8 μL) was slowly added. The mixture was stirred at 0° C. for 80 minutes, then concentrated, chromatographed (2→5% methanol: $CH_2Cl_2$) to give analog 284 (68.9 mg, 33% yield) and analog 289 (21.6 mg, 10% yield).

Example 100. Synthesis of Analog 285: Analog 034 (25 mg) was dissolved in ethanol, and O-(tert-Butyldimethylsilyl) hydroxylamine (25 mg) was added followed by stirring for 2 hours at RT. The secondary amine intermediate (9 mg) was recovered by chromatography (30% ethyl acetate: hexane), dissolved in $CH_2Cl_2$, and reacted with sulfamoyl chloride ($ClSO_2NH_2$, 5 mg) and DABCO (2 mg) with stirring for one hour, then additional sulfamoyl chloride (6 mg) was added with stirring for another 1.5 hours. The TPS blocked product was recovered by chromatography (30% ethyl acetate:hexane), and the TPS group was removed in THF by adding TBAF (Tetra-n-butylammonium fluoride). The TPS group can also be removed by dissolving the TPS product in pyridine and THF at 0° C., then adding HF-pyridine overnight. After TPS deblocking the mixture was chromatographed (50% ethyl acetate: hexane) to give analog 285.

Example 101. Synthesis of Analog 286 and analog 287 (prepared together): The ketone groups on 5-fluorouracil are first blocked with TMS groups by dissolving 5-fluorouracil (610 mg) and $(NH_4)_2SO_4$ in HMDS (10 mL) under a nitrogen atmosphere. The solution was refluxed at 142° C. for 2.5 hours, cooled to 60° C. and excess HMDS distilled off, then concentrated to dryness under high vacuum. Analog 034 (180 mg) and the di-TMS 5-fluorouracil are dissolved in $CH_2Cl_2$ (5.0 mL) with stirring and the mixture cooled to 0° C. Then $SnCL_4$ (120 μL) was slowly added drop wise. The mixture was stirred at 0° C. for 3.5 hours, then concentrated, chromatographed (80% ethyl acetate: hexane) to give analog 286 (18.9 mg, 9% yield) and analog 287 (84 mg, 38% yield).

Example 102. Synthesis of Analog 289: See the preparation of analog 284 for the preparation of analog 289 (284 and 289 prepared simultaneously then separated by chromatography).

Example 103. Analogs 299 and 300 (prepared together): Analogs 299 and 300 are prepared in equal amounts from Illudin S using the Mitsunobu reaction. Illudin S was directly reacted with $HN_3$ (PPh3, DEAD, benzene) at 0° C. under nitrogen for 45 minutes. Mitsunobu, O. *Synthesis* 1:1-28, 1981.

Example 104. Synthesis of Analog 301: Irofulven (31.6 mg, 0.128 mmol), 5-benzoylvaleric acid (35.8 mg, 0.174 mmol) and DMAP (4.7 mg) was dissolved in $CH_2Cl_2$ (2 mL) under a nitrogen atmosphere, cooled to 0° C., the DCC added (170 μL of 1.0M solution in $CH_2Cl_2$). The mixture was stirred for 60 minutes then diluted with hexane (10 mL) and filtered. The organic layer was further diluted with $CH_2Cl_2$, washed with water, then saturated $NaHCO_3$ then brine, dried with $MgSO_4$, concentrated, then dissolved in $CH_2Cl_2$, filtered and chromatographed (10:3 hexane:ethyl acetate), appropriate fractions collected, pooled, concentrated then chromatographed (3:1 hexane:ethyl acetate) to give analog 301 (23.2 mg, 42% yield).

Example 105. Analogs 302 and analog 303 (prepared together): Illudin S (100 mg, 0.378 mmol) was benzoylated by dissolving in pyridine (1.0 mL) then adding 3, 5-dintirobenzoyl chloride (110 mg, 0.5 mmol) at RT and stirring for 24 hours. The mixture was poured onto crushed ice then extracted with $CH_2Cl_2$ (10 mL), which was washed twice with water (20 mL). The organic layer was dried over $Na_2SO_4$ and concentrated to yield analogs 302 and 303. The two analogs can be separated by column chromatography (1:1 hexane:ethyl acetate).

Example 106. Synthesis of Analog 304: Analog 009 (84.6 mg) was dissolved in anhydrous $CH_2Cl_2$ (3.0 mL), DCC added (81.2 mg), mixture cooled to 0° C., propiolic acid (35 μL) added, then the reaction started with DMAP (15 mg), stirred and allowed to warm to RT over 1 hour. The mixture was filtered to remove solids then chromatographed (30% ethyl acetate in hexane) to give analog 304 (60% yield).

Example 107. Synthesis of Analog 305: Analog 009 (99.1 mg) was dissolved in anhydrous $CH_2Cl_2$ (3.0 mL), pyridine (150 μL) added, then p-nitrophenylchloroformate and stirred for 3.5 hours at RT. The mixture was concentrated, hexane (20 mL) added, and precipitate filtered before chromatographing (50% ethyl acetate in hexane) to give analog 305 (50% yield).

Example 108. Synthesis of Analog 306: Analog 009 (244 mg) was dissolved in anhydrous $CH_2Cl_2$ (4.0 mL), tosyl chloride (181 mg) added, the mixture cooled to 0° C., to which an aliquot of pyridine (80 μL) was added. The mixture stirred at 0° C. for 1 hour, and allowed to warm to RT while being stirred for an additional 20 hours. The mixture was concentrated then chromatographed (50% ethyl acetate in hexane) to yield analog 306.

Example 109. Synthesis of Analog 307: A solution of 1.0 M $N_3H$ in benzene was first prepared by mixing 654 mg $N_3H$, 0.65 mL water, in 10 mL of benzene. The mixture was cooled to 0° C., 0.5 mL of concentrated $H_2SO_4$ added, and allowed to warm slowly to RT and then stirred for 80 minutes. Next $PPh_3$ (590 mg) was dissolved in anhydrous THF (1.5 mL) and cooled to 0° C. Then 2.1 mL of $N_3H$ 1.0 M solution was added, followed by DEAD (0.475 mL) then Illudin S (282 mg in 1.0 mL anhydrous THF). The mixture was stirred for 3 hours at 0° C., warmed, concentrated, followed by chromatography (30% ethyl acetate in hexane) to give analog 307.

Example 110. Synthesis of Analog 308: Analog 307 (100 mg) was dissolved in anhydrous THF (3.0 mL) at RT and PPH3 added (306 mg, 3 equivalents). The mixture was stirred for 5 hours at RT, then the reaction stooped by adding water (0.15 mL). The mixture was heated to 85° C. for 30 minutes, then concentrated and chromatographed (20% methanol in ethyl acetate) to give analog 308.

Example 111. Synthesis of Analog 309: Analog 204 was reacted with $HN_3$ (DEAD, THF) to yield the azide analog 309 at 68% yield.

Example 112. Synthesis of Analog 310: Irofulven (42.9 mg), 4-carboxybenzene sulfonamide (41.4 mg), and DCC (38.4 mg) were dissolved in anhydrous DMF (1.0 mL) at RT, stirred and then DMAP (10 mg) added. The mixture was stirred for 75 minutes at RT then solid material was filtered off. The mixture was then chromatographed (1:1 ethyl acetate: hexane) to give analog 310 (40% yield).

Example 113. Synthesis of Analog 311: Illudin M (32.4 mg), 4-carboxybenzene sulfonamide (39.7 mg), and DCC (24.4 mg) were dissolved in anhydrous DMF (1.0 mL) at RT, stirred, then DMAP (15 mg) added. The mixture was stirred for 75 minutes at RT, allowed to warm to RT, then stirred for 22 hours. The solid material was filtered off and the mixture was then chromatographed (1:1 ethyl acetate: hexane) to give analog 311 (35% yield).

Example 114. Synthesis of Analog 312: Irofulven (1.18 grams) was dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to RT while being stirred for an additional 3 hours. The mixture was concentrated then chromatographed (50% ethyl acetate in hexane) to yield analog 312.

Example 115. Synthesis of Analog 313: Analog 308 (31 mg) was dissolved in anhydrous $CH_2Cl_2$, cooled to 0° C., with stirring then diisopropylethylamine added (45 μL), then fluorophenylsulfonyl chloride added (36 μL) for 3 hours at 0° C. Mixture was directly chromatographed (20% ethyl acetate: hexane) to give analog 313 (23.3 mg).

Example 116. Synthesis of Analog 314: Analog 009 was dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to RT while being stirred for an additional 3 hours. The mixture was concentrated then chromatographed (50% ethyl acetate in hexane) to yield analog 314.

Example 117. Synthesis of Analog 315: Irofulven was dissolved in a solution of 2,5 dimethylpyrrole (4 fold excess molar solution) in 5 mL of dry $CH_2Cl_2$ at −78° C. Boron trifluoride (equivalent molar amount to the irofulven) was slowly added with stirring. The reaction was allowed to stir for 2 more hours at −78° C., then water slowly added. The mixture was extracted twice with 2 fold equivalent volumes of ethyl acetate, the organic extracts combined, washed with saturated $NaHCO_3$, water, brine, then dried over $MgSO_4$. The solution was concentrated under vacuum until a red residue remained, which was chromatographed on silica gel (50% ethyl acetate in hexane) to yield analog 315 (30% yield).

Example 118. Synthesis of Analog 316: Analog 316 was prepared by dissolving Illudin S (20 mg) in pyridine (0.5 mL) and then 4-fluorosulfonylbenzoly chloride (equivalent molar amount) was added to the mixture in an ice bath. The solution was allowed to warm slowly and then react overnight. The liquid was then removed under reduced pressure until a crude residue remained. Rather than recrystallize from chloroform, the residue was instead chromatographed on a standard silica gel column using hexane-ethyl acetate (1:1). The mono-adduct (analog 316), a di-adduct and a small amount of unreacted Illudin S were recovered in separate eluates.

Example 119. $N_3H$ 1.0 M Solution: A solution of 1.0 M N3H in benzene was first prepared by mixing 654 mg $N_3H$, 0.65 mL water, in 10 mL of benzene. The mixture was cooled to 0° C., 0.5 mL of concentrated $H_2SO_4$ added, and allowed to warm slowly to RT and then stirred for 80 minutes.

Example 120. Synthesis of Analog 193: Irofulven (221 mg, 0.897 umol) was dissolved in anhydrous THF (1.5 mL), then $PPh_3$ (261 mg, 0.995 umol) was added, then 1.0 M $N_3H$ solution (1.0 mL, 1.0 mmol) under nitrogen atmosphere. The solution was cooled to −40° C., and then DIAD (0.21 mL, 1.013 umol) added and stirred for 30 minutes at 0° C. then diluted with hexane, and filtered to remove precipitate. The mixture was concentrated then chromatographed (30% ethyl acetate: hexane) to give analog 193 (171 mg, 71%).

Example 121. Synthesis of Analog 195: Analog 009 (31.9 mg, 116 umol) was dissolved in anhydrous THF (3.0 mL), then $PPh_3$ (33 mg, 126 umol) was added, then 1.0 M $N_3H$ solution (0.3061 mL) under nitrogen atmosphere. The solution was cooled to 0° C., DIAD (30 μL, 145 umol) added and stirred for 30 minutes at 0° C. then water (5 μL) was added to destroy the $PPh_3$. The mixture was concentrated then chromatographed (30% ethyl acetate: hexane) to give analog 195 (24.9 mg, 72%).

Example 122. Synthesis of Analog 317: Analog 219 (33 mg) was dissolved in anhydrous acetonitrile (0.5 mL) and pyridine (0.1 mL) at 0° C. under nitrogen. Then add HF-pyridine solution (7 uL, 0.245 mmol, 35M, 6.6 equiv). After 10 minutes $K_2CO_3$ was added (0.5 mL, 0.5M) and the mixture concentrated then chromatographed using $CH_2Cl_2$, methanol, triethylamine (5:0.5:0.1) to yield analog 317.

Example 123. Synthesis of Analog 318: Illudin S (30 mg) was dissolved in 1.0 mL of anhydrous pyridine under a nitrogen atmosphere, then DMAP (5.0 mg) was added, followed by excess 4-fluorosulfonyl-benzoyl chloride (190 mg). The mixture was stirred for 90 minutes at RT then diluted with 5.0 mL of ethyl acetate, washed once with saturated copper sulfate solution, washed twice with water, then dried over $MgSO_4$, concentrated then chromatographed (20% ethyl acetate: hexane) to give analog 318.

Example 124. Synthesis of Analog 332: Analog 034 (200 mg) was dissolved in ethanol (95%) at RT, then 300 mg of O-methylhydroxylamine hydrochloride ($NH_2OMe$ HCl; Note O-methyl not the N-methyl compound) was added with sodium acetate (300 mg), stirred for 6 hours, concentrated, then chromatographed (15% ethyl acetate/hexanes) to yield the analog 332.

Example 125. Synthesis of Analog 333: Prepared by dissolving analog 159 and p-nitrophenylchloroformate in anhydrous $CH_2Cl_2$ under nitrogen for 5 hours at 0° C. with 1.5 equivalents of DIPEA and 1.0 equivalents of DMAP. The $CH_2Cl_2$ was removed and analog 333 was purified using a 7% ethyl acetate/hexane column. Yield was 70%.

Example 126. Synthesis of Analog 334: Prepared by dissolving analog 159 and p-nitrophenylchloroformate in anhydrous $CH_2Cl_2$ under nitrogen at 0° C. with 1.5 equivalents of DIPEA and 1.0 equivalents of DMAP. After 5 hours the Boc-N,N'-dimethylaminoethane was added and the mixture kept at 0° C. under nitrogen for 2 hours then allowed to warm up to RT and react overnight. The $CH_2Cl_2$ was removed and analog 334 purified using a 15% ethyl acetate/hexane column.

Example 127. Synthesis of Analog 335: Analog 334 (19 μmole) was dissolved in 1 mL of methanol and then sodium methoxide in methanol (0.5 M, 100 μmole) was added at RT with stirring for 30 minutes. The reaction was quenched by addition of excess acetic acid (40 μmole). The methanol was removed and analog 335 purified using a 25% ethyl acetate/hexane column.

Example 128. Synthesis of Analog 336: Analog 002 (200 mg) was placed in a dry round bottom, add 10 mL anhydrous $CH_2Cl_2$, stir at 0° C. under nitrogen, add aluminum trichloride (AlCl3). The mixture will turn dark orange, stir additional 10 min at 0° C., add 20 mL of ethylene oxide/$CH_2Cl_2$ solution at 0° C., stir for 30 minutes at 0° C. Wash twice with 10% HCV/ice cold water (2×50 mL), then twice with water (2×25 mL), dry over $Na_2SO_4$, concentrate under reduced pressure and chromatograph using ethyl acetate/hexane mixture.

Example 129. Synthesis of Analog 337: Analog 270 (244 mg) was dissolved in 5.0 mL of $CH_2Cl_2$ and DABCO added (153 mg), and solution cooled to 0° C. Then p-nitrophenylchloroformate (162 mg) was added with stirring for 3 hours at 0° C. Mixture was concentrated and chromatographed (50% ethyl acetate 50% hexanes) to yield 201 mg of analog 337 as a yellow liquid.

Example 130. Synthesis of Analog 338: Analog 211 (82 mg) was dissolved in 5.0 mL of $CH_2Cl_2$ and DABCO added (42 mg), and solution cooled to 0° C. Then p-nitrophenylchloroformate (51 mg) was added with stirring for 5 hours at 0° C. Mixture was concentrated and chromatographed (50% ethyl acetate 50% hexanes) to yield 63 mg of analog 338 as a yellow liquid.

Example 131. Synthesis of Analog 339: Illudin S is dissolved in anhydrous $CH_2Cl_2$ (4.0 mL), tosyl chloride (1.1 equivalent) added, the mixture cooled to C, then pyridine (400 uL) added. The mixture stirred at 0 C for 1 hour, and allowed to warm to RT while being stirred for an additional 3 hours. The mixture is concentrated then chromatographed (50% ethyl acetate in hexane) to yield analog 339.

Example 132. Synthesis of Analog 340: Analog 270 (146 mg), DABCO (90 mg) was dissolved in DMF/$CH_2Cl_2$ (1:3; 5.0 mL), cooled to 0° C., then methane sulfonyl chloride (55 uL; Cl—$SO_2$—$CH_3$) added with stirring for 2 hours at 0° C., concentrated then chromatographed using ethyl acetate/hexane=(1:1) to yield analog 340 as a yellow liquid.

Example 133. Synthesis of Analog 347: Illudin S (35 mg) was dissolved in 1.0 mL of anhydrous pyridine under a nitrogen atmosphere, then DMAP (5.0 mg) was added, followed by 4-sulfamidobenzoyl chloride (90 mg). The mixture was stirred for 90 minutes at RT then diluted with ethyl acetate, washed once with saturated copper sulfate solution, washed twice with water, then dried over MgSO4, concentrated, then chromatographed (20% ethyl acetate: hexane) to give analog 347.

Example 134. Synthesis of Analog 348: Illudin M (15 mg) was dissolved in 1.0 mL of anhydrous pyridine under a nitrogen atmosphere, then DMAP (3.0 mg) was added, followed by 4-sulfamidobenzoyl chloride (33 mg). The mixture was stirred for 90 minutes at RT then diluted with ethyl acetate, washed once with saturated copper sulfate solution, washed twice with water, then dried over $MgSO_4$, concentrated then chromatographed (20% ethyl acetate: hexane) to give analog 348.

Example 135. Synthesis of Analog 353: Analog 334 was dissolved in anhydrous $CH_2Cl_2$ at 0° C. and TFA added to a final concentration of 40% for 40 minutes to remove the Boc protecting group. The reaction was stopped by adding additional anhydrous $CH_2Cl_2$ to dilute the final TFA concentration to 10%, then solvent and TFA removed using a roto-evaporator without heat. Next the residue was dissolved in peptide synthesis grade DMF (so no solvent amines are present) and commercially available analog 388 was added at 0° C., followed by triethylamine (8.0 equivalents) with stirring overnight. After concentration the material was purified by preparative HPLC. Solvent A (aqueous) was 0.1% TFA in water. Solvent B (organic) was 60% acetonitrile, 39.9% water, and 0.1% TFA. HPLC gradient was initially 60% B increasing to 100% B over 45 minutes, with analog 353 eluting at approximately 40 minutes.

Example 136. Synthesis of Analog 356: Dissolve analog 334 in $CH_2Cl_2$ at 0° C., then add ice cold TFA to a final concentration of 25%, for 30 minutes to remove Boc group. Excess TFA removed by evaporating to dryness under vacuum, then add 0.5 ml $CH_2Cl_2$, evaporating to dryness under vacuum, repeat $CH_2Cl_2$ addition and evaporation a total of 3 times and keep on ice/cold the entire time. Add 1 ml dry DMF, add triethylamine (5 equiv), and keep on ice. Part B: Take Fmoc-triglycine-OH peptide (1.1 equiv) and dissolve in 3 mls dry DMF at RT, then add EDC (1.1 equiv) and NHS (N-hydroxysuccinimide, 1.1 equiv) to form the active ester, and cool on ice. Add solution B to A on ice, then allow to warm in chiller to RT overnight to produce 356 (yield 60%).

Example 137. Synthesis of Analog 357: Prepared by dissolving analog 359 in $CH_2Cl_2$ at 0° C., then adding ice cold TFA to a final concentration of 25%, for 30 minutes. Excess TFA removed by evaporating to dryness under vacuum, adding 0.5 ml $CH_2Cl_2$, evaporating to dryness under vacuum total of 3 times.

Example 138. Synthesis of Analog 359: Part A: Dissolve analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum, repeat $CH_2Cl_2$ addition and evaporation a total of 3 times, and keep on ice/cold the entire time. Add 1 ml dry DMF, add triethylamine (5 equiv), and keep on ice. Part B: Take Boc-triglycine-OH peptide (1.1 equiv) and dissolve in 3 ml dry DMF at RT, then add EDC (1.1 equiv) and NHS (N-hydroxysuccinimide, 1.1 equiv) to form the active ester, and cool on ice. Add solution from Part B to solution from Part A on ice, then allow to warm in chiller to RT overnight to produce analog 359.

Example 139. Synthesis of Analog 361: Add analog 159 and N,N'-Disuccinimidyl carbonate (1.1 equiv) in anhydrous dichloromethane, DIPEA (1.1 equiv) and DMAP (1.1 equiv), reflux for four hours.

Example 140. Synthesis of Analog 362: Illudin S and 1.2 equivalents of mesylate anhydride, and 1.2 equivalents of 2,4,6-collidine into dry $CH_2Cl_2$, use molecular sieves. Start the reaction at 0° C. (on ice) then let sit overnight, gradually warming up to RT. The reaction mixture remained colorless, and analog 362 was isolated as a white crystalline material using ethyl acetate/hexane chromatography.

Example 141. Synthesis of Analog 363: Parik-Doering reaction was used with analog 383 in which pyridine sulfur trioxide was used in combination with DIPEA and DMSO under strict anhydrous conditions. At 0° C. the reaction mix contained a minor amount of product compatible with analog 383 when analyzed by LC/MS. When the reaction was precooled to −20° C., allowed to react with illudin S, and then slowly warmed to 0° C., analog 383 was produced at ~60% yield. Analog 383 was reacted with $NH_2$—Boc in the presence of TFA and triethylsilane under the same conditions that analog 002 was reacted with $NH_2$—Boc to produce analog 366. However, the yields were very low at <15%. Analog 383 and 1.1 equivalent of $NH_2$—Boc were dissolved in anhydrous DCM with molecular sieves, 0.2 equivalents of acetic acid added (to produce the —C═N—HR intermediate), and allowed to sit overnight. In the morning sodium triacetoxyborohydride was added (4 equivalents) and the reaction allowed to proceed for 6 hours to produce analog 389. Analog 389 was converted to the primary amine analog 363 using standard Boc deprotection method.

Example 142. Synthesis of Analog 365. Illudin S (150 mg) was reacted with Dess Martin Periodinane reagent (1.1 equiv) for 60 minutes at RT in 15 mls $CH_2Cl_2$ (no molecular sieves are used as traces of water accelerate the reaction). Solvent removed and analog 365 (110 mg) recovered using ethyl acetate/hexane chromatography.

Example 143. Synthesis of Analog 366. Add 5 mg of analog 002 into a small vial with 50 uL of acetone, added $BocNH_2$ 6.5 mg (2.5 equiv), started reaction with 20 ul of 1 N $H_2SO_4$, allowed to go overnight at RT. The yield was >80%.

Example 144. Synthesis of Analog 367: Analog 010 (80 mg) was dissolved in 3 ml of anhydrous acetonitrile with molecular sieves. Add 102 mg $NH_2Boc$ (3 equiv), 140 ul $Et_3SiH$ (3 equiv) stirred at RT for 30 minutes with sieves under nitrogen, added 63 uL of TFA (2.9 equiv). Within 30 minutes solution turning from yellow to red. Eventually turns dark brown (amine product). The solvent was removed, and compound isolated using ethyl acetate/hexane chromatography.

Example 145. Synthesis of Analog 368: Illudin S (185 mg, 0.522 mmol), DIPEA 329 mg/444 ul (5 equiv), was dissolved in 5 ml THF, add acetic anhydride 260 ul (5 equiv) and DMAP 62 mg (1 equiv) and monitor reaction at RT. To recover and purify use an acetone/hexane column (0% acetone, then 2, 4, 6% etc.).

Example 146. Synthesis of Analog 369. Illudin S (1.025 grams) and 385.1 mg of imidazole (1.46 equiv) into 8 mls dry DMF with molecular sieves and stirred for 25 minutes at RT under nitrogen, then 686 mg of TBDMSCl added (1.17 equiv) in two equal portions. The reaction was over in 20 minutes per TLC. Add saturated sodium bicarbonate to quench reaction, extracted ethyl acetate three times, organic phase recovered and washed with brine, and dried with anhydrous magnesium sulfate, then solvent removed under high vacuum and temperature of 45° C.

Example 147. Synthesis of Analog 370: Analog 369 was dissolved in DMF then added to 10 mls of $CH_2Cl_2$, then 316 mg of sodium acetate added (1 equiv), stirred for RT for 15 minutes, then acetic anhydride added (1.02 equiv), and allowed to react overnight. The reaction may not progress unless DMAP was added (0.2 equiv). The next day additional sodium acetate (150 mg, 0.3 equiv) and acetic anhydride (185 ul; 0.5 equiv) and DMAP (0.2 equiv) added. The next day solvent removed under high vacuum and temperature of 45° C.

Example 148. Synthesis of Analog 371: Analog 368 was dissolved in excess 7N $NH_3$/methanol and allow to react slowly for 48 to 72 hours at 40° C. then the primary acetate was selectively removed and analog 371 was primarily produced with a yield of ~65% (illudin S was the other product at ~35%).

Example 149. Synthesis of Analog 372: Dissolve 320 mg of #371 and 620 mg of Dess Martin (1.2 equiv) into 4 mls $CH_2Cl_2$ (no molecular sieves are used as traces of water accelerate the reaction), allowed to react for 45 minutes. Then added 3 ms of saturated bicarbonate, 3 mls of saturated $Na_2S_2O_3$ (to quench Dess Martin reagent), then 15 mls of diethyl ether. Wash the reaction mixture twice more with diethyl ether, dry with anhydrous sodium sulfate and then remove the ether. Store overnight then purified with column (elutes at 15% ethyl acetate/hexane).

Example 150. Synthesis of Analog 373: Place 4.5 mg of analog 372 in 200 ul anhydrous $CH_2Cl_2$ with several molecular sieves. Add triethylsilane (3.0 equiv), TFA (2.9 equiv) and $FmocNH_2$ (3.0 equiv) in dry THF at RT for 6 hours under nitrogen. Purify by ethyl acetate/hexane gradient column. Yield ~40%.

Example 151. Synthesis of Analog 374: The Fmoc moiety of analog 373 was removed using 4-methylpyridine (20% final) in DMF at RT for 30 minutes.

Example 152. Synthesis of Analog 377: Dissolve analog 159 into dry $CH_2Cl_2$ with molecular sieves, add imidazole (1.1 equiv) and stir for 30 minutes at RT. Then 1.2 equiv of TBSCl (chlorotributyl silane) added. After 15 minutes add 0.3 equiv of additional TBSCl.

Example 153. Synthesis of Analog 378: 4.5 mg of analog 372 in 200 ul DMF with molecular sieves under nitrogen. Add triethylsilane (3.0 equiv), TFA (2.9 equiv) and $BocNH_2$ (3.0 equiv) at RT for 6 hours under nitrogen. Purify by ethyl acetate/hexane gradient column. Yield ~40%.

Example 154. Synthesis of Analog 379: Analog 359: Part A: Dissolving analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum total of 3 times and keep on ice/cold the entire time. Add 1 ml dry DMF, triethylamine (5 equiv), and keep on ice. Part B: Take Fmoc-triglycine-Val-cit-PNP peptide (1.1 equiv) and dissolve in 3 mls of dry DMF at 0° C. Add solution B to A on ice, then allow to warm in chiller to RT overnight to produce 379.

Example 155. Synthesis of Analog 380: Prepare from analog 379 by removing Fmoc using 4-methylpyridine (20% final) in DMF at RT for 30 minutes.

Example 156. Synthesis of Analog 381: Prepare from analog 377 using lithium hydroxide (LiOH) (1.0 equiv) in 10% methanol/THF at 4° C. One must have methanol otherwise LiOH acts as a nucleophile and removes the TBS, not the acetate protective group. After 1 hour then add additional 0.2 equiv LiOH, then after 30 minutes remove THF/methanol. Purify immediately using ethyl acetate/hexane column to prevent degradation.

Example 157. Synthesis of Analog 382. Add 0.5 equiv of Dess Martin periodinane reagent to analog 381 at RT in $CH_2Cl_2$. Add another 0.5 equiv after 30 minutes, then another 0.2 equiv after 30 minutes. Added 3 ml saturated bicarbonate, 3 ml of saturated $Na_2S_2O_3$ (to quench Dess Martin reagent), then 15 mls of diethyl ether. Wash reaction mix 2 more times with diethyl ether, dry with anhydrous sodium sulfate and remove ether. The product can be stored overnight then purified with column.

Example 158. Synthesis of Analog 383: Prepared from Analog 382 by treating with 1.5% HCl/methanol at RT for 60 minutes. If one sees a smear by TLC, then leave at 4° C. overnight, and in the morning one will see a main product by TLC that was analog 383. Yield was poor as normally less than 25%.

Example 159. Synthesis of Analog 384: Analog 382 was dissolved in 1.5 ml anhydrous acetonitrile, then add $BocNH_2$ (3.0 equiv), then triethylsilane (3.0 equiv), followed by TFA (2.9 equiv) for 5 hours at RT. Best to add TFA in aliquots so as to not remove the protecting silyl group. Recover product using 10% acetone/hexane column (not ethyl acetate column), but still the yield was low at ~15%.

Example 160. Synthesis of Analog 385: Illudin S (10 mg) was dissolved in anhydrous methanol with molecular sieves; add 0.5 equiv of Indium (II) chloride, 2.0 equiv of triethylsilane). Let sit at RT overnight, remove methanol, and purify using an ethyl acetate/hexane column.

Example 161. Synthesis of Analog 387: Dissolve the boc-triglycine (20 mg/ml) in DMF, then add EDC (0.98 equiv) and pentafluorophenol (1.15 equiv) at RT for 2 hours. Evaporate with high vacuum at 40° C. then add ethyl acetate. If solids present remove by filtration. Wash with saturated sodium bicarbonate solution to remove unreacted triglycine acid and unreacted pentafluorophenol, then wash with brine, dry and evaporate to a flaky white solid. (when an oil was obtained simply add diethyl ether to precipitate a flaky white solid).

Example 162. Synthesis of Analog 389: Analog 383 and 1.1 equivalent of $BocNH_2$ are dissolved in anhydrous $CH_2Cl_2$ with molecular sieves, 0.2 equivalents of acetic acid added (to produce the —C═N—HR intermediate), and allowed to sit overnight. In the morning sodium triacetoxyborohydride was added (4 equivalents) and the reaction allowed to proceed for 6 hours to produce analog 389. Product was purified using an ethyl acetate/hexane column. The yield was ~25%.

Example 163: Synthesis of Analog 392: Part A: Dissolve analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum, repeat $CH_2Cl_2$ addition and evaporation a total of 3 times, and keep on ice/cold the entire time. Add 1 ml dry DMF, add triethylamine (5 equiv), and keep on ice. Part B: Take the Azide $N_3$-triglycine-OH peptide (1.1 equiv) and dissolve in 3 ml dry DMF at RT, then add EDC (1.1 equiv) and NHS (N-hydroxysuccinimide, 1.1 equiv) to form the active ester, and cool on ice. Add solution from Part B to solution from Part A on ice, then allow to warm in chiller to RT overnight to produce analog 392.

Example 164: Synthesis of Analog 394: Dissolve analog 235 into $CH_2CL_2$, chill on ice then add TFA to a final concentration of 10%, and allow to incubate on ice for 60 minutes. Solvent is removed using high vacuum, then the product is purified using an ethyl acetate/hexane column. The yield is ~90%.

Example 165: Synthesis of Analog 397: Into a 50 ml round bottom flask is placed 400 mg of Illudin S and then 20 ml of anhydrous DCM added along with molecular sieves. The reaction is allowed to stir at RT for 30 minutes to extract any water contained in the Illudin S. Then 1.06 ml of DIPEA is added with stirring for 15 minutes. Next the mixture is cooled to −70° C., then 1.0 g of sulfur trioxide pyridine complex (Sigma Aldrich catalog #S7556) is dissolved into 1 ml of anhydrous DMSO containing molecular sieves at RT. The sulfur trioxide pyridine/DMSO oxidizing complex is slowly added to the Illudin S solution at −70° C. with stirring. The reaction is allowed to slowly warm to −20° C., and maintained at that temperature for 15 minutes. The reaction is quenched with 10 ml of water followed immediately by 10 ml of ethyl acetate. Next 300 μl of 20% aqueous ammonia hydroxide is added whereupon a bright red color appears in the aqueous portion. The organic portion is removed, and the aqueous portion is extracted 3 more times with the ammonia hydroxide/ethyl acetate procedure. The organic phases are combined, washed with saturated bicarbonate, and then washed with saturated brine. Finally the organic phase is dried then the solvent removed. The product is purified using by silica gel chromatography using an ethyl acetate/hexane gradient to yield the intermediate primary aldehyde. Yield is approximately 30%. This primary aldehyde of Illudin S is then dissolved in anhydrous THF, then 2 equivalents of anhydrous sodium sulfate added, and the mixture cooled to 4° C. under nitrogen. Then 3.0 equivalents of N-Boc Hydroxylamine are added. After 15 minutes, 3.5 μl of glacial acetic acid are added, followed by 6.0 equivalents of sodium triacetoxy borohydride. The reaction is allowed to proceed for 18 hours at 4° C. under nitrogen. The mixture is filtered and the organic solvent removed by vacuum. The product is purified using silica gel chromatography with an ethyl acetate/hexane gradient to yield the hydroxylamine Boc derivative analog 397.

Example 166: Synthesis of Analog 398: Analog 397 is dissolved in anhydrous THF, without molecular sieves, under nitrogen and cooled to 0° C. Then TFA is added to a final concentration of 35% for 25 minutes. The THF and TFA are removed by high vacuum without external heat to yield the hydroxylamine analog 398 (final yield approximately 20%).

Example 167: Synthesis of Analog 399: Illudin S (700 mg) is dissolved in 70 ml of anhydrous DCM and 5.0 ml of peptide synthesis grade DMF at RT. Then molecular sieves are added and the mixture is stirred at RT for 30 minutes under nitrogen, and 2,4,6-trimethylpyridine (5.7 equivalents) is slowly added until the Illudin S is dissolved. The mixture is then cooled to −4° C. and sulfamoyl chloride (1.2 equivalents) is slowly added over a 15 minute period. The reaction is allowed to proceed for 4 hours at −4° C., then allowed to slowly warm and react overnight at RT for 16 hours. The DCM/DMF reaction mixture is washed with saturated sodium bicarbonate to remove residual sulfonic and hydrochloric acids. The remaining organic phase is dried then removed with high vacuum. The product is purified using silica gel chromatography with an ethyl acetate/hexane gradient to yield analog 399. Yield is approximately 25%. The product should be stored at −20° C.

Example 168: Synthesis of Analog 401: Illudin S (500 mg) is dissolved in a mixture of 300 mg of sodium acetate and 6.0 ml of acetic anhydride. The reaction is allowed to proceed at RT with stirring and monitored. After 3 to 4 hours the reaction is quenched by adding 100 ml of saturated sodium bicarbonate solution. The aqueous solution is extracted four times with ethyl acetate and the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next 1.5 equivalents of DIPEA and 1.0 equivalents of DMAP are slowly added with stirring. Then the Boc-N,N'-dimethylaminoethane reagent (3.0 equivalents) is slowly added and the mixture is kept at 0° C. under nitrogen for 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at −70° C. under an inert gas. The intermediate (41 mg) is dissolved in 1.5 ml of anhydrous $CH_2Cl_2$ under nitrogen at 0° C. into a 25 ml round bottom flask, and 50 µl of anisole is added. Next 1.2 ml of trifluoroacetic acid is slowly added in 6 equal aliquots. The reaction is left stirring on ice, under nitrogen, for 45 minutes. Then 10 ml of pre-cooled (−20C) $CHCl_3$ is quickly added. All liquid is quickly removed under high vacuum. The residue is placed back into the ice bath and 1.5 ml of pre-cooled (−20C) DMF added. After 15 minutes the Fmoc-Val-Cit-PAB-PNP linker (62 mg, Axis Pharma catalog #AP10017) is added with stirring. After 15 minutes triethylamine (217 µl) is added. The mixture is stirred under nitrogen at 0° C. for 1 hour, then allowed to slowly warm to RT. If desired, the $CH_2Cl_2$ is removed and the product is purified by silica gel chromatography using an ethyl acetate/hexane gradient to yield the desired product analog 401.

Example 169: Synthesis of Analog 404: Analog 401 can be redissolved in 1.5 ml of anhydrous $CH_2Cl_2$ under nitrogen at 0° C., then 200 µl of triethylamine added, the vial sealed and allowed to react at 4° C. for 18 hours. The mixture is purified by silica gel chromatography using an ethanol/chloroform gradient to yield the desired product analog 404 (final yield approximately 20%).

Example 170: Synthesis of Analog 405: 50 mg of VP-PEG4-Acid (1-(6-methyl-4-vinylpyridin-2-yl)-3-oxo-7,110,13,16-tetraoxa-4-azanonadecan-19-oic acid) and N-hydroxysuccinimide (16 mg, 1.20 equivalents) are dissolved in 20 ml of anhydrous $CH_2Cl_2$ under nitrogen. The EDC (1-ethyl-3-(3-dimethylaminopropyl)carbodiimide, 21 mg, 1.20 equivalents) is added and allowed to react at RT for 24 hours to produce the compound VP-PEG4-NHS (2,5-dioxopyrrolidin-1-yl 1-(6-methyl-4-vinylpyridin-22-yl)-3-oxo-7,10,13,16-tetraoxa-4-azanondecane-19-oate). The $CH_2Cl_2$ mixture containing the VP-PEG4-NHS is washed with water, then quickly dried and the $CH_2Cl_2$ removed by vacuum. Next analog 404 (74 mg) is dissolved in 3.0 ml of DMF, and then added to the VP-PEG-NHS compound. The mixture is placed under nitrogen, cooled to 0° C., then 210 µl of triethylamine added, and the reaction allowed to continue overnight in the cold. The desired product, analog 405, is recovered using reverse phase HPLC (approximately 50% yield of initial starting material analog 404).

Example 171: Synthesis of Analog 402 and Analog 403: Illudin S (0.95 grams) is dissolved in 100 ml of water, and then 100 ml of hexane is added to form an upper organic layer. With rapid stirring, 2.06 ml of concentrated sulfuric acid is added slowly. After 1 hour the hexane is removed and another 100 ml of hexane is added. This process is repeated one more time. The hexane layers are combined washed with a saturated sodium bicarbonate solution to neutralize residual acid, dried with anhydrous magnesium, then solvent removed to yield a bright yellow oil (AF1). Next paraformaldehyde (0.66 g) is dissolved in 60 ml of water, and concentrated sulfuric acid (5.0 ml) is slowly added. The cloudy solution is slowly heated until the solution is clear. This paraformaldehyde solution is allowed to slowly cool to 30° C. Then the previously prepared bright yellow intermediate (AF1) is dissolved in acetone, and the mixture slowly added with continuous stirring for 24 hours. The reaction mixture is extracted three times with ethyl acetate (100 ml), the extracts are combined, washed with saturated sodium bicarbonate, dried over anhydrous magnesium sulfate, then the organic solvent removed by vacuum. The residue is purified by silica gel chromatography using an ethyl acetate/hexane gradient to yield a bright orange intermediate (IRO1). IRO1 is dissolved in anhydrous dichloromethane, under nitrogen, and 2,4,6-trimethylpyridine (3.0 equivalents) is added, then the mixture is cooled to 0° C. Sulfamoyl chloride (1.15 equivalents) is dissolved in anhydrous peptide-grade DMF (1 ml), and is slowly added to the dichloromethane solution, with mixing. The solution is mixed for one hour at 0° C., then slowly allowed to warm to RT, and continued to react for a total of 4 hours. The reaction mixture is concentrated by vacuum, then purified by silica gel chromatography using an ethyl acetate/hexane gradient to yield analog 402 and analog 403 (final yield of both products is approximately 15%).

Example 172: Synthesis of Analog 407: Illudin S (100 mg) is dissolved in 20 ml of anhydrous DCM and 5.0 ml of DMF at RT. Then molecular sieves are added and the mixture is stirred at RT for 30 minutes under nitrogen, and 2,4,6-trimethylpyridine (5.7 equivalents) is slowly added until the Illudin S is dissolved. The mixture is then cooled to −4° C. and the trifluormethanesulfanyl chloride (Aldrich Catakog #164798, 1.2 equivalents) is slowly added over a 15 minute period. The reaction is allowed to proceed for 4 hours at −4° C., and then allowed to slowly warm and react overnight at RT for 16 hours. The DCM/DMF reaction mixture is washed with saturated sodium bicarbonate to remove residual sulfonic and hydrochloric acids. The remaining organic phase is dried then removed with high vacuum. The product is purified using by silica gel chromatography using an ethyl acetate/hexane gradient to yield analog 407. Yield is approximately 15%. The product is unstable and should be stored at −70° C. under an inert gas.

Example 173: Synthesis of Analog 408: Illudin S (500 mg) is dissolved in a mixture of 300 mg of sodium acetate and 6.0 ml of acetic anhydride. The reaction is allowed to proceed at RT with stirring and monitored. After 3 to 4 hours the reaction is quenched by adding 100 ml of saturated sodium bicarbonate solution. The aqueous solution is extracted four times with ethyl acetate and the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next 1.5 equivalents of DIPEA and 1.0 equivalents of DMAP are slowly added with stirring. After the Boc-N,N'-dimethylaminoethane reagent (3.0 equivalents) is added and the mixture is kept at 0° C. under nitrogen for an 2 hours then allowed to warm up to RT and react overnight. The $CH_2Cl_2$ is removed and the product is purified by silica gel chromatography using an ethyl acetate/hexane gradient to yield the desired intermediate product. If not used immediately this intermediate should be stored at −70° C. under an inert gas. The intermediate (41 mg) is dissolved in 1.5 ml of anhydrous $CH_2Cl_2$ under nitrogen at 0° C. into a 25 ml round bottom flask, and 50 μl of anisole is added. Next 1.2 ml of trifluoroacetic acid is slowly added in 6 equal aliquots. The reaction is left stirring on ice, under nitrogen, for 45 minutes. Then 10 ml of precooled (−20C) $CHCl_3$ added. All liquid is removed under high vacuum. The residue is placed back in to the ice bath and 1.5 ml of pre-cooled (−20° C.) DMF added. This solution is added to a solution of 3 ml of DMF containing the Fmoc-Gly3-Val-Cit-PNP peptide (Levena Biopharma Catalog #H1002, 1.1 equivalent) at 0° C. The solution is allowed to slowly warm to RT and react overnight. The desired intermediate is recovered by precipitation with excess diethyl ether. The precipitate is washed twice with ice cold ether, dried to remove the ether, then redissolved in 1.5 ml of DMF, 200 μl of triethylamine added, and the reaction allowed to proceed at 4° C. for 48 hours to produce analog 408 (final yield is approximately 20%).

Example 174: Synthesis of Analog 409: Illudin S (500 mg) is dissolved in a mixture of 300 mg of sodium acetate and 6.0 ml of acetic anhydride. The reaction is allowed to proceed at RT with stirring and monitored. The reaction is quenched after 3-4 hours by adding 100 ml of saturated sodium bicarbonate solution. The aqueous solution is extracted four times with ethyl acetate, the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next is added with stirring 1.5 equivalents of DIPEA and 1.0 equivalents of DMAP. After the Boc-N,N'-dimethylaminoethane reagent (3.0 equivalents) is added and the mixture is kept at 0° C. under nitrogen for an additional 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at −70° C. under an inert gas. This intermediate (41 mg) is dissolved in 1.5 ml of anhydrous $CH_2Cl_2$ under nitrogen at 0° C. into a 2 5 ml round bottom flask, and 50 μl of anisole is added. Next 1.2 ml of trifluoroacetic acid is slowly added in 6 equal aliquots. The reaction is left stirring on ice, under nitrogen, for 45 minutes. Then 10 ml of precooled (−20C) $CHCl_3$ is added. All liquid is removed under high vacuum. The residue is placed back in to the ice bath and 1.5 ml of pre-cooled (−20° C.) peptide synthesis grade DMF added. After 15 minutes the Fmoc-Val-Cit-PAB-PNP linker (62 mg. Axis Pharma catalog #AP10017) is added with stirring. After 15 minutes then triethylamine (217 μl) is added. The mixture is stired under nitrogen at 0° C. for 1 hour, then allowed to slowly warm to RT. If desired, the $CH_2Cl_2$ is removed and the product is purified by silica gel chromatography using an ethyl acetate/hexane gradient to yield the desired intermediate product. The intermediate can be redissolved in 1.5 ml of anhydrous $CH_2Cl_2$ under nitrogen at 0° C., then 200 μl of triethylamine added, the vial sealed and allowed to react at 4 C for 18 hours. The desired intermediate is recovered by precipitation with excess ice-cold diethyl ether. The precipitate is washed twice with ice cold ether, dried to remove the ether, then redissolved in 1.5 ml of DMF and 200 μl of triethylamine is added, and the reaction allowed to proceed at 4° C. for 48 hours to produce analog 409 (final yield approximately 30%).

Example 175: Synthesis of Analog 410: Illudin S (500 mg) is dissolved in a mixture of 300 mg of sodium acetate and 6.0 mls of acetic anhydride. The reaction is allowed to proceed at RT with stirring and monitored. The reaction is quenched after 3-4 hours by adding 100 ml of saturated sodium bicarbonate solution. The aqueous solution is extracted four times with ethyl acetate, the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next is added with stirring 1.5 equivalents of DIPEA and 1.0 equivalents of DMAP. After the Boc-N,N'-dimethylaminoethane reagent (3.0 equivalents) is added, the mixture is kept at 0° C. under nitrogen for an additional 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at −70° C. under an inert gas. This intermediate (41 mg) is dissolved in 1.5 mls of anhydrous $CH_2Cl_2$ under nitrogen at 0° C. into a 25 ml round bottom flask, and 50 μl of anisole is added. Next 1.2 ml of trifluoroacetic acid is slowly added in 6 equal aliquots. The reaction is left stirring on ice, under nitrogen, for 45 minutes. Then 10 ml of pre-cooled (−20C) $CHCl_3$ is added. All liquid is removed under high vacuum. The residue is placed back in to the ice bath and 1.5 ml of pre-cooled (−20° C.) DMF added. Next MC-Val-Cit-PAB-PNP (Levena Biopharma Catalog #VC1004, 1.2 equivalents) is directly added with stirring while maintaining the temperature at 0° C. Once all solid material is dissolved then triethylamine (8.0 equivalents) is added and the reaction continued at 4° C. for 48 hours. Analog 410 is recovered by preparative HPLC using an acetonitrile gradient (5% to 95%) with 0.05% trifluoroacetic acid (final yield approximately 15%).

Abbreviations used include: DMAP=4-dimethylaminopyridine; DCC=N,N'-dicycyclohexylcarbodiimide; ODHBt=3,4,-dihydroxy-4-oxo-1,2,3-benzo-triazine-3-yl ester; NMM=N-methylmorpholine; EDC=1-(3-dimethylaminopropyl)-3-ethylcarbodiimide hydrochloride; DIAD=diisopropyl azodicarboxylate; DEAD=diethyl azodicarboxylate; and DIPC=N,N'-diisopropylcarbodiimide. $Boc_2O$=anhydrous Boc; $BocNH_2$=t-butyl carbamate; DIPEA=N,N-diisopropylethylamine; ODHBt=3,4,-dihydroxy-4-oxo-1,2,3-benzo-triazine-3-yl ester (refers to ester made from HOOBt); HOOBt=(Hydroxy-3,4-dihydro-4-oxo-1,2,3-benzotriazine); NMM=N-methylmorpholine; RT—room temperature; TBDMSCl=t-butyldimethyl silyl chloride; TEA=triethanolamine.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

TABLE I

Cytotoxic data $IC_{50}$ values (micromolar, 2 hour exposure, N = 3, mean ± SD) for Illudin M, analog 108 and analog 110 for cells expressing the estrogen receptor (ER) (MCF7) and cells not expressing the ER (HT29).

| Analog | HT29 (ER Negative) | MCF7 (ER positive) |
| --- | --- | --- |
| Illudin M | 0.52 ± 0.10 | 0.48 ± 0.13 |
| 108 | >55 | 14.1 ± 2.8 |
| 110 | >19 | 2.0 ± 0.1 |

TABLE II

Activity of PSA cleavable illudofulvene analogs (210, 215, 216, 221) compared with Illudin S and illudofulvene precursor analogs (204, 207, 211, 212, 213, 214) against PSA negative and PSA positive cell line (48 hour exposure, N = 3; mean ± SD; IC50 values in nM).

| Analog | Prostate PC3 (negative PSA) | Prostate DuPro (trace PSA) | Prostate LnCAP (positive PSA) |
| --- | --- | --- | --- |
| Illudin | 16 ± 5 | 11 ± 3 | 15 ± 3 |
| 204 | n.t. | n.t. | 3,300 ± 1,000 |
| 207 | 880 ± 330 | 450 ± 40 | 560 ± 60 |
| 211 | 350 ± 80 | 280 ± 20 | 270 ± 50 |
| 212 | 120 ± 20 | 20 ± 2 | 120 ± 30 |
| 213 | 2,200 ± 100 | 360 ± 80 | 900 ± 200 |
| 214 | 300 ± 50 | 90 ± 10 | 190 ± 30 |
| 210 | 4,700 ± 500 | 3,500 ± 400 | 810 ± 130 |
| 215 | n.t. | n.t. | >20,000 |
| 216 | 190 ± 10 | 280 ± 60 | 190 ± 30 |
| 221 | >21,000 | 13,000 ± 1,000 | 800 ± 100 |

n.t. denotes not tested

TABLE III

| Peptides cleaved by various proteases. | | |
| --- | --- | --- |
| Protease | Peptide | SEQ. ID's |
| PSA | His-Ser-Ser-Lys-Leu-Gln-X | SEQ. ID. 104 |
|  | Mu-His-Ser-Ser-Lys-Leu-Gln-X |  |
|  | Mu-His-Ser-Ser-Lys-Leu-Gln-Lys-X | SEQ. ID. 106 |
|  | Mu-His-Ser-Ser-Lys-Leu-EDA-Lys-X | SEQ. ID. 108 |
|  | Mc-His-Ser-Ser-Lys-Leu-Gln-X |  |
|  | Mc-His-Ser-Ser-Lys-Leu-Gln-X |  |
|  | Hyp-Ala-Ser-Chg-Gln-Ser-X | SEQ. ID. 111 |
|  | Hyp-Ala-Ser-Chg-Gln-Ser-Leu-X | SEQ. ID. 116 |
|  | Mu-Hyp-Ala-Ser-Chg-Gln-Ser-X |  |
|  | Mu-Hyp-Ala-Ser-Chg-Gln-Ser-Leu-X |  |
|  | Mc-Hyp-Ala-Ser-Chg-Gln-Ser-X |  |
|  | Mc-Hyp-Ala-Ser-Chg-Gln-Ser-Leu-X |  |
|  | Hyp-Ser-Ser-Chg-Gln-Ser-Ser-Pro-X | SEQ. ID. 127 |
|  | Mu-Hyp-Ser-Ser-Chg-Gln-Ser-Ser-Pro-X |  |
|  | Mc-Hyp-Ser-Ser-Chg-Gln-Ser-Ser-Pro-X |  |
|  | 4-O-Ac-Hyp-Ser-Ser-Chg-Gln-Ser-Ser-Pro-X | SEQ. ID. 131 |
|  | Arg-Arg-Ser-Ser-Tyr-Tyr-Ser-Gly-X | SEQ. ID. 132 |
|  | Mu-Arg-Arg-Ser-Ser-Tyr-Tyr-Ser-Gly-X |  |
|  | Mc-Arg-Arg-Ser-Ser-Tyr-Tyr-Ser-Gly-X |  |
|  | Mc-Ser-Ser-Lys-Tyr-Gln-Leu-X | SEQ. ID. 136 |
|  | Mu-Ser-Ser-Lys-Tyr-Gln-Leu-X |  |
|  | N-glutaryl-Hyp-Ala-Ser-chGly-Gln-Ser-Leu | SEQ. ID. 137 |
|  | Mu-N-glutaryl-Hyp-Ala-Ser-chGly-Gln-Ser-Leu |  |
|  | Mc-N-glutaryl-Hyp-Ala-Ser-chGly-Gln-Ser-Leu |  |
| Caspase-3 | Asp-Glu-Val-Asp-Pro-X | SEQ. ID. 138 |
|  | Mu-Asp-Glu-Val-Asp-Pro-X |  |
|  | Mc-Asp-Glu-Val-Asp-Pro-X |  |

TABLE III-continued

| Peptides cleaved by various proteases. | | |
|---|---|---|
| Protease | Peptide | SEQ. ID's |
| | Lys-Gly-Ser-Gly-Asp-Val-Glu-Gly-X | SEQ. ID. 139 |
| | Mu-Lys-Gly-Ser-Gly-Asp-Val-Glu-Gly-X | |
| | Mc-Lys-Gly-Ser-Gly-Asp-Val-Glu-Gly-X | |
| Cathepsin B | PLE-X | |
| | Gly-Phe-Leu-Gly-X | SEQ. ID. 141 |
| | Lys-Lys-Phe-D-Ala-X | SEQ. ID. 142 |
| | D-Ala-Phe-Lys-Lys-X | SEQ. ID. 144 |
| | Mc-Poly-L-glutamic acid-X | |
| | Mc-Gly-Phe-Leu-Gly-X | SEQ. ID. 145 |
| | Mc-Lys-Lys-Phe-D-Ala-X | |
| | Mc-D-Ala-Phe-Lys-Lys-X | |
| | Mu-Poly-L-glutamic acid-X | |
| | Mu-Gly-Phe-Leu-Gly-X | |
| | Mu-Lys-Lys-Phe-D-Ala-X | |
| | Mu-D-Ala-Phe-Lys-Lys-X | |
| | Val-Cit-X | |
| FAP | Lys-Gln-Glu-Gln-Asn-Pro-Gly-Ser-Thr-X | SEQ. ID. 146 |
| | Mu-Lys-Gln-Glu-Gln-Asn-Pro-Gly-Ser-Thr-X | |
| | Mc-Lys-Gln-Glu-Gln-Asn-Pro-Gly-Ser-Thr-X | |
| Kallikrein 2 | Gly-Lys-Ala-Phe-Arg-Arg-X | SEQ. ID. 171 |
| | Mu-Gly-Lys-Ala-Phe-Arg-Arg-X | |
| | Mc-Gly-Lys-Ala-Phe-Arg-Arg-X | |
| MMP-2/-9/ | Glu-Pro-Cit-Gly-Hof-Tyr-Leu-X | SEQ. ID. 172 |
| | Mu-Glu-Pro-Cit-Gly-Hof-Tyr-Leu-X | |
| | Mc-Glu-Pro-Cit-Gly-Hof-Tyr-Leu-X | |
| | Gly-Ile-Leu-Gly-Val-Pro-X | SEQ. ID. 173 |
| | Mu-Gly-Ile-Leu-Gly-Val-Pro-X | |
| | Mc-Gly-Ile-Leu-Gly-Val-Pro-X | |
| | Gly-Pro-Leu-Gly-Ile-Ala-Gly-Gln-X | SEQ. ID. 174 |
| | Mu-Gly-Pro-Leu-Gly-Ile-Ala-Gly-Gln-X | |
| | Mc-Gly-Pro-Leu-Gly-Ile-Ala-Gly-Gln-X | |
| MMP-7 | Lys-Arg-Ala-Leu-Gly-Leu-Pro-Gly | SEQ. ID. 175 |
| | Mu-Lys-Arg-Ala-Leu-Gly-Leu-Pro-Gly | |
| | Mc-Lys-Arg-Ala-Leu-Gly-Leu-Pro-Gly | |
| | Arg-Pro-Leu-Ala-Leu-Trp-Arg-Ser | SEQ. ID. 176 |
| | Mu-Arg-Pro-Leu-Ala-Leu-Trp-Arg-Ser | |
| | Mc-Arg-Pro-Leu-Ala-Leu-Trp-Arg-Ser | |
| TOP | Ala-L-L-Ala-L-Ile | |
| | Mu-Ala-L-L-Ala-L-Ile | |
| | Mc-Ala-L-L-Ala-L-Ile | |
| uPA | D-Ala-Phe-Lys or | |
| | D-Ala-Phe-Lys-PABC | SEQ. ID. 177 |
| Cathepsin K | Gly-Gly-Pro-Nle-X | SEQ. ID. 178 |
| | Mu-Gly-Gly-Pro-Nle-X | |
| | Mc-Gly-Gly-Pro-Nle-X | |
| Plasmin | D-Ala-Phe-Lys-Lys-X | SEQ. ID. 179 |
| | Mu-D-Ala-Phe-Lys-Lys-X | |
| | Mc-D-Ala-Phe-Lys-Lys-X | |
| | D-Ala-Phe-Lys-X | |
| | Mu-D-Ala-Phe-Lys-X | |
| | Mc-D-Ala-Phe-Lys-X | |
| Thrombin | Poly-L-Lys-Gly-D-Phe-Pip-Arg-Ser-Gly-Gly-Gly-Gly-Gly-X | SEQ. ID. 180 |
| Trypsin | Poly-L-Lysine-Gly-Ala-Ser-D-Arg-Phe-Thr-Gly-X | SEQ. ID. 181 |

In Table III, the letter 'X' denotes the end attached to the medicant, Chg denotes cyclohexyl glycine, Cit denotes citrulline, EDA denotes ethanyl-D-Alanine, Hof denotes homophenylalanine, Hyp denotes 4-hydroxyproline, Mc denotes morpholinocarbonyl (carboxy-terminal protecting group), Mu denotes 4-morpholine-carbonyl (amino-terminal protecting group), Nle denotes norleucine, PABC denotes para-aminobenzoylcarboxyl, PLE denotes Poly-L-glutamic acid, and Pip denotes piperidine.

TABLE IV

Mechanisms of Drug Resistance.

| Mechanism of Multi-drug Resistance | Resistance to illudofulvenes |
|---|---|
| Gp170/MDR1 | No |
| Gp180/MRP | No |
| Topoisomerase I | No |
| Topoisomerase II | No |
| MVP/LRP (vault) | No |
| Thiol content/GST pi | No |
| DNA repair | No |
| Myc expression | No |
| Bcl-2 expression | No |
| BRCA status | No |
| P53 status | No |
| P21 status | No |
| MGMT expression | No |
| Micro tubulin alteration | No |

TABLE V

IUPAC names of the Illudofulvene analogs.

| Entry # | Illudofulvene Analog | IUPAC Name of Illudofulvene Analog |
|---|---|---|
| 1 | 001 | (R)-6'-hydroxy-2',4',6'-trimethylspiro[cyclopropane-1,5'-inden]-7'(6'H)-one |
| 2 | 002 | (6'R)-6'-hydroxy-3'-(hydroxymethyl)-2',4',6'-trimethylspiro[cyclopropane-1,5'-inden]-7'(6'H)-one |
| 3 | 003 | (6'R,6'''R)-3',3-methylenebis(6'-hydroxy-2',4',6'-trimethylspiro[cyclopropane-1,5'-inden]-7'(6'H)-one) |
| 4 | 004 | (R)-3'-bromo-6'-hydroxy-2',4',6'-trimethylspiro[cyclopropane-1,5'-inden]-7'(6'H)-one |
| 5 | 005 | (R)-6'-hydroxy-3'-iodo-2',4',6'-trimethylspiro[cyclopropane-1,5'-inden]-7'(6'H)-one |
| 6 | 006 | (R)-6'-hydroxy-3'-(4-hydroxybenzyl)-2',4',6'-trimethylspiro[cyclopropane-1,5'-inden]-7'(6'H)-one |
| 7 | 007 | (R)-6'-hydroxy-3'-(4-methoxybenzyl)-2',4',6'-trimethylspiro[cyclopropane-1,5'-inden]-7'(6'H)-one |
| 8 | 008 | (R)-((6'-hydroxy-2',4',6'-trimethyl-7'-oxo-6',7'-dihydrospiro[cyclopropane-1,5'-inden]-3'-yl)methoxy)methyl acetate |
| 9 | 009 | (R)-6'-hydroxy-3'-(3-hydroxypropyl)-2',4',6'-trimethylspiro[cyclopropane-1,5'-inden]-7'(6'H)-one |
| 10 | 010 | (R)-3-(6'-hydroxy-2',4',6'-trimethyl-7'-oxo-6',7'-dihydrospiro[cyclopropane-1,5'-inden]-3'-yl)propanal |
| 11 | 011 | (R)-6'-hydroxy-2',4',6'-trimethyl-7'-oxo-6',7'-dihydrospiro[cyclopropane-1,5'-indene]-3'-carbaldehyde |
| 12 | 012 | (R)-6'-hydroxy-2',4',6'-trimethyl-3'-nitrospiro[cyclopropane-1,5'-inden]-7'(6'H)-one |
| 13 | 013 | 4-hydroxy-5-(((R)-6'-hydroxy-2',4',6'-trimethyl-7'-oxo-6',7'-dihydrospiro[cyclopropane-1,5'-inden]-3'-yl)methyl)cyclohexane-1,3-dicarbaldehyde |
| 14 | 014 | (4a'S,7'R,9b'S)-7'-hydroxy-4a',7',9'-trimethyl-4a',9b'-dihydro-4'H-spiro[cyclopropane-1,8'-indeno[1,2-d][1,3]dioxin]-6'(7'H)-one |
| 15 | 015 | (R)-3'-(hydroxymethyl)-2',4',6'-trimethyl-7'-oxo-6',7'-dihydrospiro[cyclopropane-1,5'-inden]-6'-yl acetate |
| 16 | 016 | (R)-3'-(ethoxymethyl)-6'-hydroxy-2',4',6'-trimethylspiro[cyclopropane-1,5'-inden]-7'(6'H)-one |
| 17 | 017 | (6'R,6'''R)-3',3'''-(oxybis(methylene))bis(6'-hydroxy-2',4',6'-trimethylspiro[cyclopropane-1,5'-inden]-7'(6'H)-one) |
| 18 | 018 | (R)-6'-hydroxy-2',4',6'-trimethyl-3'-((((2R,3S,4R,5R,6S)-3,4,5-trihydroxy-6-(hydroxymethyl)tetrahydro-2H-pyran-2-yl)oxy)methyl)spiro[cyclopropane-1,5'-inden]-7'(6'H)-one |
| 19 | 019 | (6'R)-3'-((2,3-dihydroxypropoxy)methyl)-6'-hydroxy-2',4',6'-trimethylspiro[cyclopropane-1,5'-inden]-7'(6'H)-one |
| 20 | 020 | (R)-3'-((2-bromoethoxy)methyl)-6'-hydroxy-2',4',6'-trimethylspiro[cyclopropane-1,5'-inden]-7'(6'H)-one |
| 21 | 021 | (R)-6'-hydroxy-3'-(((2-methoxypropan-2-yl)oxy)methyl)-2',4',6'-trimethylspiro[cyclopropane-1,5'-inden]-7'(6'H)-one |
| 22 | 022 | (R)-6'-hydroxy-3'-((2-hydroxyethoxy)methyl)-2',4',6'-trimethylspiro[cyclopropane-1,5'-inden]-7'(6'H)-one |
| 23 | 023 | (R)-6'-hydroxy-3'-(((4-hydroxyphenyl)thio)methyl)-2',4',6'-trimethylspiro[cyclopropane-1,5'-inden]-7'(6'H)-one |
| 24 | 024 | (R)-3'-((benzylthio)methyl)-6'-hydroxy-2',4',6'-trimethylspiro[cyclopropane-1,5'-inden]-7'(6'H)-one |

TABLE V-continued

IUPAC names of the Illudofulvene analogs.

| Entry # | Illudofulvene Analog | IUPAC Name of Illudofulvene Analog |
|---|---|---|
| 25 | 025 | methyl (R)-2-(((6'-hydroxy-2',4',6'-trimethyl-7'-oxo-6',7'-dihydrospiro[cyclopropane-1,5'-inden]-3'-yl)methyl)thio)acetate |
| 26 | 026 | (R)-6'-hydroxy-2',4',6'-trimethyl-3'-((p-tolylthio)methyl)spiro[cyclopropane-1,5'-inden]-7'(6'H)-one |
| 27 | 027 | (R)-(6'-hydroxy-2',4',6'-trimethyl-7'-oxo-6',7'-dihydrospiro[cyclopropane-1,5'-inden]-3'-yl)methyl phenyl carbonate |
| 28 | 028 | (R)-(6'-hydroxy-2',4',6'-trimethyl-7'-oxo-6',7'-dihydrospiro[cyclopropane-1,5'-inden]-3'-yl)methyl benzoate |
| 29 | 029 | (R)-2-(((6'-hydroxy-2',4',6'-trimethyl-7'-oxo-6',7'-dihydrospiro[cyclopropane-1,5'-inden]-3'-yl)methyl)thio)acetic acid |
| 30 | 030 | methyl (R)-2-(((6'-hydroxy-1'-((2-methoxy-2-oxoethyl)thio)-2',4',6'-trimethyl-7'-oxo-6',7'-dihydrospiro[cyclopropane-1,5'-inden]-3'-yl)methyl)thio)acetate |
| 31 | 031 | methyl 2-((((6'R)-6',7a'-dihydroxy-1'-((2-methoxy-2-oxoethyl)thio)-2',4',6'-trimethyl-7'-oxo-1',6',7',7a'-tetrahydrospiro[cyclopropane-1,5'-inden]-3'-yl)methyl)thio)acetate |
| 32 | 032 | (6'R)-3'-(((2,3-dihydroxypropyl)thio)methyl)-6'-hydroxy-2',4',6'-trimethylspiro[cyclopropane-1,5'-inden]-7'(6'H)-one |
| 33 | 033 | 7'-methyl-4'H-dispiro[cyclopropane-1,6'-indene-5',2''-[1,3]dioxolan]-4'-one |
| 34 | 034 | (R)-(6'-hydroxy-2',4',6'-trimethyl-7'-oxo-6',7'-dihydrospiro[cyclopropane-1,5'-inden]-3'-yl)methyl acetate |
| 35 | 035 | 6'-hydroxy-4'-methylspiro[cyclopropane-1,5'-inden]-7'(6'H)-one |
| 36 | 036 | (R)-3'-((1H-imidazol-1-yl)methyl)-6'-hydroxy-2',4',6'-trimethylspiro[cyclopropane-1,5'-inden]-7'(6'H)-one |
| 37 | 037 | 1-carboxy-2-((((R)-6'-hydroxy-2',4',6'-trimethyl-7'-oxo-6',7'-dihydrospiro[cyclopropane-1,5'-inden]-3'-yl)methyl)thio)ethan-1-aminium |
| 38 | 038 | (R)-3-(6'-hydroxy-2',4',6'-trimethyl-7'-oxo-6',7'-dihydrospiro[cyclopropane-1,5'-inden]-3'-yl)propanoic acid |
| 39 | 039 | (R)-3'-(3,3-dimethoxypropyl)-6'-hydroxy-2',4',6'-trimethylspiro[cyclopropane-1,5'-inden]-7'(6'H)-one |
| 40 | 040 | (R)-3'-(3,3-diethoxypropyl)-6'-hydroxy-2',4',6'-trimethylspiro[cyclopropane-1,5'-inden]-7'(6'H)-one |
| 41 | 041 | (R,Z)-3-(6'-hydroxy-2',4',6'-trimethyl-7'-oxo-6',7'-dihydrospiro[cyclopropane-1,5'-inden]-3'-yl)acrylaldehyde |
| 42 | 042 | (R)-3'-(hydroxymethyl)-4',6'-dimethyl-6'-((triethylsilyl)oxy)spiro[cyclopropane-1,5'-inden]-7'(6'H)-one |
| 43 | 043 | (R)-6'-hydroxy-2',4',6'-trimethyl-3'-(((triethylsilyl)oxy)methyl)spiro[cyclopropane-1,5'-inden]-7'(6'H)-one |
| 44 | 044 | (R)-2',4',6'-trimethyl-6'-((triethylsilyl)oxy)-3'-(((triethylsilyl)oxy)methyl)spiro[cyclopropane-1,5'-inden]-7'(6'H)-one |
| 45 | 045 | methyl 2-((7-hydroxy-5-(2-hydroxyethyl)-3-(hydroxymethyl)-2,4,6-trimethyl-1H-inden-1-yl)thio)acetate |
| 46 | 046 | (R)-3-(6'-hydroxy-2',4',6'-trimethyl-7'-oxo-6',7'-dihydrospiro[cyclopropane-1,5'-inden]-3'-yl)propyl acetate |
| 47 | 047 | (6'R)-3'-(2-(1,7-dihydroxy-2,4,6-trimethyl-1H-inden-5-yl)ethyl)-6'-hydroxy-2',4',6'-trimethylspiro[cyclopropane-1,5'-inden]-7'(6'H)-one |
| 48 | 048 | (R)-6'-hydroxy-2',4',6'-trimethyl-1'-(p-tolylthio)-3'-((p-tolylthio)methyl)spiro[cyclopropane-1,5'-inden]-7'(6'H)-one |
| 49 | 049 | (R)-6'-hydroxy-2',4',6'-trimethyl-3'-(p-tolylthio)spiro[cyclopropane-1,5'-inden]-7'(6'H)-one |
| 50 | 050 | (R)-6'-hydroxy-2',4',6'-trimethyl-1',3'-bis(p-tolylthio)spiro[cyclopropane-1,5'-inden]-7'(6'H)-one |
| 51 | 051 | (R)-2-(2-(((6'-hydroxy-2',4',6'-trimethyl-7'-oxo-6',7'-dihydrospiro[cyclopropane-1,5'-inden]-3'-yl)methyl)thio)acetoxy)ethyl 2-mercaptoacetate |
| 52 | 052 | ethane-1,2-diyl bis(2-((((R)-6'-hydroxy-2',4',6'-trimethyl-7'-oxo-6',7'-dihydrospiro[cyclopropane-1,5'-inden]-3'-yl)methyl)thio)acetate) |
| 53 | 053 | (R)-3'-((2-(2-bromoethoxy)ethoxy)methyl)-6'-hydroxy-2',4',6'-trimethylspiro[cyclopropane-1,5'-inden]-7'(6'H)-one |
| 54 | 054 | (R)-6'-hydroxy-1'-(((R)-6'-hydroxy-2',4',6'-trimethyl-7'-oxo-6',7'-dihydrospiro[cyclopropane-1,5'-inden]-3'-yl)methyl)-3'-(hydroxymethyl)-2',4',6'-trimethylspiro[cyclopropane-1,5'-inden]-7'(6'H)-one |
| 55 | 055 | 5-(2-hydroxyethyl)-1-((4-hydroxyphenyethio)-3-(((4-hydroxyphenyl)thio)methyl)-2,4,6-trimethyl-1H-inden-7-ol |
| 56 | 056 | (R)-6'-hydroxy-3'-((4-hydroxyphenyl)thio)-2',4',6'-trimethylspiro[cyclopropane-1,5'-inden]-7'(6'H)-one |

TABLE V-continued

IUPAC names of the Illudofulvene analogs.

| Entry # | Illudofulvene Analog | IUPAC Name of Illudofulvene Analog |
|---|---|---|
| 57 | 057 | (R)-6'-hydroxy-1'-((4-hydroxyphenyl)thio)-2',4',6'-trimethylspiro[cyclopropane-1,5'-inden]-7'(6'H)-one |
| 58 | 058 | (R)-6'-hydroxy-1',3'-bis((4-hydroxyphenyl)thio)-2',4',6'-trimethylspiro[cyclopropane-1,5'-inden]-7'(6'H)-one |
| 59 | 059 | (6'S,7'R)-4'-methyl-6'-((triethylsilyl)oxy)-6',7'-dihydrospiro[cyclopropane-1,5'-inden]-7'-ol |
| 60 | 060 | (R)-7'-methyl-4'H-dispiro[cyclopropane-1,6'-indene-5',2''-[1,3]dioxolan]-4'-ol |
| 61 | 061 | (S)-4'-methyl-6'-((triethylsilyl)oxy)spiro[cyclopropane-1,5'-inden]-7'(6'H)-one |
| 62 | 062 | (R)-6'-hydroxy-2'-(hydroxymethyl)-4',6'-dimethylspiro[cyclopropane-1,5'-inden]-7'(6'H)-one |
| 63 | 063 | (R)-6'-hydroxy-2',3'-bis(hydroxymethyl)-4',6'-dimethylspiro[cyclopropane-1,5'-inden]-7'(6'H)-one |
| 64 | 064 | N-acetyl-S-(((R)-6'-hydroxy-2',4',6'-trimethyl-7'-oxo-6',7'-dihydrospiro[cyclopropane-1,5'-inden]-3'-yl)methyl)-L-cysteine |
| 65 | 065 | (R)-2-acetamido-3-((((R)-6'-hydroxy-4',6'-dimethyl-7'-oxo-6',7'-dihydrospiro[cyclopropane-1,5'-inden]-3'-yl)methyl)thio)-N-((S)-1-phenylethyl)propanamide |
| 66 | 066 | (S)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-phenylethyl)propanamide |
| 67 | 067 | 4-methyl-2,3-dihydro-5H-indeno[5,6-b]furan-5-one |
| 68 | 068 | 5-hydroxy-6-(2-hydroxyethyl)-7-methyl-1H-inden-1-one |
| 69 | 069 | 5-(2-hydroxyethoxy)-6-(2-hydroxyethyl)-7-methyl-1H-inden-1-one |
| 70 | 070 | (3a'R,4'R)-4'-hydroxy-7'-methyl-3a',4'-dihydro-1'H-dispiro[cyclopropane-1,6'-indene-5',2''-[1,3]dioxolan]-1'-one |
| 71 | 071 | (3a'R,4'R)-7'-methyl-4'-((triethylsilyl)oxy)-3a',4'-dihydro-1'H-dispiro[cyclopropane-1,6'-indene-5',2''-[1,3]dioxolan]-1'-one |
| 72 | 072 | (7'R,7a'R)-7'-hydroxy-4'-methyl-7',7a'-dihydrospiro[cyclopropane-1,5'-indene]-3',6'-dione |
| 73 | 073 | (7'R,7a'R)-4'-methyl-7'-((triethylsilyl)oxy)-7',7a'-dihydrospiro[cyclopropane-1,5'-indene]-3',6'-dione |
| 74 | 074 | (6'R)-3'-((((2,2-dimethyl-1,3-dioxolan-4-yl)methyl)thio)methyl)-6'-hydroxy-2',4',6'-trimethylspiro[cyclopropane-1,5'-inden]-7'(6'H)-one |
| 75 | 075 | (R)-(6'-hydroxy-4',6'-dimethyl-7'-oxo-6',7'-dihydrospiro[cyclopropane-1,5'-inden]-2'-yl)methyl acetate |
| 76 | 076 | (R)-(6'-hydroxy-4',6'-dimethyl-7'-oxo-6',7'-dihydrospiro[cyclopropane-1,5'-indene]-2',3'-diyl)bis(methylene) diacetate |
| 77 | 077 | (R)-(6'-hydroxy-3'-(hydroxymethyl)-4',6'-dimethyl-7'-oxo-6',7'-dihydrospiro[cyclopropane-1,5'-inden]-2'-yl)methyl acetate |
| 78 | 078 | (R)-(6'-hydroxy-2'-(hydroxymethyl)-4',6'-dimethyl-7'-oxo-6',7'-dihydrospiro[cyclopropane-1,5'-inden]-3'-yl)methyl acetate |
| 79 | 079 | (R)-6'-hydroxy-2'-(methoxymethyl)-4',6'-dimethylspiro[cyclopropane-1,5'-inden]-7'(6'H)-one |
| 80 | 080 | (R)-6'-hydroxy-3'-(methoxymethyl)-2',4',6'-trimethylspiro[cyclopropane-1,5'-inden]-7'(6'H)-one |
| 81 | 081 | (R)-6'-hydroxy-2'-(hydroxymethyl)-3'-(methoxymethyl)-4',6'-dimethylspiro[cyclopropane-1,5'-inden]-7'(6'H)-one |
| 82 | 082 | (R)-6'-hydroxy-2',3'-bis(methoxymethyl)-4',6'-dimethylspiro[cyclopropane-1,5'-inden]-7'(6'H)-one |
| 83 | 083 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-((2-(((S)-4-methyl-1-oxopentan-2-yl)amino)-2-oxoethyl)amino)-1-oxo-3-phenylpropan-2-yl)propanamide |
| 84 | 084 | (S)-24(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-(2-oxo-2-(((R)-1-oxo-3-phenylpropan-2-yl)amino)ethyl)pentanamide |
| 85 | 085 | (S)-24(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((S)-4-methyl-1-oxo-1-(((R)-1-oxo-3-phenylpropan-2-yl)amino)pentan-2-yl)pentanamide |
| 86 | 086 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-(2-oxo-2-(((R)-1-oxo-3-phenylpropan-2-yl)amino)ethyl)propanamide |
| 87 | 087 | (S)-24(R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((R)-4-methyl-1-(((S)-4-methyl-1-oxopentan-2-yl)amino)-1-oxopentan-2-yl)pentanamide |
| 88 | 088 | (R)-(6'-acetoxy-2',4',6'-trimethyl-7'-oxo-6',7'-dihydrospiro[cyclopropane-1,5'-inden]-3'-yl)methyl acetate |

TABLE V-continued

| IUPAC names of the Illudofulvene analogs. | | |
|---|---|---|
| Entry # | Illudofulvene Analog | IUPAC Name of Illudofulvene Analog |
| 89 | 089 | N5-((R)-1-((carboxymethyl)amino)-3-((((R)-6'-hydroxy-2',4',6'-trimethyl-7'-oxo-6',7'-dihydrospiro[cyclopropane-1,5'-inden]-3'-yl)methyl)thio)-1-oxopropan-2-yl)-D-glutamine |
| 90 | 090 | (R)-2'-(hydroxymethyl)-4',6'-dimethyl-7'-oxo-6',7'-dihydrospiro[cyclopropane-1,5'-inden]-6'-yl acetate |
| 91 | 091 | (R)-3-(6'-hydroxy-2',4',6'-trimethyl-7'-oxo-6',7'-dihydrospiro[cyclopropane-1,5'-inden]-3'-yl)propanoic acid |
| 92 | 092 | (R)-6'-hydroxy-3'-(3-methoxypropyl)-2',4',6'-trimethylspiro[cyclopropane-1,5'-inden]-7'(6'H)-one |
| 93 | 093 | (R)-3'-(3,3-diethoxypropyl)-6'-hydroxy-2',4',6'-trimethylspiro[cyclopropane-1,5'-inden]-7'(6'H)-one |
| 94 | 094 | (R)-3-(6'-hydroxy-2',4',6'-trimethyl-7'-oxo-6',7'-dihydrospiro[cyclopropane-1,5'-inden]-3'-yl)propyl acetate |
| 95 | 095 | (R)-6'-hydroxy-3'-(3-methoxypropyl)-2',4',6'-trimethylspiro[cyclopropane-1,5'-inden]-7'(6'H)-one |
| 96 | 096 | (R)-6'-hydroxy-2',4',6'-trimethyl-3'-(((1-methyl-1H-imidazol-2-yl)thio)methyl)spiro[cyclopropane-1,5'-inden]-7'(6'H)-one |
| 97 | 097 | S-(((R)-6'-hydroxy-2',4',6'-trimethyl-7'-oxo-6',7'-dihydrospiro[cyclopropane-1,5'-inden]-3'-yl)methyl)homocysteine |
| 98 | 098 | ((S)-3-((((R)-6'-hydroxy-2',4',6'-trimethyl-7'-oxo-6',7'-dihydrospiro[cyclopropane-1,5'-inden]-3'-yl)methyl)thio)-2-methylpropanoyl)proline |
| 99 | 099 | (2'S,6'R)-6'-hydroxy-2'-(hydroxymethyl)-2',4',6'-trimethylspiro[cyclopropane-1,5'-indene]-3',7'(2'H,6'H)-dione |
| 100 | 100 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-1-asparaginylglycyl-L-arginylcysteine |
| 101 | 101 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-arginylglycyl-L-asparaginylcysteine |
| 102 | 102 | S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 103 | 103 | (R)-(6'-acetoxy-2'-(hydroxymethyl)-4',6'-dimethyl-7'-oxo-6',7'-dihydrospiro[cyclopropane-1,5'-inden]-3'-yl)methyl acetate |
| 104 | 104 | (R)-8'-hydroxy-6',8'-dimethyl-1',5'-dihydrospiro[cyclopropane-1,7'-indeno[1,2-e][1,3]dioxepin]-9'(8'H)-one |
| 105 | 105 | (E)-2-((2R,4S)-4-hydroxy-2-((1R,2S)-2-hydroxy-4,4-dimethylcyclopentyl)-2-methylcyclobutylidene)propanal |
| 106 | 106 | 5-(((3'S,6'R)-6'-hydroxy-2',2',4',6'-tetramethyl-7'-oxo-2',3',6',7'-tetrahydrospiro[cyclopropane-1,5'-inden]-3'-yl)oxy)-5-oxopentanoicacid |
| 107 | 107 | (3'S,6'R)-6'-hydroxy-2',2',4',6'-tetramethyl-7'-oxo-2',3',6',7'-tetrahydrospiro[cyclopropane-1,5'-inden]-3'-yl ((13S)-13-methyl-17-oxo-7,8,9,11,12,13,14,15,16,17-decahydro-6H-cyclopenta[a]phenanthren-3-yl) glutarate |
| 108 | 108 | (13S)-17-hydroxy-13-methyl-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 109 | 109 | (13S)-17-hydroxy-13-methyl-7,8,9,11,12,13,14,15,16,17-decahydro-6H-cyclopenta[a]phenanthren-3-yl ((3'S,6'R)-6'-hydroxy-2',2',4',6'-tetramethyl-7'-oxo-2',3',6',7'-tetrahydrospiro[cyclopropane-1,5'-inden]-3'-yl) glutarate |
| 110 | 110 | (13S)-13-methyl-17-oxo-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 111 | 111 | (10R,13S)-10,13-dimethyl-3-oxo-2,3,6,7,8,9,10,11,12,13,14,15,16,17-tetradecahydro-1H-cyclopenta[a]phenanthren-17-yl 3-(6'-hydroxy-2',4'-dimethyl-7'-oxo-6',7'-dihydrospiro[cyclopropane-1,5'-inden]-3'-yl)propanoate |
| 112 | 112 | (13S)-10,13-dimethyl-17-oxohexadecahydro-1H-cyclopenta[a]phenanthren-3-yl 3(((R)-6'-hydroxy-2',4',6'-trimethyl-7'-oxo-6',7'-dihydrospiro[cyclopropane-1,5'-inden]-3'-yl)propanoate |
| 113 | 113 | (R)-3'-(but-3-en-1-yl)-6'-hydroxy-2',4',6'-trimethylspiro[cyclopropane-1,5'-inden]-7'(6'H)-one |
| 114 | 114 | (6'R)-6'-hydroxy-2',4',6'-trimethyl-3'-(2-(oxiran-2-yl)ethyl)spiro[cyclopropane-1,5'-inden]-7'(6'H)-one |
| 115 | 115 | (R)-3-(6'-hydroxy-2',4',6'-trimethyl-7'-oxo-6',7'-dihydrospiro[cyclopropane-1,5'-inden]-3'-yl)propanal oxime |

TABLE V-continued

IUPAC names of the Illudofulvene analogs.

| Entry # | Illudofulvene Analog | IUPAC Name of Illudofulvene Analog |
|---|---|---|
| 116 | 116 | (R)-3'-(tert-butoxymethyl)-6'-hydroxy-2',4',6'-trimethylspiro[cyclopropane-1,5'-inden]-7'(6'H)-one |
| 117 | 117 | 5-(((2'S,6'R)-3'-((4-carboxybutanoyl)oxy)-6'-hydroxy-2',4',6'-trimethyl-7'-oxo-2',3',6',7'-tetrahydrospiro[cyclopropane-1,5'-inden]-2'-yl)methoxy)-5-oxopentanoic acid |
| 118 | 118 | 5-(((2'S,6'R)-2'-(((3,5-dinitrobenzoyl)oxy)methyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 119 | 119 | (6'R)-3'-(3,4-dihydroxybutyl)-6'-hydroxy-2',4',6'-trimethylspiro[cyclopropane-1,5'-inden]-7'(6'H)-one |
| 120 | 120 | (R)-6'-hydroxy-3'-(3-((3-((S)-6'-hydroxy-2',4',6'-trimethyl-7'-oxo-6',7'-dihydrospiro[cyclopropane-1,5'-inden]-3'-yl)propylidene)hydrazineylidene)propyl)-2',4',6'-trimethylspiro[cyclopropane-1,5'-inden]-7'(6'H)-one |
| 121 | 121 | (R)-2-(3-(6'-hydroxy-2',4',6'-trimethyl-7'-oxo-6',7'-dihydrospiro[cyclopropane-1,5'-inden]-3'-yl)propylidene)hydrazine-1-carboxamide |
| 122 | 122 | (R)-6'-hydroxy-2',4',6'-trimethyl-3'-(3-(2-phenylhydrazineylidene)propyl)spiro[cyclopropane-1,5'-inden]-7'(6'H)-one |
| 123 | 123 | (R)-N'-(3-(6'-hydroxy-2',4',6'-trimethyl-7'-oxo-6',7'-dihydrospiro[cyclopropane-1,5'-inden]-3'-yl)propylidene)-4-methylbenzenesulfonohydrazide |
| 124 | 124 | (R)-3-(6'-hydroxy-2',4',6'-trimethyl-7'-oxo-6',7'-dihydrospiro[cyclopropane-1,5'-inden]-3'-yl)propanal O-acetyl oxime |
| 125 | 125 | (R)-3'-(3-(2-(2,4-dinitrophenyl)hydrazineylidene)propyl)-6'-hydroxy-2',4',6'-trimethylspiro[cyclopropane-1,5'-inden]-7'(6'H)-one |
| 126 | 126 | (R)-6'-hydroxy-2',4',6'-trimethyl-7'-oxo-6',7'-dihydrospiro[cyclopropane-1,5'-indene]-3'-carbaldehyde oxime |
| 127 | 127 | 2-hydroxy-4-((R)-6'-hydroxy-2',4',6'-trimethyl-7'-oxo-6',7'-dihydrospiro[cyclopropane-1,5'-inden]-3'-yl)butanenitrile |
| 128 | 128 | (6'R)-6'-hydroxy-3'-(3-hydroxybutyl)-2',4',6'-trimethylspiro[cyclopropane-1,5'-inden]-7'(6'H)-one |
| 129 | 129 | (6'R)-2',4',6'-trimethyl-6',7'-dihydrospiro[cyclopropane-1,5'-indene]-6',7'-diol |
| 130 | 130 | (R)-6'-hydroxy-3'-(3-(hydroxyamino)propyl)-2',4',6'-trimethylspiro[cyclopropane-1,5'-inden]-7'(6'H)-one |
| 131 | 131 | (R)-N-benzyl-3-(6'-hydroxy-2',4',6'-trimethyl-7'-oxo-6',7'-dihydrospiro[cyclopropane-1,5'-inden]-3'-yl)propanamide |
| 132 | 133 | (E)-7-(chloromethylene)-5-hydroxy-5,9-dimethylspiro[3.5]non-8-en-6-one |
| 133 | 134 | (E)-6-(chloromethylene)-4-hydroxy-4,8-dimethylspiro[2.5]oct-7-en-5-one |
| 134 | 135 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-nitrobenzoate |
| 135 | 136 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 136 | 137 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-nitrobenzoate |
| 137 | 138 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-(N-acetoxyacetamido)benzoate |
| 138 | 139 | (2'S,6'R)-6'-hydroxy-2',4',6'-trimethyl-2'-(((4-nitrobenzoyl)oxy)methyl)-7'-oxo-2',3',6',7'-tetrahydrospiro[cyclopropane-1,5'-inden]-3'-yl 4-nitrobenzoate |
| 139 | 140 | ((2'S,6'R)-3'4(4-(N-acetoxyacetamido)benzoyl)oxy)-6'-hydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 140 | 141 | dimethyl (5'R)-4',5'-dihydroxy-5',7',9'-trimethyl-4',5'-dihydro-1'H-spiro[cyclopropane-1,6'-[1,3a]ethenoindene]-2',3'-dicarboxylate |
| 141 | 142 | dimethyl (5'R)-5'-hydroxy-5',7',9'-trimethyl-4'-oxo-4',5'-dihydro-1'H-spiro[cyclopropane-1,6'-[1,3a]ethenoindene]-2',3'-dicarboxylate |
| 142 | 143 | (R)-6'-hydroxy-1',2',4',6'-tetramethylspiro[cyclopropane-1,5'-inden]-7'(6'H)-one |
| 143 | 144 | (R)-2-((2'-ethyl-6'-hydroxy-4',6'-dimethyl-7'-oxo-6',7'-dihydrospiro[cyclopropane-1,5'-inden]-3'-yl)methoxy)ethyl acetate |
| 144 | 145 | (R)-5-((6'-hydroxy-2',4',6'-trimethyl-7'-oxo-6',7'-dihydrospiro[cyclopropane-1,5'-inden]-3'-yl)methoxy)-5-oxopentanoic acid |

TABLE V-continued

IUPAC names of the Illudofulvene analogs.

| Entry # | Illudofulvene Analog | IUPAC Name of Illudofulvene Analog |
|---|---|---|
| 145 | 146 | (R)-4-(6'-hydroxy-2',4',6'-trimethyl-7'-oxo-6',7'-dihydrospiro[cyclopropane-1,5'-inden]-3'-yl)butanenitrile |
| 146 | 147 | (R)-3'-((benzo[d]thiazol-2-ylthio)methyl)-6'-hydroxy-2',4',6'-trimethylspiro[cyclopropane-1,5'-inden]-7'(6'H)-one |
| 147 | 148 | (R)-3'-((benzo[d]oxazol-2-ylthio)methyl)-6'-hydroxy-2',4',6'-trimethylspiro[cyclopropane-1,5'-inden]-7'(6'H)-one |
| 148 | 149 | (R)-6'-hydroxy-2',4',6'-trimethyl-3'-(((l-methyl-1H-tetrazol-5-yl)thio)methyl)spiro[cyclopropane-1,5'-inden]-7'(6'H)-one |
| 149 | 150 | (R)-6'-hydroxy-2',4',6'-trimethyl-3'-(((5-methyl-1H-benzo[d]imidazol-2-yl)thio)methyl)spiro[cyclopropane-1,5'-inden]-7'(6'H)-one |
| 150 | 151 | (R)-6'-hydroxy-2',4',6'-trimethyl-3'-(((1-phenyl-1H-tetrazol-5-yl)thio)methyl)spiro[cyclopropane-1,5'-inden]-7'(6'H)-one |
| 151 | 152 | (R)-6'-hydroxy-2',4',6'-trimethyl-3'-(((5-nitro-1H-benzo[d]imidazol-2-yl)thio)methyl)spiro[cyclopropane-1,5'-inden]-7'(6'H)-one |
| 152 | 153 | (R)-3'-(((1H-1,2,4-triazol-3-yl)thio)methyl)-6'-hydroxy-2',4',6'-trimethylspiro[cyclopropane-1,5'-inden]-7'(6'H)-one |
| 153 | 154 | (R)-6'-hydroxy-3'-(((4-hydroxypteridin-2-yl)thio)methyl)-2',4',6'-trimethylspiro[cyclopropane-1,5'-inden]-7'(6'H)-one |
| 154 | 155 | (R)-6'-hydroxy-3'-(((1-(4-hydroxyphenyl)-1H-tetrazol-5-yl)thio)methyl)-2',4',6'-trimethylspiro[cyclopropane-1,5'-inden]-7'(6'H)-one |
| 155 | 156 | (R)-4-(5-(((6'-hydroxy-2',4',6'-trimethyl-7'-oxo-6',7'-dihydrospiro[cyclopropane-1,5'-inden]-3'-yl)methyl)thio)-1H-tetrazol-1-yl)phenyl acetate |
| 156 | 157 | 7'-methyl-4'H-dispiro[cyclobutane-1,6'-indene-5',2''-[1,3]dioxolan]-4'-one |
| 157 | 158 | 5-hydroxy-2,2,6,8a-tetramethyl-2,3,3a,8,8a,8b-hexahydro-1H-cyclobuta[d]cyclopenta[b]oxepin-7(5H)-one |
| 158 | 159 | ((6'R)-3',6'-dihydroxy-2',4',6'-trimethyl-7'-oxo-2',3',6',7'-tetrahydrospiro[cyclopropane-1,5'-inden]-2'-yl)methyl acetate |
| 159 | 160 | 5-(((6'R)-2'-(acetoxymethyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 160 | 161 | ((6'R)-6'-hydroxy-2',4',6'-trimethyl-3',7'-dioxo-2',3',6',7'-tetrahydrospiro[cyclopropane-1,5'-inden]-2'-yl)methyl acetate |
| 161 | 162 | 5-(((6'R)-6'-hydroxy-2',4',6'-trimethyl-3',7'-dioxo-2',3',6',7'-tetrahydrospiro[cyclopropane-1,5'-inden]-2'-yl)methoxy)-5-oxopentanoic acid |
| 162 | 163 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl 2-chloroacetate |
| 163 | 164 | (R)-(6'-hydroxy-2',4',6'-trimethyl-7'-oxo-6',7'-dihydrospiro[cyclopropane-1,5'-inden]-3'-yl)methyl 2-chloroacetate |
| 164 | 165 | (R)-(6'-hydroxy-2',4',6'-trimethyl-7'-oxo-6',7'-dihydrospiro[cyclopropane-1,5'-inden]-3'-yl)methyl 2-morpholinoacetate |
| 165 | 166 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl methyl glutarate |
| 166 | 167 | (6'R)-6'-hydroxy-2'-(hydroxymethyl)-2',4',6'-trimethyl-7'-oxo-2',3',6',7'-tetrahydrospiro[cyclopropane-1,5'-inden]-3'-yl methyl glutarate |
| 167 | 168 | ((6'R)-6'-hydroxy-2',4',6'-trimethyl-3',7'-dioxo-2',3',6',7'-tetrahydrospiro[cyclopropane-1,5'-inden]-2'-yl)methyl methyl glutarate |
| 168 | 169 | ((6'R)-6'-hydroxy-2',4',6'-trimethyl-3',7'-dioxo-2',3',6',7'-tetrahydrospiro[cyclopropane-1,5'-inden]-2'-yl)methyl 2-chloroacetate |
| 169 | 170 | 5-(2-hydroxyethyl)-3-(hydroxymethyl)-2,4,6-trimethyl-1H-inden-7-ol |
| 170 | 171 | 6-(2-hydroxyethyl)-2,5,7-trimethyl-1-methylene-1H-inden-4-ol |
| 171 | 172 | 6-ethyl-2,5,7-trimethyl-1-methylene-1H-inden-4-ol |
| 172 | 173 | 2-(4-hydroxy-2,5,7-trimethyl-1-methylene-1H-inden-6-yl)ethyl acetate |
| 173 | 174 | 5-(2-hydroxyethyl)-3-(hydroxymethyl)-2,4,6-trimethyl-1H-indene-1,7-diol |
| 174 | 175 | (2S,3S,4R,5S,6R)-2-(acetoxymethyl)-6-(((R)-6'-hydroxy-2',4',6'-trimethyl-7'-oxo-6',7'-dihydrospiro[cyclopropane-1,5'-inden]-3'-yl)methoxy)tetrahydro-2H-pyran-3,4,5-triyl triacetate |
| 175 | 176 | 3-((R)-6'-hydroxy-2',4',6'-trimethyl-7'-oxo-6',7'-dihydrospiro[cyclopropane-1,5'-inden]-3'-yl)propyl leucinate |

TABLE V-continued

IUPAC names of the Illudofulvene analogs.

| Entry # | Illudofulvene Analog | IUPAC Name of Illudofulvene Analog |
|---|---|---|
| 176 | 177 | (R)-5-(3-(6'-hydroxy-2',4',6'-trimethyl-7'-oxo-6',7'-dihydrospiro[cyclopropane-1,5'-inden]-3'-yl)propoxy)-5-oxopentanoic acid |
| 177 | 178 | (R)-4-(3-(6'-hydroxy-2',4',6'-trimethyl-7'-oxo-6',7'-dihydrospiro[cyclopropane-1,5'-inden]-3'-yl)propoxy)-4-oxobutanoic acid |
| 178 | 179 | (R)-3-(6'-hydroxy-2',4',6'-trimethyl-7'-oxo-6',7'-dihydrospiro[cyclopropane-1,5'-inden]-3'-yl)propyl glycinate |
| 179 | 180 | (1a'R,3'R,7'S,7a'R)-3',7'-dihydroxy-1a',3',6',6'-tetramethyl-6',7'-dihydro-1a'H-spiro[cyclopropane-1,2'-indeno[3a,4-b]oxiren]-4'(3'H)-one |
| 180 | 181 | ((1a'R,3'R,6'S,7'S,7a'R)-3',7'-dihydroxy-1a',3',6'-trimethyl-4'-oxo-3',4',6',7'-tetrahydro-1a'H-spiro[cyclopropane-1,2'-indeno[3a,4-b]oxiren]-6'-yl)methyl acetate |
| 181 | 182 | (2'R,7'S,7a'S)-2'-chloro-7'-hydroxy-2',4'-dimethyl-1',2',7',7a'-tetrahydrospiro[cyclopropane-1,5'-indene]-3',6'-dione |
| 182 | 183 | (2'S,7'S,7a'S)-7'-hydroxy-2'-isopropoxy-2',4'-dimethyl-1',2',7',7a'-tetrahydrospiro[cyclopropane-1,5'-indene]-3',6'-dione |
| 183 | 184 | (R)-1-hydroxy-1-((6'-hydroxy-2',4',6'-trimethyl-7'-oxo-6',7'-dihydrospiro[cyclopropane-1,5'-inden]-3'-yl)methyl)urea |
| 184 | 185 | (S)-6'-hydroxy-2',4',6'-trimethylspiro[cyclopropane-1,5'-inden]-7'(6'H)-one |
| 185 | 186 | (6'S,7'R)-6',7'-dihydroxy-2',4',6'-trimethyl-7',7a'-dihydrospiro[cyclopropane-1,5'-inden]-3'(6'H)-one |
| 186 | 187 | (S)-6'-hydroxy-3'-(hydroxymethyl)-2',4',6'-trimethylspiro[cyclopropane-1,5'-inden]-7'(6'H)-one |
| 187 | 188 | (6'S,6'''S)-3',3'''-methylenebis(6'-hydroxy-2',4',6'-trimethylspiro[cyclopropane-1,5'-inden]-7'(6'H)-one) |
| 188 | 189 | (R)-1-((6'-hydroxy-2',4',6'-trimethyl-7'-oxo-6',7'-dihydrospiro[cyclopropane-1,5'-inden]-3'-yl)methyl)-1H-pyrrole-2,5-dione |
| 189 | 190 | (R)-1-(3-(6'-hydroxy-2',4',6'-trimethyl-7'-oxo-6',7'-dihydrospiro[cyclopropane-1,5'-inden]-3'-yl)propyl)-1H-pyrrole-2,5-dione |
| 190 | 191 | 6'-hydroxy-4',6'-dimethylspiro[cyclobutane-1,5'-inden]-7'(6'H)-one |
| 191 | 192 | (R)-2-((6'-hydroxy-2',4',6'-trimethyl-7'-oxo-6',7'-dihydrospiro[cyclopropane-1,5'-inden]-3'-yl)methyl)isoindoline-1,3-dione |
| 192 | 193 | (R)-3'-(azidomethyl)-6'-hydroxy-2',4',6'-trimethylspiro[cyclopropane-1,5'-inden]-7'(6'H)-one |
| 193 | 194 | (R)-3'-(((R)-3'-(azidomethyl)-6'-hydroxy-2',4',6'-trimethyl-7'-oxo-6',7'-dihydrospiro[cyclopropane-1,5'-inden]-1'-yl)methyl)-6'-hydroxy-2',4',6'-trimethylspiro[cyclopropane-1,5'-inden]-7'(6'H)-one |
| 194 | 195 | (R)-3'-(3-azidopropyl)-6'-hydroxy-4',6'-dimethylspiro[cyclopropane-1,5'-inden]-7'(6'H)-one |
| 195 | 196 | 3-((R)-6'-hydroxy-2',4',6'-trimethyl-7'-oxo-6',7'-dihydrospiro[cyclopropane-1,5'-inden]-3'-yl)propyl L-prolinate |
| 196 | 197 | (R)-2-(3-(6'-hydroxy-2',4',6'-trimethyl-7'-oxo-6',7'-dihydrospiro[cyclopropane-1,5'-inden]-3'-yl)propyl)isoindoline-1,3-dione |
| 197 | 198 | (R)-6'-hydroxy-2',4',6'-trimethyl-3'-((4-nitrophenoxy)methyl)spiro[cyclopropane-1,5'-inden]-7'(6'H)-one |
| 198 | 199 | (R)-6'-hydroxy-2',4',6'-trimethyl-3'-(phenoxymethyl)spiro[cyclopropane-1,5'-inden]-7'(6'H)-one |
| 199 | 200 | (R)-6'-hydroxy-3'-(2-hydroxybenzyl)-2',4',6'-trimethylspiro[cyclopropane-1,5'-inden]-7'(6'H)-one |
| 200 | 201 | (R)-N-(3-(6'-hydroxy-2',4',6'-trimethyl-7'-oxo-6',7'-dihydrospiro[cyclopropane-1,5'-inden]-3'-yl)propyl)acetamide |
| 201 | 202 | (S)-N-(3-((R)-6'-hydroxy-2',4',6'-trimethyl-7'-oxo-6',7'-dihydrospiro[cyclopropane-1,5'-inden]-3'-yl)propyl)pyrrolidine-2-carboxamide |
| 202 | 203 | 3-((R)-6'-hydroxy-2',4',6'-trimethyl-7'-oxo-6',7'-dihydrospiro[cyclopropane-1,5'-inden]-3'-yl)propyl L-seryl-L-prolinate |
| 203 | 204 | 2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 204 | 205 | (2'R,3'S,6'R)-3'-amino-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 205 | 206 | (2'R,3'S,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 206 | 207 | (S)-2-amino-N-(3-((R)-6'-hydroxy-2',4',6'-trimethyl-7'-oxo-6',7'-dihydrospiro[cyclopropane-1,5'-inden]-3'-yl)propyl)-4-methylpentanamide |

TABLE V-continued

| IUPAC names of the Illudofulvene analogs. | | |
|---|---|---|
| Entry # | Illudofulvene Analog | IUPAC Name of Illudofulvene Analog |
| 207 | 208 | 3-((R)-6'-hydroxy-2',4',6'-trimethyl-7'-oxo-6',7'-dihydrospiro[cyclopropane-1,5'-inden]-3'-yl)propyl (tert-butoxycarbonyl)-L-seryl-L-prolinate |
| 208 | 209 | 3-((R)-6'-hydroxy-2',4',6'-trimethyl-7'-oxo-6',7'-dihydrospiro[cyclopropane-1,5'-inden]-3'-yl)propyl L-seryl-L-seryl-L-prolinate |
| 209 | 210 | 3-((R)-6'-hydroxy-2',4',6'-trimethyl-7'-oxo-6',7'-dihydrospiro[cyclopropane-1,5'-inden]-3'-yl)propyl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 210 | 211 | (R)-3'-(3-aminopropyl)-6'-hydroxy-2',4',6'-trimethylspiro[cyclopropane-1,5'-inden]-7'(6'H)-one |
| 211 | 212 | (3'S,6'R)-6'-hydroxy-2',2',4',6'-tetramethyl-7'-oxo-2',3',6',7'-tetrahydrospiro[cyclopropane-1,5'-inden]-3'-yl L-prolinate |
| 212 | 213 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-prolinate |
| 213 | 214 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-seryl-L-seryl-L-prolinate |
| 214 | 215 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 215 | 216 | (3'S,6'R)-6'-hydroxy-2',2',4',6'-tetramethyl-7'-oxo-2',3',6',7'-tetrahydrospiro[cyclopropane-1,5'-inden]-3'-yl ((S)-2-((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 216 | 217 | (R)-(6'-hydroxy-2',4',6'-trimethyl-7'-oxo-6',7'-dihydrospiro[cyclopropane-1,5'-inden]-3'-yl)methyl 6-(2,5-dioxo-2,5-dihydro-1H-pyrrol-1-yl)hexanoate |
| 217 | 218 | (3'S,6'R)-6'-hydroxy-2',2',4',6'-tetramethyl-7'-oxo-2',3',6',7'-tetrahydrospiro[cyclopropane-1,5'-inden]-3'-yl 6-(2,5-dioxo-2,5-dihydro-1H-pyrrol-1-yl)hexanoate |
| 218 | 219 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl 4-(fluorosulfonyl)benzoate |
| 219 | 220 | (R)-1-acetoxy-1-((6'-hydroxy-2',4',6'-trimethyl-7'-oxo-6',7'-dihydrospiro[cyclopropane-1,5'-inden]-3'-yl)methyl)urea |
| 220 | 221 | (S)-2-((3S,6S,9S,12S,15S)-3-((1H-imidazol-4-yl)methyl)-12-(4-aminobutyl)-6,9-bis(hydroxymethyl)-15-isobutyl-1-morpholino-1,4,7,10,13-pentaoxo-2,5,8,11,14-pentaazahexadecan-16-amido)-N1-((S)-1-((3-((R)-6'-hydroxy-2',4',6'-trimethyl-7'-oxo-6',7'-dihydrospiro[cyclopropane-1,5'-inden]-3'-yl)propyl)amino)-4-methyl-1-oxopentan-2-yl)pentanediamide |
| 221 | 222 | (3'S,6'R)-6'-hydroxy-2',2',4',6'-tetramethyl-7'-oxo-2',3',6',7'-tetrahydrospiro[cyclopropane-1,5'-inden]-3'-yl 4-(fluorosulfonyl)benzoate |
| 222 | 223 | 3-((R)-6'-hydroxy-2',4',6'-trimethyl-7'-oxo-6',7'-dihydrospiro[cyclopropane-1,5'-inden]-3'-yl)propyl ((4R,7S,13S)-13-(2-amino-2-oxoethyl)-7-(3-guanidinopropyl)-6,9,12,15-tetraoxo-1,2-dithia-5,8,14-triazacycloheptadecane-4-carbonyl)glycinate |
| 223 | 224 | (R,E)-6'-hydroxy-2',4',6'-trimethylspiro[cyclopropane-1,5'-inden]-7'(6'H)-one oxime |
| 224 | 225 | (2'R,3'R,6'R,E)-2',3',6'-trihydroxy-2',4',6'-trimethyl-2',3'-dihydrospiro[cyclopropane-1,5'-inden]-7'(6'H)-one oxime |
| 225 | 226 | (R)-(6'-hydroxy-2',4',6'-trimethyl-7'-oxo-6',7'-dihydrospiro[cyclopropane-1,5'-inden]-3'-yl)methyl (E)-octadec-9-enoate |
| 226 | 227 | (R)-3-(6'-hydroxy-2',4',6'-trimethyl-7'-oxo-6',7'-dihydrospiro[cyclopropane-1,5'-inden]-3'-yl)propyl (E)-octadec-9-enoate |
| 227 | 228 | (2'S,6'R)-6'-hydroxy-2',4',6'-trimethyl-2'-((((E)-octadec-9-enoyl)oxy)methyl)-7'-oxo-2',3',6',7'-tetrahydrospiro[cyclopropane-1,5'-inden]-3'-yl (E)-octadec-9-enoate |
| 228 | 229 | (R,E)-N-(3-(6'-hydroxy-2',4',6'-trimethyl-7'-oxo-6',7'-dihydrospiro[cyclopropane-1,5'-inden]-3'-yl)propyl)octadec-9-enamide |

TABLE V-continued

IUPAC names of the Illudofulvene analogs.

| Entry # | Illudofulvene Analog | IUPAC Name of Illudofulvene Analog |
|---|---|---|
| 229 | 230 | N-((3'R,6'R)-6'-hydroxy-2',2',4',6'-tetramethyl-7'-oxo-2',3',6',7'-tetrahydrospiro[cyclopropane-1,5'-inden]-3'-yl)methanesulfonamide |
| 230 | 231 | N-((3'R,6'R)-6'-hydroxy-2',2',4',6'-tetramethyl-7'-oxo-2',3',6',7'-tetrahydrospiro[cyclopropane-1,5'-inden]-3'-yl)-4-methylbenzenesulfonamide |
| 231 | 232 | (R)-3-(6'-hydroxy-2',4',6'-trimethyl-7'-oxo-6',7'-dihydrospiro[cyclopropane-1,5'-inden]-3'-yl)propyl hydroxycarbamate |
| 232 | 233 | ethyl (R)-hydroxy((6'-hydroxy-2',4',6'-trimethyl-7'-oxo-6',7'-dihydrospiro[cyclopropane-1,5'-inden]-3'-yl)methyl)carbamate |
| 233 | 234 | benzyl (R)-hydroxy((6'-hydroxy-2',4',6'-trimethyl-7'-oxo-6',7'-dihydrospiro[cyclopropane-1,5'-inden]-3'-yl)methyl)carbamate |
| 234 | 235 | tert-butyl (R)-hydroxy((6'-hydroxy-2',4',6'-trimethyl-7'-oxo-6',7'-dihydrospiro[cyclopropane-1,5'-inden]-3'-yl)methyl)carbamate |
| 235 | 236 | (R)-6'-hydroxy-3'-(hydroxymethyl)-1',2',4',6'-tetramethylspiro[cyclopropane-1,5'-inden]-7'(6'H)-one |
| 236 | 237 | (R)-3-(6'-hydroxy-2',4',6'-trimethyl-7'-oxo-6',7'-dihydrospiro[cyclopropane-1,5'-inden]-3'-yl)propyl(2-bromoethyl)carbamate |
| 237 | 238 | (R)-3-(6'-hydroxy-2',4',6'-trimethyl-7'-oxo-6',7'-dihydrospiro[cyclopropane-1,5'-inden]-3'-yl)propyl (2-chloroethyl)carbamate |
| 238 | 239 | (R)-3-(6'-hydroxy-2',4',6'-trimethyl-7'-oxo-6',7'-dihydrospiro[cyclopropane-1,5'-inden]-3'-yl)propyl(2-hydroxyethyl)carbamate |
| 239 | 240 | (R)-3-(6'-hydroxy-2',4',6'-trimethyl-7'-oxo-6',7'-dihydrospiro[cyclopropane-1,5'-inden]-3'-yl)propyl acetoxy(acetyl)carbamate |
| 240 | 241 | (R)-N-(3-(6'-hydroxy-2',4',6'-trimethyl-7'-oxo-6',7'-dihydrospiro[cyclopropane-1,5'-inden]-3'-yl)propyl)methanesulfonamide |
| 241 | 242 | (R)-N-(3-(6'-hydroxy-2',4',6'-trimethyl-7'-oxo-6',7'-dihydrospiro[cyclopropane-1,5'-inden]-3'-yl)propyl)-4-methylbenzenesulfonamide |
| 242 | 243 | (R)-3-(6'-hydroxy-2',4',6'-trimethyl-7'-oxo-6',7'-dihydrospiro[cyclopropane-1,5'-inden]-3'-yl)propyl (2-fluoroethyl)carbamate |
| 243 | 244 | (R)-1-hydroxy-1-(3-(6'-hydroxy-2',4',6'-trimethyl-7'-oxo-6',7'-dihydrospiro[cyclopropane-1,5'-inden]-3'-yl)propyl)urea |
| 244 | 245 | (R)-1-hydroxy-1-(3-(6'-hydroxy-2',4',6'-trimethyl-7'-oxo-6',7'-dihydrospiro[cyclopropane-1,5'-inden]-3'-yl)propyl)thiourea |
| 245 | 246 | (R)-3-(6'-hydroxy-2',4',6'-trimethyl-7'-oxo-6',7'-dihydrospiro[cyclopropane-1,5'-inden]-3'-yl)propylmorpholine-4-carboxylate |
| 246 | 247 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 247 | 248 | (R)-3-(6'-hydroxy-2',4',6'-trimethyl-7'-oxo-6',7'-dihydrospiro[cyclopropane-1,5'-inden]-3'-yl)propyl [1,4'-bipiperidine]-1'-carboxylate |
| 248 | 249 | (R)-6'-hydroxy-2'-(hydroxymethyl)-3',4',6'-trimethylspiro[cyclopropane-1,5'-inden]-7'(6'H)-one |
| 249 | 250 | ((1a'R,2'S,3'R,6'R,7a'S)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 250 | 251 | ((1a'S,2'S,3'R,6'R,7a'R)-3'-acetoxy-6'-hydroxy-2',4',6'-trimethyl-7'-oxo-1',1a',2',3',6',7'-hexahydrospiro[cyclopropane-1,5'-cyclopropalclinden]-2'-yl)methyl acetate |
| 251 | 252 | (1a'R,3'S,6'R,7a'S)-3',6'-dihydroxy-2',2',4',6'-tetramethyl-1',1a',2',3'-tetrahydrospiro[cyclopropane-1,5'-cyclopropa[c]inden]-7'(6'H)-one |
| 252 | 253 | (1a'S,3'S,6'R,7a'R)-3',6'-dihydroxy-2',2',4',6'-tetramethyl-1',1a',2',3'-tetrahydrospiro[cyclopropane-1,5'-cyclopropa[c]inden]-7'(6'H)-one |
| 253 | 254 | (R)-3-(6'-hydroxy-2',4',6'-trimethyl-7'-oxo-6',7'-dihydrospiro[cyclopropane-1,5'-inden]-3'-yl)propyl 4-sulfamoylbenzoate |
| 254 | 255 | (R)-3-(6'-hydroxy-2',4',6'-trimethyl-7'-oxo-6',7'-dihydrospiro[cyclopropane-1,5'-inden]-3'-yl)propyl sulfamate |
| 255 | 256 | 3-((R)-6'-hydroxy-2',4',6'-trimethyl-7'-oxo-6',7'-dihydrospiro[cyclopropane-1,5'-inden]-3'-yl)propyl 1-(3(((R)-6'-hydroxy-2',4',6'-trimethyl-7'-oxo-6',7'-dihydrospiro[cyclopropane-1,5'-inden]-3'-yl)propyl)-1H-1,2,3-triazole-4-carboxylate |

TABLE V-continued

| IUPAC names of the Illudofulvene analogs. | | |
|---|---|---|
| Entry # | Illudofulvene Analog | IUPAC Name of Illudofulvene Analog |
| 256 | 257 | 3-((R)-6'-hydroxy-2',4',6'-trimethyl-7'-oxo-6',7'-dihydrospiro[cyclopropane-1,5'-inden]-3'-yl)propyl 1-(((R)-6'-hydroxy-2',4',6'-trimethyl-7'-oxo-6',7'-dihydrospiro[cyclopropane-1,5'-inden]-3'-yl)methyl)-1H-1,2,3-triazole-4-carboxylate |
| 257 | 258 | (4-carboxy-4-(4-carboxy-4-((3-((R)-6'-hydroxy-2',4',6'-trimethyl-7'-oxo-6',7'-dihydrospiro[cyclopropane-1,5'-inden]-3'-yl)propyl)amino)butanamido)butanoyl)glutamic acid |
| 258 | 259 | (R)-3'-((S)-2,2-dioxido-1,2,3-oxathiazinan-4-yl)-6'-hydroxy-2',4',6'-trimethylspiro[cyclopropane-1,5'-inden]-7'(6'H)-one |
| 259 | 260 | (R)-N-(3-(6'-hydroxy-2',4',6'-trimethyl-7'-oxo-6',7'-dihydrospiro[cyclopropane-1,5'-inden]-3'-yl)propyl)-[1,4'-bipiperidine]-1'-carboxamide |
| 260 | 261 | (R)-3-(6'-hydroxy-2',4',6'-trimethyl-7'-oxo-6',7'-dihydrospiro[cyclopropane-1,5'-inden]-3'-yl)propyl 1H-imidazole-1-carboxylate |
| 261 | 262 | methyl (R)-2-(((6'-hydroxy-2',4',6'-trimethyl-7'-oxo-6',7'-dihydrospiro[cyclopropane-1,5'-inden]-3'-yl)methyl)sulfonyl)acetate |
| 262 | 263 | methyl 2-((((R)-6'-hydroxy-2',4',6'-trimethyl-7'-oxo-6',7'-dihydrospiro[cyclopropane-1,5'-inden]-3'-yl)methyl)sulfinyl)acetate |
| 263 | 264 | N-[3-(6'-hydroxy-2',6'-dimethyl-7'-oxo-6',7'-dihydrospiro[cyclopropane-1,5'-inden]-3'-yl)propyl]sulfuric diamide |
| 264 | 265 | N-hydroxy-N'-[3-(6'-hydroxy-2',6'-dimethyl-7'-oxo-6',7'-dihydrospiro[cyclopropane-1,5'-inden]-3'-yl)propyl]sulfuric diamide |
| 265 | 266 | N-[3-(6'-hydroxy-2',6'-dimethyl-7'-oxo-6',7'-dihydrospiro[cyclopropane-1,5'-inden]-3'-yl)propyl]-N-methoxysulfuric diamide |
| 266 | 267 | (R)-2-amino-N-((6'-hydroxy-2',4',6'-trimethyl-7'-oxo-6',7'-dihydrospiro[cyclopropane-1,5'-inden]-3'-yl)methyl)-N-methoxyacetamide |
| 267 | 268 | (R)-2,2,2-trifluoro-N-(3-(6'-hydroxy-2',4',6'-trimethyl-7'-oxo-6',7'-dihydrospiro[cyclopropane-1,5'-inden]-3'-yl)propyl)acetamide |
| 268 | 269 | (R)-(6'-hydroxy-2',4',6'-trimethyl-7'-oxo-6',7'-dihydrospiro[cyclopropane-1,5'-inden]-3'-yl)methyl (4-methoxyphenyl)sulfamate |
| 269 | 270 | (R)-3'-(aminomethyl)-6'-hydroxy-2',4',6'-trimethylspiro[cyclopropane-1,5'-inden]-7'(6'H)-one |
| 270 | 271 | (R)-N-((6'-hydroxy-2',4',6'-trimethyl-7'-oxo-6',7'-dihydrospiro[cyclopropane-1,5'-inden]-3'-yl)methyl)methanesulfonamide |
| 271 | 272 | (5S,6S,7S)-3-(((3(((R)-6'-hydroxy-2',4',6'-trimethyl-7'-oxo-6',7'-dihydrospiro[cyclopropane-1,5'-inden]-3'-yl)propanoyl)oxy)methyl)-8-oxo-7-(2-(thiophen-2-yl)acetamido)-5-thia-1-azabicyclo[4.2.0]oct-2-ene-2-carboxylic acid 5-oxide |
| 272 | 273 | (5S,6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5-oxide |
| 273 | 274 | (6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5,5-dioxide |
| 274 | 275 | N-(((R)-6'-hydroxy-2',4',6'-trimethyl-7'-oxo-6',7'-dihydrospiro[cyclopropane-1,5'-inden]-3'-yl)methyl)pyrrolidine-2-carboxamide |
| 275 | 276 | 2-amino-N-(((R)-6'-hydroxy-2',4',6'-trimethyl-7'-oxo-6',7'-dihydrospiro[cyclopropane-1,5'-inden]-3'-yl)methyl)-4-methylpentanamide |
| 276 | 277 | (R)-1-hydroxy-3-((6'-hydroxy-2',4',6'-trimethyl-7'-oxo-6',7'-dihydrospiro[cyclopropane-1,5'-inden]-3'-yl)methyl)urea |
| 277 | 278 | (R)-1-((6'-hydroxy-2',4',6'-trimethyl-7'-oxo-6',7'-dihydrospiro[cyclopropane-1,5'-inden]-3'-yl)methyl)-3-methoxyurea |
| 278 | 279 | (R)-1-((6'-hydroxy-2',4',6'-trimethyl-7'-oxo-6',7'-dihydrospiro[cyclopropane-1,5'-inden]-3'-yl)methyl)-3-(2-hydroxyethyl)urea |
| 279 | 280 | (R)-1-(3-(6'-hydroxy-2',4',6'-trimethyl-7'-oxo-6',7'-dihydrospiro[cyclopropane-1,5'-inden]-3'-yl)propyl)-3-(2-hydroxyethyl)urea |
| 280 | 281 | (R)-1-(2-chloroethyl)-3-(3-(6'-hydroxy-2',4',6'-trimethyl-7'-oxo-6',7'-dihydrospiro[cyclopropane-1,5'-inden]-3'-yl)propyl)urea |

TABLE V-continued

| IUPAC names of the Illudofulvene analogs. | | |
|---|---|---|
| Entry # | Illudofulvene Analog | IUPAC Name of Illudofulvene Analog |
| 281 | 282 | (R)-1-(2-chloroethyl)-3-((6'-hydroxy-2',4',6'-trimethyl-7'-oxo-6',7'-dihydrospno[cyclopropane-1,5'-inden]-3'-yl)methyl)urea |
| 282 | 283 | N-[(6'-hydroxy-2',6'-dimethyl-7'-oxo-6',7'-dihydrospiro[cyclopropane-1,5'-inden]-3'-yl)methyl]sulfuric diamide |
| 283 | 284 | (R)-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 284 | 285 | N-hydroxy-N-[(6'-hydroxy-2',6'-dimethyl-7'-oxo-6',7'-dihydrospiro[cyclopropane-1,5'-inden]-3'-yl)methyl]sulfuric diamide |
| 285 | 286 | (R)-5-fluoro-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 286 | 287 | (R)-5-fluoro-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 287 | 288 | (R)-1-hydroxy-3-(3-(6'-hydroxy-2',4',6'-trimethyl-7'-oxo-6',7'-dihydrospiro[cyclopropane-1,5'-inden]-3'-yl)propyl)urea |
| 288 | 289 | (R)-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 289 | 290 | ((S)-6'-hydroxy-2',4',6'-trimethyl-7'-oxo-6',7'-dihydrospiro[cyclopropane-1,5'-inden]-3'-yl)methyl 5-oxo-5-(((S)-1,2,3,10-tetramethoxy-9-oxo-5,6,7,9-tetrahydrobenzo[a]heptalen-7-yl)amino)pentanoate |
| 290 | 291 | 3-((S)-6'-hydroxy-2',4',6'-trimethyl-7'-oxo-6',7'-dihydrospiro[cyclopropane-1,5'-inden]-3'-yl)propyl 5-oxo-5-(((S)-1,2,3,10-tetramethoxy-9-oxo-5,6,7,9-tetrahydrobenzo[a]heptalen-7-yl)amino)pentanoate |
| 291 | 292 | N1-(((S)-6'-hydroxy-2',4',6'-trimethyl-7'-oxo-6',7'-dihydrospiro[cyclopropane-1,5'-inden]-3'-yl)methyl)-N5-((S)-1,2,3,10-tetramethoxy-9-oxo-5,6,7,9-tetrahydrobenzo[a]heptalen-7-yl)glutaramide |
| 292 | 293 | 3-((S)-6'-hydroxy-2',4',6'-trimethyl-7'-oxo-6',7'-dihydrospiro[cyclopropane-1,5'-inden]-3'-yl)-N-((S)-1,2,3,10-tetramethoxy-9-oxo-5,6,7,9-tetrahydrobenzo[a]heptalen-7-yl)propanamide |
| 293 | 294 | 2-amino-N-(((R)-6'-hydroxy-2',4',6'-trimethyl-7'-oxo-6',7'-dihydrospiro[cyclopropane-1,5'-inden]-3'-yl)methyl)-N-methoxypropanamide |
| 294 | 295 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-methylpentanamide |
| 295 | 296 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-(methylthio)butanamide |
| 296 | 297 | 2-amino-N-(((R)-6'-hydroxy-2',4',6'-trimethyl-7'-oxo-6',7'-dihydrospiro[cyclopropane-1,5'-inden]-3'-yl)methyl)-3-(1H-indol-3-yl)-N-methoxypropanamide |
| 297 | 298 | (R)-3-(6'-hydroxy-2',4',6'-trimethyl-7'-oxo-6',7'-dihydrospiro[cyclopropane-1,5'-inden]-3'-yl)propyl (tert-butoxycarbonyl)glycinate |
| 298 | 299 | (2'S,3'R,6'R)-2'-(azidomethyl)-3',6'-dihydroxy-2',4',6'-trimethyl-2',3'-dihydrospiro[cyclopropane-1,5'-inden]-7'(6'H)-one |
| 299 | 300 | (2'R,3'R,6'R)-3'-azido-6'-hydroxy-2'-(hydroxymethyl)-2',4',6'-trimethyl-2',3'-dihydrospiro[cyclopropane-1,5'-inden]-7'(6'H)-one |
| 300 | 301 | (R)-6'-hydroxy-2',4',6'-trimethyl-7'-oxo-6',7'-dihydrospiro[cyclopropane-1,5'-inden]-3'-yl 6-oxo-6-phenylhexanoate |
| 301 | 302 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 3,5-dinitrobenzoate |
| 302 | 303 | (2'S,3'R,6'R)-2'-(((3,5-dinitrocyclohexa-2,4-diene-1-carbonyl)oxy)methyl)-6'-hydroxy-2',4',6'-trimethyl-7'-oxo-2',3',6',7'-tetrahydrospiro[cyclopropane-1,5'-inden]-3'-yl 3,5-dinitrobenzoate |
| 303 | 304 | (R)-3-(6'-hydroxy-2',4',6'-trimethyl-7'-oxo-6',7'-dihydrospiro[cyclopropane-1,5'-inden]-3'-yl)propyl propiolate |
| 304 | 305 | (R)-3-(6'-hydroxy-2',4',6'-trimethyl-7'-oxo-6',7'-dihydrospiro[cyclopropane-1,5'-inden]-3'-yl)propyl (4-nitrophenyl) carbonate |
| 305 | 306 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |

TABLE V-continued

| IUPAC names of the Illudofulvene analogs. | | |
|---|---|---|
| Entry # | Illudofulvene Analog | IUPAC Name of Illudofulvene Analog |
| 306 | 307 | (3'R,6'R)-3'-azido-6'-hydroxy-2',2',4',6'-tetramethyl-2',3'-dihydrospiro[cyclopropane-1,5'-inden]-7'(6'H)-one |
| 307 | 308 | (3'R,6'R)-3'-amino-6'-hydroxy-2',2',4',6'-tetramethyl-2',3'-dihydrospiro[cyclopropane-1,5'-inden]-7'(6'H)-one |
| 308 | 309 | (2'R,3'S,6'R)-3'-azido-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 309 | 310 | (R)-(6'-hydroxy-2',4',6'-trimethyl-7'-oxo-6',7'-dihydrospiro[cyclopropane-1,5'-inden]-3'-yl)methyl4-sulfamoylbenzoate |
| 310 | 311 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 311 | 312 | (R)-(6'-hydroxy-2',4',6'-trimethyl-7'-oxo-6',7'-dihydrospiro[cyclopropane-1,5'-inden]-3'-yl)methyl 4-methylbenzenesulfonate |
| 312 | 313 | 2,3,4,5,6-pentafluoro-N-((3'R,6'R)-6'-hydroxy-2',2',4',6'-tetramethyl-7'-oxo-2',3',6',7'-tetrahydrospiro[cyclopropane-1,5'-inden]-3'-yl)benzenesulfonamide |
| 313 | 314 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 314 | 315 | (R)-3'-((2,5-dimethyl-1H-pyrrol-3-yl)methyl)-6'-hydroxy-2',4',6'-trimethylspiro[cyclopropane-1,5'-inden]-7'(6'H)-one |
| 315 | 316 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 316 | 317 | (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl 4-(fluorosulfonyl)benzoate |
| 317 | 318 | ((2'S,3'R,6'R)-3'-((4-(fluorosulfonyl)benzoyl)oxy)-6'-hydroxy-2',4',6'-trimethyl-7'-oxo-2',3',6',7'-tetrahydrospiro[cyclopropane-1,5'-inden]-2'-yl)methyl 4-(fluorosulfony)benzoate |
| 318 | 332 | (R)-6'-hydroxy-3'-((methoxyamino)methyl)-2',4',6'-trimethylspiro[cyclopropane-1,5'-inden]-7'(6'H)-one |
| 319 | 333 | ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate |
| 320 | 334 | ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 321 | 335 | tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 322 | 337 | 4-nitrophenyl (R)-((6'-hydroxy-2',4',6'-trimethyl-7'-oxo-6',7'-dihydrospiro[cyclopropane-1,5'-inden]-3'-yl)methyl)carbamate |
| 323 | 338 | 4-nitrophenyl (R)-(3-(6'-hydroxy-2',4',6'-trimethyl-7'-oxo-6',7'-dihydrospiro[cyclopropane-1,5'-inden]-3'-yl)propyl)carbamate |
| 324 | 339 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate |
| 325 | 340 | (R)-N-((6'-hydroxy-2',4',6'-trimethyl-7'-oxo-6',7'-dihydrospiro[cyclopropane-1,5'-inden]-3'-yl)methyl)methanesulfonamide |
| 326 | 345 | (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |
| 327 | 346 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate |
| 328 | 347 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-sulfamoylbenzoate |
| 330 | 348 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 331 | 351 | (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |

TABLE V-continued

IUPAC names of the Illudofulvene analogs.

| Entry # | Illudofulvene Analog | IUPAC Name of Illudofulvene Analog |
|---|---|---|
| 332 | 353 | ((6'R)-3'-(((2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 333 | 354 | 4-((S)-2-((S)-2-(6-(2,5-dioxo-2,5-dihydro-1H-pyrrol-1-yl)hexanamido)-3-methylbutanamido)-5-ureidopentanamido)benzyl (2-(3-((S)-6'-hydroxy-2',4',6'-trimethyl-7'-oxo-6',7'-dihydrospiro[cyclopropane-1,5'-inden]-3'-yl)propylidene)hydrazine-1-carbonyl)carbamate |
| 334 | 356 | ((2'S,3'S,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 335 | 357 | ((2'S,3'S,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 336 | 359 | ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate |
| 337 | 361 | ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate |
| 338 | 362 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate |
| 339 | 363 | (2'S,3'R,6'R)-2'-(aminomethyl)-3',6'-dihydroxy-2',4',6'-trimethyl-2',3'-dihydrospiro[cyclopropane-1,5'-inden]-7'(6'H)-one |
| 340 | 364 | (2'R,3'R,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 341 | 366 | tert-butyl (R)-((6'-hydroxy-2',4',6'-trimethyl-7'-oxo-6',7'-dihydrospiro[cyclopropane-1,5'-inden]-3'-yl)methyl)carbamate |
| 342 | 367 | tert-butyl (R)-(3-(6'-hydroxy-2',4',6'-trimethyl-7'-oxo-6',7'-dihydrospiro[cyclopropane-1,5'-inden]-3'-yl)propyl)carbamate |
| 343 | 368 | ((2'S,3'R,6'R)-3'-acetoxy-6'-hydroxy-2',4',6'-trimethyl-7'-oxo-2',3',6',7'-tetrahydrospiro[cyclopropane-1,5'-inden]-2'-yl)methyl acetate |
| 344 | 369 | (2'S,3'R,6'R)-2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 345 | 370 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate |
| 346 | 371 | (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate |
| 347 | 372 | (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate |
| 348 | 373 | (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate |
| 349 | 374 | (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate |
| 350 | 377 | ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate |
| 351 | 378 | (2'S,3'R,6'R)-2'-(((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate |
| 352 | 379 | ((2'S,3'R,6'R)-3'-(((2-((((4-((14S,17S)-1-(9H-fluoren-9-yl)-14-isopropyl-3,6,9,12,15-pentaoxo-17-(3-ureidopropyl)-2-oxa-4,7,10,13,16-pentaazaoctadecan-18-amido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 353 | 380 | ((2'S,3'R,6'R)-3'-(((2-((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |

TABLE V-continued

IUPAC names of the Illudofulvene analogs.

| Entry # | Illudofulvene Analog | IUPAC Name of Illudofulvene Analog |
|---|---|---|
| 354 | 381 | (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one |
| 355 | 382 | (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde |
| 356 | 383 | (2'R,3'R,6'R)-3',6'-dihydroxy-2',4',6'-trimethyl-7'-oxo-2',3',6',7'-tetrahydrospiro[cyclopropane-1,5'-indene]-2'-carbaldehyde |
| 357 | 384 | tert-butyl (((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl)carbamate |
| 358 | 389 | tert-butyl(((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)carbamate |
| 359 | 392 | ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 360 | 393 | ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 361 | 394 | (R)-6'-hydroxy-3'-((hydroxyamino)methyl)-2',4',6'-trimethylspiro[cyclopropane-1,5'-inden]-7'(6'H)-one |
| 362 | 397 | tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)(hydroxy)carbamate |
| 363 | 398 | (2'S,3'R,6'R)-3',6'-dihydroxy-2'-((hydroxyamino)methyl)-2',4',6'-trimethyl-2',3'-dihydrospiro[cyclopropane-1,5'-inden]-7'(6'H)-one |
| 364 | 399 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl sulfamate |
| 365 | 401 | ((6'R)-3'-(((2-((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)ethyl)(methyl) carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 366 | 402 | (R)-(6'-hydroxy-2',4',6'-trimethyl-7'-oxo-6',7'-dihydrospiro[cyclopropane-1,5'-inden]-3'-yl)methyl sulfamate |
| 367 | 403 | ((2'S,6'R)-6'-hydroxy-2',6'-dimethyl-4'-methylene-7'-oxo-2',4',6',7'-tetrahydrospiro[cyclopropane-1,5'-inden]-2'-yl)methyl methanesulfonate |
| 368 | 404 | ((6'R)-3'-(((2-((((4-((S)-2-((S)-2-amino-3-methylbutanamido)-5-ureidopentanamido)benzyl)oxy)carbonyl)(methyl)amino)ethyl)(methyl) carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 369 | 405 | ((2'S,3'S,6'R)-6'-hydroxy-3'-(((2-((((4-((2S,5S)-5-isopropyl-25-(6-methyl-4-vinylpyridin-2-yl)-4,7,23-trioxo-2-(3-ureidopropyl)-10,13,16,19-tetraoxa-3,6,22-triazapentacosanamido)benzyl)oxy)carbonyl)(methyl)amino)ethyl) (methyl)carbamoyl)oxy)-2',4',6'-trimethyl-7'-oxo-2',3',6',7'-tetrahydrospiro[cyclopropane-1,5'-inden]-2'-yl)methyl acetate |
| 370 | 407 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl trifluoromethanesulfonate |
| 371 | 408 | 4-((2S,5S)-14-amino-5-isopropyl-4,7,10,13-tetraoxo-2-(3-ureidopropyl)-3,6,9,12-tetraazatetradecanamido)benzyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 372 | 409 | 4-((S)-2-((S)-2-amino-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 373 | 410 | 4-((S)-2-((S)-2-(6-(2,5-dioxo-2,5-dihydro-1H-pyrrol-1-yl)hexanamido)-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |

TABLE VI

Summary NCI DTP 60 Cell Line Data.

| NAME/NSC | Mean GI50 inhibition | Mean TGI cytostatic | Mean LD50 cytotoxic |
|---|---|---|---|
| Pyrrolobenzodiazepines 694501 | 7 nM | 302 nM | >23,000 nM* |
| Maytansine** 153858 | 19 nM | 318 nM | 49,200 nM |
| Fumagillol 642492 | 6,130 nM | 9,850 nM | >50,000 nM |
| Dolstatin-10 376128 | 17 nM | 2,680 nM | >50,000 nM |
| Auristatins 654663 | 1.4 nM | 902** nM | >5,000 nM** |
| Enadiyne 157365 | 2,900 nM | >100,000 nM | >100,000 nM |
| Halichondrin B 609395 | 1.2 nM | 199 nM | >1,000 nM |
| Tubulysin A | 12 nM | 1,318 nM | >10,000 nM |
| Illudin S | 10 nM | 64 nM | 511 nM |
| Illudin M | 3 nM | 20 nM | 291 nM |

TABLE VII

Ability of Illudofulvene analogs to inhibit tumor cell growth.

| Analog | Mean IC50 value (nM) ± SD, N = 3 unless otherwise indicated | | | |
|---|---|---|---|---|
| | MV522 Target Cell Line | | 8392B Nontarget Cell Line | |
| Number | 2 hr exposure | 48 hr exposure | 2 hr exposure | 48 hr exposure |
| 001 | 2200 ± 100 | 350 ± 20 | | 830 ± 100 |
| 002 | 110 ± 40 | 70 ± 10 | 26000 ± 4500 | 800 ± 100 |
| 004 | 4200 | 600 | | |
| 008 | 870 ± 90 | 630 ± 80 | 12200 ± 700 | 15100 ± 2200 |
| 009 | 500 ± 30 | 850 ± 180 | 47100 ± 11000 | 43200 ± 2300 |
| 010 | 8900 ± 1500 | 170 ± 60 | 29400 ± 1600 | 14500 ± 1700 |
| 011 | 4900 ± 900 | 1200 (N = 2) | >100000 | 40400 ± 6700 |
| 012 | 5150 ± 1350 | 320 ± 90 | 42200 ± 5000 | 18800 ± 2800 |
| 013 | 5100 ± 700 | 270 ± 130 | 11900 ± 1300 | 4200 ± 400 |
| 014 | 115 ± 30 | 460 ± 120 | 9650 ± 200 | 1100 ± 300 |
| 015 | 1800 ± 200 | 480 ± 110 | 810 ± 260 | 1300 ± 150 |
| 016 | 490 ± 130 | 440 ± 90 | >100000 | 870 ± 60 |
| 017 | 2400 ± 360 | 320 ± 60 | 14700 ± 900 | |
| 018 | 8800 ± 2900 | | 4200 ± 1300 | |
| 019 | 470 ± 60 | 660 ± 80 | >75000 | |
| 020 | 530 ± 140 | 230 ± 10 | 25000 ± 3100 | |
| 021 | 2400 ± 1000 | 930 ± 250 | 34400 ± 9400 | |
| 022 | 700 ± 200 | 680 ± 180 | 31700 ± 1400 | |
| 023 | 2900 ± 1140 | 2750 ± 500 | >138000 | |
| 024 | 1800 ± 200 | 1200 ± 300 | 12800 ± 2100 | |
| 025 | 1300 ± 310 | 1200 ± 100 | >25000 | |
| 030 | | >3000 | | |
| 031 | | >3000 | | |
| 032 | 600 ± 190 | 210 ± 30 | >30000 | |
| 033 | 10000 ± 1100 | 4600 ± 200 | 29900 ± 3300 | |
| 034 | 1400 ± 170 | 490 ± 40 | >100000 | 4400 ± 200 |
| 035 | 5600 ± 600 | | >150000 | |
| 037 | 26000 ± 5000 | 29200 ± 2300 | >85000 | |
| 038 = 091 | 750 ± 60 | | 24900 ± 8000 | |
| 039 = 092 | 1500 ± 240 | 600 ± 40 | 24600 ± 2400 | 820 ± 250 |
| 040 = 093 | 3400 ± 360 | 700 ± 90 | 24000 ± 3300 | 5200 ± 470 |
| 060 | 19400 ± 1800 | | 27600 ± 3000 | |
| 062 | 2600 ± 300 | 660 ± 200 | 37100 ± 2300 | |
| 063 | 43000 ± 5700 | 580 ± 250 | | |
| 064 | 28000 ± 4600 | 1200 ± 300 | | |
| 065 | 6200 ± 1100 | 2500 ± 1200 | | |
| 075 | 19600 ± 9700 | | 62000 ± 3600 | |
| 076 | 24000 ± 6100 | | 39500 ± 7200 | |
| 077 | 9200 ± 1200 | | | |
| 078 | 20400 ± 6300 | | >100000 | |
| 079 | 7700 ± 3500 | | >100000 | |
| 080 | 8800 ± 2400 | | >100000 | |
| 081 | >80000 | | >80000 | |
| 082 | 50600 ± 7100 | | >100000 | |
| 083 | | 37200 ± 2900 | | >42000 |
| 084 | | 28200 ± 1400 | | >42000 |
| 085 | >40000 | >40000 | | |
| 087 | >40000 | 24700 ± 3900 | >40000 | |
| 089 | 19300 ± 5700 | 15500 ± 2800 | >60000 | |
| 090 | 2500 ± 400 | 2900 ± 400 | 1600 ± 200 | 3800 ± 300 |

TABLE VII-continued

Ability of Illudofulvene analogs to inhibit tumor cell growth.

Mean IC50 value (nM) ± SD, N = 3 unless otherwise indicated

| Analog | MV522 Target Cell Line | | 8392B Nontarget Cell Line | |
|---|---|---|---|---|
| Number | 2 hr exposure | 48 hr exposure | 2 hr exposure | 48 hr exposure |
| 094 | 800 ± 100 | 210 ± 20 | 9000 ± 1700 | 110 ± 10 |
| 096 | 2700 ± 400 | 6200 ± 600 | >88000 | >3000 |
| 097 | 2900 ± 100 | | >82000 | |
| 098 | 18800 ± 2500 | 4600 ± 250 | >65000 | 11700 ± 1800 |
| 099 | 8400 ± 1100 | 1800 ± 200 | 4000 ± 400 | 300 ± 20 |
| 100 | >10000 | 1700 ± 500 | | |
| 101 | >8000 | >7500 | | |
| 102 | >13000 | 1300 ± 100 | | |
| 103 | 31800 ± 4900 | 5900 ± 400 | 12100 ± 2000 | 2300 ± 200 |
| 104 | 6300 ± 400 | 6000 ± 500 | 36400 ± 6500 | 2700 ± 600 |
| 105 | 7300 ± 1200 | 2100 ± 400 | >100000 | |
| 106 | 5200 ± 1000 | | >83000 | |
| 107 | >50000 | 1600 ± 100 | >50000 | |
| 108 | 12300 ± 2300 | 520 ± 50 | >55000 | 6000 ± 1600 |
| 109 | >50000 | | >50000 | |
| 110 | >55000 | 1400 ± 100 | >55000 | 25300 ± 2100 |
| 111 | 16700 ± 2100 | 11900 ± 2800 | 34600 ± 2100 | 10200 ± 1000 |
| 112 | 10000 ± 2000 | 6700 ± 1200 | 14900 ± 100 | 5200 ± 300 |
| 113 | 85000 ± 700 | 14100 ± 3000 | >93000 | 7800 ± 1000 |
| 114 | 1500 ± 100 | 260 ± 70 | 25100 ± 1000 | 700 ± 100 |
| 115 | 1500 ± 100 | 70 ± 5 | 1600 ± 700 | 630 ± 60 |
| 116 | 400 ± 100 | 1000 ± 50 | 7000 ± 400 | 170 ± 30 |
| 117 | 1100 ± 100 | 100 ± 30 | 7900 ± 1600 | 10 ± 2 |
| 118 | 14000 ± 2000 | 740 ± 120 | 24500 ± 4500 | 2000 ± 400 |
| 119 | 1100 ± 70 | 270 ± 40 | >33000 | >10000 |
| 120 | 2800 ± 900 | 600 ± 100 | 19100 ± 4600 | 510 ± 110 |
| 121 | 300 ± 10 | 90 ± 10 | 15200 ± 6000 | 1300 ± 500 |
| 122 | 6400 ± 300 | 2400 ± 300 | 14500 ± 1200 | 1100 ± 300 |
| 123 | 1900 ± 400 | 600 ± 60 | 450 ± 30 | 2400 ± 500 |
| 124 | 2800 ± 700 | 870 ± 350 | >30000 | 2400 ± 550 |
| 125 | 3700 ± 600 | 1200 ± 200 | 15500 ± 1400 | 600 ± 100 |
| 126 | 2100 ± 500 | 900 ± 100 | >30000 | 330 ± 80 |
| 127 | 870 ± 30 | 340 ± 90 | >30000 | 100 ± 40 |
| 128 | 840 ± 230 | 370 ± 50 | >35000 | 800 ± 70 |
| 129 | >136000 | 19700 ± 1900 | >136000 | 39400 ± 9200 |
| 130 | 700 ± 100 | 130 ± 40 | 27,000 ± 7000 | 4400 ± 500 |
| 133 | 58800 ± 6600 | 15800 ± 2600 | 12200 ± 2300 | 2700 ± 400 |
| 134 | 50000 ± 6000 | 28000 ± 4000 | 43900 ± 5100 | 8500 ± 2000 |
| 135 | 1600 ± 300 | 22 ± 4 | 70 ± 20 | 22 ± 2 |
| 136 | 430 ± 10 | 130 ± 10 | >6200 | 25 ± 2 |
| 137 | 850 ± 110 | 1200 ± 100 | 8500 ± 1200 | 710 ± 60 |
| 138 | 2100 ± 200 | 1000 ± 200 | 5400 ± 200 | 820 ± 230 |
| 139 | 6400 ± 900 | 3400 ± 500 | 11600 ± 900 | 2600 ± 1000 |
| 140 | 17100 ± 5100 | >14000 | 12700 ± 300 | >14000 |
| 141 | 11400 ± 1000 | 3700 ± 800 | 13700 ± 1900 | 1100 ± 140 |
| 142 | 90 ± 10 | 24 ± 7 | 6400 ± 1100 | 80 ± 6 |
| 143 | 43500 ± 11300 | 11400 ± 1800 | 56500 ± 20000 | 3600 ± 700 |
| 146 | 2500 ± 400 | 740 ± 280 | 13,000 ± 1200 | |
| 147 | >76000 | 26100 ± 12900 | >76000 | 43800 ± 3000 |
| 148 | 17100 ± 1100 | 6800 ± 1100 | 61000 ± 11600 | 6700 ± 1600 |
| 149 | 2900 ± 1000 | 1500 ± 500 | 44600 ± 1400 | 4100 ± 900 |
| 150 | 9500 ± 1600 | 1400 ± 400 | 59000 ± 5500 | 10600 ± 800 |
| 151 | 7900 ± 400 | 4200 ± 1600 | 25500 ± 1200 | 6600 ± 2300 |
| 152 | | 6400 ± 1200 | 49000 ± 7700 | 9100 ± 100 |
| 153 | 8700 ± 2700 | 10900 ± 3400 | >90000 | 15800 ± 9600 |
| 154 | >70000 | 61300 ± 10000 | >70000 | 46,700 ± 13100 |
| 155 | 8200 ± 1200 | 3600 ± 400 | 17,000 ± 4000 | 9100 ± 1100 |
| 156 | 7200 ± 500 | 3100 ± 100 | 32,300 ± 9,400 | 5500 ± 1200 |
| 157 | >400,000 | >123,000 | >350,000 | 13100 ± 1600 |
| 158 | >175,000 | >175,000 | >200,000 | 61,000 ± 9,000 |
| 159 | 2700 ± 400 | 120 ± 10 | 13,700 ± 4,200 | <10 nM |
| 160 | 1900 ± 200 | 500 ± 200 | 52,400 ± 17,800 | 3200 ± 1100 |
| 161 | 2800 ± 500 | 3300 ± 700 | 13,800 ± 3,400 | >10,000 |
| 163 | 3500 ± 800 | 820 ± 40 | 18600 ± 800 | 910 ± 100 |
| 164 | | 70 ± 10 | 3500 ± 1600 | 130 ± 40 |
| 165 | 7700 ± 1100 | 290 ± 40 | 11000 ± 3300 | 11000 ± 1000 |
| 166 | 6500 ± 600 | 7200 ± 1900 | 6500 ± 2100 | 6000 ± 1500 |
| 167 | 14800 ± 2200 | | 18500 ± 2300 | |
| 169 | 7100 ± 600 | | 2300 ± 600 | |
| 177 | 7500 ± 800 | 1900 ± 800 | 73000 ± 5000 | 4100 ± 1300 |
| 178 | 21000 ± 4000 | 1000 ± 100 | 32000 ± 9000 | >8000 |
| 180 | 19900 ± 300 | >4000 | 5200 ± 1800 | 660 ± 50 |

TABLE VII-continued

| Ability of Illudofulvene analogs to inhibit tumor cell growth. | | | | |
|---|---|---|---|---|
| | Mean IC50 value (nM) ± SD, N = 3 unless otherwise indicated | | | |
| Analog | MV522 Target Cell Line | | 8392B Nontarget Cell Line | |
| Number | 2 hr exposure | 48 hr exposure | 2 hr exposure | 48 hr exposure |
| 182 | 99000 ± 12000 | 38000 ± 8200 | 39000 ± 7000 | 18700 ± 2700 |
| 183 | >120,000 | >275,000 | >120,000 | >235,000 |
| 184 | 800 ± 300 | 210 ± 20 | >100,000 | >10000 |
| 185 | 1700 ± 600 | 1900 ± 100 | | |
| 186 | 144000 ± 32000 | 70000 ± 16000 | 79000 ± 24000 | 48000 ± 2000 |
| 187 | 1300 ± 400 | 900 ± 200 | 3200 ± 800 | 3200 ± 700 |
| 189 | 8900 ± 2500 | 6100 ± 2600 | 41,000 ± 3700 | |
| 190 | 19,000 ± 4000 | >9,000 | 56,000 ± 2000 | >9,000 |
| 191 | >140,000 | 49,000 ± 13000 | >140,000 | 15000 ± 4000 |
| 192 | 1,600 ± 200 | 700 ± 100 | 8700 ± 1700 | 200 ± 30 |
| 193 | 1400 ± 400 | 2500 ± 600 | 48,000 ± 7000 | >11,000 |
| 195 | 1400 ± 200 | 390 ± 120 | 21,000 ± 6000 | 4300 ± 1200 |
| 196 | 840 ± 100 | 450 ± 120 | 80,000 ± 5000 | >9,200 |
| 197 | 950 ± 70 | 500 ± 100 | 9500 ± 400 | 11,300 ± 100 |
| 198 | 700 ± 100 | 2800 ± 600 | >8,200 | >82,000 |
| 199 | 4700 ± 600 | 2500 ± 1100 | >93,000 | >9,300 |
| 201 | 360 ± 110 | 260 ± 70 | 13,000 ± 1700 | 26,000 ± 7000 |
| 202 | 1200 ± 100 | 650 ± 100 | >62,000 | >6200 |
| 203 | 760 ± 170 | 940 ± 330 | 48,000 ± 6000 | >5500 |
| 204 | 220 ± 40 | 1600 ± 300 | 4100 ± 800 | 8600 ± 800 |
| 205 | 8400 ± 2200 | 1200 ± 400 | >185,000 | >2,600 |
| 206 | 610 ± 40 | 230 ± 20 | 20,000 ± 1000 | 8200 ± 200 |
| 207 | 570 ± 60 | 410 ± 60 | | |
| 208 | 1200 ± 100 | 930 ± 160 | 25,000 ± 3000 | |
| 209 | 3900 ± 1100 | 610 ± 100 | >90,000 | |
| 210 | 40,000 ± 4000 | 5500 ± 600 | | |
| 211 | 470 ± 120 | 430 ± 100 | 59,000 ± 9000 | |
| 212 | 80 ± 10 | 55 ± 5 | | |
| 213 | 2300 ± 700 | 1700 ± 700 | | |
| 214 | 2900 ± 800 | 360 ± 30 | | |
| 215 | 26,000 ± 3000 | 490 ± 120 | | |
| 216 | 460 ± 60 | 150 ± 40 | | |
| 217 | 2,200 ± 100 | 2,200 ± 100 | 43,000 ± 4,000 | >7,000 |
| 218 | 10,000 ± 3,000 | 600 ± 200 | 15,000 ± 6,000 | 600 ± 100 |
| 219 | >52,000 | >52,00 | >52,000 | >52,000 |
| 220 | 90 ± 10 | 130 ± 10 | 101,000 ± 18,000 | 40,000 ± 3,000 |
| 221 | >21,000 | 2,500 ± 200 | >21,000 | >21,000 |
| 222 | 5,000 ± 100 | 1,100 ± 100 | 9,300 ± 200 | 330 ± 60 |
| 223 | 20,000 ± 3,700 | 2,700 ± 300 | >185,000 | >55,000 |
| 224 | >200,000 | >130,000 | >200,000 | >130,000 |
| 225 | 47,000 ± 4,000 | 55,000 ± 11,000 | >350,000 | 33,000 ± 13,000 |
| 226 | >59,000 | >59,000 | >59,000 | >59,000 |
| 227 | >57,000 | 4,400 ± 700 | >57,000 | 16,000 ± 4,000 |
| 228 | >38,000 | >38,000 | 24,000 ± 3,000 | >38,000 |
| 229 | >56,000 | >2,000 | >56,000 | >2,000 |
| 230 | 620 ± 80 | 100 ± 10 | 38,000 ± 5,000 | 1,000 ± 200 |
| 231 | 1,500 ± 100 | 280 ± 10 | 14,000 ± 4,000 | |
| 232 | 700 ± 100 | 460 ± 60 | 42,000 ± 6,000 | 3,300 ± 600 |
| 233 | 3,200 ± 300 | 350 ± 80 | >150,000 | 2,400 ± 700 |
| 234 | 3,000 ± 300 | 1,100 ± 400 | 24,000 ± 6,000 | 9,000 ± 1,000 |
| 235 | 3,500 ± 400 | 2,200 ± 400 | 49,000 ± 6,000 | 6,500 ± 1,600 |
| 236 | 49,000 ± 11,000 | 29,000 ± 5,000 | 48,000 ± 10,000 | |
| 237 | 1,200 ± 300 | 730 ± 140 | 22,000 ± 1,000 | 6,600 ± 900 |
| 238 | 780 ± 190 | 57 ± 8 | 23,000 ± 2,000 | 4,700 ± 1,200 |
| 239 | 420 ± 60 | 70 ± 20 | 39,000 ± 3,000 | 28,000 ± 4,000 |
| 240 | 2,900 ± 100 | 1,300 ± 200 | >24,000 | 1,300 ± 100 |
| 241 | 560 ± 90 | 110 ± 20 | >28,000 | 18,000 ± 4,000 |
| 242 | 2,400 ± 400 | 580 ± 150 | 18,000 ± 2,000 | 2,900 ± 600 |
| 243 | 2,200 ± 500 | 670 ± 240 | 64,000 ± 10,000 | 26,000 ± 6,000 |
| 244 | 1,600 ± 400 | 150 ± 10 | 87,000 ± 11,000 | 35,000 ± 7,000 |
| 245 | 3,400 ± 1000 | 440 ± 90 | 79,000 ± 7,000 | 14,000 ± 1,700 |
| 246 | 2,800 ± 260 | 1,900 ± 450 | 14,000 ± 2,000 | 6,200 ± 1,300 |
| 247 | 6,100 ± 2,000 | 1,200 ± 250 | 10,000 ± 1,400 | 7,100 ± 1,700 |
| 248 | 830 ± 100 | 200 ± 25 | 23,000 ± 1,000 | 610 ± 120 |
| 249 | 4,100 ± 820 | 420 ± 100 | 18,000 ± 3,500 | 19,000 ± 3,800 |
| 250 | 99,000 ± 21,000 | 137,000 ± 14,000 | >275,000 | 137,000 ± 10,000 |
| 251 | 128,000 ± 4,000 | 51,000 ± 1,000 | >275,000 | 82,000 ± 8,000 |
| 252 | >380,000 | 33,000 ± 3,000 | >380,000 | >380,000 |
| 253 | >380,000 | >38,000 | >380,000 | >380,000 |
| 254 | 2,700 ± 800 | 1,100 ± 100 | 43,000 ± 6,000 | >65,000 |
| 255 | 2,900 ± 500 | 55 ± 2 | 119,000 ± 15,000 | 99,000 ± 4,000 |
| 256 | 1,500 ± 200 | 880 ± 200 | 7,500 ± 800 | 7,100 ± 300 |

TABLE VII-continued

Ability of Illudofulvene analogs to inhibit tumor cell growth.

Mean IC50 value (nM) ± SD, N = 3 unless otherwise indicated

| Analog | MV522 Target Cell Line | | 8392B Nontarget Cell Line | |
|---|---|---|---|---|
| Number | 2 hr exposure | 48 hr exposure | 2 hr exposure | 48 hr exposure |
| 257 | 2,800 ± 600 | 320 ± 30 | 25,000 ± 2,000 | 26,000 ± 3,000 |
| 258 | >45,000 | >45,000 | >45,000 | >45,000 |
| 259 | 16000 ± 3000 | 2400 ± 200 | >85,000 | 4700 ± 400 |
| 260 | 1600 ± 500 | 150 ± 20 | >64,000 | 19000 ± 4500 |
| 261 | 6300 ± 1100 | 1000 ± 150 | 64000 ± 2000 | 38000 ± 2100 |
| 262 | 8700 ± 1300 | 3900 ± 570 | 287000 ± 14000 | 73000 ± 17000 |
| 263 | 2000 ± 300 | 1400 ± 200 | 124000 ± 18000 | 39000 ± 7000 |
| 264 | 1400 ± 100 | 76 ± 17 | >85,000 | 54000 ± 20000 |
| 265 | 810 ± 20 | 8 ± 1 | 1100 ± 200 | 250 ± 80 |
| 266 | 140 ± 20 | 70 ± 18 | 56000 ± 15000 | 32000 ± 7000 |
| 267 | 900 ± 160 | 160 ± 20 | >90,000 | 28000 ± 8000 |
| 268 | 2100 ± 200 | 330 ± 90 | 54,000 ± 16000 | >8,000 |
| 269 | 11000 ± 3000 | 850 ± 320 | 52000 ± 4000 | >7,000 |
| 270 | 8000 ± 1500 | 1300 ± 100 | >84,000 | 7100 ± 700 |
| 271 | 1700 ± 200 | 200 ± 90 | >93,000 | >9,300 |
| 272 | >46,000 | >4,700 | >47,000 | >4,700 |
| 273 | 30000 ± 5000 | >1,500 | >45,000 | >4,500 |
| 274 | 39000 ± 3000 | 1200 ± 300 | >46,000 | >4,500 |
| 275 | 1500 ± 300 | 370 ± 40 | >62,000 | >6,200 |
| 276 | 1500 ± 200 | 760 ± 100 | >61,000 | >6,100 |
| 277 | 760 ± 70 | 190 ± 20 | 31,000 ± 6000 | 9,800 ± 1000 |
| 278 | 1000 ± 100 | 270 ± 10 | >94000 | >9,400 |
| 279 | 1700 ± 400 | 190 ± 20 | >90000 | >9,000 |
| 280 | 2400 ± 800 | <80 | >83000 | >2,800 |
| 281 | 1800 ± 700 | 170 ± 10 | 27000 ± 2000 | 5000 ± 700 |
| 282 | 680 ± 60 | 110 ± 10 | >85000 | >8,500 |
| 283 | 2900 ± 1200 | 300 ± 20 | 40000 ± 4000 | >9,300 |
| 284 | 13,600 (N = 2) | 340 ± 20 | | >8,800 |
| 285 | 3800 ± 1100 | 310 ± 20 | 84000 ± 9000 | 2000 ± 100 |
| 286 | 48000 ± 10000 | 6300 ± 200 | 51000 ± 1700 | >8,800 |
| 287 | 455000 ± 22000 | 1100 ± 100 | 567000 ± 17000 | 4700 ± 400 |
| 288 | 1800 ± 600 | 150 ± 20 | 11000 ± 3200 | ~9,000 |
| 289 | 51 ± 4 | 530 ± 150 | >290000 | >8,800 |
| 294 | 960 ± 170 | | | |
| 295 | 200 ± 44 | | | |
| 296 | 250 (N = 2) | | | |
| 297 | 2200 (N = 1) | | | |
| 298 | >7000 | | | |

TABLE VIII

Screening of Analogs from the National Cancer Institute (NCI) Developmental Therapeutics Program (DTP) NCI 60 cell line screen assay.

| Analog | Activity Value* | Cytotoxicity | MDR Activity |
|---|---|---|---|
| Epothilone A | +31 | No | No |
| MMAE | +21 | No | No |
| DM1 | +8 | No | No |
| 002 | −15 | Yes | Yes |
| 142 | −5 | Yes | Yes |
| 159 | −25 | Yes | Yes |
| 176 | −11 | Yes | Yes |
| 334 | −11 | Yes | Yes |
| 362 | −9 | Yes | Yes |
| 371 | −18 | Yes | Yes |
| 383 | −1 | Yes | Yes |
| 394 | −2 | Yes | Yes |

*Activity Value = the lower or more negative the activity value is an indication of the more active the compound was against tumor cells in the 60 cell line panel. A positive value indicates tumor cells could grow but at a slower rate. A value of Zero (0) indicates that while no cell growth was detected there was no evidence of cell death occurring (i.e., when the drug is removed the cells could grow again). A negative value indicates that the compounds actually lyse tumor cells.

What is claimed is:

1. A compound selected from the group consisting of:

analog 333 ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate;

analog 334 ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 335 tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 339 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate;

analog 345 (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 346 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate;

analog 351 (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 353 ((6'R)-3'-(((2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 356 ((2'S,3'S,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 357 ((2'S,3'S,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 359 ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate;

analog 361 ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate;

analog 362 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate;

analog 363 (2'S,3'R,6'R)-2'-(aminomethyl)-3',6'-dihydroxy-2',4',6'-trimethyl-2',3'-dihydrospiro[cyclopropane-1,5'-inden]-7'(6'H)-one;

analog 370 (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate;

analog 371 (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate;

analog 372 (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate;

analog 373 (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 374 (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate;

analog 377 ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate;

analog 378 (2'S,3'R,6'R)-2'-(((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 379 ((2'S,3'R,6'R)-3'-(((2-((((4-((14S,17S)-1-(9H-fluoren-9-yl)-14-isopropyl-3,6,9,12,15-pentaoxo-17-(3-ureidopropyl)-2-oxa-4,7,10,13,16-pentaazaoctadecan-18-amido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 380 ((2'S,3'R,6'R)-3'-(((2-((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 381 (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one;

analog 382 (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde;

analog 384 tert-butyl (((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl)carbamate;

analog 389 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)carbamate;

analog 392 ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 393 ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 397 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)(hydroxy)carbamate;

analog 398 (2'S,3'R,6'R)-3',6'-dihydroxy-2'-((hydroxyamino)methyl)-2',4',6'-trimethyl-2',3'-dihydrospiro[cyclopropane-1,5'-inden]-7'(6'H)-one;

analog 399 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl sulfamate;

analog 401 ((6'R)-3'-(((2-((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 403 ((2'S,6'R)-6'-hydroxy-2',6'-dimethyl-4'-methylene-7'-oxo-2',4',6',7'-tetrahydrospiro[cyclopropane-1,5'-inden]-2'-yl)methyl methanesulfonate;

analog 404 ((6'R)-3'-(((2-((((4-((S)-2-((S)-2-amino-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 405 ((2'S,3'S,6'R)-6'-hydroxy-3'-(((2-((((4-((2S,5S)-5-isopropyl-25-(6-methyl-4-vinylpyridin-2-yl)-4,7,23-trioxo-2-(3-ureidopropyl)-10,13,16,19-tetraoxa-3,6,22-triazapentacosanamido)benzyl)oxy)carbonyl)(methyl)amino)ethyl)(methyl)carbamoyl)oxy)-2',4',6'-trimethyl-7'-oxo-2',3',6',7'-tetrahydrospiro[cyclopropane-1,5'-inden]-2'-yl)methyl acetate;

analog 407 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl trifluoromethanesulfonate;

analog 408 4-((2S,5S)-14-amino-5-isopropyl-4,7,10,13-tetraoxo-2-(3-ureidopropyl)-3,6,9,12-tetraazatetradecanamido)benzyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 409 4-((S)-2-((S)-2-amino-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate); and analog 410 4-((S)-2-((S)-2-(6-(2,5-dioxo-2,5-dihydro-1H-pyrrol-1-yl)hexanamido)-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate).

2. A composition comprising enantiomers and racemic mixtures of the compound of claim 1.

3. A composition comprising the composition of claim 2, and a physiologically compatible carrier for treating cancer.

4. A composition comprising the composition of claim 2, in the form of a liposomal particle, a nanoparticle, or a PEGylated compound.

5. A composition comprising the composition of claim 4, and a physiologically compatible carrier for treating cancer.

6. A compound comprising an illudofulvene moiety and a linker, where the illudofulvene moiety is selected from the group consisting of:

analog 333 ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate;

analog 334 ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 335 tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 339 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate;

analog 345 (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 346 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate;

analog 351 (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 353 ((6'R)-3'-(((2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 356 ((2'S,3'S,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 357 ((2'S,3'S,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 359 ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate;

analog 361 ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate;

analog 362 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate;

analog 363 (2'S,3'R,6'R)-2'-(aminomethyl)-3',6'-dihydroxy-2',4',6'-trimethyl-2',3'-dihydrospiro[cyclopropane-1,5'-inden]-7'(6'H)-one;

analog 370 (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate;

analog 371 (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate;

analog 372 (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate;

analog 373 (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 374 (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate;

analog 377 ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate;

analog 378 (2'S,3'R,6'R)-2'-(((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 379 ((2'S,3'R,6'R)-3'-(((2-((((4-((14S,17S)-1-(9H-fluoren-9-yl)-14-isopropyl-3,6,9,12,15-pentaoxo-17-(3-ureidopropyl)-2-oxa-4,7,10,13,16-pentaazaoctadecan-18-amido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 380 ((2'S,3'R,6'R)-3'-(((2-((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 381 (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one;

analog 382 (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde;

analog 384 tert-butyl (((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl)carbamate;

analog 389 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)carbamate;

analog 392 ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 393 ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 397 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)(hydroxy)carbamate;

analog 398 (2'S,3'R,6'R)-3',6'-dihydroxy-2'-((hydroxyamino)methyl)-2',4',6'-trimethyl-2',3'-dihydrospiro[cyclopropane-1,5'-inden]-7'(6'H)-one;

analog 399 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl sulfamate;

analog 401 ((6'R)-3'-(((2-((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 403 ((2'S,6'R)-6'-hydroxy-2',6'-dimethyl-4'-methylene-7'-oxo-2',4',6',7'-tetrahydrospiro[cyclopropane-1,5'-inden]-2'-yl)methyl methanesulfonate;

analog 404 ((6'R)-3'-(((2-((((4-((S)-2-((S)-2-amino-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 405 ((2'S,3'S,6'R)-6'-hydroxy-3'-(((2-((((4-((2S,5S)-5-isopropyl-25-(6-methyl-4-vinylpyridin-2-yl)-4,7,23-trioxo-2-(3-ureidopropyl)-10,13,16,19-tetraoxa-3,6,22-triazapentacosanamido)benzyl)oxy)carbonyl)(methyl)amino)ethyl)(methyl)carbamoyl)oxy)-2',4',6'-trimethyl-7'-oxo-2',3',6',7'-tetrahydrospiro[cyclopropane-1,5'-inden]-2'-yl)methyl acetate;

analog 407 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl trifluoromethanesulfonate;

analog 408 4-((2S,5S)-14-amino-5-isopropyl-4,7,10,13-tetraoxo-2-(3-ureidopropyl)-3,6,9,12-tetraazatetradecanamido)benzyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 409 4-((S)-2-((S)-2-amino-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate); and analog 410 4-((S)-2-((S)-2-(6-(2,5-dioxo-2,5-dihydro-1H-pyrrol-1-yl)hexanamido)-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate).

7. A composition comprising enantiomers and racemic mixtures of the compound of claim 6.

8. A composition comprising the composition of claim 7, and a physiologically compatible carrier for treating cancer.

9. A composition comprising the composition of claim 7, in the form of a liposomal particle, a nanoparticle, or a PEGylated compound.

10. A composition comprising the composition of claim 9, and a physiologically compatible carrier for treating cancer.

11. The compound of claim 6, where the linker is selected from the group consisting of a 4-fluorosulfonyl benzoyl linker, a 3-fluorosulfonyl benzoyl linker a 2-fluorosulfonyl benzoyl linker, a maleimide linker, an azlactone linker and a bridging amino acid linker.

12. A compound comprising an illudofulvene moiety, a linker and an affinity moiety, where the illudofulvene moiety is selected from the group consisting of:

analog 333 ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate;

analog 334 ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 335 tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 339 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate;

analog 345 (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 346 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate;

analog 351 (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate;

analog 353 ((6'R)-3'-(((2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 356 ((2'S,3'S,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 357 ((2'S,3'S,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 359 ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate;

analog 361 ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate;

analog 362 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate;

analog 363 (2'S,3'R,6'R)-2'-(aminomethyl)-3',6'-dihydroxy-2',4',6'-trimethyl-2',3'-dihydrospiro[cyclopropane-1,5'-inden]-7'(6'H)-one;

analog 370 (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate;

analog 371 (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate;

analog 372 (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate;

analog 373 (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 374 (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate;

analog 377 ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate;

analog 378 (2'S,3'R,6'R)-2'-(((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate;

analog 379 ((2'S,3'R,6'R)-3'-(((2-((((4-((14S,17S)-1-(9H-fluoren-9-yl)-14-isopropyl-3,6,9,12,15-pentaoxo-17-(3-ureidopropyl)-2-oxa-4,7,10,13,16-pentaazaoctadecan-18-amido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 380 ((2'S,3'R,6'R)-3'-(((2-((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 381 (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one;

analog 382 (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde;

analog 384 tert-butyl (((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl)carbamate;

analog 389 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)carbamate;

analog 392 ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 393 ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 397 tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)(hydroxy)carbamate;

analog 398 (2'S,3'R,6'R)-3',6'-dihydroxy-2'-((hydroxyamino)methyl)-2',4',6'-trimethyl-2',3'-dihydrospiro[cyclopropane-1,5'-inden]-7'(6'H)-one;

analog 399 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl sulfamate;

analog 401 ((6'R)-3'-(((2-((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 403 ((2'S,6'R)-6'-hydroxy-2',6'-dimethyl-4'-methylene-7'-oxo-2',4',6',7'-tetrahydrospiro[cyclopropane-1,5'-inden]-2'-yl)methyl methanesulfonate;

analog 404 ((6'R)-3'-(((2-((((4-((S)-2-((S)-2-amino-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate;

analog 405 ((2'S,3'S,6'R)-6'-hydroxy-3'-(((2-((((4-((2S,5S)-5-isopropyl-25-(6-methyl-4-vinylpyridin-2-yl)-4,7,23-trioxo-2-(3-ureidopropyl)-10,13,16,19-tetraoxa-3,6,22-triazapentacosanamido)benzyl)oxy)carbonyl)(methyl)amino)ethyl)(methyl)carbamoyl)oxy)-2',4',6'-trimethyl-7'-oxo-2',3',6',7'-tetrahydrospiro[cyclopropane-1,5'-inden]-2'-yl)methyl acetate;

analog 407 ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl trifluoromethanesulfonate;

analog 408 4-((2S,5S)-14-amino-5-isopropyl-4,7,10,13-tetraoxo-2-(3-ureidopropyl)-3,6,9,12-tetraazatetradecanamido)benzyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate);

analog 409 4-((S)-2-((S)-2-amino-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate); and analog 410 4-((S)-2-((S)-2-(6-(2,5-dioxo-2,5-dihydro-1H-pyrrol-1-yl)hexanamido)-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate), where the affinity moiety is selected from the group consisting of an antibody, an antibody fragment, a protein, a growth factor, a peptide, and a non-peptide moiety.

13. A composition comprising enantiomers and racemic mixtures of the compound of claim 12.

14. A composition comprising the composition of claim 13, and a physiologically compatible carrier for treating cancer.

15. A composition comprising the composition of claim 13, in the form of a liposomal particle, a nanoparticle, or a PEGylated compound.

16. A composition comprising the composition of claim 15, and a physiologically compatible carrier for treating cancer.

17. The compound of claim 12, where the peptide is selected from the group consisting of a peptidic growth factor, a specific binding peptide, a protease cleavable, a glycopeptide, an integrin binding peptide, and a peptidic toxin.

18. The compound of claim 12, where the protein is selected from the group consisting of transferrin, epidermal growth factors, bombesin, gastrin, gastrin-releasing peptide, platelet-derived growth factor, IL-2, IL-6, transforming growth factor-alpha, transforming growth factor-beta, vaccinia growth factor, insulin, insulin-like growth factor I, insulin-like growth factor II, somatostatin, and apoprotein from low density lipoprotein.

19. The compound of claim 12, where the non-peptide moiety is selected from the group consisting of a steroid, a carbohydrate, a nucleic acid, a viral antigen, a microbial antigen, a lectin, and an oligonucleotide.

20. The compound of claim 12, where the linker is selected from the group consisting of a 4-fluorosulfonyl benzoyl linker, a 3-fluorosulfonyl benzoyl linker a 2-fluorosulfonyl benzoyl linker, a maleimide linker, an azlactone linker, and a bridging amino acid linker.

* * * * *

SEQUENCE LISTING

<160> NUMBER OF SEQ ID NOS: 926

<210> SEQ ID NO 1
<211> LENGTH: 1962
<212> TYPE: DNA
<213> ORGANISM: Homo sapiens

<400> SEQUENCE: 1

```
gctgttccag tcccgcccct gagctctgtc atggcgacgt ccagtgctcc agccggtgtg     60
aggacacgat atgctggggt ttttgtccgc acgccaaacg ggtttggagg accctcttcg    120
ccttcggaga gcagagtcaa cacggagagt tttgggactg gaattaaata aagacagaga    180
tgttgaaaga atccacggcg gtggaattaa cacccttgac attgaacctg ttgaagggag    240
atacatgtta tcaggtggtt cagatggtgt gattgtactt tatgaccttg agaactccag    300
cagacaatct tattacacat gtaaagcagt gtgttccatt ggcagagatc atcctgatgt    360
tcacagatac agtgtggaga ctgtacagtg gtatcctcat gacactggca tgttcacatc    420
aagctcattt gataaaactc tgaaagtatg ggatacaaat acattacaat tggtactaga    480
ggacccaaag tacaactttg tgacttgaag tctggatcct gttctcacat tctacagggt    540
cacagacaag aaatattagc agtttcctgg tctccacgtt atgactatat cttggcaaca    600
gcaagtgctg acagtagagt aaaattatgg gatgtgagaa gagcatcagg atgtttgatt    660
actcttgatc aacataatgg gaaaaagtca caagctgttg aatcagcaaa cactgctcat    720
aatgggaaag ttaatggctt atgttttaca agtgatggac ttcacctcct cactgttggt    780
acagataatc gaatgaggct ctggaatagt tccaatggag aaaacacact tgtgaactat    840
ggaaaagttt gtaataacag taaaaaagga ttgaaattca ctgtctcctg tggctgcagt    900
tcagaatttg tttttgtacc atatggtagc accattgctg tttatacagt ttactcagga    960
gaacagataa ctatgcttaa gggacattat aaaactgttg actgctgtgt atttcagtca   1020
aatttccagg aactttatag tggtagcaga gactgcaaca ttctggcttg ggttccatcc   1080
ttatatgaac cagttcctga tgatgatgag actacaacaa aatcacaatt aaatccggcc   1140
tttgaagatg cctggagcag cagtgatgaa gaaggatgaa tatcatcttt agtacctttt   1200
tgtctctgct gaaacttttt aaatgagact gtgttttttt caactgtatg gtctattcct   1260
gacagctaaa ttagccctaa atgtgggtaa tatttttcct catgttttaa aatgaggtta   1320
atatttgcat aaaatcctaa aacagacttc tgtatagttt atttagtcaa aatgtgttcc   1380
ttgatcccag atgttgtggc ctgggaaagc cctcattgct acagtacaag taacacaagt   1440
cgttgtacct cagttgtgac cttcagcaga ttttatgaac tataagatgc agtctcagag   1500
gatcagcaag tggaggccat cagtattgac tttctcttac ttgctgtact atcagcctgc   1560
tcgtttccac ctttaagaat gattttgcca agaatgatta tatcaaaaat agtagttgaa   1620
atggtaacat caaaattatt ttattctttc ttcttcatgt attcacattt ttcagtggtt   1680
tcatttaatt aaccatgctt tatgttaaac attttggggc tcaatgtctc ctactatcca   1740
aaatgtgcat cacaggaggc ttttaacttt gtgaaaatcc catgtttgct ttattttatt   1800
ttaatgtcag aaggcagttt gcgctaatgc ttgaactctt tttctgtgaa actcattaag   1860
gtatgaccaa atcctgcctc attaattcaa gcagaaaata tcctggcagg gaatctggct   1920
taaacatgaa atgctgtaat aaaatttcta tgttattgtc tc                       1962
```

<210> SEQ ID NO 2
<211> LENGTH: 396
<212> TYPE: PRT
<213> ORGANISM: Homo sapiens

<400> SEQUENCE: 2

```
Met Leu Gly Phe Leu Ser Ala Arg Gln Thr Gly Leu Glu Asp Pro Leu
1               5                   10                  15
```

```
Arg Leu Arg Arg Ala Glu Ser Thr Arg Arg Val Leu Gly Leu Glu Leu
            20                  25                  30

Asn Lys Asp Arg Asp Val Glu Arg Ile His Gly Gly Gly Ile Asn Thr
        35                  40                  45

Leu Asp Ile Glu Pro Val Glu Gly Arg Tyr Met Leu Ser Gly Gly Ser
    50                  55                  60

Asp Gly Val Ile Val Leu Tyr Asp Leu Glu Asn Ser Ser Arg Gln Ser
65                  70                  75                  80

Tyr Tyr Thr Cys Lys Ala Val Cys Ser Ile Gly Arg Asp His Pro Asp
                85                  90                  95

Val His Arg Tyr Ser Val Glu Thr Val Gln Trp Tyr Pro His Asp Thr
            100                 105                 110

Gly Met Phe Thr Ser Ser Ser Phe Asp Lys Thr Leu Lys Val Trp Asp
        115                 120                 125

Thr Asn Thr Leu Gln Thr Ala Asp Val Phe Asn Phe Glu Glu Thr Val
    130                 135                 140

Tyr Ser His His Met Ser Pro Val Ser Thr Lys His Cys Leu Val Ala
145                 150                 155                 160

Val Gly Thr Arg Gly Pro Lys Val Gln Leu Cys Asp Leu Lys Ser Gly
                165                 170                 175

Ser Cys Ser His Ile Leu Gln Gly His Arg Gln Glu Ile Leu Ala Val
            180                 185                 190

Ser Trp Ser Pro Arg Tyr Asp Tyr Ile Leu Ala Thr Ala Ser Ala Asp
        195                 200                 205

Ser Arg Val Lys Leu Trp Asp Val Arg Arg Ala Ser Gly Cys Leu Ile
    210                 215                 220

Thr Leu Asp Gln His Asn Gly Lys Lys Ser Gln Ala Val Glu Ser Ala
225                 230                 235                 240

Asn Thr Ala His Asn Gly Lys Val Asn Gly Leu Cys Phe Thr Ser Asp
                245                 250                 255

Gly Leu His Leu Leu Thr Val Gly Thr Asp Asn Arg Met Arg Leu Trp
            260                 265                 270

Asn Ser Ser Asn Gly Glu Asn Thr Leu Val Asn Tyr Gly Lys Val Cys
        275                 280                 285

Asn Asn Ser Lys Lys Gly Leu Lys Phe Thr Val Ser Cys Gly Cys Ser
    290                 295                 300

Ser Glu Phe Val Phe Val Pro Tyr Gly Ser Thr Ile Ala Val Tyr Thr
305                 310                 315                 320

Val Tyr Ser Gly Glu Gln Ile Thr Met Leu Lys Gly His Tyr Lys Thr
                325                 330                 335

Val Asp Cys Cys Val Phe Gln Ser Asn Phe Gln Glu Leu Tyr Ser Gly
            340                 345                 350

Ser Arg Asp Cys Asn Ile Leu Ala Trp Val Pro Ser Leu Tyr Glu Pro
        355                 360                 365

Val Pro Asp Asp Asp Glu Thr Thr Thr Lys Ser Gln Leu Asn Pro Ala
    370                 375                 380

Phe Glu Asp Ala Trp Ser Ser Ser Asp Glu Glu Gly
385                 390                 395
```

<210> SEQ ID NO 3
<211> LENGTH: 3590
<212> TYPE: DNA
<213> ORGANISM: Homo sapiens

<400> SEQUENCE: 3

```
gcgccacggg cctccccgca ccagcagaag tcggagtcgc tgttgggggc ggtgtctatg     60
gttgagctga gggcgcaggc gccacggccc gtcgagctgg gttccaaggc ggctggcggc    120
ggtagcgtct ctgtttcctt gtgggcgctc gcgcggccct gggtagtctg tagagaatgc    180
caaatgaggg aatcccccac tcaagtcaaa ctcaggagca agactgttta cagagtcaac    240
ctgtcagtaa taatgaagaa atggcaatca agcaagaaag tggtggtgat ggggaggtgg    300
aggagtacct ctcctttcgt tctgtgggtg acgggctgtc cacctctgct gtggggtgcg    360
catcagcagc tccgaggaga gggccagccc tgctgcacat cgaccgacat cagatccagg    420
cagtagagcc tagcgcccag gcccttgagc tgcagggttt gggtgtggac gtctatgacc    480
aggacgtgct ggaacaggga gtgcttcagc aggtggacaa tgccatccat gaggccagcc    540
gtgcctccca gctcgttgac gtggagaagg agtatcggtc ggtcctggat gacctcacgt    600
catgtacgac atccctaagg caaatcaata aaattattga acagcttagc cctcaagctg    660
ccaccagcag agacatcaac aggaaactag attctgtaaa acgacagaag tataataagg    720
aacaacagct aaaaaagatc actgcaaaac aaaagcatct ccaggccatc cttggaggag    780
cagaggtgaa aattgaacta gatcacgcca gtctggagga ggatgcagag ccggggccat    840
ccagtcttgg cagcatgctc atgcctgtcc aggagactgc ctgggaagag ctcatccgca    900
ctggccagat gacacctttt ggtacccaga tccctcagaa acaggagaaa aagcccagaa    960
aaatcatgct taatgaagca tcaggcttcg aaaagtattt ggcagatcaa gcaaaactgt   1020
cttttgaaag gaagaagcaa ggttgtaata aaagagcagc tagaaaagct ccagccccag   1080
tcacgcctcc agccccagtg caaaataaaa acaaaccaaa caagaaagcc agagttctgt   1140
ccaaaaaaga ggagcgtttg aaaaagcaca tcaagaaact ccagaagagg gctttgcagt   1200
tccaggggaa agtgggattg ccaaaggcaa ggagaccttg ggagtcagac atgaggccag   1260
aggcagaggg agactctgag ggtgaagagt ctgagtattt ccccacagag gaggaggaag   1320
aggaggaaga tgacgaggtg gagggggcag aggcggacct gtctggagat ggtactgact   1380
atgagctgaa gcctctgccc aagggcggga aacggcagaa gaaagtgcca gtgcaggaga   1440
ttgatgatga ctttttccca agttctgggg aagaagctga agctgcttct gtaggagaag   1500
gaggaggagg aggtcggaaa gtgggaagat accgagatga tggagatgaa gattattata   1560
agcagcggtt aagtcccaag atgcctcgaa cactaagttt acatgaaata actgaccttt   1620
tagagacaga tgacagcata gaagcaagtg ctatagtgat acaaccacct gaaaatgcta   1680
cagcacctgt ttctgatgag gaatcaggag atgaagaagg tggaacaata aataatctgc   1740
caggttcttt gttgcacaca gctgcgtatc ttattcaaga tggctctgat gctgagtctg   1800
actcagatga tccctcatac gcacctaaag atgactctcc tgatgaagtt ccatctacgt   1860
ttactgtgca gcaacctcca ccatcaagga ggaggaaaat gacaaaaatt ctttgcaaat   1920
ggaaaaaagc cgacctaact gtacaacccg tagcaggtag agttacagca ccaccaaacg   1980
atttcttcac cgtaatgaga actcccacag aaattcttga actttttctt gatgacgagg   2040
tcattgaact cattgtcaag tactccaact tatatgcttg cagtaaaggt gtacatcttg   2100
gcttgactag ctctgaattc aaatgttttc tgggaattat ttttctgagt ggttatgtct   2160
cagttcctag aaggcgtatg ttttgggaac aaagaacaga tgtgcataat gtactggtta   2220
gtgctgccat gagacgtgac cggtttgaaa ctatattttc taatttgcat gttgctgaca   2280
atgcaaattt ggatccagtg gacaaatttt ccaaattgcg acctctcata agcaaactta   2340
```

```
atgagagatg catgaaattt gttccaaatg aaacatattt cagctttgat gaattcatgg   2400

ttccttattt tggtcgtcac gggtgcaaac aatttattcg gggaaagccc attcggtttg   2460

gctataagtt ttggtgtggt gccacctgtc tgggctacat ttgctggttt cagccgtatc   2520

agggtaaaaa cccaaatact aaacatgagg aatatggtgt cggtgcgtca cttgtccttc   2580

agtttagtga ggcacttaca gaggcacacc ctggacaata ccattttgta ttcaataact   2640

ttttcaccag tattgcactt cttgataagc tcagttcaat gggacatcag gcaacaggta   2700

cagtgagaaa ggatcacatt gacagagttc cactggaatc agatgtagct ttaaagaaaa   2760

aagaaagagg cacatttgat tatcgaattg atggcaaagg caatattgtc tgcagatgga   2820

atgataacag tgttgtcact gttgcctcat ctggtgctgg tatccatccc ctgtgtcttg   2880

tcagtcgtta ctcccagaaa ctgaaaaaga agatacaagt tcagcagcca aacatgatca   2940

aagtgtataa ccagttcatg ggaggcgtag acagagctga tgaaaacatt gataagtatc   3000

gggcatcaat ccgtggaaag aaatggtatt caagccctct tttgttctgt ttcgaactgg   3060

tcttacaaaa tgcttggcaa ttgcataaaa catatgatga gaaaccagtg gattttctgg   3120

agtttcgtcg acgtgtggta tgccattatc tggagaccca tggtcatcct ccagaacctg   3180

gccaaaaagg aagacctcag aagcgtaaca ttgactcacg ttatgatggc ataaatcatg   3240

tgatagtcaa acagggaaag caaacgcgat gcgctgaatg tcataagaac acaacttttc   3300

gatgtgaaaa atgtgatgtt gccttacatg tgaagtgttc cgttgaatat cacactgaat   3360

agcaggtgtc accacctcct gagataagaa acatagtttt atacattatg tacagtgtag   3420

cagtggtttt gcctagtgtt ccaattttgg aacgtcacat aacaatggaa cataataaat   3480

tttttttct cttcaaattt ttgttccttg aatttttcta ggtaacatat atgaatttca   3540

tgcaaaaatt caaaaaattg taacctcaga cataaatggg ttaaagatgt              3590
```

```
<210> SEQ ID NO 4
<211> LENGTH: 1493
<212> TYPE: PRT
<213> ORGANISM: Homo sapiens

<400> SEQUENCE: 4

Met Pro Asn Glu Gly Ile Pro His Ser Ser Gln Thr Gln Glu Gln Asp
1               5                   10                  15

Cys Leu Gln Ser Gln Pro Val Ser Asn Asn Glu Glu Met Ala Ile Lys
            20                  25                  30

Gln Glu Ser Gly Gly Asp Gly Glu Val Glu Glu Tyr Leu Ser Phe Arg
        35                  40                  45

Ser Val Gly Asp Gly Leu Ser Thr Ser Ala Val Gly Cys Ala Ser Ala
    50                  55                  60

Ala Pro Arg Arg Gly Pro Ala Leu Leu His Ile Asp Arg His Gln Ile
65                  70                  75                  80

Gln Ala Val Glu Pro Ser Ala Gln Ala Leu Glu Leu Gln Gly Leu Gly
                85                  90                  95

Val Asp Val Tyr Asp Gln Asp Val Leu Glu Gln Gly Val Leu Gln Gln
            100                 105                 110

Val Asp Asn Ala Ile His Glu Ala Ser Arg Ala Ser Gln Leu Val Asp
        115                 120                 125

Val Glu Lys Glu Tyr Arg Ser Val Leu Asp Asp Leu Thr Ser Cys Thr
    130                 135                 140

Thr Ser Leu Arg Gln Ile Asn Lys Ile Ile Glu Gln Leu Ser Pro Gln
```

```
145                 150                 155                 160

Ala Ala Thr Ser Arg Asp Ile Asn Arg Lys Leu Asp Ser Val Lys Arg
                165                 170                 175

Gln Lys Tyr Asn Lys Glu Gln Gln Leu Lys Lys Ile Thr Ala Lys Gln
            180                 185                 190

Lys His Leu Gln Ala Ile Leu Gly Gly Ala Glu Val Lys Ile Glu Leu
        195                 200                 205

Asp His Ala Ser Leu Glu Glu Asp Ala Glu Pro Gly Pro Ser Ser Leu
    210                 215                 220

Gly Ser Met Leu Met Pro Val Gln Glu Thr Ala Trp Glu Glu Leu Ile
225                 230                 235                 240

Arg Thr Gly Gln Met Thr Pro Phe Gly Thr Gln Ile Pro Gln Lys Gln
                245                 250                 255

Glu Lys Lys Pro Arg Lys Ile Met Leu Asn Glu Ala Ser Gly Phe Glu
            260                 265                 270

Lys Tyr Leu Ala Asp Gln Ala Lys Leu Ser Phe Glu Arg Lys Lys Gln
        275                 280                 285

Gly Cys Asn Lys Arg Ala Ala Arg Lys Ala Pro Ala Pro Val Thr Pro
    290                 295                 300

Pro Ala Pro Val Gln Asn Lys Asn Lys Pro Asn Lys Lys Ala Arg Val
305                 310                 315                 320

Leu Ser Lys Lys Glu Glu Arg Leu Lys Lys His Ile Lys Lys Leu Gln
                325                 330                 335

Lys Arg Ala Leu Gln Phe Gln Gly Lys Val Gly Leu Pro Lys Ala Arg
            340                 345                 350

Arg Pro Trp Glu Ser Asp Met Arg Pro Glu Ala Glu Gly Asp Ser Glu
        355                 360                 365

Gly Glu Glu Ser Glu Tyr Phe Pro Thr Glu Glu Glu Glu Glu Glu Glu
    370                 375                 380

Asp Asp Glu Val Glu Gly Ala Glu Ala Asp Leu Ser Gly Asp Gly Thr
385                 390                 395                 400

Asp Tyr Glu Leu Lys Pro Leu Pro Lys Gly Gly Lys Arg Gln Lys Lys
                405                 410                 415

Val Pro Val Gln Glu Ile Asp Asp Asp Phe Phe Pro Ser Ser Gly Glu
            420                 425                 430

Glu Ala Glu Ala Ala Ser Val Gly Glu Gly Gly Gly Gly Gly Arg Lys
        435                 440                 445

Val Gly Arg Tyr Arg Asp Asp Gly Asp Glu Asp Tyr Tyr Lys Gln Arg
    450                 455                 460

Leu Arg Arg Trp Asn Lys Leu Arg Leu Gln Asp Lys Glu Lys Arg Leu
465                 470                 475                 480

Lys Leu Glu Asp Asp Ser Glu Glu Ser Asp Ala Glu Phe Asp Glu Gly
                485                 490                 495

Phe Lys Val Pro Gly Phe Leu Phe Lys Lys Leu Phe Lys Tyr Gln Gln
            500                 505                 510

Thr Gly Val Arg Trp Leu Trp Glu Leu His Cys Gln Gln Ala Gly Gly
        515                 520                 525

Ile Leu Gly Asp Glu Met Gly Leu Gly Lys Thr Ile Gln Ile Ile Ala
    530                 535                 540

Phe Leu Ala Gly Leu Ser Tyr Ser Lys Ile Arg Thr Arg Gly Ser Asn
545                 550                 555                 560

Tyr Arg Phe Glu Gly Leu Gly Pro Thr Val Ile Val Cys Pro Thr Thr
                565                 570                 575
```

```
Val Met His Gln Trp Val Lys Glu Phe His Thr Trp Trp Pro Pro Phe
            580                 585                 590

Arg Val Ala Ile Leu His Glu Thr Gly Ser Tyr Thr His Lys Lys Glu
        595                 600                 605

Lys Leu Ile Arg Asp Val Ala His Cys His Gly Ile Leu Ile Thr Ser
    610                 615                 620

Tyr Ser Tyr Ile Arg Leu Met Gln Asp Asp Ile Ser Arg Tyr Asp Trp
625                 630                 635                 640

His Tyr Val Ile Leu Asp Glu Gly His Lys Ile Arg Asn Pro Asn Ala
                645                 650                 655

Ala Val Thr Leu Ala Cys Lys Gln Phe Arg Thr Pro His Arg Ile Ile
            660                 665                 670

Leu Ser Gly Ser Pro Met Gln Asn Asn Leu Arg Glu Leu Trp Ser Leu
        675                 680                 685

Phe Asp Phe Ile Phe Pro Gly Lys Leu Gly Thr Leu Pro Val Phe Met
    690                 695                 700

Glu Gln Phe Ser Val Pro Ile Thr Met Gly Gly Tyr Ser Asn Ala Ser
705                 710                 715                 720

Pro Val Gln Val Lys Thr Ala Tyr Lys Cys Ala Cys Val Leu Arg Asp
                725                 730                 735

Thr Ile Asn Pro Tyr Leu Leu Arg Arg Met Lys Ser Asp Val Lys Met
            740                 745                 750

Ser Leu Ser Leu Pro Asp Lys Asn Glu Gln Val Leu Phe Cys Arg Leu
        755                 760                 765

Thr Asp Glu Gln His Lys Val Tyr Gln Asn Phe Val Asp Ser Lys Glu
    770                 775                 780

Val Tyr Arg Ile Leu Asn Gly Glu Met Gln Ile Phe Ser Gly Leu Ile
785                 790                 795                 800

Ala Leu Arg Lys Ile Cys Asn His Pro Asp Leu Phe Ser Gly Gly Pro
                805                 810                 815

Lys Asn Leu Lys Gly Leu Pro Asp Asp Glu Leu Glu Glu Asp Gln Phe
            820                 825                 830

Gly Tyr Trp Lys Arg Ser Gly Lys Met Ile Val Val Glu Ser Leu Leu
        835                 840                 845

Lys Ile Trp His Lys Gln Gly Gln Arg Val Leu Leu Phe Ser Gln Ser
    850                 855                 860

Arg Gln Met Leu Asp Ile Leu Glu Val Phe Leu Arg Ala Gln Lys Tyr
865                 870                 875                 880

Thr Tyr Leu Lys Met Asp Gly Thr Thr Thr Ile Ala Ser Arg Gln Pro
                885                 890                 895

Leu Ile Thr Arg Tyr Asn Glu Asp Thr Ser Ile Phe Val Phe Leu Leu
            900                 905                 910

Thr Thr Arg Val Gly Gly Leu Gly Val Asn Leu Thr Gly Ala Asn Arg
        915                 920                 925

Val Val Ile Tyr Asp Pro Asp Trp Asn Pro Ser Thr Asp Thr Gln Ala
    930                 935                 940

Arg Glu Arg Ala Trp Arg Ile Gly Gln Lys Lys Gln Val Thr Val Tyr
945                 950                 955                 960

Arg Leu Leu Thr Ala Gly Thr Ile Glu Glu Lys Ile Tyr His Arg Gln
                965                 970                 975

Ile Phe Lys Gln Phe Leu Thr Asn Arg Val Leu Lys Asp Pro Lys Gln
            980                 985                 990
```

Arg Arg Phe Phe Lys Ser Asn Asp Leu Tyr Glu Leu Phe Thr Leu Thr
995 1000 1005

Ser Pro Asp Ala Ser Gln Ser Thr Glu Thr Ser Ala Ile Phe Ala
1010 1015 1020

Gly Thr Gly Ser Asp Val Gln Thr Pro Lys Cys His Leu Lys Arg
1025 1030 1035

Arg Ile Gln Pro Ala Phe Gly Ala Asp His Asp Val Pro Lys Arg
1040 1045 1050

Lys Lys Phe Pro Ala Ser Asn Ile Ser Val Asn Asp Ala Thr Ser
1055 1060 1065

Ser Glu Glu Lys Ser Glu Ala Lys Gly Ala Glu Val Asn Ala Val
1070 1075 1080

Thr Ser Asn Arg Ser Asp Pro Leu Lys Asp Asp Pro His Met Ser
1085 1090 1095

Ser Asn Val Thr Ser Asn Asp Arg Leu Gly Glu Glu Thr Asn Ala
1100 1105 1110

Val Ser Gly Pro Glu Glu Leu Ser Val Ile Ser Gly Asn Gly Glu
1115 1120 1125

Cys Ser Asn Ser Ser Gly Thr Gly Lys Thr Ser Met Pro Ser Gly
1130 1135 1140

Asp Glu Ser Ile Asp Glu Lys Leu Gly Leu Ser Tyr Lys Arg Glu
1145 1150 1155

Arg Pro Ser Gln Ala Gln Thr Glu Ala Phe Trp Glu Asn Lys Gln
1160 1165 1170

Met Glu Asn Asn Phe Tyr Lys His Lys Ser Lys Thr Lys His His
1175 1180 1185

Ser Val Ala Glu Glu Glu Thr Leu Glu Lys His Leu Arg Pro Lys
1190 1195 1200

Gln Lys Pro Lys Asn Ser Lys His Cys Arg Asp Ala Lys Phe Glu
1205 1210 1215

Gly Thr Arg Ile Pro His Leu Val Lys Lys Arg Arg Tyr Gln Lys
1220 1225 1230

Gln Asp Ser Glu Asn Lys Ser Glu Ala Lys Glu Gln Ser Asn Asp
1235 1240 1245

Asp Tyr Val Leu Glu Lys Leu Phe Lys Lys Ser Val Gly Val His
1250 1255 1260

Ser Val Met Lys His Asp Ala Ile Met Asp Gly Ala Ser Pro Asp
1265 1270 1275

Tyr Val Leu Val Glu Ala Glu Ala Asn Arg Val Ala Gln Asp Ala
1280 1285 1290

Leu Lys Ala Leu Arg Leu Ser Arg Gln Arg Cys Leu Gly Ala Val
1295 1300 1305

Ser Gly Val Pro Thr Trp Thr Gly His Arg Gly Ile Ser Gly Ala
1310 1315 1320

Pro Ala Gly Lys Lys Ser Arg Phe Gly Lys Lys Arg Asn Ser Asn
1325 1330 1335

Phe Ser Val Gln His Pro Ser Ser Thr Ser Pro Thr Glu Lys Cys
1340 1345 1350

Gln Asp Gly Ile Met Lys Lys Glu Gly Lys Asp Asn Val Pro Glu
1355 1360 1365

His Phe Ser Gly Arg Ala Glu Asp Ala Asp Ser Ser Ser Gly Pro
1370 1375 1380

Leu Ala Ser Ser Ser Leu Leu Ala Lys Met Arg Ala Arg Asn His

```
    1385                1390                1395

Leu Ile  Leu Pro Glu Arg Leu  Glu Ser Glu Ser Gly  His Leu Gln
    1400                1405                1410

Glu Ala  Ser Ala Leu Leu Pro  Thr Thr Glu His Asp  Asp Leu Leu
    1415                1420                1425

Val Glu  Met Arg Asn Phe Ile  Ala Phe Gln Ala His  Thr Asp Gly
    1430                1435                1440

Gln Ala  Ser Thr Arg Glu Ile  Leu Gln Glu Phe Glu  Ser Lys Leu
    1445                1450                1455

Ser Ala  Ser Gln Ser Cys Val  Phe Arg Glu Leu Leu  Arg Asn Leu
    1460                1465                1470

Cys Thr  Phe His Arg Thr Ser  Gly Gly Glu Gly Ile  Trp Lys Leu
    1475                1480                1485

Lys Pro  Glu Tyr Cys
    1490
```

<210> SEQ ID NO 5
<211> LENGTH: 3515
<212> TYPE: DNA
<213> ORGANISM: Homo sapiens

<400> SEQUENCE: 5

```
ctccttccgc gtggtccctc cccctcaggc cgcggtcgcg attacgctct ctacggcctg     60
cgaccgcagg gccgttgcgg gctggagaca cggcgccgac tggaaccgga ggagctctag    120
gccaaatggt tgggccagcc aggatcccag gacccttcgc cgctcgagac cggagagagg    180
aaacgaaaca ggcgggaacc cgtgggggag ggagggaact agcggaaggt gtcatggcgg    240
ccgcgctctt gagtcacgtg cccagggccc gccttgctac ttccggtcac gtgccctcag    300
actcctcgca gccagcgatg gaggcgagac cccctagtaa cagaggcggt ggctactgct    360
gcggccactg ggtttcggcc tcttcccagc agcggctcta agaagcgcag cggaactcga    420
ccggatccaa cccagttagt tacttcctgt ctagagttgt agcttccacc tgagttctcc    480
tgggaagaag tgtttgccac tcaaggaata cactcaagaa aaacctggaa atcacagaag    540
gcattgtaag atagctacag tgattctgtt aaacctcctg aaattggtcc ttgaacaatt    600
aagaggtgct acagatgacc aggaaaattt accaggcaaa ttagctgtga gacaattgac    660
catttgtgcc caatgttcgc accttctagc caccatggca acctcatctg aagaagtttt    720
gctgattgta aagaaaagtgc gtcaaaagaa gcaggatgga gctctgtacc tcatggcaga    780
aagaattgct tgggcacctg aaggcaaaga tagatttaca atcagccata tgtatgcaga    840
tattaaatgc cagaaaatta gtccagaagg aaaagctaaa attcagcttc agctggtcct    900
acatgcaggg gacacaacta acttccattt ttccaatgaa agcacagcag tgaaagagcg    960
agatgcagta aaagaccttc ttcagcagct gctgcccaaa ttcaagagga aagcaaataa   1020
agaactggaa gagaagaaca gaatgctgca agaagatcct gttttgtttc agctttataa   1080
agaccttgtt gtgagtcaag tgatcagtgc tgaggaattc tgggccaatc gtttaaatgt   1140
gaatgcaaca gatagttctt ccacatccaa tcataagcag gatgttggca tttctgctgc   1200
atttctggct gatgtccggc cccaaactga tggctgtaac ggtctaagat ataatttaac   1260
ttctgatatc attgagtcca tatttaggac ctatccagca gtaaaaatga aatatgcaga   1320
aaatgttccc cacaacatga cagagaagga attctggaca cgtttttttcc agtcccatta   1380
ttttcacagg gatcggctga atacagggtc aaaggatctc tttgcagaat gtgccaaaat   1440
```

```
agatgaaaaa ggcctaaaaa caatggtttc attaggagtg aaaaacccac tactagattt   1500

aacagctttg gaagataaac cattagatga gggctatggc atttcctctg tgccatctgc   1560

ttccaattct aaatccataa aagagaatag taatgctgcc atcatcaaga gatttaacca   1620

tcacagtgcc atggtcctgg cagctggact cagaaaacaa gaagcacaaa atgaacaaac   1680

tagtgagccc agcaacatgg atggaaattc cggagatgca gactgctttc agccagcagt   1740

caaaagggcg aaattacaag agtccattga atatgaagac ttggggaaaa ataattctgt   1800

aaaaacgatt gcactaaacc tcaagaagtc agataggtat tatcatggtc caactccaat   1860

ccagtcacta cagtatgcaa caagtcagga cattattaat tcttttcaaa gtattagaca   1920

agaaatggaa gcttatacac ccaagttaac tcaggttctc tcaagtagtg ctgccagtag   1980

taccatcaca gcactgtcac ctggaggggc acttatgcag ggaggaacac agcaagccat   2040

aaaccagatg gtgccaaatg atattcaatc tgaattgaaa cacttatatg tagctgttgg   2100

agaacttcta cgacatttct ggtcctgctt tcctgttaat acgccattcc tagaagaaaa   2160

ggtagtgaaa atgaaaagta atttggaacg attccaagtt acgaagctct gtccattcca   2220

agaaaagatt cggagacagt atttaagcac aaatttggta agtcacatag aagagatgct   2280

ccagacagcc tacaacaagc tccacacatg gcagtcacgg cgtctgatga agaaaacgtg   2340

aggtggccat gatgcttaca ggttttgtga gattgagaga actatgacct gcagcaactc   2400

tggaaacctg gcctgacaga caagcagatg acctcacagg agtgataaga aacatctgct   2460

ccacgccaac tcccagagct gatgctattg tacttgcaca ttggagactg aaaggaaaga   2520

agggactaaa tgctggggag gtaaattaag acagaaccaa atgagctaag ttgcaaatat   2580

atatatatac acacacacac atatatgtac atgtgtatgt acatatatat tttaaaagac   2640

tgtttactgc agttgctcag gaactgcttt tgattcacat taagctgctt tcagaaatta   2700

aaaaaacact ttttaaaggg tgcattgata aaatctgagg tttttggtt gtcgtttttt   2760

tctgtgtaca tttttttcct aagtttatgg cacagggtag accttaagta ttcctcctcc   2820

atccttcatt cttcaccctc cattggatcc tcaagtttta atgaattcca attatacctt   2880

acatcagcaa gttaaaaaaa gtactttaaa ataaagcaaa gggagactgt tgctcaacca   2940

tcaggaaaca gttgtcagaa gacatcattg gttctgtgtt tcctacggaa ataagaaacg   3000

ataaatattg cactgaatgt ttgtggtttg gagtccctga ataataaaga gggaatatat   3060

ttgcagaaag tcgcataggg tttttaatg cagaattttg tcagaagaca atggcgctgc   3120

atgtttttct ttgagtgcaa atgtacattg ctaagatttt tttaagatgg catgtgcttt   3180

gaaaagaaga tattgcattt ttaagagttt aaaaatctta tgagtgagaa atattaaaaa   3240

aatcttattt tcacctcttt agaagaaata aaagatgttt ctcctatctc cttttctcta   3300

gtatttgact gttactgtcc ttggcgaatc gataatcatt gcatagtgac tgaaaagcct   3360

aagtgcaaaa aaaaaaaaaa aagatgttct tgtttctgaa cttcgtgcca tattttgttc   3420

ctgatgggat caacttaatg tttaagactt tagatgtctt gtattaaaaa ttacacaaaa   3480

aaagtaaaac tttttatact taccctttta actct                               3515
```

<210> SEQ ID NO 6
<211> LENGTH: 548
<212> TYPE: PRT
<213> ORGANISM: Homo sapiens

<400> SEQUENCE: 6

Met Ala Thr Ser Ser Glu Glu Val Leu Leu Ile Val Lys Lys Val Arg

```
1               5                   10                  15

Gln Lys Lys Gln Asp Gly Ala Leu Tyr Leu Met Ala Glu Arg Ile Ala
            20                  25                  30

Trp Ala Pro Glu Gly Lys Asp Arg Phe Thr Ile Ser His Met Tyr Ala
        35                  40                  45

Asp Ile Lys Cys Gln Lys Ile Ser Pro Glu Gly Lys Ala Lys Ile Gln
    50                  55                  60

Leu Gln Leu Val Leu His Ala Gly Asp Thr Thr Asn Phe His Phe Ser
65                  70                  75                  80

Asn Glu Ser Thr Ala Val Lys Glu Arg Asp Ala Val Lys Asp Leu Leu
                85                  90                  95

Gln Gln Leu Leu Pro Lys Phe Lys Arg Lys Ala Asn Lys Glu Leu Glu
            100                 105                 110

Glu Lys Asn Arg Met Leu Gln Glu Asp Pro Val Leu Phe Gln Leu Tyr
        115                 120                 125

Lys Asp Leu Val Val Ser Gln Val Ile Ser Ala Glu Glu Phe Trp Ala
    130                 135                 140

Asn Arg Leu Asn Val Asn Ala Thr Asp Ser Ser Ser Thr Ser Asn His
145                 150                 155                 160

Lys Gln Asp Val Gly Ile Ser Ala Ala Phe Leu Ala Asp Val Arg Pro
                165                 170                 175

Gln Thr Asp Gly Cys Asn Gly Leu Arg Tyr Asn Leu Thr Ser Asp Ile
            180                 185                 190

Ile Glu Ser Ile Phe Arg Thr Tyr Pro Ala Val Lys Met Lys Tyr Ala
        195                 200                 205

Glu Asn Val Pro His Asn Met Thr Glu Lys Glu Phe Trp Thr Arg Phe
    210                 215                 220

Phe Gln Ser His Tyr Phe His Arg Asp Arg Leu Asn Thr Gly Ser Lys
225                 230                 235                 240

Asp Leu Phe Ala Glu Cys Ala Lys Ile Asp Glu Lys Gly Leu Lys Thr
                245                 250                 255

Met Val Ser Leu Gly Val Lys Asn Pro Leu Leu Asp Leu Thr Ala Leu
            260                 265                 270

Glu Asp Lys Pro Leu Asp Glu Gly Tyr Gly Ile Ser Ser Val Pro Ser
        275                 280                 285

Ala Ser Asn Ser Lys Ser Ile Lys Glu Asn Ser Asn Ala Ala Ile Ile
    290                 295                 300

Lys Arg Phe Asn His His Ser Ala Met Val Leu Ala Ala Gly Leu Arg
305                 310                 315                 320

Lys Gln Glu Ala Gln Asn Glu Gln Thr Ser Glu Pro Ser Asn Met Asp
                325                 330                 335

Gly Asn Ser Gly Asp Ala Asp Cys Phe Gln Pro Ala Val Lys Arg Ala
            340                 345                 350

Lys Leu Gln Glu Ser Ile Glu Tyr Glu Asp Leu Gly Lys Asn Asn Ser
        355                 360                 365

Val Lys Thr Ile Ala Leu Asn Leu Lys Lys Ser Asp Arg Tyr Tyr His
    370                 375                 380

Gly Pro Thr Pro Ile Gln Ser Leu Gln Tyr Ala Thr Ser Gln Asp Ile
385                 390                 395                 400

Ile Asn Ser Phe Gln Ser Ile Arg Gln Glu Met Glu Ala Tyr Thr Pro
                405                 410                 415

Lys Leu Thr Gln Val Leu Ser Ser Ser Ala Ala Ser Ser Thr Ile Thr
            420                 425                 430
```

```
Ala Leu Ser Pro Gly Gly Ala Leu Met Gln Gly Gly Thr Gln Gln Ala
        435                 440                 445

Ile Asn Gln Met Val Pro Asn Asp Ile Gln Ser Glu Leu Lys His Leu
    450                 455                 460

Tyr Val Ala Val Gly Glu Leu Leu Arg His Phe Trp Ser Cys Phe Pro
465                 470                 475                 480

Val Asn Thr Pro Phe Leu Glu Glu Lys Val Val Lys Met Lys Ser Asn
                485                 490                 495

Leu Glu Arg Phe Gln Val Thr Lys Leu Cys Pro Phe Gln Glu Lys Ile
            500                 505                 510

Arg Arg Gln Tyr Leu Ser Thr Asn Leu Val Ser His Ile Glu Glu Met
        515                 520                 525

Leu Gln Thr Ala Tyr Asn Lys Leu His Thr Trp Gln Ser Arg Arg Leu
    530                 535                 540

Met Lys Lys Thr
545


<210> SEQ ID NO 7
<211> LENGTH: 1951
<212> TYPE: DNA
<213> ORGANISM: Homo sapiens

<400> SEQUENCE: 7

ccttctagcg gcgccggtga gtccgcgtgt ggaagtctgt gaggcgcaga ggtggggcag      60

gccgtctggc tagctaggcg gctgggagcg ttttcgtggc ggggaacgga ggttgaattg     120

ccctgcctgg gctcataggg aaggaggatg tgaaggagct tgtgaaggca gaggaagatt     180

attgaataat aaaatacagt tttgaaaaaa atggatgaag aacctgaaag aactaagcga     240

tgggaaggag gctatgaaag aacatgggag attcttaaag aagatgaatc tggatcactt     300

aaagctacaa tagaagacat tctattcaag gcaaagagaa aaagagtatt tgagcaccat     360

ggacaagttc gacttggaat gatgcgccac ctttatgtgg tagtagatgg atcaagaaca     420

atggaagacc aagatttaaa gcctaataga ctgacgtgta ctttaaagtt gttggaatac     480

tttgtagagg aatattttga tcaaaatcct attagtcaga ttggaataat tgtaactaag     540

agtaaaagag ctgaaaaatt gactgaactt tcaggaaacc caagaaaaca tataacgtct     600

ttgaagaaag ctgtggatat gacctgccat ggagagccat ctctttataa ttccctaagc     660

atagctatgc agactctaaa acacatgcct ggacatacaa gtcgagaagt actaatcatc     720

tttagcagcc ttacaacttg cgatccatct aatatttatg atctaatcaa gaccctaaag     780

gcagctaaaa ttagagtatc tgttattgga ttgtctgcag aagttcgcgt ttgcactgta     840

cttgctcgtg aaactggtgg cacgtaccat gttattttag atgaaagcca ttacaaagag     900

ttgctcacac atcatgttag tcctcctcct gctagctcaa gttctgaatg ctcacttatt     960

cgtatgggat ttcctcagca caccattgct tctttatctg accaggatgc aaaaccctct    1020

ttcagcatgg cgcatttgga tggcaatact gagccagggc ttacattagg aggctatttc    1080

tgcccacagt gtcgggcaaa gtactgtgag ctacctgttg agtgtaaaat ctgtggtctt    1140

actttggtgt ctgctcccca cttggcacgg tcttaccatc atttgtttcc tttggatgct    1200

tttcaagaaa ttcccctaga agaatataat ggagaaagat tttgttatgg atgtcagggg    1260

gaattgaaag accaacatgt ttatgtttgt gctgtgtgcc aaaatgtttt ctgtgtggac    1320

tgtgatgttt ttgttcatga ttctctacac tgttgccctg gctgtattca taagattcca    1380
```

-continued

```
gctccttcag gtgtttgatt ccagcatgta gtatacattg tatgtgttaa aaagaaattt   1440

gcaactgtga ataaaaggac ttctttagaa gaagcttcat ttaaaacatg aaaggataat   1500

ctgacttaag aaactttttg ctaagaaaag gtaatatttt attaaatttt aaatttgtgt   1560

tgtcacagaa atacctgaaa ttcagtagta cttcattcaa ttaattttgt tttctattat   1620

tttgagttat actgttttca aagtcattat gcagtatgta taaacttata agaattaaat   1680

tgatgtgata attttatgtt tttataatta aatatagaat ctttatgatt tatgttaatt   1740

cattaattta gtgtaagaag aaagttaagt ctgaatgtaa attcagtgta agatgaaaat   1800

ttatcaatac ttatgaaatt aggctgggcg ctgtggctca cacctgtaat cccaacactt   1860

tgggaggctg aggtgggcag atcacctgag gtcaggagtt cgagaccagc ctggccaaca   1920

tggtgaaacc ccgtcactac taaaaataca a                                  1951


<210> SEQ ID NO 8
<211> LENGTH: 395
<212> TYPE: PRT
<213> ORGANISM: Homo sapiens

<400> SEQUENCE: 8

Met Asp Glu Glu Pro Glu Arg Thr Lys Arg Trp Glu Gly Gly Tyr Glu
1               5                   10                  15

Arg Thr Trp Glu Ile Leu Lys Glu Asp Glu Ser Gly Ser Leu Lys Ala
            20                  25                  30

Thr Ile Glu Asp Ile Leu Phe Lys Ala Lys Arg Lys Arg Val Phe Glu
        35                  40                  45

His His Gly Gln Val Arg Leu Gly Met Met Arg His Leu Tyr Val Val
    50                  55                  60

Val Asp Gly Ser Arg Thr Met Glu Asp Gln Asp Leu Lys Pro Asn Arg
65                  70                  75                  80

Leu Thr Cys Thr Leu Lys Leu Leu Glu Tyr Phe Val Glu Glu Tyr Phe
                85                  90                  95

Asp Gln Asn Pro Ile Ser Gln Ile Gly Ile Ile Val Thr Lys Ser Lys
            100                 105                 110

Arg Ala Glu Lys Leu Thr Glu Leu Ser Gly Asn Pro Arg Lys His Ile
        115                 120                 125

Thr Ser Leu Lys Lys Ala Val Asp Met Thr Cys His Gly Glu Pro Ser
    130                 135                 140

Leu Tyr Asn Ser Leu Ser Ile Ala Met Gln Thr Leu Lys His Met Pro
145                 150                 155                 160

Gly His Thr Ser Arg Glu Val Leu Ile Ile Phe Ser Ser Leu Thr Thr
                165                 170                 175

Cys Asp Pro Ser Asn Ile Tyr Asp Leu Ile Lys Thr Leu Lys Ala Ala
            180                 185                 190

Lys Ile Arg Val Ser Val Ile Gly Leu Ser Ala Glu Val Arg Val Cys
        195                 200                 205

Thr Val Leu Ala Arg Glu Thr Gly Gly Thr Tyr His Val Ile Leu Asp
    210                 215                 220

Glu Ser His Tyr Lys Glu Leu Leu Thr His His Val Ser Pro Pro Pro
225                 230                 235                 240

Ala Ser Ser Ser Ser Glu Cys Ser Leu Ile Arg Met Gly Phe Pro Gln
                245                 250                 255

His Thr Ile Ala Ser Leu Ser Asp Gln Asp Ala Lys Pro Ser Phe Ser
            260                 265                 270
```

-continued

Met Ala His Leu Asp Gly Asn Thr Glu Pro Gly Leu Thr Leu Gly Gly
275 280 285

Tyr Phe Cys Pro Gln Cys Arg Ala Lys Tyr Cys Glu Leu Pro Val Glu
290 295 300

Cys Lys Ile Cys Gly Leu Thr Leu Val Ser Ala Pro His Leu Ala Arg
305 310 315 320

Ser Tyr His His Leu Phe Pro Leu Asp Ala Phe Gln Glu Ile Pro Leu
325 330 335

Glu Glu Tyr Asn Gly Glu Arg Phe Cys Tyr Gly Cys Gln Gly Glu Leu
340 345 350

Lys Asp Gln His Val Tyr Val Cys Ala Val Cys Gln Asn Val Phe Cys
355 360 365

Val Asp Cys Asp Val Phe Val His Asp Ser Leu His Cys Cys Pro Gly
370 375 380

Cys Ile His Lys Ile Pro Ala Pro Ser Gly Val
385 390 395

<210> SEQ ID NO 9
<211> LENGTH: 3434
<212> TYPE: DNA
<213> ORGANISM: Homo sapiens

<400> SEQUENCE: 9
gggggctggc acgagtcaca gcacctcgtg cgtcacttgg cggcgccgga cgttgggctg 60
cgcaggattt gagacgctcc cctgaccacc acttgctctg cgctgaggtg ctgggacagc 120
catggtttca gacgaagatg aattgaatct tctggttatt gtagttgatg ccaacccaat 180
ttggtgggga aagcaagcat taaaggaatc tcagttcact ttatccaaat gcatagatgc 240
cgtgatggtg ctgggaaatt cgcatttatt catgaatcgt tccaacaaac ttgctgtgat 300
agcaagtcac attcaagaaa gccgattctt atatcctgga aagaatggca gacttggaga 360
cttcttcgga gaccctggca accctcctga atttaatccc tctgggagta aagatggaaa 420
atacgaactt ttaacctcag caaatgaagt tattgttgaa gagattaaag atctaatgac 480
caaaagtgac ataaagggtc aacatacaga aactttgctg gcaggatccc tggccaaagc 540
cctttgctac attcatagaa tgaacaagga agttaaagac aatcaggaaa tgaaatcaag 600
gatattggtg attaaggctg cagaagacag tgcgttgcag tatatgaact tcatgaatgt 660
catctttgca gcacagaaac agaatatttt gattgatgcc tgtgttttag actccgactc 720
agggctcctc caacaggctt gtgacatcac gggaggactg tacctgaagg tgcctcagat 780
gccttctctt ctgcagtatt tgctgtgggt gtttcttccc gatcaagatc agagatctca 840
gttaatcctc ccacccccag ttcatgttga ctacagggct gcttgcttct gtcatcgaaa 900
tctcattgaa attggttatg tctgttctgt gtgtttgtca atattctgca atttcagccc 960
catttgtact acgtgcgaga cagcctttaa aatttctctg cctccagtgc tgaaagccaa 1020
gaaaaagaaa ctgaaagtgt ctgcctgagg ataaaatatt ttccccatct tttagagctg 1080
ttaatagaaa ttatatagca gattctttgt tgggaagact gaaaaaaata aagataggta 1140
taggataatt tttaatatgg tgaccttaca gaaaatattt cccaaacatc cttttcatcc 1200
tgtgcttctg gaggactgat ttgtttgagg gaatcattct atgcattata tcctaaaata 1260
ttctatgact ggtttctgtc catgtttgtg gctttcattt ttttaatggg atgactatta 1320
gtcaaagtca gcttgtcatg actcatcata ggctttctaa cctactccct gaatccgggt 1380
cctcattgtg aaatgcatgc catacgaaat ttgaacgtag ctttggaaaa agggactatt 1440

```
tgtggagtaa tggcattaat caacatagaa catcttattt gaatcaacag ttaacttcag   1500

tagtcatgtg aataaaattc ttattgtcta aattgagaca gcctcagata tttgcagata   1560

tttactttt gtctgatatc agtacatatt tggacaaagt catctaaata atagtttgtc   1620

accaaataac tacaaaatct cattttaaat gagtaaggag aacgtgtaca gaagcaaatt   1680

ttcttcaaaa tagttgtggg aagagcttat atgtgaaagc ttatgactgg ttttgaggga   1740

gaacttactg gagaaaatgg actctatgtt aagtatggtt ttcagataga attctttcct   1800

tttttaatga ggaaaaaaaa tccacattaa tattgaaact gcacctgtaa tcccagcact   1860

ttgggaggct gaggacagag gattgcttga gcccaggagt tcgagagcag cctgggcagc   1920

aaagtgagac cccatctcta ctaaaaattt aaatgtattt attaaaactg ttctctagaa   1980

gctttggact gaatcccaaa agtgtttata agttcaaaag caaaagtatt tgtaatttca   2040

acaacaaaaa atgtatttct ttatgtaatc ttgaaattat taaaagtcct tttagcttct   2100

agcacatatt tgtacaaaga gtttaaggaa tggtggctgg tttggtttgt tttttaaaaa   2160

tgtttactga cgaggccggg cgtggtggct cacccctgca atcccagcac tttgggaggc   2220

cgaggcaggc agatcacaag gtcaggagtt caagatcagc ctggccagta tggtgaaacc   2280

ctgtctctac taaaaataga aaaattagcc atgcgaagta gcaggtgcct gtagttccag   2340

ctactcggga ggctgaggca agagaattgc ttgaatccag gaggcagagg ttgcagtgag   2400

ccaagatagc gcctctgtac tccagcctgg gtgacagagc gagactctgt atcaaaaaaa   2460

aaaaagatcg ggcacgttgg ctcacgcctg taatcccagc actttgggag gccaaggtgg   2520

gtggatcacg aggtcaggag tgatcaggct gggtttctgt tttgttttgt tttgtgagac   2580

agagtctcgc tctgttgccc aggctggggt gcagtggtgc aagctcggct ctctgcaagc   2640

tctgtctcct gggttcacgc cattctcctg cctcagcctc ccaagtagct gggattacta   2700

ctctactgaa cccatgaggc agaaatttga gaccatcctg cccaacgtgg tgaaaacatg   2760

gtgaaaccct gtctctacta aaaatacaaa aattagctgg gcgtggtggc aggtgcctgt   2820

aatcccagct actcaggaga ctgaggcagg agaattgctt gaacccagga ggtggaggtt   2880

gcagtgagcc aagatcaaga ttgcgccatt gcactccagc ctgggcgaca agaacaaaac   2940

tctgtctcaa aaaaaaaaaa aaaaaaaaag tctgtactga taaaacccat tgtgtacaaa   3000

actttgtatg taaggaagat tttaattttc tctttataca agctgagtca tatttaaata   3060

atttgatgtt ggcttagata atttcagata gattttatat tctggatttg tgtttttgtt   3120

aacaaatata caaagacttt ggtgatcact ttgcaaatat ttgttaatcc ttgagtttga   3180

gaacctgtct tttaaaaata atattttgta tactaattaa gtgtaatgga aatcacaatt   3240

ttaagtctag gaaataaagt attatatata ctttcaaaca agctagcaag gcttttatta   3300

ttactttttt atttgaaata tcttatatat ttggttagtt ctgtttaact tgtttttaac   3360

tgttgccctt atgagttatt ttatataaat ttttacaata aaataatttg attttcaaaa   3420

aaaaaaaaaa aaaa                                                      3434
```

<210> SEQ ID NO 10
<211> LENGTH: 308
<212> TYPE: PRT
<213> ORGANISM: Homo sapiens

<400> SEQUENCE: 10

```
Met Val Ser Asp Glu Asp Glu Leu Asn Leu Leu Val Ile Val Val Asp
1               5                   10                  15
```

```
Ala Asn Pro Ile Trp Trp Gly Lys Gln Ala Leu Lys Glu Ser Gln Phe
            20                  25                  30

Thr Leu Ser Lys Cys Ile Asp Ala Val Met Val Leu Gly Asn Ser His
        35                  40                  45

Leu Phe Met Asn Arg Ser Asn Lys Leu Ala Val Ile Ala Ser His Ile
    50                  55                  60

Gln Glu Ser Arg Phe Leu Tyr Pro Gly Lys Asn Gly Arg Leu Gly Asp
65                  70                  75                  80

Phe Phe Gly Asp Pro Gly Asn Pro Pro Glu Phe Asn Pro Ser Gly Ser
                85                  90                  95

Lys Asp Gly Lys Tyr Glu Leu Leu Thr Ser Ala Asn Glu Val Ile Val
            100                 105                 110

Glu Glu Ile Lys Asp Leu Met Thr Lys Ser Asp Ile Lys Gly Gln His
        115                 120                 125

Thr Glu Thr Leu Leu Ala Gly Ser Leu Ala Lys Ala Leu Cys Tyr Ile
    130                 135                 140

His Arg Met Asn Lys Glu Val Lys Asp Asn Gln Glu Met Lys Ser Arg
145                 150                 155                 160

Ile Leu Val Ile Lys Ala Ala Glu Asp Ser Ala Leu Gln Tyr Met Asn
                165                 170                 175

Phe Met Asn Val Ile Phe Ala Ala Gln Lys Gln Asn Ile Leu Ile Asp
            180                 185                 190

Ala Cys Val Leu Asp Ser Asp Ser Gly Leu Leu Gln Gln Ala Cys Asp
        195                 200                 205

Ile Thr Gly Gly Leu Tyr Leu Lys Val Pro Gln Met Pro Ser Leu Leu
    210                 215                 220

Gln Tyr Leu Leu Trp Val Phe Leu Pro Asp Gln Asp Gln Arg Ser Gln
225                 230                 235                 240

Leu Ile Leu Pro Pro Pro Val His Val Asp Tyr Arg Ala Ala Cys Phe
                245                 250                 255

Cys His Arg Asn Leu Ile Glu Ile Gly Tyr Val Cys Ser Val Cys Leu
            260                 265                 270

Ser Ile Phe Cys Asn Phe Ser Pro Ile Cys Thr Thr Cys Glu Thr Ala
        275                 280                 285

Phe Lys Ile Ser Leu Pro Pro Val Leu Lys Ala Lys Lys Lys Lys Leu
    290                 295                 300

Lys Val Ser Ala
305
```

<210> SEQ ID NO 11
<211> LENGTH: 1736
<212> TYPE: DNA
<213> ORGANISM: Homo sapiens

<400> SEQUENCE: 11

```
cttttccact cctcccctta cctcccttct cttctgaatt ctccattctg ggctcttgcc     60

tgtgaaatct ttctttgctt tccccatctt ttcctcgcat tttttcacca tctttccctc    120

aatctccagg agccaatgcg agactttggc tccgattaag cgacggcccg agactcgggg    180

tgcgcgagga ggatcgacag agtggtgatg gagagcaccc cttcaagggg actgaaccga    240

gtacacctac aatgcaggaa tctgcaggaa ttcttagggg gcctgagccc tggggtattg    300

gaccgattgt atgggcaccc tgccacatgt ctggctgtct tcagggagct cccatccttg    360

gctaagaact gggtgatgcg gatgctcttt ctggagcagc ctttgccaca ggctgctgta    420
```

```
gctctgtggg taaagaagga attcagcaag gctcaggagg aaagtacagg gctgctgagc     480
ggcctccgga tctggcacac acagctgctc ccaggcgggc tccagggcct catcctcaac     540
cccattttcc gccagaacct ccgcattgcc cttctgggtg gggggaaggc ctggtctgat     600
gacacaagtc agctgggacc agacaagcat gcccgggacg ttccctccct tgacaagtac     660
gccgaggagc gatgggaggt ggtcttgcac ttcatggtgg gctcccccag tgcagctgtc     720
agccaggact tggctcagct cctcagccag gctgggctca tgaagagtac tgaacctgga     780
gagccgccct gcattacttc cgctggcttc cagttcctgt tgctggacac cccggctcag     840
ctctggtact ttatgttgca gtatttgcag acagcccaga gccggggcat ggacctggta     900
gagattctct ccttcctctt ccagctcagc ttctctactc tgggcaagga ttactctgtg     960
gaaggtatga gtgattctct gttgaacttc ctgcaacatc tgcgtgagtt tgggcttgtt    1020
ttccagagga agaggaaatc tcggcgttac taccccacac gcctggccat caatctctca    1080
tcaggtgtct ctggagctgg gggcactgtg catcagccag gtttcattgt cgtggaaacc    1140
aattaccgac tgtatgccta cacggagtcg gagctgcaga ttgccctcat tgccctcttc    1200
tctgagatgc tctatcggtt ccccaacatg gtggtggcgc aggtgacccg ggagagtgtg    1260
cagcaggcaa tcgccagtgg catcacagcc cagcagataa tccatttcct aaggacaaga    1320
gcccacccag tgatgctcaa acagacacct gtgctgcccc ccaccatcac cgaccagatc    1380
cggctctggg agctggaaag ggacagactc cggttcactg agggtgtcct gtataaccag    1440
ttcctgtcgc aagtggactt tgagctgctg ctggcccacg cgcgggagct gggcgtgctc    1500
gtgttcgaga actcggccaa gcggctcatg gtggtgaccc cggccgggca cagcgacgtc    1560
aagcgctttt ggaagcggca gaaacatagc tcctgagagc gcgggacttg gacacggacc    1620
tcggcgggcg ggactgggcg gggcggggca tcagaactca ggtgtttttt atttacgcgt    1680
cagggctttt cttgtttaat aaagttatga tagctaaaaa aaaaaaaaaa aaaaaa        1736
```

<210> SEQ ID NO 12
<211> LENGTH: 462
<212> TYPE: PRT
<213> ORGANISM: Homo sapiens

<400> SEQUENCE: 12

```
Met Glu Ser Thr Pro Ser Arg Gly Leu Asn Arg Val His Leu Gln Cys
1               5                   10                  15

Arg Asn Leu Gln Glu Phe Leu Gly Gly Leu Ser Pro Gly Val Leu Asp
            20                  25                  30

Arg Leu Tyr Gly His Pro Ala Thr Cys Leu Ala Val Phe Arg Glu Leu
        35                  40                  45

Pro Ser Leu Ala Lys Asn Trp Val Met Arg Met Leu Phe Leu Glu Gln
    50                  55                  60

Pro Leu Pro Gln Ala Ala Val Ala Leu Trp Val Lys Lys Glu Phe Ser
65                  70                  75                  80

Lys Ala Gln Glu Glu Ser Thr Gly Leu Leu Ser Gly Leu Arg Ile Trp
                85                  90                  95

His Thr Gln Leu Leu Pro Gly Gly Leu Gln Gly Leu Ile Leu Asn Pro
            100                 105                 110

Ile Phe Arg Gln Asn Leu Arg Ile Ala Leu Leu Gly Gly Gly Lys Ala
        115                 120                 125

Trp Ser Asp Asp Thr Ser Gln Leu Gly Pro Asp Lys His Ala Arg Asp
    130                 135                 140
```

```
Val Pro Ser Leu Asp Lys Tyr Ala Glu Glu Arg Trp Glu Val Val Leu
145                 150                 155                 160

His Phe Met Val Gly Ser Pro Ser Ala Ala Val Ser Gln Asp Leu Ala
                165                 170                 175

Gln Leu Leu Ser Gln Ala Gly Leu Met Lys Ser Thr Glu Pro Gly Glu
            180                 185                 190

Pro Pro Cys Ile Thr Ser Ala Gly Phe Gln Phe Leu Leu Leu Asp Thr
        195                 200                 205

Pro Ala Gln Leu Trp Tyr Phe Met Leu Gln Tyr Leu Gln Thr Ala Gln
    210                 215                 220

Ser Arg Gly Met Asp Leu Val Glu Ile Leu Ser Phe Leu Phe Gln Leu
225                 230                 235                 240

Ser Phe Ser Thr Leu Gly Lys Asp Tyr Ser Val Glu Gly Met Ser Asp
                245                 250                 255

Ser Leu Leu Asn Phe Leu Gln His Leu Arg Glu Phe Gly Leu Val Phe
            260                 265                 270

Gln Arg Lys Arg Lys Ser Arg Arg Tyr Tyr Pro Thr Arg Leu Ala Ile
        275                 280                 285

Asn Leu Ser Ser Gly Val Ser Gly Ala Gly Gly Thr Val His Gln Pro
    290                 295                 300

Gly Phe Ile Val Val Glu Thr Asn Tyr Arg Leu Tyr Ala Tyr Thr Glu
305                 310                 315                 320

Ser Glu Leu Gln Ile Ala Leu Ile Ala Leu Phe Ser Glu Met Leu Tyr
                325                 330                 335

Arg Phe Pro Asn Met Val Val Ala Gln Val Thr Arg Glu Ser Val Gln
            340                 345                 350

Gln Ala Ile Ala Ser Gly Ile Thr Ala Gln Gln Ile Ile His Phe Leu
        355                 360                 365

Arg Thr Arg Ala His Pro Val Met Leu Lys Gln Thr Pro Val Leu Pro
    370                 375                 380

Pro Thr Ile Thr Asp Gln Ile Arg Leu Trp Glu Leu Glu Arg Asp Arg
385                 390                 395                 400

Leu Arg Phe Thr Glu Gly Val Leu Tyr Asn Gln Phe Leu Ser Gln Val
                405                 410                 415

Asp Phe Glu Leu Leu Leu Ala His Ala Arg Glu Leu Gly Val Leu Val
            420                 425                 430

Phe Glu Asn Ser Ala Lys Arg Leu Met Val Val Thr Pro Ala Gly His
        435                 440                 445

Ser Asp Val Lys Arg Phe Trp Lys Arg Gln Lys His Ser Ser
    450                 455                 460
```

<210> SEQ ID NO 13
<211> LENGTH: 7503
<212> TYPE: DNA
<213> ORGANISM: Homo sapiens

<400> SEQUENCE: 13

```
ggcgcactct gccggcaacg ccgaggcgct tctgcatctg tgggccgagc attcttcagg      60

tcatctgaac cttctgagaa aacatggtca acgtcttgaa aggagtgctt atagaatgtg     120

atcctgccat gaagcagttt ctgctgtact tggatgagtc caatgccctg ggaagaagt      180

tcatcattca agacattgat gacactcacg tctttgtaat agcagaattg gttaatgtcc     240

tccaggagcg agtgggtgaa ttaatggacc aaaatgcttt ttcccttacc cagaaatgaa     300
```

-continued

```
aatactcaat atggaccatt taggaattat aagcagcaac tgtgaaagac ttgccactca    360
atatcttagg tgactgatta gacatagagg gttgttttag gagcatgcca cgggaaagac    420
tgagggatca tgatcatttg ttcagaaaaa aagcccctga actgattttg ttaccataga    480
atttaaaaaa aaaaaaagct ttaacagttg gctgtaattt ggcttttatt atcctttatt    540
aaaatacaaa tgtcaatgct tttcctgcct ttttaatacc atgtcagtgt aacataggta    600
tttattttgc tcatccctgt gatctgtgca tttttgctgc gtggatgtga ttgtttggtt    660
tcagttagaa acgtcataga tttgctgttt gaatatgcca aggtggggac ttagacatta    720
tgtacgtctc acaaatccta cctgcatacc agtcagctct attgaggaag acaatgtaaa    780
actaatgtaa actacagttt gcatttccct gaaaacagaa tattgttttt aagagggtta    840
gaaacaacca gtgggaaagg cacatgctgc tttgtttagt ttttccttgt tcaaactttg    900
ttggtcacat tttcccatct gtattctttt ttattaagaa aacagcttag ggaggctgag    960
gtgggaggat tgcttgagcc caggagtccg aggttgctac aaaaacacca ttgcactctg   1020
gcctggacaa cagagagacc ctgcctcaaa aaaaaaaaaa aaaaaaaaaa aaattctact   1080
tgtaccttat tccctatgag aatacttatc aaacttatct aaaaaagaaa aataggaaca   1140
gccatatgca aagtcagccc aacaggaaag gacatattag attaaaatac attgcggcct   1200
gggcttagtg gctcacacct gtaatcccag cactttggga ggctgaggca ggcagatcgc   1260
ttgagtccag gagtcgaaac cctgtctcta caaaaaaaaa aatacaaaaa tctgcctgtt   1320
gtcccagcca ctggggaggc tgaggtagga ggtcaaggct gcagtgaacc ttgatcattg   1380
ctactgccac tccagcctag gtgacagagt gagaccctgt ctccaaaaaa aaaagtgtat   1440
atgtatgtgt gtatatatag caagagagag ttctgtgatc aattgaaggc aaaaacagta   1500
acactgagag gggctttgct tcccttcctg aagatcatgt cattggggtg ggttcctgta   1560
aagggaattt tccaagagaa aagagaattt tcatgacctg tagactctta caaatccatt   1620
ttacctgctt ccttatggta tgtttattca aagcacctgt gtaccatatt tattcactta   1680
cacagcatta ctgaatctgg aaattttcag ttaggtatat tttacataat tcccacccat   1740
ataactcagt ccatacagtt cacagttttc attccctcat agcaatgcaa aaaattttga   1800
tgagttacta ctactaaaac tagttaagta aaagatgatt cttaagaatt tccaggctgg   1860
gcacggtggc tcacgcctgt aatcccagca ctttgggagg ctgaggcagg cagctcacga   1920
ggtcaggaga tcgagaccat cctgctcggt gaaaccccat ctctattaaa aatacaaaaa   1980
attagccggg cctggtggcg ggtgcctgta gtcccatcta ctcaggaggc tgaggcagga   2040
gaatggcgtg aacccgggag gcggagcttg cagtaagctg agattgtgcc actgcactcc   2100
agcctgggcg acagagggag actccatctc aaaaaaaaaa aaaaaaaaaa atgaatttcc   2160
agctatacca aaatgttact aatgtatctt atatttcagg catgtctaaa tcaactttta   2220
gtatgcctca ggcatttgtc accaaccttt tatattaaca tgaaacttag aaaatttttg   2280
atagaatccc agagttcaaa aggtattagg atttttgcca ctgaagtaaa aaagagaaaa   2340
aaagatattt atgagaaaac tattgaacag tgactgtgtt gtacccgagc aagttagagg   2400
aacgccacac tttgagacga atttaaaagt cctttattta gctggcagcc aagaggtggc   2460
tcacacttgg aattctctca gctccgagga aggggcttga ttttccttta tactttggtt   2520
taggaagggg acgggagctc agttgcaaca attctacaga agtaaaaaca tgcaaaaaat   2580
taaaaagaca aatggttaca gagaaacaaa cagttccagg tgcaggggct ctaaatctat   2640
cataagatgt caggtgtggg ggctctgcca gacacaaact caaggcttta tggtgtatct   2700
```

cttgagcgaa atcctgggaa cttcgtacat tgcttgcttc agtaccttat gagttaattg 2760
gactctttga tatgttgaga gtcagcttac acaagttaac tccttgagga aagggggtgg 2820
gtaaggagtc cttgatgtcc tgtaaatgaa ggaaccaaat ggagttcctc cggctttctc 2880
agctaaggga gagcttattc acatggaaac aaggctaggt gattaaggga gaaagggaca 2940
gtctgaaaac aaggttagta aaaacaaggt taggtattag aactgcaaag agtattaagt 3000
gaaataagtg aaggaaaata tgagctctta tttttaaaaa gttgtgttgg ggcaaatgtt 3060
aaatatcttt ctttctctgg acattattaa gaaagataga gtgatgtgaa tgataggaag 3120
cccacctgta accacttagc tgacatgtcc aactatgggt gaacaggaaa taagcgacat 3180
tcacctaggc tgtttattgg aatctgacta gcattatttg atttggcata ctttacatgt 3240
ccagaacaag gctgttggtg cttggcacca agaaatttat gacttttttt ttttttttaa 3300
ataaagtcct aaaggtagca ttaaaatgac ttaactggag gcaggaggat cactgaagcc 3360
caggagtttg aagctgcagt aagctaagaa ggtgccactg cactgcagcc tggatgacag 3420
agtgaaactt tgtctcttaa tagaactatg gactgaagtt gtgatattga gtgttatatt 3480
tctcaataaa ggtttttttct tttaatactg tattaggtca aattcaaggt cttaattcct 3540
tgaattccaa tttccttgtg aaatttcatg tgattaattt aaaattccag ggatcctatc 3600
taacatcaca gttgatggat ataacaatgt attttgagaa atcagttttg gtgaacagta 3660
acagcattac tgataatagg caacaaacac tactgcattt tatttctgat aggcattata 3720
ggtggtaatc caaatgatta atgattttat tgctctttac attttctaga acaggtgatt 3780
tgacataatt gtactttttt ctgagaagtt ggtagtgtac ttactactct attttgcagt 3840
tatacaataa atcttactta gctgacaact aggagtaaaa gctctgacaa aaagcctctg 3900
ctgtaactaa aatactgaga tcattctatc ttaacaaact taacagatgg ggaaggggta 3960
tattttaaag atggagaaat gatgcagttt gcaaatatag tcaataaata ttctcaagtg 4020
tacgtagctc aatttcattt gcagcaaaga taacactgaa atgtctatgg atgagattat 4080
tggataaact tttttaaaaa cactgttctc aagataggca agtgattaag agcactgact 4140
gggccgggcg cggtggctca cgtctataat cctagcactt tgggaggccg aggcgggcaa 4200
atcacaaggt caggagatca aaacaatcct ggctaacaag gtgaaacccc gtctctacta 4260
aaaatacaaa aaaattagct gggcatggtg gtggacgcct gtagtcccag ctactcggga 4320
ggctgaggca ggagaatggt gtaatcccgg gaggtggagg ttgcagtgag ccgagatcgt 4380
gccactgcac tccagccggg gtgacagagc gagactccca cccatctcaa aaaaaataaa 4440
aatgaaaagc actgattgaa tctagattcc ttgagtccaa gtgtcagatc tctgcttact 4500
agctctggga tctcagatgt ttcgttgatt ggatttcttt gtgctcattt gtgtaaacag 4560
gaatgcccgt ctttaaagac tattaaaatg aatgtgagtt aacacacaag aggtcttcaa 4620
aaagttgatg gaaaatgcat attatgaaaa aaattatgca tagatttcaa aaatctttgc 4680
agcaaaataa actcatcatt ataacatgtc tgaacaggat ctagtttgag gcactaagaa 4740
ggatatcagt ttaaatagag cccctgtcag aacaatatga attctgctaa aactgaagca 4800
agaacaaaca tcaaatttat ggcaaagctt aggtggaaga atggtgcaat cattgatgct 4860
ttgcaaaaag tttatgggaa caacgcccca aggaaatcag tttacaaatg gataattcat 4920
tttaagaaag gacaagacaa tgttgaagat gaaacctaca gcagcagacc atgccacttc 4980
gtgaggaaaa aattatctca ttcatgccct acttgaagag gaccaatgat taacagcaga 5040

-continued aacgatagcc aacacaatat gctcctcagt tggttcagct tttataaatc tgactgaaaa 5100
attaaagttg agcacacttt ccactcaatg gataccaaaa ccatccagcc caggtcagct 5160
gcagacaaaa gcagagcttt cgatggaaat gtcaaacaag tgagatcaag atcctgaagc 5220
atttcttcaa agaattgtag caaaaacaga cttttaaaac cttgaattca gagacaggta 5280
taaagactgc ttggtgattt tgaaaggact gagatcattt tgggagagat catcttcaga 5340
aaatgaccag atacaacaag aatttaacat ggcagccaaa ccaacccact aacacacatt 5400
taaataagat acccaaatgc agaaagaaaa gcacagtcgt catgcaaaat agtcactact 5460
cattcaaaaa ctctatagtt gtctgagtcg ttatgctcaa aatatccaat aatatttctt 5520
ttgctgagct gtaaaataat tattttgcaa acataaaaga aaaaaaaaag aattgtaaca 5580
gaaacatggc tttaccagta tgaccctcaa gacaaaatac aaaacaatgg ctaccaagag 5640
gtggaagtgg cccagtcaca gcaagagcag attgatcaag agcaaaggtc atggtaacag 5700
ttttttggat cctcaagtca ttttgcttgt tgactttttg gagggccaaa taaagatatc 5760
atctgcttat tatgagagtg tttcgagaga aatccaaagc ttagcagaga aacgcctggg 5820
aaagcttcac cagagggtct tccaccgtga cagttcccct gcgcattcct ctcataaagc 5880
aagggcagtt tagctagaat ttctatcaaa aatcattagg tatccatctc ccagtcctga 5940
tttggctcct tctgacttct ttttgtttcc caatcttaaa aaaatccctg aagggcacct 6000
gtttttcttc agctaataaa aaagacatgg ttaatttccc aggaccctca gttctttagg 6060
gatagactga atggctggta tcattgcttg aacttaatgg agcttatgtt gagaaataaa 6120
agaaattata ttttattttt atcttttaat tctatttttc catgaacttt ttgaagtccc 6180
ctcagatata aagcagaacg ttatgaaact gagttacctt gaatctagaa gagtacaatg 6240
ataaagggga agatagaaac acacacatat gcgttgtttt ccccactttc acaatgccgt 6300
gcagaaacta acagatgaag gaggagaatc cctaaaaaca gagcattggg tagctagtcc 6360
accagcggtc tgatgctttc attgatctca aaactgtctc tgagtaactc taccaggaaa 6420
gttgtctgga gggttaacat ttctgaaacc atttttatct ttgccttcat tcttgaatga 6480
taattagtct cgaatgtttg gatcacaatc cattgaaaga ctaggctatt ttttcactgt 6540
cctcagacat ttactgagtc cagtttggac tttattttat tttatttttt ttgaaacaag 6600
atctcgctct gttgctcagg ctgaagtgca atagcgcaaa ctcggctcac tgcaacctcc 6660
caggttcaag caattctcgt gcctcagcca tccctatagg catgcgccac cacactttgc 6720
taatcttgta tttttggtag agacggggtt tgcaccatgt tggccaggct ggtctcgaac 6780
tcccaacctc aagtaatctg gcctcccaaa gtggtgggat tacaggcgtg agccagcgcg 6840
cccggcctgg acttaacttc tgaagaactc tttctgttta gattgcagga gcgttctctc 6900
ggctcatctc ttgttttctc acccagctgt tcttcttcta gttggccatc attcttcatc 6960
cctccctccc tttcctgcag ttaattattt ctttgaaatt ttaaaacttc ttaatgttgc 7020
ctggaataca tgagtcttcc tgatctcttc aaacggggtt tgttttgttt tgctttgggg 7080
agaattcttt tgacgttttt gaataagctg ttaacaactt taatacctgt cttgtttgtt 7140
ttcttcagaa atttgttaat tctccatgat tagcaccttt atgtggttat ctcattattt 7200
tcattccttt ttaattctct gttttaggaa tgcttgtcaa attcgtcact aaaattgatt 7260
tactttcttg aaaacctgtt tctgctgctc ccaacatgat ttaatcttgg ctactgagct 7320
tttggttacg ttgcactccc tttaaaatta ctccgtttaa gtacagtgtt cactctttgg 7380
gtaatgtgta caatagaagc ccaatcccca cctataccca atatatccat gggacaagca 7440
tgtacatgca ccccctgagt ctaaaataaa aattttaaaa aaactaaaaa aaaaaaaaaa 7500
aaa 7503

<210> SEQ ID NO 14
<211> LENGTH: 71
<212> TYPE: PRT
<213> ORGANISM: Homo sapiens

<400> SEQUENCE: 14

Met Val Asn Val Leu Lys Gly Val Leu Ile Glu Cys Asp Pro Ala Met
1 5 10 15

Lys Gln Phe Leu Leu Tyr Leu Asp Glu Ser Asn Ala Leu Gly Lys Lys
20 25 30

Phe Ile Ile Gln Asp Ile Asp Asp Thr His Val Phe Val Ile Ala Glu
35 40 45

Leu Val Asn Val Leu Gln Glu Arg Val Gly Glu Leu Met Asp Gln Asn
50 55 60

Ala Phe Ser Leu Thr Gln Lys
65 70

<210> SEQ ID NO 15
<211> LENGTH: 5831
<212> TYPE: DNA
<213> ORGANISM: Homo sapiens

<400> SEQUENCE: 15
gacatttcac gccgccgcca ttttgagagc gagccgagcc gagctgccgg gcgccgcgtc 60
cgctgccgga gccccgacga cgacgccgag gaggcggagg ccgcggctct cggaacgcgg 120
ccggcccgtc gcccgcccgc tccgccgctc ccgccggccc cagggcccgc aggcccgccg 180
cggccggcca ggcctcccgt ccgccgcgcc cggcccgagg cggggctgac tccgcggccc 240
ccgaccggcc gccctccgcc cccggccggc ccgcggcccc gcagccccgg ccccggcccc 300
ggcggcggga ggcgggcccc gcggcggcgg cggcggcggc cgcagcgagc gacgaggccg 360
cccggcccgg cccgccggcc gcccgcccgc ctcggcgccg agattgggcg aatcgcgagc 420
aagtacgtgc gcgtctccct gccgccgccg ccgcccgccg cgggccgccc cggggccgcc 480
gtcgccgacg acgcgcggga ggaggaggag gaggccgccc cgccgccgcc gccgccgccg 540
ccgccccggc tcgccgccgc ccgcccgccg ggctcgcagc cccggccccc ggccgcaggc 600
gaggcccagg ccgcggccga catgaaccac cagcagcagc agcagcagca gaaagcgggc 660
gagcagcagt tgagcgagcc cgaggacatg gagatggaag cgggagatac agatgaccca 720
ccaagaatta ctcagaaccc tgtgatcaat gggaatgtgg ccctgagtga tggacacaac 780
accgcggagg aggacatgga ggatgacacc agttggcgct ccgaggcaac ctttcagttc 840
actgtggagc gcttcagcag actgagtgag tcggtcctta gccctccgtg ttttgtgcga 900
aatctgccat ggaagattat ggtgatgcca cgcttttatc cagacagacc acaccaaaaa 960
agcgtaggat tctttctcca gtgcaatgct gaatctgatt ccacgtcatg gtcttgccat 1020
gcacaagcag tgctgaagat aataaattac agagatgatg aaaagtcgtt cagtcgtcgt 1080
attagtcatt tgttcttcca taaagaaaat gattggggat tttccaattt tatggcctgg 1140
agtgaagtga ccgatcctga gaaaggattt atagatgatg acaaagttac ctttgaagtc 1200
tttgtacagg cggatgctcc ccatggagtt gcgtgggatt caaagaagca cacaggctac 1260
gtcggcttaa agaatcaggg agcgacttgt tacatgaaca gcctgctaca gacgttattt 1320
ttcacgaatc agctacgaaa ggctgtgtac atgatgccaa ccgaggggga tgattcgtct 1380
aaaagcgtcc ctttagcatt acaaagagtg ttctatgaat tacagcatag tgataaacct 1440
gtaggaacaa aaaagttaac aaagtcattt gggtgggaaa ctttagatag cttcatgcaa 1500
catgatgttc aggagctttg tcgagtgttg ctcgataatg tggaaaataa gatgaaaggc 1560
acctgtgtag agggcaccat acccaaatta ttccgcggca aaatggtgtc ctatatccag 1620
tgtaaagaag tagactatcg gtctgataga agagaagatt attatgatat ccagctaagt 1680
atcaaaggaa agaaaaatat atttgaatca tttgtggatt atgtggcagt agaacagctc 1740
gatggggaca ataaatacga cgctggggaa catggcttac aggaagcaga gaaaggtgtg 1800
aaattcctaa cattgccacc agtgttacat ctacaactga tgagatttat gtatgaccct 1860
cagacggacc aaaatatcaa gatcaatgat aggtttgaat tcccagagca gttaccactt 1920
gatgaatttt tgcaaaaaac agatcctaag gaccctgcaa attatattct tcatgcagtc 1980
ctggttcata gtggagataa tcatggtgga cattatgtgg tttatctaaa ccccaaaggg 2040
gatggcaaat ggtgtaaatt tgatgacgac gtggtgtcaa ggtgtactaa agaggaagca 2100
attgagcaca attatggggg tcacgatgac gacctgtctg ttcgacactg cactaatgct 2160
tacatgttag tctacatcag ggaatcaaaa ctgagtgaag ttttacaggc ggtcaccgac 2220
catgatattc ctcagcagtt ggtggagcga ttacaagaag agaaaaggat cgaggctcag 2280
aagcggaagg agcggcagga agcccatctc tatatgcaag tgcagatagt cgcagaggac 2340
cagttttgtg gccaccaagg gaatgacatg tacgatgaag aaaaagtgaa atacactgtg 2400
ttcaaagtat tgaagaactc ctcgcttgct gagtttgttc agagcctctc tcagaccatg 2460
ggatttccac aagatcaaat tcgattgtgg cccatgcaag caaggagtaa tggaacaaaa 2520
cgaccagcaa tgttagataa tgaagccgac ggcaataaaa caatgattga gctcagtgat 2580
aatgaaaacc cttggacaat attcctggaa acagttgatc ccgagctggc tgctagtgga 2640
gcgaccttac ccaagtttga taaagatcat gatgtaatgt tatttttgaa gatgtatgat 2700
cccaaaacgc ggagcttgaa ttactgtggg catatctaca caccaatatc ctgtaaaata 2760
cgtgacttgc tcccagttat gtgtgacaga gcaggattta ttcaagatac tagccttatc 2820
ctctatgagg aagttaaacc gaatttaaca gagagaattc aggactatga cgtgtctctt 2880
gataaagccc ttgatgaact aatggatggt gacatcatag tatttcagaa ggatgaccct 2940
gaaaatgata acagtgaatt acccaccgca aaggagtatt tccgagatct ctaccaccgc 3000
gttgatgtca ttttctgtga taaaacaatc cctaatgatc ctggatttgt ggttacgtta 3060
tcaaatagaa tgaattattt tcaggttgca aagacagttg cacagaggct caacacagat 3120
ccaatgttgc tgcagttttt caagtctcaa ggttataggg atggcccagg taatcctctt 3180
agacataatt atgaaggtac tttaagagat cttctacagt tcttcaagcc tagacaacct 3240
aagaaacttt actatcagca gcttaagatg aaaatcacag actttgagaa caggcgaagt 3300
tttaaatgta tatggttaaa cagccaattt agggaagagg aaataacact atatccagac 3360
aagcatgggt gtgtccggga cctgttagaa gaatgtaaaa aggccgtgga gcttggggag 3420
aaagcatcag ggaaacttag gctgctagaa attgtaagct acaaaatcat tggtgttcat 3480
caagaagatg aactattaga atgtttatct cctgcaacga gccggacgtt tcgaatagag 3540
gaaatccctt tggaccaggt ggacatagac aaagagaatg agatgcttgt cacagtggcg 3600
catttccaca aagaggtctt cggaacgttc ggaatcccgt tttgctgag gatacaccag 3660

```
ggcgagcatt ttcgagaagt gatgaagcga atccagagcc tgctggacat ccaggagaag   3720
gagtttgaga agtttaaatt tgcaattgta atgatgggcc gacaccagta cataaatgaa   3780
gacgagtatg aagtaaattt gaaagacttt gagccacagc ccggtaatat gtctcatcct   3840
cggccttggc tagggctcga ccacttcaac aaagccccaa agaggagtcg ctacacttac   3900
cttgaaaagg ccattaaaat ccataactga tttccaagct ggtgtgttca aggcgaggac   3960
ggtgtgtggg tggcccctta acagcctaga actttggtgc acgtgccctc tagccgaagt   4020
cttcagcaag aggattcgct gctggtgtta attttatttt attgaggctg ttcagtttgg   4080
cttctctgta tctattgact gcccttttg agcaaaatga agatgttttt ataaagcttg   4140
gatgccaatg agagttattt tatggtaacc acagtgcaag gcaactgtca gcgcaatggg   4200
ggagaagagg ttagtggatc gggggtccct ggctcaaggt ctctgggctg tccctagtgg   4260
gcacgagtgg ctcggctgcc ttcctggggt cccgtgcacc agccctgcag ctagcaagtc   4320
ttgtgtttag gctcgtctga cctatttcct tcagttatac tttcaatgac cttttgtgca   4380
tctgttaagg caaaacagag aaactcacaa cctaataaat agcgctcttc ccttcattgt   4440
gtgcattgtc ggcccttcct cgggttctcc tcctccagct gcctgggggc tttttaataa   4500
acttgtctca cctcgtcagc cactactgtc tgcagcccct ttgcaaagtg gatgcactga   4560
atacagtccg gacagacatt gtgggggtct ttttattaaa tcaagaacat tgttaaattc   4620
aattaaggtt tactctgctg ccttggcaga cttacgatct caacagttca tacgagcagg   4680
tgaaaggatt ataaatagaa tttcgttaaa gtggaacaga cgacaagaaa gccttttagc   4740
aagagggcat gctcactagt ggttagtaag ctgtcgactt tgtaaaaaag ttaaaaatga   4800
aaaaaaaagg aaaaatgaat tgtatattta atgaatgaac atgtacaatt tgccactggg   4860
aggaggttcc tttttgttgg gtgagtctgc aagtgaattt cactgatgtt gatattcatt   4920
gtgtgtagtt ttatttcggt cccagccccg tttcctttta ttttggagct aatgccagct   4980
gcgtgtctag ttttgagtgc agtaaaatag aatcagcaaa tcactcttat ttttcatcct   5040
tttccggtat tttttgggtt gtttctgtgg gagcagtgta caccaactct tcctgtatat   5100
tgcctttttg ctggaaaatg ttgtatgttg aataaaattt tctataaaaa ttataattca   5160
gtgagttacg tggaagtgga ggaagatttc tactctccct ggaaacaggc ctgggaaacc   5220
ttggcatttg taacaaggtt tcactgagat gtacttttcc ttctaattcc gttttgcggg   5280
ggcagggtct cttgtttctt ttttttttt ttttttttt tagcctctaa ctagtcacat   5340
ttactcttaa gaaatgaaag gttttccagg agagaactgt gtacaaataa ggtgactgga   5400
gatgtgacct gatgtgtcac gaggcccttc ggggcggcag gcgctatcgt gggcgtggtc   5460
cttgcaccgt cccatcggcc ttgccttcca gctccgtggc acggtttcct ggtctttggg   5520
ccagtgtgta ccttggagtg acttcctttc tcaacttcca ctgcagtgtg tgtgccttct   5580
gctctgagag ctgccttgtg acccgtgtga tagaaagcag ggagtgaggg tccccgcgga   5640
cctggccctt ccctccttcc tcccccagaa agaggagtta gagcaggggt gcgagagccg   5700
ttcgctgtgg gtttgtcttt gaacaaacat taaggtgtct tgtttttgtt ctgggctggg   5760
ggttggctgt agtcttaggt aactgaaagt tcctactctc ccttaaggta ttaaatgact   5820
ctttttccaa a                                                        5831
```

<210> SEQ ID NO 16
<211> LENGTH: 1102
<212> TYPE: PRT
<213> ORGANISM: Homo sapiens

<400> SEQUENCE: 16

Met Asn His Gln Gln Gln Gln Gln Gln Gln Lys Ala Gly Glu Gln Gln
1 5 10 15

Leu Ser Glu Pro Glu Asp Met Glu Met Glu Ala Gly Asp Thr Asp Asp
20 25 30

Pro Pro Arg Ile Thr Gln Asn Pro Val Ile Asn Gly Asn Val Ala Leu
35 40 45

Ser Asp Gly His Asn Thr Ala Glu Glu Asp Met Glu Asp Asp Thr Ser
50 55 60

Trp Arg Ser Glu Ala Thr Phe Gln Phe Thr Val Glu Arg Phe Ser Arg
65 70 75 80

Leu Ser Glu Ser Val Leu Ser Pro Pro Cys Phe Val Arg Asn Leu Pro
85 90 95

Trp Lys Ile Met Val Met Pro Arg Phe Tyr Pro Asp Arg Pro His Gln
100 105 110

Lys Ser Val Gly Phe Phe Leu Gln Cys Asn Ala Glu Ser Asp Ser Thr
115 120 125

Ser Trp Ser Cys His Ala Gln Ala Val Leu Lys Ile Ile Asn Tyr Arg
130 135 140

Asp Asp Glu Lys Ser Phe Ser Arg Arg Ile Ser His Leu Phe Phe His
145 150 155 160

Lys Glu Asn Asp Trp Gly Phe Ser Asn Phe Met Ala Trp Ser Glu Val
165 170 175

Thr Asp Pro Glu Lys Gly Phe Ile Asp Asp Asp Lys Val Thr Phe Glu
180 185 190

Val Phe Val Gln Ala Asp Ala Pro His Gly Val Ala Trp Asp Ser Lys
195 200 205

Lys His Thr Gly Tyr Val Gly Leu Lys Asn Gln Gly Ala Thr Cys Tyr
210 215 220

Met Asn Ser Leu Leu Gln Thr Leu Phe Phe Thr Asn Gln Leu Arg Lys
225 230 235 240

Ala Val Tyr Met Met Pro Thr Glu Gly Asp Asp Ser Ser Lys Ser Val
245 250 255

Pro Leu Ala Leu Gln Arg Val Phe Tyr Glu Leu Gln His Ser Asp Lys
260 265 270

Pro Val Gly Thr Lys Lys Leu Thr Lys Ser Phe Gly Trp Glu Thr Leu
275 280 285

Asp Ser Phe Met Gln His Asp Val Gln Glu Leu Cys Arg Val Leu Leu
290 295 300

Asp Asn Val Glu Asn Lys Met Lys Gly Thr Cys Val Glu Gly Thr Ile
305 310 315 320

Pro Lys Leu Phe Arg Gly Lys Met Val Ser Tyr Ile Gln Cys Lys Glu
325 330 335

Val Asp Tyr Arg Ser Asp Arg Arg Glu Asp Tyr Tyr Asp Ile Gln Leu
340 345 350

Ser Ile Lys Gly Lys Lys Asn Ile Phe Glu Ser Phe Val Asp Tyr Val
355 360 365

Ala Val Glu Gln Leu Asp Gly Asp Asn Lys Tyr Asp Ala Gly Glu His
370 375 380

Gly Leu Gln Glu Ala Glu Lys Gly Val Lys Phe Leu Thr Leu Pro Pro
385 390 395 400

Val Leu His Leu Gln Leu Met Arg Phe Met Tyr Asp Pro Gln Thr Asp

```
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
        435                 440                 445

Ile Leu His Ala Val Leu Val His Ser Gly Asp Asn His Gly Gly His
    450                 455                 460

Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Asp Leu Ser Val Arg His Cys Thr Asn
            500                 505                 510

Ala Tyr Met Leu Val Tyr Ile Arg Glu Ser Lys Leu Ser Glu Val Leu
        515                 520                 525

Gln Ala Val Thr Asp His Asp Ile Pro Gln Gln Leu Val Glu Arg Leu
    530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
    610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
    690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765

Gln Lys Asp Asp Pro Glu Asn Asp Asn Ser Glu Leu Pro Thr Ala Lys
    770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830
```

```
Asp Pro Met Leu Leu Gln Phe Phe Lys Ser Gln Gly Tyr Arg Asp Gly
        835                 840                 845

Pro Gly Asn Pro Leu Arg His Asn Tyr Glu Gly Thr Leu Arg Asp Leu
    850                 855                 860

Leu Gln Phe Phe Lys Pro Arg Gln Pro Lys Lys Leu Tyr Tyr Gln Gln
865                 870                 875                 880

Leu Lys Met Lys Ile Thr Asp Phe Glu Asn Arg Arg Ser Phe Lys Cys
                885                 890                 895

Ile Trp Leu Asn Ser Gln Phe Arg Glu Glu Glu Ile Thr Leu Tyr Pro
            900                 905                 910

Asp Lys His Gly Cys Val Arg Asp Leu Leu Glu Glu Cys Lys Lys Ala
        915                 920                 925

Val Glu Leu Gly Glu Lys Ala Ser Gly Lys Leu Arg Leu Leu Glu Ile
    930                 935                 940

Val Ser Tyr Lys Ile Ile Gly Val His Gln Glu Asp Glu Leu Leu Glu
945                 950                 955                 960

Cys Leu Ser Pro Ala Thr Ser Arg Thr Phe Arg Ile Glu Glu Ile Pro
                965                 970                 975

Leu Asp Gln Val Asp Ile Asp Lys Glu Asn Glu Met Leu Val Thr Val
            980                 985                 990

Ala His Phe His Lys Glu Val Phe  Gly Thr Phe Gly Ile  Pro Phe Leu
        995                 1000                 1005

Leu Arg  Ile His Gln Gly Glu  His Phe Arg Glu Val  Met Lys Arg
    1010                 1015                 1020

Ile Gln  Ser Leu Leu Asp Ile  Gln Glu Lys Glu Phe  Glu Lys Phe
    1025                 1030                 1035

Lys Phe  Ala Ile Val Met Met  Gly Arg His Gln Tyr  Ile Asn Glu
    1040                 1045                 1050

Asp Glu  Tyr Glu Val Asn Leu  Lys Asp Phe Glu Pro  Gln Pro Gly
    1055                 1060                 1065

Asn Met  Ser His Pro Arg Pro  Trp Leu Gly Leu Asp  His Phe Asn
    1070                 1075                 1080

Lys Ala  Pro Lys Arg Ser Arg  Tyr Thr Tyr Leu Glu  Lys Ala Ile
    1085                 1090                 1095

Lys Ile  His Asn
    1100
```

<210> SEQ ID NO 17
<211> LENGTH: 4674
<212> TYPE: DNA
<213> ORGANISM: Homo sapiens

<400> SEQUENCE: 17

```
gccagggcgt gtcccgtgtg cccgagagcg ccggcggcgg ggccggaggg cgggccctgg      60

gccgagtgac aggccgcagc cccccgagca ccgtcgaagc cggcgcgccc gcccggtgca     120

gccgctgtgc gagagcgacc ccgcggtcca agcctcgcgt ggccctgccg ggccccttct     180

ttccccgagt agggcgcagc ttcccagcct ccgccccggc ctcgcctggc gcttccttcc     240

gggtccttcg gcctttccct ggcggtgcgg caggccctcg cctcatccca ccaggcacgc     300

cgcggtgctc ggccctgggt atccgggcag gctgcctccg ttagggccgc ccctgctctc     360

cggacgcgac ttttcattgg tctcagaatt tcttggctcc tcttggcctc tgcagccttg     420

ctggaggctg ccctgcggaa tctgaatatg gatcagaaac tttcgaagtt ggtagaagag     480
```

-continued

```
ctcacaactt caggagaacc ccgactaaat cctgagaaaa tgaaggaact gaagaaaatt    540
tgcaagtctt cagaggagca gctgagccgc gcctaccgcc tgctgatagc acagctgacc    600
caggagcacg ccgagatccg tctctcagcc ttccagattg tggaggaact cttcgtcagg    660
tctcaccagt tccggatgct ggttgtttcc aacttccagg agttcctgga gctcacgctg    720
ggcacagacc ccgcacagcc tctgccgccc cccagggagg cggcacagag gctgaggcag    780
gcgaccaccc gggccgtgga agggtggaat gagaagtttg gggaggccta caagaagctt    840
gccttgggct accacttctt aagacacaac aaaaaggtgg attttcaaga cacgaatgct    900
cggagtctgg cagaaaggaa gagagaagag gagaagcaga agcacttgga taaaatttat    960
caagaaagag ccagccaggc ggagagggag atgcaagaaa tgtctggaga aattgaatcc   1020
tgcttgacgg aggtagagag ctgctttagg ctgctggtgc cttttgactt tgacccgaac   1080
ccggagacgg aatcccttgg catggcttct ggcatgtccg atgcccttcg ctcctcctgc   1140
gcgggccagg tgggcccctg ccggtctggc acccctgacc cccgggacgg ggagcagccc   1200
tgctgcagta gagacctgcc tgcctctgca ggccaccccca gagcgggcgg cggggcacag   1260
ccatcccaga cagccacagg tgacccctca gatgaggacg aggacagcga cctcgaggag   1320
tttgtgcgga gccacgggct gggctcgcac aagtacacgc tggatgtgga gctctgctca   1380
gagggcctga aggtgcagga gaacgaggac aaccttgctc tcatccacgc cgcccgcgac   1440
acactcaagc tcatccggaa caagttcctg ccggctgtgt gctcgtggat ccagcgcttc   1500
acccgcgtcg ggacccacgg tggatgttta aagcgtgcca ttgacctgaa ggctgaattg   1560
gagctcgtac tgagaaaata caaggagctg gacatcgagc ctgagggagg ggaaaggcgc   1620
aggacagaag ccctgggggga tgcggaggaa gatgaggacg atgaggactt tgtggaggtc   1680
cctgagaagg aggggtatga gccacacatc cccgaccact tgcggcctga gtatgggctg   1740
gaggcagcac cagagaaaga cacagttgtg cggtgcttgc ggacgaggac gaggatggac   1800
gaggaggtgt cggaccccac ctctgcggct gctcagctgc ggcagctccg ggaccacttg   1860
cctccaccct catctgccag cccctccaga gcgttgccag agccacagga ggcccagaag   1920
ctggcagcag agcgggcccg ggcgcctgtg gtgccctacg gcgtggacct gcactactgg   1980
ggccaggagc tccccacagc cgggaagatt gtcaagtctg actcccagca ccgcttctgg   2040
aagcccagcg aggtggagga ggaagtggtc aatgccgaca tctccgagat gctccggagc   2100
cgccacatca cttttgccgg gaagtttgag cctgtgcagc actggtgccg tgccccgagg   2160
ccagacggcc ggctctgtga gcgccaagac cggctgaagt gccctttcca tgggaagatt   2220
gttccacggg acgacgaagg acggccgctc gacccggaag acagggctcg tgagcagcgg   2280
cggcagctgc agaagcagga gcgcccggaa tggcaggacc ctgagttgat gagagacgtg   2340
gaagcagcca cagggcagga tctcggctca tccaggtaca gcgggaaagg caggggggaag   2400
aagaggaggt accccagcct caccaacctg aaggctcagg ctgataccgc ccgcgctcgc   2460
attgggagaa aagtcttcgc caaggcagct gtgcggaggg tagtggcagc catgaaccgg   2520
atggaccaga agaagcacga gaagttttca aaccagttta actacgcact gaactagaga   2580
gcggggccca gtgcactggc catcagcact ttctccctct gccagtgtct caggacagca   2640
gagtgggcgt gggtctgggc agtaaccatg ctttgtctat tactgtgttt gatgtaaaga   2700
aatggtgtgt tgcaatgccc tgaaggtacg gccgctctgc tgctacaggg ttcggcatcg   2760
tctggtgatg ggtctggcct cgcagaagag gccctcgggc ctggagatgt gaacacaggc   2820
agcgaccctg ttccagaggg cttctgcgag tcctcgtgag accagtgctt gtcgtggtgt   2880
```

-continued

```
ggggttcagc acggacggaa tgtgtgtgca gctcagcctt cagagcgtgc attccccagc   2940

caggaggcga ccactcagag gaactctggg aaacccactt ttgtgcaaat gctgttttta   3000

acacaaacac aaaggctagt gaaccgttca gtcatctgct ttctgtttct ggatgtgcct   3060

tttcatacat gtgtcctctt gtccctggct tcttacactt ggcgttgttt ttaaggttta   3120

tccatgcagt tcccctccaa tgtataaaac aaaggaggtg aaaacctgtc catgcggaag   3180

cttgtgcacc catgttcaca gcagcattgg agaaggatac cgaacatctt ctcgtgggct   3240

tactggccat ttgtgtatct cctttggaga ggagtctatt caaacctctt gcctattttt   3300

aattgaatga tttatcttga gttgtaacag ttgttttttt tgtttttcct tttagagatg   3360

ggcttttgct cttacccagg ctgagtgcag tggcagaatc atagctcagt gcagcctcaa   3420

actcctgggc tcaagccatc cttccacgtc agcctcccag gtagctggga ctacaggcac   3480

acaccacaac acctggctaa tttttttaaat tttttgtaga gatgaggtct cactgtgttg   3540

cccacggtga tctcgaactc ctagcctcaa gcgatcctcc tgcttcggtc tcccaaagtg   3600

ttgggattac aggcatgagc caccactcct ggccaggagt ttatatgtat actgtggata   3660

ctagatcctc atgtgatttg caaaaacttt atttatttat ttatttattt ttgaaatgga   3720

atcttgctct gtcgccaggc tggagtgcaa tggcgtgatc tcggctcact gcaactacca   3780

cctcctgggt tcaagcgatt cgcctgcgtc agcgtcctga gtagctggga ctacaggcgc   3840

gcaccaccac gcccagctaa tttttgtatt tttagtagag acgggatttc actgtgttgg   3900

ctgggatggt cttgatctct tgacctcgtg atccacccac ctcggcctcc catagtgctg   3960

ggattacagg tgtgagccac cgcactcagc tgatttgcaa aaactttctt ccatactgtt   4020

gtttcacttt ctggatagtg tcctctgaag cacaaaagtt aattttgatg aagtacagca   4080

atttatctgt tttttttcttt tgttgcttat gcttttgctg tcacatttca gaagccatca   4140

cctaatccaa gatcacagag atttacacct agtttctaat aagcatttta taatttcagc   4200

tcttatgtgt agatctttga tccattgtga attaagtttt gtgtgtggtg taagagccca   4260

cattcttttg catgtggata tccagttgtc ccagcaccat ttgttgaaaa cattattttt   4320

ccccattgaa ttatcttcgc accattattg ataatcagtt gaccaaaaat gtacaggctt   4380

atttctgggc acttgactct attccattga cctgtttaac cttatgccag tgccacagtg   4440

ccttgatcag tgctgctttg ttgtgagaag ttttactttg ttctgcttca aggctgtttt   4500

gactcttctg catctcttgc atttccaaat gaattttagg atccactcat cagtttcttc   4560

aaaaaaaaaa aaaaagcagc tgagattttt gataggaatt acattaaatc tagagattgc   4620

tttggaatgt attaccgtct taatattaaa tcttctgagt catgaaaaaa aaaa         4674
```

<210> SEQ ID NO 18
<211> LENGTH: 709
<212> TYPE: PRT
<213> ORGANISM: Homo sapiens

<400> SEQUENCE: 18

```
Met Asp Gln Lys Leu Ser Lys Leu Val Glu Glu Leu Thr Thr Ser Gly
1               5                   10                  15

Glu Pro Arg Leu Asn Pro Glu Lys Met Lys Glu Leu Lys Lys Ile Cys
            20                  25                  30

Lys Ser Ser Glu Glu Gln Leu Ser Arg Ala Tyr Arg Leu Leu Ile Ala
        35                  40                  45

Gln Leu Thr Gln Glu His Ala Glu Ile Arg Leu Ser Ala Phe Gln Ile
```

```
    50                  55                  60

Val Glu Glu Leu Phe Val Arg Ser His Gln Phe Arg Met Leu Val Val
65                  70                  75                  80

Ser Asn Phe Gln Glu Phe Leu Glu Leu Thr Leu Gly Thr Asp Pro Ala
                85                  90                  95

Gln Pro Leu Pro Pro Pro Arg Glu Ala Ala Gln Arg Leu Arg Gln Ala
            100                 105                 110

Thr Thr Arg Ala Val Glu Gly Trp Asn Glu Lys Phe Gly Glu Ala Tyr
        115                 120                 125

Lys Lys Leu Ala Leu Gly Tyr His Phe Leu Arg His Asn Lys Lys Val
    130                 135                 140

Asp Phe Gln Asp Thr Asn Ala Arg Ser Leu Ala Glu Arg Lys Arg Glu
145                 150                 155                 160

Glu Glu Lys Gln Lys His Leu Asp Lys Ile Tyr Gln Glu Arg Ala Ser
                165                 170                 175

Gln Ala Glu Arg Glu Met Gln Glu Met Ser Gly Glu Ile Glu Ser Cys
            180                 185                 190

Leu Thr Glu Val Glu Ser Cys Phe Arg Leu Leu Val Pro Phe Asp Phe
        195                 200                 205

Asp Pro Asn Pro Glu Thr Glu Ser Leu Gly Met Ala Ser Gly Met Ser
    210                 215                 220

Asp Ala Leu Arg Ser Ser Cys Ala Gly Gln Val Gly Pro Cys Arg Ser
225                 230                 235                 240

Gly Thr Pro Asp Pro Arg Asp Gly Glu Gln Pro Cys Cys Ser Arg Asp
                245                 250                 255

Leu Pro Ala Ser Ala Gly His Pro Arg Ala Gly Gly Gly Ala Gln Pro
            260                 265                 270

Ser Gln Thr Ala Thr Gly Asp Pro Ser Asp Glu Asp Glu Asp Ser Asp
        275                 280                 285

Leu Glu Glu Phe Val Arg Ser His Gly Leu Gly Ser His Lys Tyr Thr
    290                 295                 300

Leu Asp Val Glu Leu Cys Ser Glu Gly Leu Lys Val Gln Glu Asn Glu
305                 310                 315                 320

Asp Asn Leu Ala Leu Ile His Ala Ala Arg Asp Thr Leu Lys Leu Ile
                325                 330                 335

Arg Asn Lys Phe Leu Pro Ala Val Cys Ser Trp Ile Gln Arg Phe Thr
            340                 345                 350

Arg Val Gly Thr His Gly Gly Cys Leu Lys Arg Ala Ile Asp Leu Lys
        355                 360                 365

Ala Glu Leu Glu Leu Val Leu Arg Lys Tyr Lys Glu Leu Asp Ile Glu
    370                 375                 380

Pro Glu Gly Gly Glu Arg Arg Arg Thr Glu Ala Leu Gly Asp Ala Glu
385                 390                 395                 400

Glu Asp Glu Asp Asp Glu Asp Phe Val Glu Val Pro Glu Lys Glu Gly
                405                 410                 415

Tyr Glu Pro His Ile Pro Asp His Leu Arg Pro Glu Tyr Gly Leu Glu
            420                 425                 430

Ala Ala Pro Glu Lys Asp Thr Val Val Arg Cys Leu Arg Thr Arg Thr
        435                 440                 445

Arg Met Asp Glu Glu Val Ser Asp Pro Thr Ser Ala Ala Ala Gln Leu
    450                 455                 460

Arg Gln Leu Arg Asp His Leu Pro Pro Pro Ser Ser Ala Ser Pro Ser
465                 470                 475                 480
```

```
Arg Ala Leu Pro Glu Pro Gln Glu Ala Gln Lys Leu Ala Ala Glu Arg
                485                 490                 495

Ala Arg Ala Pro Val Val Pro Tyr Gly Val Asp Leu His Tyr Trp Gly
            500                 505                 510

Gln Glu Leu Pro Thr Ala Gly Lys Ile Val Lys Ser Asp Ser Gln His
        515                 520                 525

Arg Phe Trp Lys Pro Ser Glu Val Glu Glu Glu Val Val Asn Ala Asp
    530                 535                 540

Ile Ser Glu Met Leu Arg Ser Arg His Ile Thr Phe Ala Gly Lys Phe
545                 550                 555                 560

Glu Pro Val Gln His Trp Cys Arg Ala Pro Arg Pro Asp Gly Arg Leu
                565                 570                 575

Cys Glu Arg Gln Asp Arg Leu Lys Cys Pro Phe His Gly Lys Ile Val
            580                 585                 590

Pro Arg Asp Asp Glu Gly Arg Pro Leu Asp Pro Glu Asp Arg Ala Arg
        595                 600                 605

Glu Gln Arg Arg Gln Leu Gln Lys Gln Glu Arg Pro Glu Trp Gln Asp
    610                 615                 620

Pro Glu Leu Met Arg Asp Val Glu Ala Ala Thr Gly Gln Asp Leu Gly
625                 630                 635                 640

Ser Ser Arg Tyr Ser Gly Lys Gly Arg Gly Lys Lys Arg Arg Tyr Pro
                645                 650                 655

Ser Leu Thr Asn Leu Lys Ala Gln Ala Asp Thr Ala Arg Ala Arg Ile
            660                 665                 670

Gly Arg Lys Val Phe Ala Lys Ala Ala Val Arg Arg Val Val Ala Ala
        675                 680                 685

Met Asn Arg Met Asp Gln Lys Lys His Glu Lys Phe Ser Asn Gln Phe
    690                 695                 700

Asn Tyr Ala Leu Asn
705


<210> SEQ ID NO 19
<211> LENGTH: 2947
<212> TYPE: DNA
<213> ORGANISM: Homo sapiens

<400> SEQUENCE: 19

tgctgtagct gccatgggca aaagagaccg agcggaccgc ggtgagacgt tgcgcgggca      60

cgctcagcca cgactgccct tgccggccct gcccccgct ctgcctcgga gctgctccgg     120

gcctctgcgc cggccgaccc tgctggccct cccgcgcgca ccccgttggg acaggccttt     180

gggcgggaga gatgctggac ctgggcgcag cccagcgaac tcggcctagg ggagacgggt     240

gaggggcgca acgcctgcgg gatgcaggtg gctcttagct aggagtttgc ggcggcgcag     300

acaagaagaa atccaggaag cggcactatg aggatgaaga ggatgatgaa gaggacgccc     360

cggggaacga ccctcaggaa gcggttccct cggcggcggg gaagcaggtg gatgagtcag     420

gcaccaaagt ggatgaatat ggagccaagg actacaggct gcaaatgccg ctgaaggacg     480

accacacctc caggcccctc tgggtggctc ccgatggcca tatcttcttg gaagccttct     540

ctccagttta caaatatgcc caagacttct tggtggctat tgcagagcca gtgtgccgac     600

caacccatgt gcatgagtac aaactaactg cctactcctt gtatgcagct gtcagcgttg     660

ggctgcaaac cagtgacatc accgagtacc tcaggaagct cagcaagact ggagtccctg     720

atggaattat gcagtttatt aagttgtgta ctgtcagcta tggaaaagtc aagctggtct     780
```

tgaagcacaa cagatacttc gttgaaagtt gccaccctga tgtaatccag catcttctcc 840
aggaccccgt gatccgagaa tgccgcttaa gaaactctga aggggaggcc actgagctca 900
tcacagagac tttcacaagc aaatctgcca tttctaagac tgctgaaagc agtggtgggc 960
cctccacttc ccgagtgaca gatccacagg gtaaatctga catccccatg gacctgtttg 1020
acttctatga gcaaatggac aaggatgaag aagaagaaga agagacacag acagtgtctt 1080
ttgaagtcaa gcaggaaatg attgaggaac tccagaaacg ttgcatccac ctggagtacc 1140
ctctgttggc agaatatgac ttccggaatg attctgtcaa ccctgatatc aacattgacc 1200
taaagcccac agctgtcctc agaccctatc aggagaagag cttgcgaaag atgtttggaa 1260
acgggcgtgc acgttcgggg gtcattgttc ttccctgcgg tgctggaaag tccctggttg 1320
gtgtgactgc tgcatgcact gtcagaaaac gctgtctggt gctgggcaac tcagctgttt 1380
ctgtggagca gtggaaagcc cagttcaaga tgtggtccac cattgacgac agccagatct 1440
gccggttcac ctccgatgcc aaggacaagc ccatcggctg ctccgttgcc attagcacct 1500
actccatgct gggccacacc accaaaaggt cctgggaggc cgagcgagtc atggagtggc 1560
tcaagaccca ggagtggggc ctcatgatcc tggatgaagt gcacaccata ccagccaaga 1620
tgttccgaag ggtgctcacc atcgtgcagg cccactgtaa gctgggtttg actgcgaccc 1680
tcgtccgcga agatgacaaa attgtggatt taaattttct gattgggcct aagctctacg 1740
aagccaactg gatggagctg cagaataatg gctacatcgc caaagtccag tgtgctgagg 1800
tctggtgccc tatgtctcct gaattttacc gggaatatgt ggcaatcaaa accaagaaac 1860
gaatcttgct gtacaccatg aaccccaaca aatttagagc ttgccagttt ctgatcaagt 1920
ttcatgaaag gaggaatgac aagattattg tctttgctga caatgtgttt gccctaaagg 1980
aatatgccat tcgactgaac aaaccctata tctacggacc tacgtctcag gggaaaagga 2040
tgcaaattct ccagaatttc aagcacaacc ccaaaattaa caccatcttc atatccaagg 2100
taggtgacac ttcgtttgat ctgccggaag caaatgtcct cattcagatc tcatcccatg 2160
gtggctccag gcgtcaggaa gcccaaaggc tagggcgggt gcttcgagct aaaaaaggga 2220
tggttgcaga agagtacaat gcctttttct actcactggt atcccaggac acacaggaaa 2280
tggcttactc aaccaagcgg cagagattct tggtagatca aggttatagc ttcaaggtga 2340
tcacgaaact cgctggcatg gaggaggaag acttggcgtt ttcgacaaaa gaagagcaac 2400
agcagctctt acagaaagtc ctggcagcca ctgacctgga tgccgaggag gaggtggtgg 2460
ctggggaatt tggctccaga tccagccagg catctcggcg ctttggcacc atgagttcta 2520
tgtctggggc cgacgacact gtgtacatgg agtaccactc atcgcggagc aaggcgccca 2580
gcaaacatgt acacccgctc ttcaagcgct ttaggaaatg atgcttaggc agggtacttc 2640
gttcaagacc ggcgcttggc acccttgttg gaaagggatt ttcagcataa cattttcctt 2700
ccacctcttt gaccttccct ccagcgttgg ccaaattgtg ctgaggaaga tgcatcaagg 2760
gcttggctgt gccttcatag gtcatctagg gttttataaa ggaggaggag acaatatttt 2820
ttcaaacttt ttggggagtg gggtcatttc tgtatataaa aaatgttaat atttaaggtg 2880
tatttatgtt accgttctga ataaacagaa tggaccattg aaccagtaaa aaaaaaaaaa 2940
aaaaaaa 2947

<210> SEQ ID NO 20
<211> LENGTH: 718
<212> TYPE: PRT

<213> ORGANISM: Homo sapiens

<400> SEQUENCE: 20

Met Pro Leu Lys Asp Asp His Thr Ser Arg Pro Leu Trp Val Ala Pro
1 5 10 15

Asp Gly His Ile Phe Leu Glu Ala Phe Ser Pro Val Tyr Lys Tyr Ala
20 25 30

Gln Asp Phe Leu Val Ala Ile Ala Glu Pro Val Cys Arg Pro Thr His
35 40 45

Val His Glu Tyr Lys Leu Thr Ala Tyr Ser Leu Tyr Ala Ala Val Ser
50 55 60

Val Gly Leu Gln Thr Ser Asp Ile Thr Glu Tyr Leu Arg Lys Leu Ser
65 70 75 80

Lys Thr Gly Val Pro Asp Gly Ile Met Gln Phe Ile Lys Leu Cys Thr
85 90 95

Val Ser Tyr Gly Lys Val Lys Leu Val Leu Lys His Asn Arg Tyr Phe
100 105 110

Val Glu Ser Cys His Pro Asp Val Ile Gln His Leu Leu Gln Asp Pro
115 120 125

Val Ile Arg Glu Cys Arg Leu Arg Asn Ser Glu Gly Glu Ala Thr Glu
130 135 140

Leu Ile Thr Glu Thr Phe Thr Ser Lys Ser Ala Ile Ser Lys Thr Ala
145 150 155 160

Glu Ser Ser Gly Gly Pro Ser Thr Ser Arg Val Thr Asp Pro Gln Gly
165 170 175

Lys Ser Asp Ile Pro Met Asp Leu Phe Asp Phe Tyr Glu Gln Met Asp
180 185 190

Lys Asp Glu Glu Glu Glu Glu Glu Thr Gln Thr Val Ser Phe Glu Val
195 200 205

Lys Gln Glu Met Ile Glu Glu Leu Gln Lys Arg Cys Ile His Leu Glu
210 215 220

Tyr Pro Leu Leu Ala Glu Tyr Asp Phe Arg Asn Asp Ser Val Asn Pro
225 230 235 240

Asp Ile Asn Ile Asp Leu Lys Pro Thr Ala Val Leu Arg Pro Tyr Gln
245 250 255

Glu Lys Ser Leu Arg Lys Met Phe Gly Asn Gly Arg Ala Arg Ser Gly
260 265 270

Val Ile Val Leu Pro Cys Gly Ala Gly Lys Ser Leu Val Gly Val Thr
275 280 285

Ala Ala Cys Thr Val Arg Lys Arg Cys Leu Val Leu Gly Asn Ser Ala
290 295 300

Val Ser Val Glu Gln Trp Lys Ala Gln Phe Lys Met Trp Ser Thr Ile
305 310 315 320

Asp Asp Ser Gln Ile Cys Arg Phe Thr Ser Asp Ala Lys Asp Lys Pro
325 330 335

Ile Gly Cys Ser Val Ala Ile Ser Thr Tyr Ser Met Leu Gly His Thr
340 345 350

Thr Lys Arg Ser Trp Glu Ala Glu Arg Val Met Glu Trp Leu Lys Thr
355 360 365

Gln Glu Trp Gly Leu Met Ile Leu Asp Glu Val His Thr Ile Pro Ala
370 375 380

Lys Met Phe Arg Arg Val Leu Thr Ile Val Gln Ala His Cys Lys Leu
385 390 395 400

-continued

Gly Leu Thr Ala Thr Leu Val Arg Glu Asp Asp Lys Ile Val Asp Leu
405 410 415

Asn Phe Leu Ile Gly Pro Lys Leu Tyr Glu Ala Asn Trp Met Glu Leu
420 425 430

Gln Asn Asn Gly Tyr Ile Ala Lys Val Gln Cys Ala Glu Val Trp Cys
435 440 445

Pro Met Ser Pro Glu Phe Tyr Arg Glu Tyr Val Ala Ile Lys Thr Lys
450 455 460

Lys Arg Ile Leu Leu Tyr Thr Met Asn Pro Asn Lys Phe Arg Ala Cys
465 470 475 480

Gln Phe Leu Ile Lys Phe His Glu Arg Arg Asn Asp Lys Ile Ile Val
485 490 495

Phe Ala Asp Asn Val Phe Ala Leu Lys Glu Tyr Ala Ile Arg Leu Asn
500 505 510

Lys Pro Tyr Ile Tyr Gly Pro Thr Ser Gln Gly Glu Arg Met Gln Ile
515 520 525

Leu Gln Asn Phe Lys His Asn Pro Lys Ile Asn Thr Ile Phe Ile Ser
530 535 540

Lys Val Gly Asp Thr Ser Phe Asp Leu Pro Glu Ala Asn Val Leu Ile
545 550 555 560

Gln Ile Ser Ser His Gly Gly Ser Arg Arg Gln Glu Ala Gln Arg Leu
565 570 575

Gly Arg Val Leu Arg Ala Lys Lys Gly Met Val Ala Glu Glu Tyr Asn
580 585 590

Ala Phe Phe Tyr Ser Leu Val Ser Gln Asp Thr Gln Glu Met Ala Tyr
595 600 605

Ser Thr Lys Arg Gln Arg Phe Leu Val Asp Gln Gly Tyr Ser Phe Lys
610 615 620

Val Ile Thr Lys Leu Ala Gly Met Glu Glu Glu Asp Leu Ala Phe Ser
625 630 635 640

Thr Lys Glu Glu Gln Gln Gln Leu Leu Gln Lys Val Leu Ala Ala Thr
645 650 655

Asp Leu Asp Ala Glu Glu Glu Val Val Ala Gly Glu Phe Gly Ser Arg
660 665 670

Ser Ser Gln Ala Ser Arg Arg Phe Gly Thr Met Ser Ser Met Ser Gly
675 680 685

Ala Asp Asp Thr Val Tyr Met Glu Tyr His Ser Ser Arg Ser Lys Ala
690 695 700

Pro Ser Lys His Val His Pro Leu Phe Lys Arg Phe Arg Lys
705 710 715

<210> SEQ ID NO 21
<211> LENGTH: 2568
<212> TYPE: DNA
<213> ORGANISM: Homo sapiens

<400> SEQUENCE: 21
ttcatgaggg aggcgggtcg accccgctgc acagtccggc cggcgccatg aagctcaacg 60
tggacgggct cctggtctac ttcccgtacg actacatcta ccccgagcag ttctcctaca 120
tgcgggagct caaacgcacg ctggacgcca agggtcatgg agtcctggag atgccctcag 180
gcaccgggaa gacagtatcc ctgttggccc tgatcatggc ataccagaga gcatatccgc 240
tggaggtgac caaactcatc tactgctcaa gaactgtgcc agagattgag aaggtgattg 300
aagagcttcg aaagttgctc aacttctatg agaagcagga gggcgagaag ctgccgtttc 360

```
tgggactggc tctgagctcc cgcaaaaact tgtgtattca ccctgaggtg acacccctgc    420
gctttgggaa ggacgtcgat gggaaatgcc acagcctcac agcctcctat gtgcgggcgc    480
agtaccagca tgacaccagc ctgccccact gccgattcta tgaggaattt gatgcccatg    540
ggcgtgaggt gcccctcccc gctggcatct acaacctgga tgacctgaag gccctggggc    600
ggcgccaggg ctggtgccca tacttccttg ctcgatactc aatcctgcat gccaatgtgg    660
tggtttatag ctaccactac ctcctggacc ccaagattgc agacctggtg tccaaggaac    720
tggcccgcaa ggccgtcgtg gtcttcgacg aggcccacaa cattgacaac gtctgcatcg    780
actccatgag cgtcaacctc acccgccgga cccttgaccg gtgccagggc aacctggaga    840
ccctgcagaa gacggtgctc aggatcaaag agacagacga gcagcgcctg cgggacgagt    900
accggcgtct ggtggagggg ctgcgggagg ccagcgccgc ccgggagacg gacgcccacc    960
tggccaaccc cgtgctgccc gacgaagtgc tgcaggaggc agtgcctggc tccatccgca   1020
cggccgagca tttcctgggc ttcctgaggc ggctgctgga gtacgtgaag tggcggctgc   1080
gtgtgcagca tgtggtgcag gagagcccgc ccgccttcct gagcggcctg gcccagcgcg   1140
tgtgcatcca gcgcaagccc ctcagattct gtgctgaacg cctccggtcc ctgctgcata   1200
ctctggagat caccgacctt gctgacttct ccccgctcac cctccttgct aactttgcca   1260
cccttgtcag cacctacgcc aaaggcttca ccatcatcat cgagcccttt gacgacagaa   1320
ccccgaccat tgccaacccc atcctgcact tcagctgcat ggacgcctcg ctggccatca   1380
aacccgtatt tgagcgtttc cagtctgtca tcatcacatc tgggacactg tccccgctgg   1440
acatctaccc caagatcctg gacttccacc ccgtcaccat ggcaaccttc accatgacgc   1500
tggcacgggt ctgcctctgc cctatgatca tcggccgtgg caatgaccag gtggccatca   1560
gctccaaatt tgagacccgg gaggatattg ctgtgatccg gaactatggg aacctcctgc   1620
tggagatgtc cgctgtggtc cctgatggca tcgtggcctt cttcaccagc taccagtaca   1680
tggagagcac cgtggcctcc tggtatgagc aggggatcct tgagaacatc cagaggaaca   1740
agctgctctt tattgagacc caggatggtg ccgaaaccag tgtcgccctg gagaagtacc   1800
aggaggcctg cgagaatggc cgcggggcca tcctgctgtc agtggcccgg ggcaaagtgt   1860
ccgagggaat cgactttgtg caccactacg ggcgggccgt catcatgttt ggcgtcccct   1920
acgtctacac acagagccgc attctcaagg cgcggctgga atacctgcgg gaccagttcc   1980
agattcgtga gaatgacttt cttaccttcg atgccatgcg ccacgcggcc cagtgtgtgg   2040
gtcgggccat caggggcaag acggactacg gcctcatggt ctttgccgac aagcggtttg   2100
cccgtgggga caagcggggg aagctgcccc gctggatcca ggagcacctc acagatgcca   2160
acctcaacct gaccgtggac gagggtgtcc aggtggccaa gtacttcctg cggcagatgg   2220
cacagccctt ccaccgggag gatcagctgg gcctgtccct gctcagcctg gagcagctag   2280
aatcagagga gacgctgaag aggatagagc agattgctca gcagctctga gtggggcggg   2340
tggggccata aacggttcct ggtgactcct gagtcttgcc tggccctggt tcccagcggc   2400
ggtggtgcta gaaggtctta tgaagtcagg tgacatttct cactgtcacg tccacagcct   2460
ttaatcgcag gagaaggcag ctatccacca ggtacccaga ggcaaggggg ggccaggaga   2520
tgatagaccc cctctcaccc caccagccca tccctcctgc actgttcc                2568
```

<210> SEQ ID NO 22
<211> LENGTH: 760
<212> TYPE: PRT

<213> ORGANISM: Homo sapiens

<400> SEQUENCE: 22

```
Met Lys Leu Asn Val Asp Gly Leu Leu Val Tyr Phe Pro Tyr Asp Tyr
1               5                   10                  15

Ile Tyr Pro Glu Gln Phe Ser Tyr Met Arg Glu Leu Lys Arg Thr Leu
            20                  25                  30

Asp Ala Lys Gly His Gly Val Leu Glu Met Pro Ser Gly Thr Gly Lys
        35                  40                  45

Thr Val Ser Leu Leu Ala Leu Ile Met Ala Tyr Gln Arg Ala Tyr Pro
    50                  55                  60

Leu Glu Val Thr Lys Leu Ile Tyr Cys Ser Arg Thr Val Pro Glu Ile
65                  70                  75                  80

Glu Lys Val Ile Glu Glu Leu Arg Lys Leu Leu Asn Phe Tyr Glu Lys
                85                  90                  95

Gln Glu Gly Glu Lys Leu Pro Phe Leu Gly Leu Ala Leu Ser Ser Arg
            100                 105                 110

Lys Asn Leu Cys Ile His Pro Glu Val Thr Pro Leu Arg Phe Gly Lys
        115                 120                 125

Asp Val Asp Gly Lys Cys His Ser Leu Thr Ala Ser Tyr Val Arg Ala
    130                 135                 140

Gln Tyr Gln His Asp Thr Ser Leu Pro His Cys Arg Phe Tyr Glu Glu
145                 150                 155                 160

Phe Asp Ala His Gly Arg Glu Val Pro Leu Pro Ala Gly Ile Tyr Asn
                165                 170                 175

Leu Asp Asp Leu Lys Ala Leu Gly Arg Arg Gln Gly Trp Cys Pro Tyr
            180                 185                 190

Phe Leu Ala Arg Tyr Ser Ile Leu His Ala Asn Val Val Val Tyr Ser
        195                 200                 205

Tyr His Tyr Leu Leu Asp Pro Lys Ile Ala Asp Leu Val Ser Lys Glu
    210                 215                 220

Leu Ala Arg Lys Ala Val Val Val Phe Asp Glu Ala His Asn Ile Asp
225                 230                 235                 240

Asn Val Cys Ile Asp Ser Met Ser Val Asn Leu Thr Arg Arg Thr Leu
                245                 250                 255

Asp Arg Cys Gln Gly Asn Leu Glu Thr Leu Gln Lys Thr Val Leu Arg
            260                 265                 270

Ile Lys Glu Thr Asp Glu Gln Arg Leu Arg Asp Glu Tyr Arg Arg Leu
        275                 280                 285

Val Glu Gly Leu Arg Glu Ala Ser Ala Ala Arg Glu Thr Asp Ala His
    290                 295                 300

Leu Ala Asn Pro Val Leu Pro Asp Glu Val Leu Gln Glu Ala Val Pro
305                 310                 315                 320

Gly Ser Ile Arg Thr Ala Glu His Phe Leu Gly Phe Leu Arg Arg Leu
                325                 330                 335

Leu Glu Tyr Val Lys Trp Arg Leu Arg Val Gln His Val Val Gln Glu
            340                 345                 350

Ser Pro Pro Ala Phe Leu Ser Gly Leu Ala Gln Arg Val Cys Ile Gln
        355                 360                 365

Arg Lys Pro Leu Arg Phe Cys Ala Glu Arg Leu Arg Ser Leu Leu His
    370                 375                 380

Thr Leu Glu Ile Thr Asp Leu Ala Asp Phe Ser Pro Leu Thr Leu Leu
385                 390                 395                 400
```

```
Ala Asn Phe Ala Thr Leu Val Ser Thr Tyr Ala Lys Gly Phe Thr Ile
                405                 410                 415

Ile Ile Glu Pro Phe Asp Asp Arg Thr Pro Thr Ile Ala Asn Pro Ile
            420                 425                 430

Leu His Phe Ser Cys Met Asp Ala Ser Leu Ala Ile Lys Pro Val Phe
        435                 440                 445

Glu Arg Phe Gln Ser Val Ile Ile Thr Ser Gly Thr Leu Ser Pro Leu
    450                 455                 460

Asp Ile Tyr Pro Lys Ile Leu Asp Phe His Pro Val Thr Met Ala Thr
465                 470                 475                 480

Phe Thr Met Thr Leu Ala Arg Val Cys Leu Cys Pro Met Ile Ile Gly
                485                 490                 495

Arg Gly Asn Asp Gln Val Ala Ile Ser Ser Lys Phe Glu Thr Arg Glu
            500                 505                 510

Asp Ile Ala Val Ile Arg Asn Tyr Gly Asn Leu Leu Leu Glu Met Ser
        515                 520                 525

Ala Val Val Pro Asp Gly Ile Val Ala Phe Phe Thr Ser Tyr Gln Tyr
    530                 535                 540

Met Glu Ser Thr Val Ala Ser Trp Tyr Glu Gln Gly Ile Leu Glu Asn
545                 550                 555                 560

Ile Gln Arg Asn Lys Leu Leu Phe Ile Glu Thr Gln Asp Gly Ala Glu
                565                 570                 575

Thr Ser Val Ala Leu Glu Lys Tyr Gln Glu Ala Cys Glu Asn Gly Arg
            580                 585                 590

Gly Ala Ile Leu Leu Ser Val Ala Arg Gly Lys Val Ser Glu Gly Ile
        595                 600                 605

Asp Phe Val His His Tyr Gly Arg Ala Val Ile Met Phe Gly Val Pro
    610                 615                 620

Tyr Val Tyr Thr Gln Ser Arg Ile Leu Lys Ala Arg Leu Glu Tyr Leu
625                 630                 635                 640

Arg Asp Gln Phe Gln Ile Arg Glu Asn Asp Phe Leu Thr Phe Asp Ala
                645                 650                 655

Met Arg His Ala Ala Gln Cys Val Gly Arg Ala Ile Arg Gly Lys Thr
            660                 665                 670

Asp Tyr Gly Leu Met Val Phe Ala Asp Lys Arg Phe Ala Arg Gly Asp
        675                 680                 685

Lys Arg Gly Lys Leu Pro Arg Trp Ile Gln Glu His Leu Thr Asp Ala
    690                 695                 700

Asn Leu Asn Leu Thr Val Asp Glu Gly Val Gln Val Ala Lys Tyr Phe
705                 710                 715                 720

Leu Arg Gln Met Ala Gln Pro Phe His Arg Glu Asp Gln Leu Gly Leu
                725                 730                 735

Ser Leu Leu Ser Leu Glu Gln Leu Glu Ser Glu Glu Thr Leu Lys Arg
            740                 745                 750

Ile Glu Gln Ile Ala Gln Gln Leu
        755                 760
```

<210> SEQ ID NO 23
<211> LENGTH: 6765
<212> TYPE: DNA
<213> ORGANISM: Homo sapiens

<400> SEQUENCE: 23

```
agagcttcca tggagtcagg gcagccggct cgacggattg ccatggcgcc gctgctggag      60
```

-continued

```
tacgagcgac agctggtgct ggaactgctc gacactgacg ggctagtagt gtgcgcccgc    120
gggctcggcg cggaccggct cctctaccac tttctccagc tgcactgcca cccagcctgc    180
ctggtgctgg tgctcaacac gcagccggcc gaggaggagt attttatcaa tcagctgaag    240
atagaaggag ttgaacacct ccctcgccgt gtaacaaatg aaatcacaag caacagtcgc    300
tatgaagttt acacacaagg tggtgttata tttgcgacaa gtaggatact tgtggttgac    360
ttcttgactg atagaatacc ttcagattta attactggca tcttggtgta tagagcccac    420
agaataatcg agtcttgtca agaagcattc atcttgcgcc tctttcgcca gaaaaacaaa    480
cgtggtttta ttaaagcttt cacagacaat gctgttgcct ttgatactgg tttttgtcat    540
gtggaaagag tgatgagaaa tctttttgtg aggaaactgt atctgtggcc aaggttccat    600
gtagcagtaa actcattttt agaacagcac aaacctgaag ttgtagaaat ccatgtttct    660
atgacaccta ccatgcttgc tatacagact gctatactgg acattttaaa tgcatgtcta    720
aaggaactaa aatgccataa cccatcgctt gaagtggaag atttatcttt agaaaatgct    780
attggaaaac cttttgacaa gacaatccgc cattatctgg atcctttgtg gcaccagctt    840
ggagccaaga ctaaatcctt agttcaggat ttgaagatat tacgaacttt gctgcagtat    900
ctctctcagt atgattgtgt cacatttctt aatcttctgg aatctctgag agcaacggaa    960
aaagcttttg gtcagaattc aggttggctg tttcttgact ccagcacctc gatgtttata   1020
aatgctcgag caagggttta tcatcttcca gatgccaaaa tgagtaaaaa agaaaaaaata   1080
tctgaaaaaa tggaaattaa agaaggggaa gaaacaaaaa aggaactggt cctagaaagc   1140
aacccaaagt gggaggcact gactgaagta ttaaaagaaa ttgaggcaga aaataaggag   1200
agtgaagctc ttggtggtcc aggtcaagta ctgatttgtg caagtgatga ccgaacatgt   1260
tcccagctga gagactatat cactcttgga gcggaggcct tcttattgag gctctacagg   1320
aaaacctttg agaaggatag caaagctgaa gaagtctgga tgaaatttag gaaggaagac   1380
agttcaaaga gaattaggaa atctcacaaa agacctaaag acccccaaaa caaagaacgg   1440
gcttctacca aagaaagaac cctcaaaaag aaaaaacgga agttgacctt aactcaaatg   1500
gtaggaaaac ctgaagaact ggaagaggaa ggagatgtcg aggaaggata tcgtcgagaa   1560
ataagcagta gcccagaaag ctgcccggaa gaaattaagc atgaagaatt tgatgtaaat   1620
ttgtcatcgg atgctgcttt cggaatcctg aaagaacccc tcactatcat ccatccgctt   1680
ctgggttgca gcgaccccta tgctctgaca agggtactac atgaagtgga gccaagatac   1740
gtggttcttt atgacgcaga gctaaccttt gttcggcagc ttgaaattta cagggcgagt   1800
aggcctggga aacctctgag ggtttacttt cttatatacg gaggttcaac tgaggaacaa   1860
cgctatctca ctgctttgcg gaaagaaaag gaagcttttg aaaaactcat aagggaaaaa   1920
gcaagcatgg ttgtccctga agaaagagaa ggcagagatg aaacaaactt agacctagta   1980
agaggcacag catctgcaga tgtttccact gacactcgga aagccggtgg ccaggaacag   2040
aatggtacac agcaaagcat agttgtggat atgcgtgaat ttcgaagtga gcttccatct   2100
ctgatccatc gtcggggcat tgacattgaa cccgtgactt tagaggttgg agattacatc   2160
ctcactccag aaatgtgcgt ggagcgcaag agtatcagtg atttaatcgg ctctttaaat   2220
aacggccgcc tctacagcca gtgcatctcc atgtcccgct actacaagcg tcccgtgctt   2280
ctgattgagt ttgaccctag caagcctttc tctctcactt cccgaggtgc cttgtttcag   2340
gagatctcca gcaatgacat tagttccaaa ctcactcttc ttacacttca cttccccaga   2400
ctacggattc tctggtgccc ctctcctcat gcaacggcgg agttgtttga ggagctgaaa   2460
```

```
caaagcaagc cacagcctga tgcggcgaca gcactggcca ttacagcaga ttctgaaacc   2520
cttcccgagt cagagaagta taatcctggt ccccaagact tcttgttaaa aatgccaggg   2580
gtgaatgcca aaaactgccg ctccttgatg caccacgtta agaacatcgc agaattagca   2640
gccctgtcac aagacgagct cacgagtatt ctggggaatg ctgcaaatgc caaacagctt   2700
tatgatttca ttcacacctc ttttgcagaa gtcgtatcaa aaggaaaagg gaaaaagtga   2760
acagtgatgg ctgttttctt atcccatgcc tgtacttttc agcggctcct tgccagacat   2820
cataggtcat tattaattat tggtttgcta tttcattctt ttccaatgct cttaatgatt   2880
gtacggtgga ccagaagcca ggattcctct ctgaactctg cagttaggca tcacttgaac   2940
ttgcctgtgc ctgctctttt tcctccctgc accgtctatg ccgggcttag catgtttctt   3000
tttaaatgag gtttgtcagg atcaggtaaa gttcctacaa gtgattacag aaggtagaaa   3060
ctttacctga tcctaacaga tctcatttag aaaggaatat gctaagcctg gcatggacgg   3120
tgcagggagg gaaaagagca ggcacaagaa agctaccatt tttaacagtc cttgttatct   3180
agtgcaacat aaataacagt cttaattgca cttataccca tgtcctgtgg ctctccaaat   3240
ctggtctttg ctgttgtgtc tgctggacgc ttgaactgat gtttgtgtag gaaatcatgt   3300
tctgaccctt tgtctacaaa ggagccttct ggaacactga gaagaaacat ctctttgcca   3360
ttcctgacca gttctctcta ccacattttc ttcagctcca tacttctgcc tgtctgctct   3420
aaggaaattt catggagcct tcctactact aattcaagac agtctcctca aaaactggtt   3480
gactagtctt ctaatgaccc taacatatgt agcatatact ataatttcat tgttccaaat   3540
tagtattttt aaagcaaaat gaattacctg tttgcaaaag ttaatgatga aggagctctt   3600
agaattctca atttttgcac atattcagtc tcctaatatc agagatccct aagtccagct   3660
ggctagttac agagtttttt cagacttcct cgtttctcag ctcttatatc ctaagacacc   3720
agcatcatat cctctagaaa tacaacctaa ttggcagtga gccgagatcg caccactgca   3780
cccctgcctg ggcgacagag tgagactttg tctctattac aaaaagaaaa gaaaagaaat   3840
acaacctaag ctcacctgcc tgtgattcct catttctcac catcctgtgc cagggtggct   3900
acttctctct gtgaggactc aaatacaagc caatgagtgg cccactaagc ttttaagatt   3960
tgattttcct gccttgagat aaaaaggagt gtaggtaaat gaaagatcaa tgtatggaat   4020
atataaaaat acgaaagaaa tatatacgtt taaaaatcca taaagaaaaa aatctcattc   4080
taaacctgat taagttggct ttttacgtaa gtgtacaaat aggatattca cagcatcttt   4140
gtgcagtttt taaactttta tatttaaaca ttattaagtt ggcttttgtt cacatgttga   4200
gtaatgggta gtaaattttc tacctcagga gctgatatag acatcagttc tgctagccat   4260
atcacatatt ttaatgtttc atcaacatca gctgtttttt tgtttgctac actatttgaa   4320
ctaatagaca gtggatcatg taacacaaaa ttgtcttcaa ctttaacaaa attgtcattg   4380
ttattttttt ttgagacaga gtctccctct gttgcccagg ctggagtgca gtggcgcaat   4440
ctcggctcac tgcaacctcg cctgctgggt tcaagcagtt ctcccacctc agcctcccaa   4500
gtagctggga ttataggtgt gcaccaccag acccggctaa tttttgtatt tttagtagag   4560
acggggtttc accatgttgg ccaggctggt ctcaaactac tgacctcagg tgatccaccc   4620
accttggcct cccaaagtgc tgagataaca ggcgtgagcc accgcaccca cccaacaaaa   4680
ttatttttaa ctgtcgtttc tgaactgaac ctctcacatt ggcatcttga tttattggta   4740
cttaacagta tatatggatt ttgaactcta cacaagggta taaccagaat gaattgaggg   4800
```

-continued

```
gtatcaagaa ccagattggt tacagtagaa ctctgtaaga tgatgtggag agtaaggaaa   4860
aggagaagaa ataaaaatta gtttaagatg gaataaagat ttgggctgct aattttttcc   4920
caggattcaa aatatacccg ctagaatgga aaacaaaaat ttgaatgatt acaacattat   4980
cgttaacatt caattttgta tttattgttt tattgaatat agttcagagt atattaaaat   5040
agacctacca cttcaaatga taatgattat tataatgtct cttcacccta ttctagcact   5100
tctgcttgca gtatgtggtt tctatttttt tcctcttgta taattccact tgcttttaat   5160
tgttgtttca ttatataaaa ggaacatctt cccatagcat attctatgaa aggggtttca   5220
ttccaagttg agttttcaaa aaaaaggtct tcctaaagct accattttca accgtccttg   5280
ttatctagta caacataaat aacagtctta aaaattgcac taataccagt gccccccctgg   5340
ctctccaaat ctgttctttg ctcttgtatc tgctggacgc ttgaagacag gtgcactgtc   5400
tcgtatgtat ttgaattatg aacagtaatt tctaatgaat tctaaaatgg tcattgtaag   5460
tgaaagcctc tcgctaccac ttcctcttcc aactacataa atatatttca atgtatttcc   5520
agttttggaa agttttcaat acatacatca agtgtttact tagattttta taaaaatttt   5580
ttttacaatc taataatctt tggtaaagga actagagatg catgcagttg caaaattaat   5640
gtatttattt tccagcataa ttttattaac ttcacttttt ttctctctag taaatatcca   5700
gtgtacttat gaactcatgt ttggctcttt taaaaccttt tctaaaagct agatcagcat   5760
ttttctattt tacaagtttt ttgtataaaa aggtgaacat atgagatatt gtgagaaatc   5820
attttaagtt tcatttaaat catggtgcct cttttgatac tttcttaaaa ttgtgcaaga   5880
agaaatcatt tttagtagtg gtcataaata ttatcctttt ggcagtaagc tattactaat   5940
tcagcctgaa gctcggtaga caatatgtct acatgtgttt gagtacatcc tggatacagt   6000
ttcccagctc atgagggact gaaaatagtc ttattcatca acccactagg atgtgaaggg   6060
ttaagtctag atttggtcgc attgaaaccc cacaatatag aattaataaa tggccttcag   6120
taggaaaacc tacactaaag caaatccgaa gaagtggggc agggggaaag aggcattact   6180
ggtctttcct tttgttttgc aagcataatt tgattttcct ttggctcaga aaactcattt   6240
ggggaaattc tcttttgtgt tcagtttaac ctagaaaggt cctcttgaaa aaccaacatt   6300
ttaggaaagt tcttttttca ggatggagta tattaaaatt aagccaggct ttgacgtgaa   6360
ttatcacttt tctttattat tttgttttct attttggttt atagctattt ctggttcagt   6420
tctgaacttc agcacttaat catccttatc aaccaggctt ttggtagcct aaaccgctat   6480
gctgttgttt ttttaattta aagatgtata agccaaaatt tggatgggag tgagacataa   6540
ctgatttata tgaattttaa cagagttgta tttgtgtgtg tttaataaaa tatatattta   6600
ttcagtactt tcctcagtat tttatgggca aagtaaaaat aacaatgcat agtgaaaggg   6660
catatattac cagcagtaat aattcaaaat cctgaaaatg tttcattttt tttgtttttg   6720
ttatgcagaa taaacaaggc agaaatgctc tttgaaccac taaaa                    6765
```

<210> SEQ ID NO 24
<211> LENGTH: 916
<212> TYPE: PRT
<213> ORGANISM: Homo sapiens

<400> SEQUENCE: 24

```
Met Glu Ser Gly Gln Pro Ala Arg Arg Ile Ala Met Ala Pro Leu Leu
1               5                   10                  15

Glu Tyr Glu Arg Gln Leu Val Leu Glu Leu Leu Asp Thr Asp Gly Leu
            20                  25                  30
```

-continued

```
Val Val Cys Ala Arg Gly Leu Gly Ala Asp Arg Leu Leu Tyr His Phe
        35                  40                  45

Leu Gln Leu His Cys His Pro Ala Cys Leu Val Leu Val Leu Asn Thr
    50                  55                  60

Gln Pro Ala Glu Glu Glu Tyr Phe Ile Asn Gln Leu Lys Ile Glu Gly
65                  70                  75                  80

Val Glu His Leu Pro Arg Arg Val Thr Asn Glu Ile Thr Ser Asn Ser
                85                  90                  95

Arg Tyr Glu Val Tyr Thr Gln Gly Gly Val Ile Phe Ala Thr Ser Arg
            100                 105                 110

Ile Leu Val Val Asp Phe Leu Thr Asp Arg Ile Pro Ser Asp Leu Ile
        115                 120                 125

Thr Gly Ile Leu Val Tyr Arg Ala His Arg Ile Ile Glu Ser Cys Gln
    130                 135                 140

Glu Ala Phe Ile Leu Arg Leu Phe Arg Gln Lys Asn Lys Arg Gly Phe
145                 150                 155                 160

Ile Lys Ala Phe Thr Asp Asn Ala Val Ala Phe Asp Thr Gly Phe Cys
                165                 170                 175

His Val Glu Arg Val Met Arg Asn Leu Phe Val Arg Lys Leu Tyr Leu
            180                 185                 190

Trp Pro Arg Phe His Val Ala Val Asn Ser Phe Leu Glu Gln His Lys
        195                 200                 205

Pro Glu Val Val Glu Ile His Val Ser Met Thr Pro Thr Met Leu Ala
    210                 215                 220

Ile Gln Thr Ala Ile Leu Asp Ile Leu Asn Ala Cys Leu Lys Glu Leu
225                 230                 235                 240

Lys Cys His Asn Pro Ser Leu Glu Val Glu Asp Leu Ser Leu Glu Asn
                245                 250                 255

Ala Ile Gly Lys Pro Phe Asp Lys Thr Ile Arg His Tyr Leu Asp Pro
            260                 265                 270

Leu Trp His Gln Leu Gly Ala Lys Thr Lys Ser Leu Val Gln Asp Leu
        275                 280                 285

Lys Ile Leu Arg Thr Leu Leu Gln Tyr Leu Ser Gln Tyr Asp Cys Val
    290                 295                 300

Thr Phe Leu Asn Leu Leu Glu Ser Leu Arg Ala Thr Glu Lys Ala Phe
305                 310                 315                 320

Gly Gln Asn Ser Gly Trp Leu Phe Leu Asp Ser Ser Thr Ser Met Phe
                325                 330                 335

Ile Asn Ala Arg Ala Arg Val Tyr His Leu Pro Asp Ala Lys Met Ser
            340                 345                 350

Lys Lys Glu Lys Ile Ser Glu Lys Met Glu Ile Lys Glu Gly Glu Glu
        355                 360                 365

Thr Lys Lys Glu Leu Val Leu Glu Ser Asn Pro Lys Trp Glu Ala Leu
    370                 375                 380

Thr Glu Val Leu Lys Glu Ile Glu Ala Glu Asn Lys Glu Ser Glu Ala
385                 390                 395                 400

Leu Gly Gly Pro Gly Gln Val Leu Ile Cys Ala Ser Asp Asp Arg Thr
                405                 410                 415

Cys Ser Gln Leu Arg Asp Tyr Ile Thr Leu Gly Ala Glu Ala Phe Leu
            420                 425                 430

Leu Arg Leu Tyr Arg Lys Thr Phe Glu Lys Asp Ser Lys Ala Glu Glu
        435                 440                 445
```

```
Val Trp Met Lys Phe Arg Lys Glu Asp Ser Ser Lys Arg Ile Arg Lys
    450                 455                 460

Ser His Lys Arg Pro Lys Asp Pro Gln Asn Lys Glu Arg Ala Ser Thr
465                 470                 475                 480

Lys Glu Arg Thr Leu Lys Lys Lys Lys Arg Lys Leu Thr Leu Thr Gln
                485                 490                 495

Met Val Gly Lys Pro Glu Glu Leu Glu Glu Glu Gly Asp Val Glu Glu
            500                 505                 510

Gly Tyr Arg Arg Glu Ile Ser Ser Ser Pro Glu Ser Cys Pro Glu Glu
        515                 520                 525

Ile Lys His Glu Glu Phe Asp Val Asn Leu Ser Ser Asp Ala Ala Phe
    530                 535                 540

Gly Ile Leu Lys Glu Pro Leu Thr Ile Ile His Pro Leu Leu Gly Cys
545                 550                 555                 560

Ser Asp Pro Tyr Ala Leu Thr Arg Val Leu His Glu Val Glu Pro Arg
                565                 570                 575

Tyr Val Val Leu Tyr Asp Ala Glu Leu Thr Phe Val Arg Gln Leu Glu
            580                 585                 590

Ile Tyr Arg Ala Ser Arg Pro Gly Lys Pro Leu Arg Val Tyr Phe Leu
        595                 600                 605

Ile Tyr Gly Gly Ser Thr Glu Glu Gln Arg Tyr Leu Thr Ala Leu Arg
    610                 615                 620

Lys Glu Lys Glu Ala Phe Glu Lys Leu Ile Arg Glu Lys Ala Ser Met
625                 630                 635                 640

Val Val Pro Glu Glu Arg Glu Gly Arg Asp Glu Thr Asn Leu Asp Leu
                645                 650                 655

Val Arg Gly Thr Ala Ser Ala Asp Val Ser Thr Asp Thr Arg Lys Ala
            660                 665                 670

Gly Gly Gln Glu Gln Asn Gly Thr Gln Gln Ser Ile Val Val Asp Met
        675                 680                 685

Arg Glu Phe Arg Ser Glu Leu Pro Ser Leu Ile His Arg Arg Gly Ile
    690                 695                 700

Asp Ile Glu Pro Val Thr Leu Glu Val Gly Asp Tyr Ile Leu Thr Pro
705                 710                 715                 720

Glu Met Cys Val Glu Arg Lys Ser Ile Ser Asp Leu Ile Gly Ser Leu
                725                 730                 735

Asn Asn Gly Arg Leu Tyr Ser Gln Cys Ile Ser Met Ser Arg Tyr Tyr
            740                 745                 750

Lys Arg Pro Val Leu Leu Ile Glu Phe Asp Pro Ser Lys Pro Phe Ser
        755                 760                 765

Leu Thr Ser Arg Gly Ala Leu Phe Gln Glu Ile Ser Ser Asn Asp Ile
    770                 775                 780

Ser Ser Lys Leu Thr Leu Leu Thr Leu His Phe Pro Arg Leu Arg Ile
785                 790                 795                 800

Leu Trp Cys Pro Ser Pro His Ala Thr Ala Glu Leu Phe Glu Glu Leu
                805                 810                 815

Lys Gln Ser Lys Pro Gln Pro Asp Ala Ala Thr Ala Leu Ala Ile Thr
            820                 825                 830

Ala Asp Ser Glu Thr Leu Pro Glu Ser Glu Lys Tyr Asn Pro Gly Pro
        835                 840                 845

Gln Asp Phe Leu Leu Lys Met Pro Gly Val Asn Ala Lys Asn Cys Arg
    850                 855                 860

Ser Leu Met His His Val Lys Asn Ile Ala Glu Leu Ala Ala Leu Ser
```

```
865                 870                 875                 880

Gln Asp Glu Leu Thr Ser Ile Leu Gly Asn Ala Ala Asn Ala Lys Gln
                885                 890                 895

Leu Tyr Asp Phe Ile His Thr Ser Phe Ala Glu Val Val Ser Lys Gly
            900                 905                 910

Lys Gly Lys Lys
        915


<210> SEQ ID NO 25
<211> LENGTH: 4091
<212> TYPE: DNA
<213> ORGANISM: Homo sapiens

<400> SEQUENCE: 25

atttttcatg ggtttgcgga cccaccagcg aaggcgggag gtgtcgcagg gacatcttct     60

ggctgtttcc gtcgcctgcg tggcccttgc accccggtct tccattagcg gcgcagacgt    120

ttgggcctaa gcgctgggcg aggcgaggcc ctgcccctcc ccgccaacgg ccattctctg    180

gacctgtctt tcttccggga ggcggtgaca gctgctgaga cgtgttgcag ccagagtctc    240

tccgctttaa tgcgctccca ttagtgccgt cccccactgg aaaaccgtgg cttctgtatt    300

atttgccatc tttgttgtgt aggagcaggg agggcttcct cccggggtcc taggcggcgg    360

tgcagtccgt cgtagaagaa ttagagtaga agttgtcggg gtccgctctt aggacgcagc    420

cgcctcatgg gggtccaggg gctctggaag ctgctggagt gctccgggcg gcaggtcagc    480

cccgaagcgc tggaagggaa gatcctggct gttgatatta gcatttggtt aaaccaagca    540

cttaaaggag tccgggatcg ccatgggaac tcaatagaaa atcctcatct tctcactttg    600

tttcatcggc tctgcaaact cttatttttt cgaattcgtc ctatttttgt gtttgatggg    660

gatgctccac tattgaagaa acagactttg gtgaagagaa ggcagagaaa ggacttagcg    720

tccagtgact ccaggaaaac gacagagaag cttctgaaaa catttttgaa aagacaagcc    780

atcaaaactg ccttcagaag caaaagagat gaagcactac ccagtcttac ccaagttcga    840

agagaaaacg acctctatgt tttgcctcct ttacaagagg aagaaaaaca cagttcagaa    900

gaggaagatg aaaaagaatg gcaagaaaga atgaatcaaa aacaagcatt acaggaagag    960

ttctttcata atcctcaagc gatagatatt gagtctgagg acttcagcag cctgcccccct   1020

gaagtaaagc atgaaatctt gactgatatg aaagagttca ccaagcgcag aagaacatta   1080

tttgaagcaa tgccagagga gtctgatgac ttttcacagt accaactcaa aggcttgctt   1140

aaaaagaact atctgaacca gcatatagaa catgtccaaa aggaaatgaa tcagcaacat   1200

tcaggacaca tccgaaggca gtatgaagat gaagggggct ttctgaagga ggtagagtca   1260

aggagagtgg tctctgaaga cacttcacat tacatcttga taaaaggtat tcaagctaag   1320

acagttgcag aagtggattc agagtctctt ccttcttcca gcaaaatgca cggcatgtct   1380

tttgacgtga agtcatctcc atgtgaaaaa ctgaagacag agaaagagcc tgatgctacc   1440

cctccttctc caagaacttt actagctatg caagctgccc tgctgggaag tagctcagaa   1500

gaggagctgg agagtgaaaa tcgaaggcag gcccgtggga ggaacgcacc tgctgctgta   1560

gacgaaggct ccatatcacc ccggactctt tcagccatta agagagctct tgacgatgac   1620

gaagatgtaa aagtgtgtgc tggggatgat gtgcagacgg gagggccagg agcagaagaa   1680

atgcgtataa acagctccac cgagaacagt gatgaaggac ttaaagtgag agatggaaaa   1740

ggaataccgt ttactgcaac acttgcgtca tctagtgtga actctgcaga ggagcacgta   1800
```

-continued

```
gccagcacta atgaggggag agagcccaca gactcagttc caaaagaaca aatgtcactt   1860
gttcacgtgg ggactgaagc ctttccgata agtgatgagt ctatgattaa ggacagaaaa   1920
gatcggctgc ctctggagag tgcagtggtt agacatagtg acgcacctgg gctcccgaat   1980
ggaagggaac tgacaccggc atctccaact tgtacaaatt ctgtgtcaaa gaatgaaaca   2040
catgctgaag tgcttgagca gcagaacgaa ctttgcccat atgagagtaa attcgattct   2100
tctcttcttt caagtgatga tgaaacaaaa tgtaaaccga attctgcttc tgaagtcatt   2160
ggccctgtca gtttgcaaga aacaagtagc atagtaagtg tcccttcaga ggcagtagat   2220
aatgtggaaa atgtggtgtc atttaatgct aaagagcatg agaattttct ggaaaccatc   2280
caagaacagc agaccactga atctgcaggc caggatttaa tttccattcc aaaggccgtg   2340
gaaccaatgg aaattgactc ggaagaaagt gaatctgatg gaagtttcat tgaagtgcaa   2400
agtgtgatta gtgatgagga acttcaagca gaattccctg aaacttccaa acctccctca   2460
gaacaaggcg aagaggaact ggtaggaact agggagggag aagcccctgc tgagtccgag   2520
agcctcctga gggacaactc tgagagggac gacgtggatg gtgagccaca ggaagctgag   2580
aaagatgcgg aagattcgct ccatgaatgg caagatatta atttggagga gttggaaact   2640
ctggagagca acctcttagc acagcagaat tcactgaaag ctcaaaaaca gcagcaagaa   2700
cggatcgctg ctactgtcac cggacagatg ttcctggaaa gccaggaact cctgcgcctg   2760
ttcggcattc cctacatcca ggctcccatg gaagcagagg cgcagtgcgc catcctggac   2820
ctgactgatc agacttccgg aaccatcact gatgacagtg atatctggct gtttggagcg   2880
cggcatgtct atagaaactt ttttaataaa aacaagtttg tagaatatta tcaatatgtg   2940
gactttcaca atcaattggg attggaccgg aataagttaa taaatttggc ttatttgctt   3000
ggaagtgatt ataccgaagg aataccaact gtgggttgtg taaccgccat ggaaattctc   3060
aatgaattcc ctgggcatgg cctggaacct ctcctaaaat tctcagaatg gtggcatgaa   3120
gctcaaaaaa atccaaagat aagacctaat cctcatgaca ccaaagtgaa aaaaaaatta   3180
cggacattgc aactcacccc tggctttcct aacccagctg ttgccgaggc ctacctcaaa   3240
cccgtggtgg atgactcgaa gggatccttt ctgtggggga aacctgatct cgacaaaatt   3300
agagaatttt gtcagcggta tttcggctgg aacagaacga agacagatga atctctgttt   3360
cctgtattaa agcaactcga tgcccagcag acacagctcc gaattgattc cttctttaga   3420
ttagcacaac aggagaaaga agatgctaaa cgtattaaga gccagagact aaacagagct   3480
gtgacatgta tgctaaggaa agagaaagaa gcagcagcca gcgaaataga agcagtttct   3540
gttgccatgg agaaagaatt tgagctactt gataaggcaa aacgaaaaac ccagaagaga   3600
ggcataacaa ataccttaga agagtcatca agcctgaaaa gaaagaggct ttcagattct   3660
aaacgaaaga atacatgcgg tggatttttg ggggagacct gcctctcaga atcatctgat   3720
ggatcttcaa gtgaagatgc tgaaagttca tctttaatga atgtacaaag gagaacagct   3780
gcgaaagagc caaaaaccag tgcttcagat tcgcagaact cagtgaagga agctcccgtg   3840
aagaatggag gtgcgaccac cagcagctct agtgatagtg atgacgatgg agggaaagag   3900
aagatggtcc tcgtgaccgc cagatctgtg tttgggaaga aaagaaggaa actaagacgt   3960
gcgaggggaa gaaaaaggaa aacctaatta aaaaatatgt atcctctata attagttatg   4020
acagccattt gtaatgaatt tgtcgcaaag acgtaataaa attaactggt ggcacggtct   4080
ttgtaaaaaa a                                                        4091
```

<210> SEQ ID NO 26
<211> LENGTH: 1186
<212> TYPE: PRT
<213> ORGANISM: Homo sapiens

<400> SEQUENCE: 26

```
Met Gly Val Gln Gly Leu Trp Lys Leu Leu Glu Cys Ser Gly Arg Gln
1               5                   10                  15

Val Ser Pro Glu Ala Leu Glu Gly Lys Ile Leu Ala Val Asp Ile Ser
            20                  25                  30

Ile Trp Leu Asn Gln Ala Leu Lys Gly Val Arg Asp Arg His Gly Asn
        35                  40                  45

Ser Ile Glu Asn Pro His Leu Leu Thr Leu Phe His Arg Leu Cys Lys
    50                  55                  60

Leu Leu Phe Phe Arg Ile Arg Pro Ile Phe Val Phe Asp Gly Asp Ala
65                  70                  75                  80

Pro Leu Leu Lys Lys Gln Thr Leu Val Lys Arg Arg Gln Arg Lys Asp
                85                  90                  95

Leu Ala Ser Ser Asp Ser Arg Lys Thr Thr Glu Lys Leu Leu Lys Thr
            100                 105                 110

Phe Leu Lys Arg Gln Ala Ile Lys Thr Ala Phe Arg Ser Lys Arg Asp
        115                 120                 125

Glu Ala Leu Pro Ser Leu Thr Gln Val Arg Arg Glu Asn Asp Leu Tyr
    130                 135                 140

Val Leu Pro Pro Leu Gln Glu Glu Glu Lys His Ser Ser Glu Glu Glu
145                 150                 155                 160

Asp Glu Lys Glu Trp Gln Glu Arg Met Asn Gln Lys Gln Ala Leu Gln
                165                 170                 175

Glu Glu Phe Phe His Asn Pro Gln Ala Ile Asp Ile Glu Ser Glu Asp
            180                 185                 190

Phe Ser Ser Leu Pro Pro Glu Val Lys His Glu Ile Leu Thr Asp Met
        195                 200                 205

Lys Glu Phe Thr Lys Arg Arg Arg Thr Leu Phe Glu Ala Met Pro Glu
    210                 215                 220

Glu Ser Asp Asp Phe Ser Gln Tyr Gln Leu Lys Gly Leu Leu Lys Lys
225                 230                 235                 240

Asn Tyr Leu Asn Gln His Ile Glu His Val Gln Lys Glu Met Asn Gln
                245                 250                 255

Gln His Ser Gly His Ile Arg Arg Gln Tyr Glu Asp Glu Gly Gly Phe
            260                 265                 270

Leu Lys Glu Val Glu Ser Arg Arg Val Val Ser Glu Asp Thr Ser His
        275                 280                 285

Tyr Ile Leu Ile Lys Gly Ile Gln Ala Lys Thr Val Ala Glu Val Asp
    290                 295                 300

Ser Glu Ser Leu Pro Ser Ser Ser Lys Met His Gly Met Ser Phe Asp
305                 310                 315                 320

Val Lys Ser Ser Pro Cys Glu Lys Leu Lys Thr Glu Lys Glu Pro Asp
                325                 330                 335

Ala Thr Pro Pro Ser Pro Arg Thr Leu Leu Ala Met Gln Ala Ala Leu
            340                 345                 350

Leu Gly Ser Ser Ser Glu Glu Glu Leu Glu Ser Glu Asn Arg Arg Gln
        355                 360                 365

Ala Arg Gly Arg Asn Ala Pro Ala Ala Val Asp Glu Gly Ser Ile Ser
    370                 375                 380
```

Pro Arg Thr Leu Ser Ala Ile Lys Arg Ala Leu Asp Asp Asp Glu Asp
385 390 395 400

Val Lys Val Cys Ala Gly Asp Asp Val Gln Thr Gly Gly Pro Gly Ala
405 410 415

Glu Glu Met Arg Ile Asn Ser Ser Thr Glu Asn Ser Asp Glu Gly Leu
420 425 430

Lys Val Arg Asp Gly Lys Gly Ile Pro Phe Thr Ala Thr Leu Ala Ser
435 440 445

Ser Ser Val Asn Ser Ala Glu Glu His Val Ala Ser Thr Asn Glu Gly
450 455 460

Arg Glu Pro Thr Asp Ser Val Pro Lys Glu Gln Met Ser Leu Val His
465 470 475 480

Val Gly Thr Glu Ala Phe Pro Ile Ser Asp Glu Ser Met Ile Lys Asp
485 490 495

Arg Lys Asp Arg Leu Pro Leu Glu Ser Ala Val Val Arg His Ser Asp
500 505 510

Ala Pro Gly Leu Pro Asn Gly Arg Glu Leu Thr Pro Ala Ser Pro Thr
515 520 525

Cys Thr Asn Ser Val Ser Lys Asn Glu Thr His Ala Glu Val Leu Glu
530 535 540

Gln Gln Asn Glu Leu Cys Pro Tyr Glu Ser Lys Phe Asp Ser Ser Leu
545 550 555 560

Leu Ser Ser Asp Asp Glu Thr Lys Cys Lys Pro Asn Ser Ala Ser Glu
565 570 575

Val Ile Gly Pro Val Ser Leu Gln Glu Thr Ser Ser Ile Val Ser Val
580 585 590

Pro Ser Glu Ala Val Asp Asn Val Glu Asn Val Val Ser Phe Asn Ala
595 600 605

Lys Glu His Glu Asn Phe Leu Glu Thr Ile Gln Glu Gln Gln Thr Thr
610 615 620

Glu Ser Ala Gly Gln Asp Leu Ile Ser Ile Pro Lys Ala Val Glu Pro
625 630 635 640

Met Glu Ile Asp Ser Glu Glu Ser Glu Ser Asp Gly Ser Phe Ile Glu
645 650 655

Val Gln Ser Val Ile Ser Asp Glu Glu Leu Gln Ala Glu Phe Pro Glu
660 665 670

Thr Ser Lys Pro Pro Ser Glu Gln Gly Glu Glu Glu Leu Val Gly Thr
675 680 685

Arg Glu Gly Glu Ala Pro Ala Glu Ser Glu Ser Leu Leu Arg Asp Asn
690 695 700

Ser Glu Arg Asp Asp Val Asp Gly Glu Pro Gln Glu Ala Glu Lys Asp
705 710 715 720

Ala Glu Asp Ser Leu His Glu Trp Gln Asp Ile Asn Leu Glu Glu Leu
725 730 735

Glu Thr Leu Glu Ser Asn Leu Leu Ala Gln Gln Asn Ser Leu Lys Ala
740 745 750

Gln Lys Gln Gln Gln Glu Arg Ile Ala Ala Thr Val Thr Gly Gln Met
755 760 765

Phe Leu Glu Ser Gln Glu Leu Leu Arg Leu Phe Gly Ile Pro Tyr Ile
770 775 780

Gln Ala Pro Met Glu Ala Glu Ala Gln Cys Ala Ile Leu Asp Leu Thr
785 790 795 800

Asp Gln Thr Ser Gly Thr Ile Thr Asp Asp Ser Asp Ile Trp Leu Phe

```
                805                 810                 815

Gly Ala Arg His Val Tyr Arg Asn Phe Phe Asn Lys Asn Lys Phe Val
            820                 825                 830

Glu Tyr Tyr Gln Tyr Val Asp Phe His Asn Gln Leu Gly Leu Asp Arg
        835                 840                 845

Asn Lys Leu Ile Asn Leu Ala Tyr Leu Leu Gly Ser Asp Tyr Thr Glu
    850                 855                 860

Gly Ile Pro Thr Val Gly Cys Val Thr Ala Met Glu Ile Leu Asn Glu
865                 870                 875                 880

Phe Pro Gly His Gly Leu Glu Pro Leu Leu Lys Phe Ser Glu Trp Trp
                885                 890                 895

His Glu Ala Gln Lys Asn Pro Lys Ile Arg Pro Asn Pro His Asp Thr
            900                 905                 910

Lys Val Lys Lys Lys Leu Arg Thr Leu Gln Leu Thr Pro Gly Phe Pro
        915                 920                 925

Asn Pro Ala Val Ala Glu Ala Tyr Leu Lys Pro Val Val Asp Asp Ser
    930                 935                 940

Lys Gly Ser Phe Leu Trp Gly Lys Pro Asp Leu Asp Lys Ile Arg Glu
945                 950                 955                 960

Phe Cys Gln Arg Tyr Phe Gly Trp Asn Arg Thr Lys Thr Asp Glu Ser
                965                 970                 975

Leu Phe Pro Val Leu Lys Gln Leu Asp Ala Gln Gln Thr Gln Leu Arg
            980                 985                 990

Ile Asp Ser Phe Phe Arg Leu Ala  Gln Gln Glu Lys Glu  Asp Ala Lys
        995                 1000                1005

Arg Ile  Lys Ser Gln Arg Leu  Asn Arg Ala Val Thr  Cys Met Leu
    1010                1015                1020

Arg Lys  Glu Lys Glu Ala Ala  Ala Ser Glu Ile Glu  Ala Val Ser
    1025                1030                1035

Val Ala  Met Glu Lys Glu Phe  Glu Leu Leu Asp Lys  Ala Lys Arg
    1040                1045                1050

Lys Thr  Gln Lys Arg Gly Ile  Thr Asn Thr Leu Glu  Glu Ser Ser
    1055                1060                1065

Ser Leu  Lys Arg Lys Arg Leu  Ser Asp Ser Lys Arg  Lys Asn Thr
    1070                1075                1080

Cys Gly  Gly Phe Leu Gly Glu  Thr Cys Leu Ser Glu  Ser Ser Asp
    1085                1090                1095

Gly Ser  Ser Ser Glu Asp Ala  Glu Ser Ser Ser Leu  Met Asn Val
    1100                1105                1110

Gln Arg  Arg Thr Ala Ala Lys  Glu Pro Lys Thr Ser  Ala Ser Asp
    1115                1120                1125

Ser Gln  Asn Ser Val Lys Glu  Ala Pro Val Lys Asn  Gly Gly Ala
    1130                1135                1140

Thr Thr  Ser Ser Ser Ser Asp  Ser Asp Asp Asp Gly  Gly Lys Glu
    1145                1150                1155

Lys Met  Val Leu Val Thr Ala  Arg Ser Val Phe Gly  Lys Lys Arg
    1160                1165                1170

Arg Lys  Leu Arg Arg Ala Arg  Gly Arg Lys Arg Lys  Thr
    1175                1180                1185
```

<210> SEQ ID NO 27
<211> LENGTH: 2492
<212> TYPE: DNA
<213> ORGANISM: Homo sapiens

<400> SEQUENCE: 27
cactcagaaa ggccgctggg tgcggggagc gcagaggcgg tgcagggcgg ctggctcgcc 60
tcggcgtgca gtgcgcgtgc gtggagctgg gagctaggtc ctcggagtgg gccagagatg 120
gcggcggccg acggggcttt gccggaggcg gcggctttag agcaacccgc ggagctgcct 180
gcctcggtgc gggcgagtat cgagcggaag cggcagcggg cactgatgct gcgccaggcc 240
cggctggctg cccggcccta ctcggcgacg gcggctgcgg ctactggagg tttgggccgc 300
gtccgcgctt tccccttccc tctccccgcc tccccggtcc ccagactggc tcgtgcaagc 360
cgagtcccgg ggcccggggg tcgcgtcaac tccgctggcg tatgtgtgca gattctcccc 420
gagtcggaga gggaatccgc ccagccagcc gccttgtcaa agcgtcctgt ccacgaccac 480
agagcgttcc tctgtcgcac gcgggcctcc tgacccccag ccccgggcct tcttcgctgc 540
acctcggctg ctggcagctt cgatttttcg tttagggatg cagccgcccc ggccgggagg 600
tgtcagccac tgccaggtgt cagggcctca gctgtcccgg aaagaggagt tagactagtt 660
cttgattctg gcctctatac ctagaactag ttgatggaag aggcagatct tggtgtttgt 720
tagggagagc tttcaacaat tagagttgcc aaaagtgcaa tggattgctt ctcatgagct 780
tcccgttact agaagcgctc aaataggaac tggaagaacg cttacttatg tggaggagag 840
gagattcagc aatcagaatc tcctactcag caatcagaag aagggactgg atagtaaacc 900
tttaagattc taatccatag attccatgag tctatttctt ggacatgtga cctctgcgat 960
ttcttggcaa aaactagttg ctcaaaacgt gtttattgat tgaagtaaat taaggactga 1020
tctctcattg cagattattc tcttatagaa tttgccactg gggtcaacta ataatcttta 1080
acaggatact taaaatatag tttggttgac aggcagttct tcagggctgc ctctataaca 1140
tgaagtacat gtgttcctaa agctctatac tgccctttgt cgagcacagt ttagagctgt 1200
attactcttt tttatcagcc agatgtagtg agagtgagaa gagtctgagg ctggcagcat 1260
gtcttgatgt tcatactaac accgaaactg caaattccag ctacttttga tggcatggct 1320
aatgtaaaag cagccccaaa gataattgac acaggaggag gcttcatttt agaagaggaa 1380
gaagaagaag aacagaaaat tggaaaagtt gttcatcaac caggacctgt tatggaattt 1440
gattatgtaa tatgcgaaga atgtgggaaa gaatttatgg attcttatct tatgaaccac 1500
tttgatttgc caacttgtga taactgcaga gatgctgatg ataaacacaa gcttataacc 1560
aaaacagagg caaaacaaga atatcttctg aaagactgtg atttagaaaa aagagagcca 1620
cctcttaaat ttattgtgaa gaagaatcca catcattcac aatggggtga tatgaaactc 1680
tacttaaagt tacagattgt gaagaggtct cttgaagttt ggggtagtca agaagcatta 1740
gaagaagcaa aggaagtccg acaggaaaac cgagaaaaaa tgaaacagaa gaaatttgat 1800
aaaaaagtaa aagaattgcg gcgagcagta agaagcagcg tgtggaaaag ggagacgatt 1860
gttcatcaac atgagtatgg accagaagaa aacctagaag atgacatgta ccgtaagact 1920
tgtactatgt gtggccatga actgacatat gaaaaaatgt gattttttag ttcagtgacc 1980
tgttttatag aattttatat ttaaataaag gaaatttaga ttggtccttt tcaaaattca 2040
aaaaaaaaag caacatcttc atagatgaat gaaacccttg tataagtaat acttcagtaa 2100
taattatgta tgttatggct taaaagcaag tttcagtgaa ggtcacctgg cctggttgtg 2160
tgcacaatgt catgtctgtg attgccttct tacaacagag atgggagctg agtgctagag 2220
taggtgcaga agtggtaggt cagctacaaa tttgaggaca agataccaag gcaaacccta 2280

-continued

```
gattggggta gagggaaaag ggttcaacaa aggctgaact ggattcttaa ccaagaaaca   2340

aataatagca atggtggtgc accactgtac cccaggttct agtcatgtgt tttttaggac   2400

gatttctgtc tccacgatgg tggaaacagt ggggaactac tgctggaaaa agccctaata   2460

gcagaaataa acattgagtt gtacgagtct ga                                 2492
```

<210> SEQ ID NO 28
<211> LENGTH: 273
<212> TYPE: PRT
<213> ORGANISM: Homo sapiens

<400> SEQUENCE: 28

```
Met Ala Ala Ala Asp Gly Ala Leu Pro Glu Ala Ala Ala Leu Glu Gln
1               5                   10                  15

Pro Ala Glu Leu Pro Ala Ser Val Arg Ala Ser Ile Glu Arg Lys Arg
            20                  25                  30

Gln Arg Ala Leu Met Leu Arg Gln Ala Arg Leu Ala Ala Arg Pro Tyr
        35                  40                  45

Ser Ala Thr Ala Ala Ala Ala Thr Gly Gly Met Ala Asn Val Lys Ala
    50                  55                  60

Ala Pro Lys Ile Ile Asp Thr Gly Gly Gly Phe Ile Leu Glu Glu Glu
65                  70                  75                  80

Glu Glu Glu Glu Gln Lys Ile Gly Lys Val Val His Gln Pro Gly Pro
                85                  90                  95

Val Met Glu Phe Asp Tyr Val Ile Cys Glu Glu Cys Gly Lys Glu Phe
            100                 105                 110

Met Asp Ser Tyr Leu Met Asn His Phe Asp Leu Pro Thr Cys Asp Asn
        115                 120                 125

Cys Arg Asp Ala Asp Asp Lys His Lys Leu Ile Thr Lys Thr Glu Ala
    130                 135                 140

Lys Gln Glu Tyr Leu Leu Lys Asp Cys Asp Leu Glu Lys Arg Glu Pro
145                 150                 155                 160

Pro Leu Lys Phe Ile Val Lys Lys Asn Pro His His Ser Gln Trp Gly
                165                 170                 175

Asp Met Lys Leu Tyr Leu Lys Leu Gln Ile Val Lys Arg Ser Leu Glu
            180                 185                 190

Val Trp Gly Ser Gln Glu Ala Leu Glu Glu Ala Lys Glu Val Arg Gln
        195                 200                 205

Glu Asn Arg Glu Lys Met Lys Gln Lys Lys Phe Asp Lys Lys Val Lys
    210                 215                 220

Glu Leu Arg Arg Ala Val Arg Ser Ser Val Trp Lys Arg Glu Thr Ile
225                 230                 235                 240

Val His Gln His Glu Tyr Gly Pro Glu Glu Asn Leu Glu Asp Asp Met
                245                 250                 255

Tyr Arg Lys Thr Cys Thr Met Cys Gly His Glu Leu Thr Tyr Glu Lys
            260                 265                 270

Met
```

<210> SEQ ID NO 29
<211> LENGTH: 5739
<212> TYPE: DNA
<213> ORGANISM: Homo sapiens

<400> SEQUENCE: 29

```
gacgtaatgc ggtagcgcgg ggaatttcga gtggtgttgg agcgccggag gctagtgggt     60
```

ggctgacccc cagcatcctc gggagcgacc atggactccc tggccgagtc tcggtggcct 120
ccgggcctgg cagtcatgaa gacaatagat gatttgctgc ggtgtggaat ttgcttcgag 180
tatttcaaca ttgcaatgat aatacctcag tgttcacata actactgctc tctctgtata 240
agaaaatttc tgtcctataa aactcagtgt ccaacttgct gtgtgactgt cacagagccg 300
gatctgaaaa ataaccgcat attagatgaa ctggtaaaaa gcttgaattt tgcacggaat 360
catctgctgc agtttgcttt agagtcacca gccaaatctc ctgcttcttc ctcttcaaag 420
aatcttgctg tcaaagtata tactcctgta gcctccagac agtctttaaa gcaggggagc 480
aggttaatgg ataatttctt gatcagagaa atgagtggtt ctacatcaga gttgttgata 540
aaagaaaata aaagcaaatt cagccctcaa aaagaggcga gccctgctgc aaagaccaaa 600
gagacacgtt ctgtagaaga gatcgctcca gatccctcag aggctaagcg tcctgagcca 660
ccctcgacat ccactttgaa acaagttact aaagtggatt gtcctgtttg cggggttaac 720
attccagaaa gtcacattaa taagcattta gacagctgtt tatcacgcga agagaagaag 780
gaaagcctca gaagttctgt tcacaaaagg aagccgctgc ccaaaactgt atataatttg 840
ctctctgatc gtgatttaaa gaaaaagcta aaagagcatg gattatctat tcaaggaaat 900
aaacaacagc tcattaaaag gcaccaagaa tttgtacaca tgtacaatgc ccaatgcgat 960
gctttgcatc ctaaatcagc tgctgaaata gttcgagaaa tcgaaaatat agagaagact 1020
aggatgcgtc ttgaagctag taaactcaat gaaagtgtaa tggtttttac aaaggaccaa 1080
acagaaaagg aaatagatga aatccacagt aaatatcgta aaaaacataa gagtgaattt 1140
cagcttctgg tggatcaggc tagaaaagga tacaagaaaa ttgctggaat gtcacaaaaa 1200
acagtaacaa taacaaaaga agatgaatct acagaaaagc tatcttctgt atgcatggga 1260
caggaagata atatgacctc agtaacaaac cacttttctc aatcaaagct ggactcccca 1320
gaggaattgg aacctgacag agaagaggat tcttctagct gtattgatat tcaagaagtt 1380
ctttcttcat cagaatcaga ttcatgcaat agttccagtt cagacatcat aagagatctt 1440
ttagaagaag aggaagcctg ggaagcatca cataaaaacg atcttcaaga cacagaaata 1500
agtccaagac agaatcgccg cacaagagcc gctgaaagtg ctgagattga accaagaaac 1560
aagcgtaata ggaattaatg tgggcttttg ctgacttttc aaatgcattg attagaatac 1620
cgtacttttg gttgccacag atagattttc tatttataaa tgcccaagga aagatgctaa 1680
attctaaata ttacggttag ctgatattca ttcttttctg cttttccaga ggggaaaaat 1740
gttacaaaat atccttactt ggtcagttgc ctcctgcctc taaaacatct ctctctaaaa 1800
atactgacat ttcacacagg taccagcttt gcagaggagg tagactcttt ggcactttgg 1860
cacagggatt tggtttggtt tggtttggtt tgataattaa atttcagaat gtccttaggc 1920
cattctcctt ctcttccatg gagaatccag cctcacaaaa ggattctttc aacttcttta 1980
ttgcaagaaa cagttgagtt aaatgtttgt ttttggaaag gcgggatgtc agttcacatc 2040
cttggtgtgt gtaagtaccg atgcacgcca ccaccatgcc tgtgttacag cagctccatg 2100
atggttgttg cccgaggtta atgtagttgt ttgttagacc tgtgtcttac acatttctca 2160
gagtaggata ttagtattat aatttaaagc tacgacagtc acaaagtcac aataacttag 2220
aaacattgcg catattcttc tgaaatagca cttaaaaatg attagtgtca gtatttttc 2280
acttgggtca atcaaatctg taacactgaa tccaagctat taaacaaaaa gtatgcaatg 2340
aatgaatttt gtaaatgaat agagagtatc agtttacaat aatgttctta aaacagtatc 2400
ctctggatag ttgagtatgg gttagaaatc attgaaatgg attggtcaga aattgctatc 2460

```
tgtgtaaaat gtctaccagt agccagatgc ttccagagtt cttaatgcct ctctggcatt   2520
tcagagccag catcccccaa ctcccacccc tctgccatca cccaacccaa acacatcagc   2580
tttcaaatga gatgatagta aatgcggcaa tgttaagaca agaaatttat gatttgccag   2640
attcaacatt tatgacctcc ccttccaaag actgtctccg ttgaccttgt ctttttggta   2700
tgccttgggg tttctgataa tgtgtggagt ctcattatgg ctgagagttt agtgttttca   2760
cagtgaagtg cagacatttg atttctttat gagttccctg tgttagaaat ggctatagaa   2820
aaatttgtca taataatttc atttgcatga aatcctgagg ggtgcattaa ggaaactaaa   2880
agcaccactt accaaatcta tcggcagaac tgatgtgagg taagtgagca tgtcaaacaa   2940
aataggagct cacatggata tatttatgtc actgagttgt cagaaattat gtcaaaatga   3000
aaactgtttg tttcatgaca aattatatag tctataaatt aaactggaag taattattac   3060
tttaattgca gcaaaaggag tttgtgaggg agcggtgaga cccaagattg ggaaagtagg   3120
cacatgagtt cattcagcaa atatttggtt atctatgtct gtcactgtgc tgacactggg   3180
aatacaaagg tggccaaaga tcatctagaa caatggttcc cagtggggtg ggcagaaaga   3240
ttttgccccc caggagacag ctggcaatgt gtggagacac ttttggaggt ggagggtggt   3300
gaggggtact accagtatca atgggtggag gccagggatg aggctaaaca cccaaccctc   3360
atggattagt ttgccagggc tgccgtcaca agatactgca gacggggaag cttacacaac   3420
agaaatgtgt attctcagaa ttctggaggc tggaagtcca agatcagtag ggtttcttct   3480
tcggcctctc tccttggctt ccactcatgg tgtccttgca tggtcttttc tctgtgtgca   3540
catgactgtg caggactggt gtcccgattt cttgtaggga cagcagtcat tggatcaggg   3600
cccatgcgta tggcctcatt ttacttcagt tacctctttt ttagatagag ggccctatct   3660
ctaaatactg tcacattctg agataccggc agttaagact tccaacatat ttagtggtag   3720
gggttaaggg gcacgcttta gactacaaca ctccacagta aagaattatc cagtctaaca   3780
tgtcagttgt gccaagactg agaaacctgt aatgtaaagg aactcccaag tctacctgaa   3840
aagtaaggtc taaagagcat ttattgagca ctatctgtta gcacttagca tatgtttaat   3900
attcatacat tgaaagaaat gtatgttcat atccatctga caaagattaa ggaacttaga   3960
gtaagtaata gatccaaaat tgaaactgat aaacttctgg ttctaaaatt cacctttttag  4020
tgaaaataca gtttctcacc aaacttacag taattcagag ttattaactc tttctacctc   4080
ctcactcccc tcaaagttat aacatctccc atcaacatca gctcagaatg gcagtgatgc   4140
ttatggtttg tgggggtgca ggtgagctgc tggatgcact ttagatggcc tagtatgcca   4200
ggccgtcctt tcatcctcta ctctcgtctt tctttttcga cctcatgttg aggattactg   4260
gtctagttga aaaaagaatt catacacata agaccatgta tataatagag ggaggtatgc   4320
ctttaaaaac aaaattacat ggtaaagact gatgtgtcaa cagggataga caacatagag   4380
aaggctagaa ctgtttctgg aaaaaaaccc aaaaacaatg gatttcaaac ttcttagcat   4440
ccgataaaag aaagtagcaa ttattcaaat gagaaacact tctgtctgtt atgtacatat   4500
tatgaaagta tgaacataag agggaaaacc acaaccatta catttttttac catttcagta  4560
atttttttt ggtttttagt ctgtttttag acatccttaa gaacaactat ctgaggctgt   4620
aaacaagtat ttacattaac acccatgata ctgactttat actccctacc tgcattgaga   4680
ccttaaaggg ggcatttctc cattccttct gtgtatttct gggtatcccc aggttcagat   4740
attcagaata cagatacaag tccatgcttg catatgttgc tgctcccccc gacagacttc   4800
```

```
taccagcatc tgccctcctc accgctgctc tgtcacgtgc actgcggctg gccctgctgg   4860

aaagtcctac cttgcctagg acgccatccc cgatatagcc ccaagatgca aacctgccaa   4920

gtgctagggc agccctgcct tcctgtccat ttcagtctct tggccttgct gtgttccaag   4980

tggaaatggg agtgtgcttt cctggtttgc tagtgtacta tcacccggac cacagcgtcc   5040

tgtgcaaaaa tttgcttcct ctctcttccc ctttcactct ttctcttttc tcttccccac   5100

cccctttttt ttctctttcc ccttaccttt ctttcctttc cactcttcct gtccttcctt   5160

ccttcaacta ttaggactat atgtcaagta atgtgcaaaa caaagacagt tcctgccctg   5220

atggagcttg tagatcagaa gggaagatga gcattaagta attatataga ttaatgtaca   5280

actgtgatga gtgcaacaaa agagaggttc atggcactat caaacatgca atggacggat   5340

tttgtttttg cctataaact cttgccatag aaagcttgaa aatcagtcca gggggacagc   5400

attaatcacc atgttctttc cttatccctg tcttccccaa aattcatgtg ttgaaactta   5460

acaagaggtg ggaactttag gatgtgatta agtcgtgagg gcacagctct tatagatggg   5520

gtcacggtcc ttctaaaagg gcttgaggga gtggttttgt ttccttccat cccttccgcc   5580

acatgaggac acagtcttcg ttccctctgg aggactcagc aacaacacac catcttggaa   5640

gcagagagca gtcctcacca gacacggaat ctgccagtgc cttgatcttg gacttaccag   5700

cctccatacc tgtgagaaat aaatttctat tgtctataa                           5739
```

<210> SEQ ID NO 30
<211> LENGTH: 495
<212> TYPE: PRT
<213> ORGANISM: Homo sapiens

<400> SEQUENCE: 30

```
Met Asp Ser Leu Ala Glu Ser Arg Trp Pro Pro Gly Leu Ala Val Met
1               5                   10                  15

Lys Thr Ile Asp Asp Leu Leu Arg Cys Gly Ile Cys Phe Glu Tyr Phe
            20                  25                  30

Asn Ile Ala Met Ile Ile Pro Gln Cys Ser His Asn Tyr Cys Ser Leu
        35                  40                  45

Cys Ile Arg Lys Phe Leu Ser Tyr Lys Thr Gln Cys Pro Thr Cys Cys
    50                  55                  60

Val Thr Val Thr Glu Pro Asp Leu Lys Asn Asn Arg Ile Leu Asp Glu
65                  70                  75                  80

Leu Val Lys Ser Leu Asn Phe Ala Arg Asn His Leu Leu Gln Phe Ala
                85                  90                  95

Leu Glu Ser Pro Ala Lys Ser Pro Ala Ser Ser Ser Ser Lys Asn Leu
            100                 105                 110

Ala Val Lys Val Tyr Thr Pro Val Ala Ser Arg Gln Ser Leu Lys Gln
        115                 120                 125

Gly Ser Arg Leu Met Asp Asn Phe Leu Ile Arg Glu Met Ser Gly Ser
    130                 135                 140

Thr Ser Glu Leu Leu Ile Lys Glu Asn Lys Ser Lys Phe Ser Pro Gln
145                 150                 155                 160

Lys Glu Ala Ser Pro Ala Ala Lys Thr Lys Glu Thr Arg Ser Val Glu
                165                 170                 175

Glu Ile Ala Pro Asp Pro Ser Glu Ala Lys Arg Pro Glu Pro Pro Ser
            180                 185                 190

Thr Ser Thr Leu Lys Gln Val Thr Lys Val Asp Cys Pro Val Cys Gly
        195                 200                 205
```

```
Val Asn Ile Pro Glu Ser His Ile Asn Lys His Leu Asp Ser Cys Leu
    210                 215                 220

Ser Arg Glu Glu Lys Lys Glu Ser Leu Arg Ser Ser Val His Lys Arg
225                 230                 235                 240

Lys Pro Leu Pro Lys Thr Val Tyr Asn Leu Leu Ser Asp Arg Asp Leu
                245                 250                 255

Lys Lys Lys Leu Lys Glu His Gly Leu Ser Ile Gln Gly Asn Lys Gln
            260                 265                 270

Gln Leu Ile Lys Arg His Gln Glu Phe Val His Met Tyr Asn Ala Gln
        275                 280                 285

Cys Asp Ala Leu His Pro Lys Ser Ala Ala Glu Ile Val Arg Glu Ile
    290                 295                 300

Glu Asn Ile Glu Lys Thr Arg Met Arg Leu Glu Ala Ser Lys Leu Asn
305                 310                 315                 320

Glu Ser Val Met Val Phe Thr Lys Asp Gln Thr Glu Lys Glu Ile Asp
                325                 330                 335

Glu Ile His Ser Lys Tyr Arg Lys Lys His Lys Ser Glu Phe Gln Leu
            340                 345                 350

Leu Val Asp Gln Ala Arg Lys Gly Tyr Lys Lys Ile Ala Gly Met Ser
        355                 360                 365

Gln Lys Thr Val Thr Ile Thr Lys Glu Asp Glu Ser Thr Glu Lys Leu
    370                 375                 380

Ser Ser Val Cys Met Gly Gln Glu Asp Asn Met Thr Ser Val Thr Asn
385                 390                 395                 400

His Phe Ser Gln Ser Lys Leu Asp Ser Pro Glu Glu Leu Glu Pro Asp
                405                 410                 415

Arg Glu Glu Asp Ser Ser Ser Cys Ile Asp Ile Gln Glu Val Leu Ser
            420                 425                 430

Ser Ser Glu Ser Asp Ser Cys Asn Ser Ser Ser Ser Asp Ile Ile Arg
        435                 440                 445

Asp Leu Leu Glu Glu Glu Glu Ala Trp Glu Ala Ser His Lys Asn Asp
    450                 455                 460

Leu Gln Asp Thr Glu Ile Ser Pro Arg Gln Asn Arg Arg Thr Arg Ala
465                 470                 475                 480

Ala Glu Ser Ala Glu Ile Glu Pro Arg Asn Lys Arg Asn Arg Asn
                485                 490                 495
```

<210> SEQ ID NO 31
<211> LENGTH: 4263
<212> TYPE: DNA
<213> ORGANISM: Homo sapiens

<400> SEQUENCE: 31

```
ctctccacgg cgcacagagc atgcgcgggg cgggagtgag cgaaattcaa gctccaaact     60

ctaagctcca agctccaagc tccaagctcc aagctccaaa ctcccgccgg ggtaactgga    120

acccaatccg agggtcatgg aggcatcccg aaggtttccg gaagccgagg ccttgagccc    180

agagcaggct gctcattacc taagatatgt gaaagaggcc aaagaagcaa ctaagaatgg    240

agacctggaa gaagcattta aacttttcaa tttggcaaag gacatttttc ccaatgaaaa    300

agtgctgagc agaatccaaa aaatacagga agccttggag gagttggcag aacagggaga    360

tgatgaattt acagatgtgt gcaactctgg cttgctactt tatcgagaac tgcacaacca    420

actctttgag caccagaagg aaggcatagc tttcctctat agcctgtata gggatggaag    480

aaaaggtggt atattggctg atgatatggg attagggaag actgttcaaa tcattgcttt    540
```

-continued

```
cctttccggt atgtttgatg catcacttgt gaatcatgtg ctgctgatca tgccaaccaa    600
tcttattaac acatgggtaa aagaattcat caagtggact ccaggaatga gagtcaaaac    660
ctttcatggt cctagcaagg atgaacggac cagaaacctc aatcggattc agcaaaggaa    720
tggtgttatt atcactacat accaaatgtt aatcaataac tggcagcaac tttcaagctt    780
taggggccaa gagtttgtgt gggactatgt catcctcgat gaagcacata aaataaaaac    840
ctcatctact aagtcagcaa tatgtgctcg tgctattcct gcaagtaatc gcctcctcct    900
cacaggaacc ccaatccaga ataatttaca agaactatgg tccctatttg attttgcttg    960
tcaagggtcc ctgctgggaa cattaaaaac ttttaagatg gagtatgaaa atcctattac   1020
tagagcaaga gagaaggatg ctaccccagg agaaaaagcc ttgggattta aaatatctga   1080
aaacttaatg gcaatcataa aaccctattt tctcaggagg actaaagaag acgtacagaa   1140
gaaaaagtca agcaacccag aggccagact taatgaaaag aatccagatg ttgatgccat   1200
ttgtgaaatg ccttcccttt ccaggaaaaa tgatttaatt atttggatac gacttgtgcc   1260
tttacaagaa gaaatataca ggaaatttgt gtctttagat catatcaagg agttgctaat   1320
ggagacgcgc tcacctttgg ctgagctagg tgtcttaaag aagctgtgtg atcatcctag   1380
gctgctgtct gcacgggctt gttgtttgct aaatcttggg acattctctg ctcaagatgg   1440
aaatgagggg gaagattccc cagatgtgga ccatattgat caagtaactg atgacacatt   1500
gatggaagaa tctggaaaaa tgatattcct aatggaccta cttaagaggc tgcgagatga   1560
gggacatcaa actctggtgt tttctcaatc gaggcaaatt ctaaacatca ttgaacgcct   1620
cttaaagaat aggcacttta agacattgcg aatcgatggg acagttactc atcttttgga   1680
acgagaaaaa agaattaact tattccagca aaataaagat tactctgttt ttctgcttac   1740
cactcaagta ggtggtgtcg gtttaacatt aactgcagca actagagtgg tcatttttga   1800
ccctagctgg aatcctgcaa ctgatgctca agctgtggat agagtttacc gaattggaca   1860
aaaagagaat gttgtggttt ataggctaat cacttgtggg actgtagagg aaaaaatata   1920
cagaagacag gttttcaagg actcattaat aagacaaact actggtgaaa aaaagaaccc   1980
tttccgatat tttagtaaac aagaattaag agagctcttt acaatcgagg atcttcagaa   2040
ctctgtaacc cagctgcagc ttcagtcttt gcatgctgct cagaggaaat ctgatataaa   2100
actagatgaa catattgcct acctgcagtc tttggggata gctggaatct cagaccatga   2160
tttgatgtac acatgtgatc tgtctgttaa agaagagctt gatgtggtag aagaatctca   2220
ctatattcaa caaagggttc agaaagctca attcctcgtt gaattcgagt ctcaaaataa   2280
agagttcctg atggaacaac aaagaactag aaatgagggg gcctggctaa gagaacctgt   2340
atttccttct tcaacaaaga agaaatgccc taaattgaat aaaccacagc ctcagccttc   2400
acctcttcta agtactcatc atactcagga agaagatatc agttccaaaa tggcaagtgt   2460
agtcattgat gatctgccca aagagggtga gaaacaagat ctctccagta taaaggtgaa   2520
tgttaccacc ttgcaagatg gtaaaggtac aggtagtgct gactctatag ctactttacc   2580
aaaggggttt ggaagtgtag aagaactttg tactaactct tcattgggaa tggaaaaaag   2640
ctttgcaact aaaaatgaag ctgtacaaaa agagacatta caagaggggc ctaagcaaga   2700
ggcactgcaa gaggatcctc tggaaagttt taattatgta cttagcaaat caaccaaagc   2760
tgatattggg ccaaatttag atcaactaaa ggatgatgag attttacgtc attgcaatcc   2820
ttggcccatt atttccataa caaatgaaag tcaaaatgca gaatcaaatg tatccattat   2880
```

-continued

```
tgaaatagct gatgaccttt cagcatccca tagtgcactg caggatgctc aagcaagtga   2940

ggccaagttg gaagaggaac cttcagcatc ttcaccacag tatgcatgtg atttcaatct   3000

tttcttggaa gactcagcag acaacagaca aaatttttcc agtcagtctt tagagcatgt   3060

tgagaaagaa aatagcttgt gtggctctgc acctaattcc agagcagggt ttgtgcatag   3120

caaaacatgt ctcagttggg agttttctga gaaagacgat gaaccagaag aagtagtagt   3180

taaagcaaaa atcagaagta aagctagaag gattgtttca gatggcgaag atgaagatga   3240

ttcttttaaa gatacctcaa gcataaatcc attcaacaca tctctctttc aattctcatc   3300

tgtgaaacaa tttgatgctt caactcccaa aaatgacatc agtccaccag gaaggttctt   3360

ttcatctcaa atacccagta gtgtaaataa gtctatgaac tctagaagat ctctggcttc   3420

taggaggtct cttattaata tggttttaga ccacgtggag gacatggagg aaagacttga   3480

cgacagcagt gaagcaaagg gtcctgaaga ttatccagaa gaaggggtgg aggaaagcag   3540

tggcgaagcc tccaagtata cagaagagga tccttccgga gaaacactgt cttcagaaaa   3600

caagtccagc tggttaatga cgtctaagcc tagtgctcta gctcaagaga cctctcttgg   3660

tgcccctgag cctttgtctg gtgaacagtt ggttggttct ccccaggata aggcggcaga   3720

ggctacaaat gactatgaga ctcttgtaaa gcgtggaaaa gaactaaaag agtgtggaaa   3780

aatccaggag gccctaaact gcttagttaa agcgcttgac ataaaaagtg cagatcctga   3840

agttatgctc ttgactttaa gtttgtataa gcaacttaat aacaattgag aatgtaacct   3900

gtttattgta ttttaaagtg aaactgaata tgagggaatt tttgttccca taattggatt   3960

ctttgggaac atgaagcatt caggcttaag gcaagaaaga tctcaaaaag caacttctgc   4020

cctgcaacgc cccccactcc atagtctggt attctgagca ctagcttaat atttcttcac   4080

ttgaatattc ttatatttta ggcatattct ataaatttaa ctgtgttgtt tcttggaaag   4140

ttttgtaaaa ttattctggt cattcttaat tttactctga aagtgatcat ctttgtatat   4200

aacagttcag ataagaaaat taaagttact tttctcaagt gttttccaaa aaaaaaaaaa   4260

aaa                                                                 4263
```

<210> SEQ ID NO 32
<211> LENGTH: 1250
<212> TYPE: PRT
<213> ORGANISM: Homo sapiens

<400> SEQUENCE: 32

```
Met Glu Ala Ser Arg Arg Phe Pro Glu Ala Glu Ala Leu Ser Pro Glu
1               5                   10                  15

Gln Ala Ala His Tyr Leu Arg Tyr Val Lys Glu Ala Lys Glu Ala Thr
            20                  25                  30

Lys Asn Gly Asp Leu Glu Glu Ala Phe Lys Leu Phe Asn Leu Ala Lys
        35                  40                  45

Asp Ile Phe Pro Asn Glu Lys Val Leu Ser Arg Ile Gln Lys Ile Gln
    50                  55                  60

Glu Ala Leu Glu Glu Leu Ala Glu Gln Gly Asp Asp Glu Phe Thr Asp
65                  70                  75                  80

Val Cys Asn Ser Gly Leu Leu Leu Tyr Arg Glu Leu His Asn Gln Leu
                85                  90                  95

Phe Glu His Gln Lys Glu Gly Ile Ala Phe Leu Tyr Ser Leu Tyr Arg
            100                 105                 110

Asp Gly Arg Lys Gly Gly Ile Leu Ala Asp Asp Met Gly Leu Gly Lys
        115                 120                 125
```

```
Thr Val Gln Ile Ile Ala Phe Leu Ser Gly Met Phe Asp Ala Ser Leu
    130                 135                 140

Val Asn His Val Leu Leu Ile Met Pro Thr Asn Leu Ile Asn Thr Trp
145                 150                 155                 160

Val Lys Glu Phe Ile Lys Trp Thr Pro Gly Met Arg Val Lys Thr Phe
                165                 170                 175

His Gly Pro Ser Lys Asp Glu Arg Thr Arg Asn Leu Asn Arg Ile Gln
            180                 185                 190

Gln Arg Asn Gly Val Ile Ile Thr Thr Tyr Gln Met Leu Ile Asn Asn
        195                 200                 205

Trp Gln Gln Leu Ser Ser Phe Arg Gly Gln Glu Phe Val Trp Asp Tyr
    210                 215                 220

Val Ile Leu Asp Glu Ala His Lys Ile Lys Thr Ser Ser Thr Lys Ser
225                 230                 235                 240

Ala Ile Cys Ala Arg Ala Ile Pro Ala Ser Asn Arg Leu Leu Leu Thr
                245                 250                 255

Gly Thr Pro Ile Gln Asn Asn Leu Gln Glu Leu Trp Ser Leu Phe Asp
            260                 265                 270

Phe Ala Cys Gln Gly Ser Leu Leu Gly Thr Leu Lys Thr Phe Lys Met
        275                 280                 285

Glu Tyr Glu Asn Pro Ile Thr Arg Ala Arg Glu Lys Asp Ala Thr Pro
    290                 295                 300

Gly Glu Lys Ala Leu Gly Phe Lys Ile Ser Glu Asn Leu Met Ala Ile
305                 310                 315                 320

Ile Lys Pro Tyr Phe Leu Arg Arg Thr Lys Glu Asp Val Gln Lys Lys
                325                 330                 335

Lys Ser Ser Asn Pro Glu Ala Arg Leu Asn Glu Lys Asn Pro Asp Val
            340                 345                 350

Asp Ala Ile Cys Glu Met Pro Ser Leu Ser Arg Lys Asn Asp Leu Ile
        355                 360                 365

Ile Trp Ile Arg Leu Val Pro Leu Gln Glu Glu Ile Tyr Arg Lys Phe
    370                 375                 380

Val Ser Leu Asp His Ile Lys Glu Leu Leu Met Glu Thr Arg Ser Pro
385                 390                 395                 400

Leu Ala Glu Leu Gly Val Leu Lys Lys Leu Cys Asp His Pro Arg Leu
                405                 410                 415

Leu Ser Ala Arg Ala Cys Cys Leu Leu Asn Leu Gly Thr Phe Ser Ala
            420                 425                 430

Gln Asp Gly Asn Glu Gly Glu Asp Ser Pro Asp Val Asp His Ile Asp
        435                 440                 445

Gln Val Thr Asp Asp Thr Leu Met Glu Glu Ser Gly Lys Met Ile Phe
    450                 455                 460

Leu Met Asp Leu Leu Lys Arg Leu Arg Asp Glu Gly His Gln Thr Leu
465                 470                 475                 480

Val Phe Ser Gln Ser Arg Gln Ile Leu Asn Ile Ile Glu Arg Leu Leu
                485                 490                 495

Lys Asn Arg His Phe Lys Thr Leu Arg Ile Asp Gly Thr Val Thr His
            500                 505                 510

Leu Leu Glu Arg Glu Lys Arg Ile Asn Leu Phe Gln Gln Asn Lys Asp
        515                 520                 525

Tyr Ser Val Phe Leu Leu Thr Thr Gln Val Gly Gly Val Gly Leu Thr
    530                 535                 540
```

```
Leu Thr Ala Ala Thr Arg Val Val Ile Phe Asp Pro Ser Trp Asn Pro
545                 550                 555                 560

Ala Thr Asp Ala Gln Ala Val Asp Arg Val Tyr Arg Ile Gly Gln Lys
                565                 570                 575

Glu Asn Val Val Val Tyr Arg Leu Ile Thr Cys Gly Thr Val Glu Glu
            580                 585                 590

Lys Ile Tyr Arg Arg Gln Val Phe Lys Asp Ser Leu Ile Arg Gln Thr
        595                 600                 605

Thr Gly Glu Lys Lys Asn Pro Phe Arg Tyr Phe Ser Lys Gln Glu Leu
    610                 615                 620

Arg Glu Leu Phe Thr Ile Glu Asp Leu Gln Asn Ser Val Thr Gln Leu
625                 630                 635                 640

Gln Leu Gln Ser Leu His Ala Ala Gln Arg Lys Ser Asp Ile Lys Leu
                645                 650                 655

Asp Glu His Ile Ala Tyr Leu Gln Ser Leu Gly Ile Ala Gly Ile Ser
            660                 665                 670

Asp His Asp Leu Met Tyr Thr Cys Asp Leu Ser Val Lys Glu Glu Leu
        675                 680                 685

Asp Val Val Glu Glu Ser His Tyr Ile Gln Gln Arg Val Gln Lys Ala
    690                 695                 700

Gln Phe Leu Val Glu Phe Glu Ser Gln Asn Lys Glu Phe Leu Met Glu
705                 710                 715                 720

Gln Gln Arg Thr Arg Asn Glu Gly Ala Trp Leu Arg Glu Pro Val Phe
                725                 730                 735

Pro Ser Ser Thr Lys Lys Lys Cys Pro Lys Leu Asn Lys Pro Gln Pro
            740                 745                 750

Gln Pro Ser Pro Leu Leu Ser Thr His His Thr Gln Glu Glu Asp Ile
        755                 760                 765

Ser Ser Lys Met Ala Ser Val Val Ile Asp Asp Leu Pro Lys Glu Gly
    770                 775                 780

Glu Lys Gln Asp Leu Ser Ser Ile Lys Val Asn Val Thr Thr Leu Gln
785                 790                 795                 800

Asp Gly Lys Gly Thr Gly Ser Ala Asp Ser Ile Ala Thr Leu Pro Lys
                805                 810                 815

Gly Phe Gly Ser Val Glu Glu Leu Cys Thr Asn Ser Ser Leu Gly Met
            820                 825                 830

Glu Lys Ser Phe Ala Thr Lys Asn Glu Ala Val Gln Lys Glu Thr Leu
        835                 840                 845

Gln Glu Gly Pro Lys Gln Glu Ala Leu Gln Glu Asp Pro Leu Glu Ser
    850                 855                 860

Phe Asn Tyr Val Leu Ser Lys Ser Thr Lys Ala Asp Ile Gly Pro Asn
865                 870                 875                 880

Leu Asp Gln Leu Lys Asp Asp Glu Ile Leu Arg His Cys Asn Pro Trp
                885                 890                 895

Pro Ile Ile Ser Ile Thr Asn Glu Ser Gln Asn Ala Glu Ser Asn Val
            900                 905                 910

Ser Ile Ile Glu Ile Ala Asp Asp Leu Ser Ala Ser His Ser Ala Leu
        915                 920                 925

Gln Asp Ala Gln Ala Ser Glu Ala Lys Leu Glu Glu Glu Pro Ser Ala
    930                 935                 940

Ser Ser Pro Gln Tyr Ala Cys Asp Phe Asn Leu Phe Leu Glu Asp Ser
945                 950                 955                 960

Ala Asp Asn Arg Gln Asn Phe Ser Ser Gln Ser Leu Glu His Val Glu
```

```
                965                 970                 975

Lys Glu Asn Ser Leu Cys Gly Ser Ala Pro Asn Ser Arg Ala Gly Phe
            980                 985                 990

Val His Ser Lys Thr Cys Leu Ser  Trp Glu Phe Ser Glu  Lys Asp Asp
        995                 1000                1005

Glu Pro  Glu Glu Val Val Val  Lys Ala Lys Ile Arg  Ser Lys Ala
    1010                 1015                 1020

Arg Arg  Ile Val Ser Asp Gly  Glu Asp Glu Asp Asp  Ser Phe Lys
    1025                 1030                 1035

Asp Thr  Ser Ser Ile Asn Pro  Phe Asn Thr Ser Leu  Phe Gln Phe
    1040                 1045                 1050

Ser Ser  Val Lys Gln Phe Asp  Ala Ser Thr Pro Lys  Asn Asp Ile
    1055                 1060                 1065

Ser Pro  Pro Gly Arg Phe Phe  Ser Ser Gln Ile Pro  Ser Ser Val
    1070                 1075                 1080

Asn Lys  Ser Met Asn Ser Arg  Arg Ser Leu Ala Ser  Arg Arg Ser
    1085                 1090                 1095

Leu Ile  Asn Met Val Leu Asp  His Val Glu Asp Met  Glu Glu Arg
    1100                 1105                 1110

Leu Asp  Asp Ser Ser Glu Ala  Lys Gly Pro Glu Asp  Tyr Pro Glu
    1115                 1120                 1125

Glu Gly  Val Glu Glu Ser Ser  Gly Glu Ala Ser Lys  Tyr Thr Glu
    1130                 1135                 1140

Glu Asp  Pro Ser Gly Glu Thr  Leu Ser Ser Glu Asn  Lys Ser Ser
    1145                 1150                 1155

Trp Leu  Met Thr Ser Lys Pro  Ser Ala Leu Ala Gln  Glu Thr Ser
    1160                 1165                 1170

Leu Gly  Ala Pro Glu Pro Leu  Ser Gly Glu Gln Leu  Val Gly Ser
    1175                 1180                 1185

Pro Gln  Asp Lys Ala Ala Glu  Ala Thr Asn Asp Tyr  Glu Thr Leu
    1190                 1195                 1200

Val Lys  Arg Gly Lys Glu Leu  Lys Glu Cys Gly Lys  Ile Gln Glu
    1205                 1210                 1215

Ala Leu  Asn Cys Leu Val Lys  Ala Leu Asp Ile Lys  Ser Ala Asp
    1220                 1225                 1230

Pro Glu  Val Met Leu Leu Thr  Leu Ser Leu Tyr Lys  Gln Leu Asn
    1235                 1240                 1245

Asn Asn
    1250
```

<210> SEQ ID NO 33
<211> LENGTH: 10324
<212> TYPE: DNA
<213> ORGANISM: Homo sapiens

<400> SEQUENCE: 33

```
caattcggga gcccgttctc gcgggatttt ccaagaccgg gttggaattt gcgggggtta     60

ggagacggaa gtcagagcct aggaagattt gggggtcgcc ttgccggcct cctgtcctcc    120

tccggcggcg gcggagcccg agagaactag gtgaacaccg ctttgccagc ctcacacagc    180

gtcccctggc tctgccgccg ctccggacgt cgccctcccg ttctgcttgg gtccccttag    240

tcgctacctt tgctgggatc cccctcctcc atcctgtggc ttcgggttgc cgaagagcga    300

tgctcggagg gcggccggaa gtggcgttgg ccgccattgg cctgccggcc agccaccttg    360
```

```
ctgtcctccg ccgccttccg ggtgttacat gcagccgggc tcggccccte cccctggccg    420
gatggatccg tcggcgccac agccccgcgc ggaaacctca ggcaaagaca tatggcatcc    480
aggagaaaga tgtcttgccc cttctccaga taatggaaaa ctttgtgaag caagcataaa    540
atctatcaca gtggatgaaa atggcaagtc atttgcagtc gtcttatatg cagattttca    600
agaaaggaaa atacctctta aacagcttca agaagtgaaa tttgttaaag attgccctag    660
gaatcttata tttgatgatg aagatttaga aaaaccttat ttcccaaacc gaaaatttcc    720
atcatcttct gttgctttta aattatctga caatggagac tctattcctt ataccatcaa    780
taggtatttg agagactacc aaagagaagg aacccggttt ctttatggac actacatcca    840
tggaggaggg tgcattctgg gtgatgacat gggacttgga aaaacagtac aggttatttc    900
atttctggct gcagttttgc ataaaaaggg aactcgtgag gatattgaaa ataacatgcc    960
agagttttta ctaagaagta tgaaaaagga accccttttct tctacagcaa aaaagatgtt   1020
cttaatagtt gctcctcttt ctgtcctcta caactggaag gatgaattgg acacctgggg   1080
atatttcaga gtcactgttt tacatggaaa cagaaaagat aatgaattaa ttcgtgtaaa   1140
gcagaggaaa tgtgaaattg ctctaacaac ttatgaaaca ctacgcttat gcctggatga   1200
acttaacagt ttggaatggt cagctgtcat tgtggatgaa gctcatagaa tcaagaatcc   1260
aaaagctaga gtaacagaag ttatgaaagc tttgaaatgt aatgtccgca ttggcctcac   1320
tggaaccatc cttcagaaca acatgaagga actgtggtgt gttatggact gggctgtgcc   1380
aggccttttta gggagtggga cctacttcaa gaagcagttt tctgacccag tagaacatgg   1440
tcagagacac acggcaacaa agagagaact agccactggc cgaaaggcca tgcaaagact   1500
tgccaaaaag atgtctggct ggtttctcag gcgcaccaag actcttatca aggatcagtt   1560
gcctaagaag gaagaccgga tggtgtattg ttctttgaca gatttccaga aagctgtcta   1620
tcaaacagtg ttagaaacag aggacgtgac tttgatactt caatcttctg agccttgtac   1680
ctgtaggagt ggccaaaaaa ggagaaattg ttgttataag accaattctc atggtgaaac   1740
agtgaaaacc ttgtatctca gttaccttac agtccttcag aaggtagcta accatgtcgc   1800
gctactgcaa gctgctagta cttccaaaca acaggaaaca cttatcaaaa ggatatgtga   1860
tcaggtattt tccagattcc cagattttgt gcagaaaagc aaagatgcag cctttgaaac   1920
actttctgac cctaaataca gtggaaaaat gaaggtcctt cagcagcttt taaatcattg   1980
caggaaaaac agagataaag ttcttctctt ttctttttcc accaagttgc ttgacgtgct   2040
acagcagtac tgtatggcgt ctgggcttga ttaccgacga cttgatggaa gtacaaaatc   2100
agaggaaaga ctcaagattg taaaagagtt caacagtaca caagatgtta acatttgcct   2160
tgtctctaca atggctggtg gactaggcct caattttgtc ggtgccaatg ttgttgtatt   2220
atttgatcct acttggaatc cagccaatga tcttcaagcc attgacagag catataggat   2280
tggacaatgt agagatgtca aagtgcttag gctgatatcc ttgggaactg tggaggaaat   2340
catgtattta cgacagatat acaagcagca acttcactgt gtggtggttg gaagtgaaaa   2400
tgccaaacga tattttgaag cagttcaagg atctaaagag catcaaggag agctttttgg   2460
gatccataac ctcttcaaat ttaggtccca agggtcttgt cttacgaagg acatcctgga   2520
gagagaaggc caagtagaag cagggatcat gacagccaca acatggttga aagagggacc   2580
tccagcacac aaactggaaa tgcctagaca gcctgactgt caggaatgca gaggtacaga   2640
acaagctgca gagccactgg caaaggaagc atgtgatctc tgcagtgact tcagtgatga   2700
agagccagtg ggagccacag gaataaagac tgccaaaaac aaagcacccg attcaagtaa   2760
```

agcttccagc tctccaggac agcttacctt actccagtgt ggtttctcga aattgcttga 2820
aacaaaatgt aaagcagttg aggatagtga tggaaatact gcctctgatg atgaaagttc 2880
tgatgagcag cccacatgcc tttcaacaga agccaaagat gctggttgtg agaaaaatca 2940
ggactctctt ggtacttcaa aacatcagaa attagataac atcctaaatc caaaagaaaa 3000
gcatattttt tataaaagtg agaagatttt agaacagaat atttcttcca agtctgacga 3060
gaaaaaaatt aaaaatacag ataaacattg cattttacag aatgtcacag aatcagaaga 3120
tagtgatgtc atctgtccta cacaatacac aactgagaga ttccccgaca atagtataag 3180
gtttaagcca cccttggaag gatctgagga ttctgaaaca gaacacactg taaaaacaag 3240
aaataatgat aatagtcgaa acactgatga caaaagaaat ggaataattt caaaaaagtt 3300
aagtcctgag aacacaaccc tgaaatctat tttgaaaaga aaaggcacca gtgatatcag 3360
tgatgaatct gatgacattg aaatttcttc caagtcaaga gtaagaaaga gagctagttc 3420
attgaggttt aagagaataa aagaaaccaa aaaagaactt cacaattctc ccaaaacaat 3480
gaacaaaaca aaccaagtgt atgcagcaaa tgaggatcat aactctcagt ttattgatga 3540
ttattcatcc tcagatgaga gtttatccgt cagccacttc agtttctcta aacagagcca 3600
cagaccaaga actataagag acagaactag tttttcttca aaattgccta gccataataa 3660
gaaaaatagc acttttattc caagaaaacc aatgaaatgt tcaaatgaga aagttgttaa 3720
tcaagagcag tcgtatgaat caatggataa atttttagat ggcgttcagg aagtggctta 3780
tattcactca aaccagaatg taattggatc gagcaaagct gaaaatcaca tgagccgatg 3840
ggcagcacat gacgtatttg agttgaagca gttttctcag ctgcctgcta acatagctgt 3900
ttgcagttct aagacatata aagaaaaagt ggatgcagat acattgccac acacaaagaa 3960
aggccagcaa ccgagtgaag gcagcatttc acttcctctt tacatttcaa atcctgtaaa 4020
ccagaagaag aaaaaagtct accatacaaa ccagaccacc ttcataattg gagaaacacc 4080
aaaaggaatc cgcagaaaac aatttgaaga aatggcctct tattttaact cgtcttctgt 4140
aaacgaattt gctaaacata taaccaatgc cacatcagaa gaacgacaga aaatgctaag 4200
agacttttat gcttctcaat atccagaggt aaaagaattt tttgtggatt ctgtgtcaca 4260
attcaacaat tcttcctttg agaaaggaga gcagcgcacc cggaagaaat ctgataaaag 4320
agaatctctt ataaaaccaa ggctgtcaga ttctgaaacc ttgtcattta aagattctac 4380
caacaaaatt tctcaagttt gcagcctaaa aacatataaa agaaaatcag ttaagtttca 4440
gaatcatatt tcctatagag aagaggtgtt ttttaatgat gcagaaacta agaaatcacc 4500
tgttagttct actcaagaga ttgacagtgg gaaaaacagc caggcatccg aagatactgt 4560
gacatcccgt tctctgaaca gtgagtctga aacacgtgag agaaggttag aaaataccat 4620
gaaagaccaa caggacctca caagaacggg catttcaaga aaagaacccc ttctcaaatt 4680
ggaaaacaaa aagatagaaa atccagtgct ggaaaatact tctgtgataa gcttacttgg 4740
tgatacctct attcttgatg accttttttaa aagtcatggg aacagtccca cacaactgcc 4800
aaagaaagtt ctttcagggc ccatggaaaa agcaaaacag agaccaaaag atttctggga 4860
catcttgaat gagcagaatg atgagagtct tagtaaactc acagacttgg cagtaataga 4920
gactctgtgt gaaaaagcac ctctagcagc accctttaaa aggagagaag agccagcaac 4980
ttctctttgg aaatcaaatg agaaattttt atggaagaaa tttagcccaa gtgatacaga 5040
tgaaaacgca accaatacac agagtaccac ataagcatat aaatgaatta ctgcaccagt 5100

-continued aaactgctgc catcactgtt tacggcactg gattccacac tgattctatt atcttgaaca 5160
cagttgttga catatatttt tattaaatta ttgctttagg attttttgaa gtctaaagta 5220
ttgtcatgga tctgtttttc ttgatatttg atttgatctt tcaagaatat gattgtattt 5280
atagtataaa cctctgttat gaattagaaa agattctagg tttgttaata ggagacctgg 5340
gacatctttc ttactatatt acataatgat gtgacacttg ccccggtgag cattgtttcc 5400
cagtatgaaa gatgaagagt ctgtaccgaa tcagcatgag tgtccttcca gtttaaaaaa 5460
gctttgcttc gctctcctaa tggctcatag gctgaatcat gtctgcccct caaatcaggt 5520
gtataccaat gtgtttttta ctagcacttg ggaaagttat taagtatttt ctttttccct 5580
gggcatcatg ttctattatt attttagaaa aaagtcataa ttggtactga atatatggta 5640
tatataatat taaaatggta attttgcaac agctcaaaat taaaaggtta atgttataca 5700
ctttactata tgagctgtga ttactaccat tagccacaga taccagtgcc tcaacttttt 5760
atgtacctat tgtgatttaa tgtaaataaa ggtttgtata gtacttttgt agttcttaag 5820
tatgaagaaa tgggtaaact ttttattttg ttagaaactg ttatattttg agtgtaatat 5880
ttatggttta tagcaaaatg aatgtgctta ttgttgaatg catgtattta gaagccttta 5940
ctcagcccct gtgttctgtg ctaggagctt gagctctaca ggtaaggcag agctaccggt 6000
gaatgaaagg aaatcatgtc agtgaaaaat catggtggaa agcccctggc atcacatgtg 6060
catgctgtag gcaggacctg agctgcctcc gctgcaggtt cagatgcacc gctgcagctg 6120
tccttcagtt agttcacagg gctgcaagag gaggacacat ccctccagaa aacagcctga 6180
gccgggaact ggctgtgcta aagagcactg ctatcaagtt gaggagagag ggcttccgtg 6240
tactcaggat gtagagtcat tgctcagaag tgaacaaaaa atcaaaaaca aaagtcttct 6300
caagggactg atcggccaag tatgcttttc tttagagcaa tgttttgccc tagagaattg 6360
taaaatttat gtcatgactc agtacatatg tgttcgtaca tatatgattg gaataaaatg 6420
tttatgaaat atttactcat aagccatgta acatactttg acatttttct cttctaggat 6480
tgtgtttggt agggcagtgg gtttgtgtgt gtgttaatcc tctcacaacc cactgaattg 6540
aatttcatgg cccatggtta agatccacag tgtgaaaacg ctgttttaaa ttatatgagt 6600
tcgtcatttg tttgctctgt gcagctgagt tgtgtccaga cttaccagat ggtatgtttt 6660
gccattgagg ggccttctac acaatgagtg catgatatgg tccttgatag acttgacttg 6720
tagatgtttt cagcctacaa tgtgatcagc tatctgagga actccagtaa gtagatacca 6780
cttcatttca gtttatatac aagacaatgt agttcaaaca ttttaatacc ttgtaaatta 6840
tgatattcat ataaatatta gctctatagt cttcatatat gtacagtttt tttttttttt 6900
tttttttttt tgagattgag tctcactctg tcacccaggc tggagtacag tggcatgatc 6960
ttggctcact gcaacctcca cctccctccc aaacaactct tatgcctcag cctcctgagt 7020
agctaggatt acaggtgtgt accaccacac tcagctaaac attttttttt ttttttgaga 7080
cggagtctca ctctgtcgcc aggctggagt gcagtggctc gatcttggct cactgcagcc 7140
tccgcccccc gagtcaagca attctcctgc ctcagcctcc cgagtagctg ggactacagg 7200
tgcgtgccac cacgcccagc taattttttt gtgtttttag tagggatggg gtttcaccat 7260
gttggccagg ctggtctcaa tctcctggct gcaagcgatc cacctgcctt gtcctcccaa 7320
agtgctggga ttacaggtgt gagccaccat gcccagccaa taaatgctat taaagaaact 7380
tttaggccgg gcacagtggc tcacgcctgt aatcccagca ctttgggagg ccgaggcagg 7440
cggatcacaa ggtcatgaga tcgagactat cctggctaac gcggtgaaac cccgtctcta 7500

```
ctaaaaaaaa aaaaaataca aaaattagcc aggcgtggtg gtgggcgcct gtagtcccag   7560
ctactcggga ggctgaggca ggagaatggc gtgaacctgg gaggcagagc ttgcagtgag   7620
ccaggattgt gccccctgcac cccagcctgg gtgacagagc aagactccat ctcaaaaaag   7680
gaaactttta tcaatagtag tcaaaatggg agcaaaaatg cagaactgga gtttaaaaat   7740
tagtttccaa cagttgtcag tgaaatattt atcactatta tgtaggaaag tgtgtcaggt   7800
ggaatgcaga gtccagtatg aaaaggagcc tgtttcagaa cggaaactgt caggtggagt   7860
ggactccctg caatggagtg atggaaagat ttggtacaac cattgatgac ctgagaacag   7920
acactaggaa ggtttgacaa gatccttcct acccccactc cactggtgat gtgtcaccaa   7980
gttctgctaa ctaaatgggt ggcctcaagc aaatccctta cctcctttta gccttagttt   8040
cccctttaaa ttggtgatgg attagatcag tggtggtcag ccattttctt aaagcaactg   8100
aactgtatct taatcagaaa cttaactagt aaaacaatta aaatgcaagt ctgttgcttc   8160
aagcaacacc actgtggctc catggagcac taatttgaaa accacagaga tgagatcatt   8220
tctaagaaaa cctttcaact ttgtttccat gatgctactt gccacaatct tttttactta   8280
agcaatgata ccgtttctgg ctgaacactc accacacagc tattaatatt ggaaactgag   8340
gcaagatacc aagagatttt tgcacttgaa ttcctcaggg ttctcttaca gccctgaaaa   8400
cacctcttca aggaaataaa taacatctgc aaatggtgca gctgccccta agtattcaag   8460
gcaaagaagc cttagtttgc agagatgatg ataaactttt catccttcca cagaaaatga   8520
gaaagccaca ggaaatacac ggttattttc taattaaagt tcaatgtgta cgcttttaaa   8580
ttctgaagtt atccttcttt tatgatatca aaatagccct ctttttgaa atgatggtag   8640
atcatacctt ttggtctttt tcattgtcct tacataaaag ttggtaatca tatgtcagtc   8700
ccagaagttt tatttgacac ttactggtct ataaaatcca aaggaatggg gatcactgcc   8760
tgccttaaag gtttttttgt gtgtttgttt gtttgtttgt ttgcatgtga aggattttta   8820
tgtcacaaat ccagctaaca gtggatctag gatctaggcc tcaccgagga tgtcactgaa   8880
cctgtcagcc ccaatgacag gcacacacct tcaaagagca agagtgccca tcactttcta   8940
ggctccttgc ctgctgctca ttccatcatc acggatacag acttgtttct ggtttcatct   9000
tccaccagag attgcaaagc atcctctgcc cagtgcttct aggaggcctt actgggatgg   9060
ttcataagcc actttcctct tggtgacagc ccctgtacac tgtggcatgt acggctggct   9120
ccacttggta tttgttgcag gagggaagaa catctcactt ttgcttggct aaagggccac   9180
cccaggagag ctattttgcc tcagggtctt gcagggtttc tctaggaaaa cagtgcatct   9240
gatagttact ctctgcccct aggaggaaag acagattcgc ccttccttcc caagtcccag   9300
gctgtgtggt tcccagcccc aagggtagca agtcagaacc tccggagagg cttttaagca   9360
tgcacatgtc cagggtcctc atcaagagac tgaatcaggg ggtctagggc tcagcacagg   9420
cacccttttt gtttttgcag tttcacagga attctgatgt gccagtgatt gtcaggtttg   9480
tccctgggca ggacccacct gcctgacctt ctgtccccct gggacacagt atttccagag   9540
aggtgcttca gttgccccac cacgacttcc agcgcccccc atctctgtat gcagctgagc   9600
tcatgatgga gcccactgtg tgctttttgt tgttgttaca ttcctataaa aatgtccacg   9660
catatttgaa catctgtgtt catagtggca ttattcacaa tggctacaac acgaagaaag   9720
cattccaagt acctatcgat gaataagcaa aatattacac acacaggaat attattcagc   9780
cttgaaagga aattcggaca cgtgctacaa catagatgaa tcttgaggac ggtatgcaaa   9840
```

```
gtgaaataaa tcagacacag aaggacaaat actgtatgat tccacttata taaagtacct   9900

agattagtca gattcataga gacaaagtag aatggtggtt gctagacgct ggagggaggg   9960

gagaaagggg agttattaat gggtgtagag tttctgttac acaggatgca aagtggcctg  10020

aagatggatg gtcgtgatgg ttgcacagca atgtgaattt aatgacactg aagtgtacac  10080

ttaaaagtca ttaaaatgct aaattttgta tgtgttttac aattttaaaa atggaaaaaa  10140

agtaagacca aaagcaacac ctctccagaa tgtgtgttat ataccaaatt ttgatgtatg  10200

tgagattgct gactatattt tacttatcaa tttgaaatta tattgttttt atgttgacac  10260

tccatataag ccattatttt gaaaaaaaca ttttccttat taaaagattg gaaaaaaatt  10320

caca                                                               10324


<210> SEQ ID NO 34
<211> LENGTH: 1561
<212> TYPE: PRT
<213> ORGANISM: Homo sapiens

<400> SEQUENCE: 34

Met Gln Pro Gly Ser Ala Pro Pro Pro Gly Arg Met Asp Pro Ser Ala
1               5                   10                  15

Pro Gln Pro Arg Ala Glu Thr Ser Gly Lys Asp Ile Trp His Pro Gly
            20                  25                  30

Glu Arg Cys Leu Ala Pro Ser Pro Asp Asn Gly Lys Leu Cys Glu Ala
        35                  40                  45

Ser Ile Lys Ser Ile Thr Val Asp Glu Asn Gly Lys Ser Phe Ala Val
    50                  55                  60

Val Leu Tyr Ala Asp Phe Gln Glu Arg Lys Ile Pro Leu Lys Gln Leu
65                  70                  75                  80

Gln Glu Val Lys Phe Val Lys Asp Cys Pro Arg Asn Leu Ile Phe Asp
                85                  90                  95

Asp Glu Asp Leu Glu Lys Pro Tyr Phe Pro Asn Arg Lys Phe Pro Ser
            100                 105                 110

Ser Ser Val Ala Phe Lys Leu Ser Asp Asn Gly Asp Ser Ile Pro Tyr
        115                 120                 125

Thr Ile Asn Arg Tyr Leu Arg Asp Tyr Gln Arg Glu Gly Thr Arg Phe
    130                 135                 140

Leu Tyr Gly His Tyr Ile His Gly Gly Gly Cys Ile Leu Gly Asp Asp
145                 150                 155                 160

Met Gly Leu Gly Lys Thr Val Gln Val Ile Ser Phe Leu Ala Ala Val
                165                 170                 175

Leu His Lys Lys Gly Thr Arg Glu Asp Ile Glu Asn Asn Met Pro Glu
            180                 185                 190

Phe Leu Leu Arg Ser Met Lys Lys Glu Pro Leu Ser Ser Thr Ala Lys
        195                 200                 205

Lys Met Phe Leu Ile Val Ala Pro Leu Ser Val Leu Tyr Asn Trp Lys
    210                 215                 220

Asp Glu Leu Asp Thr Trp Gly Tyr Phe Arg Val Thr Val Leu His Gly
225                 230                 235                 240

Asn Arg Lys Asp Asn Glu Leu Ile Arg Val Lys Gln Arg Lys Cys Glu
                245                 250                 255

Ile Ala Leu Thr Thr Tyr Glu Thr Leu Arg Leu Cys Leu Asp Glu Leu
            260                 265                 270

Asn Ser Leu Glu Trp Ser Ala Val Ile Val Asp Glu Ala His Arg Ile
        275                 280                 285
```

-continued

```
Lys Asn Pro Lys Ala Arg Val Thr Glu Val Met Lys Ala Leu Lys Cys
    290                 295                 300

Asn Val Arg Ile Gly Leu Thr Gly Thr Ile Leu Gln Asn Asn Met Lys
305                 310                 315                 320

Glu Leu Trp Cys Val Met Asp Trp Ala Val Pro Gly Leu Leu Gly Ser
                325                 330                 335

Gly Thr Tyr Phe Lys Lys Gln Phe Ser Asp Pro Val Glu His Gly Gln
            340                 345                 350

Arg His Thr Ala Thr Lys Arg Glu Leu Ala Thr Gly Arg Lys Ala Met
        355                 360                 365

Gln Arg Leu Ala Lys Lys Met Ser Gly Trp Phe Leu Arg Arg Thr Lys
    370                 375                 380

Thr Leu Ile Lys Asp Gln Leu Pro Lys Lys Glu Asp Arg Met Val Tyr
385                 390                 395                 400

Cys Ser Leu Thr Asp Phe Gln Lys Ala Val Tyr Gln Thr Val Leu Glu
                405                 410                 415

Thr Glu Asp Val Thr Leu Ile Leu Gln Ser Ser Glu Pro Cys Thr Cys
            420                 425                 430

Arg Ser Gly Gln Lys Arg Arg Asn Cys Cys Tyr Lys Thr Asn Ser His
        435                 440                 445

Gly Glu Thr Val Lys Thr Leu Tyr Leu Ser Tyr Leu Thr Val Leu Gln
    450                 455                 460

Lys Val Ala Asn His Val Ala Leu Leu Gln Ala Ala Ser Thr Ser Lys
465                 470                 475                 480

Gln Gln Glu Thr Leu Ile Lys Arg Ile Cys Asp Gln Val Phe Ser Arg
                485                 490                 495

Phe Pro Asp Phe Val Gln Lys Ser Lys Asp Ala Ala Phe Glu Thr Leu
            500                 505                 510

Ser Asp Pro Lys Tyr Ser Gly Lys Met Lys Val Leu Gln Gln Leu Leu
        515                 520                 525

Asn His Cys Arg Lys Asn Arg Asp Lys Val Leu Leu Phe Ser Phe Ser
    530                 535                 540

Thr Lys Leu Leu Asp Val Leu Gln Gln Tyr Cys Met Ala Ser Gly Leu
545                 550                 555                 560

Asp Tyr Arg Arg Leu Asp Gly Ser Thr Lys Ser Glu Glu Arg Leu Lys
                565                 570                 575

Ile Val Lys Glu Phe Asn Ser Thr Gln Asp Val Asn Ile Cys Leu Val
            580                 585                 590

Ser Thr Met Ala Gly Gly Leu Gly Leu Asn Phe Val Gly Ala Asn Val
        595                 600                 605

Val Val Leu Phe Asp Pro Thr Trp Asn Pro Ala Asn Asp Leu Gln Ala
    610                 615                 620

Ile Asp Arg Ala Tyr Arg Ile Gly Gln Cys Arg Asp Val Lys Val Leu
625                 630                 635                 640

Arg Leu Ile Ser Leu Gly Thr Val Glu Glu Ile Met Tyr Leu Arg Gln
                645                 650                 655

Ile Tyr Lys Gln Gln Leu His Cys Val Val Val Gly Ser Glu Asn Ala
            660                 665                 670

Lys Arg Tyr Phe Glu Ala Val Gln Gly Ser Lys Glu His Gln Gly Glu
        675                 680                 685

Leu Phe Gly Ile His Asn Leu Phe Lys Phe Arg Ser Gln Gly Ser Cys
    690                 695                 700
```

-continued

```
Leu Thr Lys Asp Ile Leu Glu Arg Glu Gly Gln Val Glu Ala Gly Ile
705                 710                 715                 720

Met Thr Ala Thr Thr Trp Leu Lys Glu Gly Pro Pro Ala His Lys Leu
                725                 730                 735

Glu Met Pro Arg Gln Pro Asp Cys Gln Glu Cys Arg Gly Thr Glu Gln
            740                 745                 750

Ala Ala Glu Pro Leu Ala Lys Glu Ala Cys Asp Leu Cys Ser Asp Phe
        755                 760                 765

Ser Asp Glu Glu Pro Val Gly Ala Thr Gly Ile Lys Thr Ala Lys Asn
    770                 775                 780

Lys Ala Pro Asp Ser Ser Lys Ala Ser Ser Ser Pro Gly Gln Leu Thr
785                 790                 795                 800

Leu Leu Gln Cys Gly Phe Ser Lys Leu Leu Glu Thr Lys Cys Lys Ala
                805                 810                 815

Val Glu Asp Ser Asp Gly Asn Thr Ala Ser Asp Asp Glu Ser Ser Asp
            820                 825                 830

Glu Gln Pro Thr Cys Leu Ser Thr Glu Ala Lys Asp Ala Gly Cys Glu
        835                 840                 845

Lys Asn Gln Asp Ser Leu Gly Thr Ser Lys His Gln Lys Leu Asp Asn
    850                 855                 860

Ile Leu Asn Pro Lys Glu Lys His Ile Phe Tyr Lys Ser Glu Lys Ile
865                 870                 875                 880

Leu Glu Gln Asn Ile Ser Ser Lys Ser Asp Glu Lys Lys Ile Lys Asn
                885                 890                 895

Thr Asp Lys His Cys Ile Leu Gln Asn Val Thr Glu Ser Glu Asp Ser
            900                 905                 910

Asp Val Ile Cys Pro Thr Gln Tyr Thr Thr Glu Arg Phe Pro Asp Asn
        915                 920                 925

Ser Ile Arg Phe Lys Pro Pro Leu Glu Gly Ser Glu Asp Ser Glu Thr
    930                 935                 940

Glu His Thr Val Lys Thr Arg Asn Asn Asp Asn Ser Arg Asn Thr Asp
945                 950                 955                 960

Asp Lys Arg Asn Gly Ile Ile Ser Lys Lys Leu Ser Pro Glu Asn Thr
                965                 970                 975

Thr Leu Lys Ser Ile Leu Lys Arg Lys Gly Thr Ser Asp Ile Ser Asp
            980                 985                 990

Glu Ser Asp Asp Ile Glu Ile Ser  Ser Lys Ser Arg Val  Arg Lys Arg
        995                 1000                1005

Ala Ser  Ser Leu Arg Phe Lys  Arg Ile Lys Glu Thr  Lys Lys Glu
    1010                1015                1020

Leu His  Asn Ser Pro Lys Thr  Met Asn Lys Thr Asn  Gln Val Tyr
    1025                1030                1035

Ala Ala  Asn Glu Asp His Asn  Ser Gln Phe Ile Asp  Asp Tyr Ser
    1040                1045                1050

Ser Ser  Asp Glu Ser Leu Ser  Val Ser His Phe Ser  Phe Ser Lys
    1055                1060                1065

Gln Ser  His Arg Pro Arg Thr  Ile Arg Asp Arg Thr  Ser Phe Ser
    1070                1075                1080

Ser Lys  Leu Pro Ser His Asn  Lys Lys Asn Ser Thr  Phe Ile Pro
    1085                1090                1095

Arg Lys  Pro Met Lys Cys Ser  Asn Glu Lys Val Val  Asn Gln Glu
    1100                1105                1110

Gln Ser  Tyr Glu Ser Met Asp  Lys Phe Leu Asp Gly  Val Gln Glu
```

```
    1115                1120                1125

Val Ala  Tyr Ile His Ser Asn  Gln Asn Val Ile Gly  Ser Ser Lys
    1130                1135                1140

Ala Glu  Asn His Met Ser Arg  Trp Ala Ala His Asp  Val Phe Glu
    1145                1150                1155

Leu Lys  Gln Phe Ser Gln Leu  Pro Ala Asn Ile Ala  Val Cys Ser
    1160                1165                1170

Ser Lys  Thr Tyr Lys Glu Lys  Val Asp Ala Asp Thr  Leu Pro His
    1175                1180                1185

Thr Lys  Lys Gly Gln Gln Pro  Ser Glu Gly Ser Ile  Ser Leu Pro
    1190                1195                1200

Leu Tyr  Ile Ser Asn Pro Val  Asn Gln Lys Lys Lys  Lys Val Tyr
    1205                1210                1215

His Thr  Asn Gln Thr Thr Phe  Ile Ile Gly Glu Thr  Pro Lys Gly
    1220                1225                1230

Ile Arg  Arg Lys Gln Phe Glu  Glu Met Ala Ser Tyr  Phe Asn Ser
    1235                1240                1245

Ser Ser  Val Asn Glu Phe Ala  Lys His Ile Thr Asn  Ala Thr Ser
    1250                1255                1260

Glu Glu  Arg Gln Lys Met Leu  Arg Asp Phe Tyr Ala  Ser Gln Tyr
    1265                1270                1275

Pro Glu  Val Lys Glu Phe Phe  Val Asp Ser Val Ser  Gln Phe Asn
    1280                1285                1290

Asn Ser  Ser Phe Glu Lys Gly  Glu Gln Arg Thr Arg  Lys Lys Ser
    1295                1300                1305

Asp Lys  Arg Glu Ser Leu Ile  Lys Pro Arg Leu Ser  Asp Ser Glu
    1310                1315                1320

Thr Leu  Ser Phe Lys Asp Ser  Thr Asn Lys Ile Ser  Gln Val Cys
    1325                1330                1335

Ser Leu  Lys Thr Tyr Lys Arg  Lys Ser Val Lys Phe  Gln Asn His
    1340                1345                1350

Ile Ser  Tyr Arg Glu Glu Val  Phe Phe Asn Asp Ala  Glu Thr Lys
    1355                1360                1365

Lys Ser  Pro Val Ser Ser Thr  Gln Glu Ile Asp Ser  Gly Lys Asn
    1370                1375                1380

Ser Gln  Ala Ser Glu Asp Thr  Val Thr Ser Arg Ser  Leu Asn Ser
    1385                1390                1395

Glu Ser  Glu Thr Arg Glu Arg  Arg Leu Glu Asn Thr  Met Lys Asp
    1400                1405                1410

Gln Gln  Asp Leu Thr Arg Thr  Gly Ile Ser Arg Lys  Glu Pro Leu
    1415                1420                1425

Leu Lys  Leu Glu Asn Lys Lys  Ile Glu Asn Pro Val  Leu Glu Asn
    1430                1435                1440

Thr Ser  Val Ile Ser Leu Leu  Gly Asp Thr Ser Ile  Leu Asp Asp
    1445                1450                1455

Leu Phe  Lys Ser His Gly Asn  Ser Pro Thr Gln Leu  Pro Lys Lys
    1460                1465                1470

Val Leu  Ser Gly Pro Met Glu  Lys Ala Lys Gln Arg  Pro Lys Asp
    1475                1480                1485

Phe Trp  Asp Ile Leu Asn Glu  Gln Asn Asp Glu Ser  Leu Ser Lys
    1490                1495                1500

Leu Thr  Asp Leu Ala Val Ile  Glu Thr Leu Cys Glu  Lys Ala Pro
    1505                1510                1515
```

```
Leu Ala  Ala Pro Phe Lys Arg  Arg Glu Glu Pro Ala  Thr Ser Leu
    1520                 1525                 1530

Trp Lys  Ser Asn Glu Lys Phe  Leu Trp Lys Lys Phe  Ser Pro Ser
    1535                 1540                 1545

Asp Thr  Asp Glu Asn Ala Thr  Asn Thr Gln Ser Thr  Thr
    1550                 1555                 1560


<210> SEQ ID NO 35
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 35

ccttgatccc agatgttgtg gcctg                                          25


<210> SEQ ID NO 36
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 36

ctgggaaagc cctcattgct acagt                                          25


<210> SEQ ID NO 37
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 37

tacctcagtt gtgaccttca gcaga                                          25


<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38

gtggaggcca tcagtattga ctttc                                          25


<210> SEQ ID NO 39
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 39

tattgacttt ctcttacttg ctgta                                          25


<210> SEQ ID NO 40
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 40
```

cttgctgtac tatcagcctg ctcgt 25

<210> SEQ ID NO 41
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 41
tgctcgtttc cacctttaag aatg 24

<210> SEQ ID NO 42
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 42
ctcaatgtct cctactatcc aaaat 25

<210> SEQ ID NO 43
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 43
atgtgcatca caggaggctc ttaac 25

<210> SEQ ID NO 44
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 44
ttgcgctaat gcttgaactc ttttt 25

<210> SEQ ID NO 45
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 45
gtatgaccaa atcctgcctc attaa 25

<210> SEQ ID NO 46
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 46
gctagaaacc acctgattct gccag 25

<210> SEQ ID NO 47
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 47
tgaaagcggg cacctgcagg aagct 25

<210> SEQ ID NO 48
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 48
gaacacgatg accttctggt ggaga 25

<210> SEQ ID NO 49
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 49
tgagaaactt catcgctttc caggc 25

<210> SEQ ID NO 50
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 50
tccaggccca cactgatggc caggc 25

<210> SEQ ID NO 51
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 51
caggccagca ccagggagat actgc 25

<210> SEQ ID NO 52
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 52
aagttatctg catcacagtc ttgtg 25

<210> SEQ ID NO 53
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 53
cagtcttgtg tcttccgaga actat 25

<210> SEQ ID NO 54
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 54
atctgtgcac tttccataga acttc 25

<210> SEQ ID NO 55
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 55
aacaacattg cttcctaaac tttca 25

<210> SEQ ID NO 56
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 56
ggaagttggc tgcacttgat gtttg 25

<210> SEQ ID NO 57
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 57
gagactgttg ctcaaccatc aggaa 25

<210> SEQ ID NO 58
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 58
gagactgttg ctcaaccatc aggaa 25

<210> SEQ ID NO 59
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 59
gcagaaagtc gcatagggtt tttta 25

<210> SEQ ID NO 60
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 60
gacaatggcg ctgcatgttt ttctt 25

<210> SEQ ID NO 61
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 61
tatctccttt tctctagtat ttgac 25

<210> SEQ ID NO 62
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 62
tttgactgtt actgtccttg gcgaa 25

<210> SEQ ID NO 63
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 63
gttactgtcc ttggcgaatc gataa 25

<210> SEQ ID NO 64
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 64
ggcgaatcga taatcattgc atagt 25

<210> SEQ ID NO 65
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 65
tagtgactga aaagcctaag tgcaa 25

<210> SEQ ID NO 66
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 66
ttcttgtttc tgaacttcgt gccat 25

<210> SEQ ID NO 67
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 67
acttcgtgcc atattttgtt cctga 25

<210> SEQ ID NO 68
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 68
tctattagag acttaccctc ctgac 25

<210> SEQ ID NO 69
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 69
cttaccctcc tgacctgata aaaag 25

<210> SEQ ID NO 70
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 70
aaagggatac ccatgtctct attaa 25

<210> SEQ ID NO 71
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 71
tacccatgtc tctattaaca gcttt 25

<210> SEQ ID NO 72
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 72
ttagttatgc ttaaggagga gttct 25

<210> SEQ ID NO 73
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 73
taatgtaaga cagttttggc cttta 25

<210> SEQ ID NO 74
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 74
attatcatga gagatccttc tgaat 25

<210> SEQ ID NO 75
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 75
ccttctgaat aggatgtctt tctga 25

<210> SEQ ID NO 76
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 76
tctttctgag ttccactatt cagtt 25

<210> SEQ ID NO 77
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 77
cagttacaaa actccttaat gctta 25

<210> SEQ ID NO 78
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 78
tactgtgtac cttttatatt taata 25

<210> SEQ ID NO 79
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 79
aagtctgtac tgataaaacc cattg 25

<210> SEQ ID NO 80
<211> LENGTH: 25

<212> TYPE: DNA
<213> ORGANISM: Artificial Sequence
<220> FEATURE:
<223> OTHER INFORMATION: Synthetic polynucleotide

<400> SEQUENCE: 80
actgataaaa cccattgtgt acaaa 25

<210> SEQ ID NO 81
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 81
ttctctttat acaagctgag tcata 25

<210> SEQ ID NO 82
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 82
gattttatat tctggatttg tgttt 25

<210> SEQ ID NO 83
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 83
agactttggt gatcactttg caaat 25

<210> SEQ ID NO 84
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 84
tggtgatcac tttgcaaata tttgt 25

<210> SEQ ID NO 85
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 85
atatttgtta atccttgagt ttgag 25

<210> SEQ ID NO 86
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 86
tgagtttgag aacctgtctt ttaaa 25

<210> SEQ ID NO 87
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 87
atactttcaa acaagctagc aaggc 25

<210> SEQ ID NO 88
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 88
ttatatattt ggttagttct gttta 25

<210> SEQ ID NO 89
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 89
ctgttgccct tatgagttat tttat 25

<210> SEQ ID NO 90
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 90
attaccgact gtatgcctac acgga 25

<210> SEQ ID NO 91
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 91
tacacggagt cggagctgca gattg 25

<210> SEQ ID NO 92
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 92
ttccccaaca tggtggtggc gcagg 25

<210> SEQ ID NO 93
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 93
gcagcaggca atcgccagtg gcatc 25

<210> SEQ ID NO 94
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 94
cagcccagca gataatccat ttcct 25

<210> SEQ ID NO 95
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 95
cagactccgg ttcactgagg gtgtc 25

<210> SEQ ID NO 96
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 96
gagggtgtcc tgtataacca gttcc 25

<210> SEQ ID NO 97
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 97
aaccagttcc tgtcgcaagt ggact 25

<210> SEQ ID NO 98
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 98
ttcgagaact cggccaagcg gctca 25

<210> SEQ ID NO 99
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 99
ggcacagcga cgtcaagcgc ttttg 25

<210> SEQ ID NO 100
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 100
gctcctgaga gcgcgggact tggac 25

<210> SEQ ID NO 101
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 101
gagcattctt caggtcatct gaacc 25

<210> SEQ ID NO 102
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 102
gagaaaacat ggtcaacgtc ttgaa 25

<210> SEQ ID NO 103
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 103
gtgcttatag aatgtgatcc tgcca 25

<210> SEQ ID NO 104
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 104
cagtttctgc tgtacttgga tgagt 25

<210> SEQ ID NO 105
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 105
ttggatgagt ccaatgccct gggga 25

<210> SEQ ID NO 106
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 106
gatgacactc acgtctttgt aatag 25

<210> SEQ ID NO 107
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 107
gcagaattgg ttaatgtcct ccagg 25

<210> SEQ ID NO 108
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 108
tgtcctccag gagcgagtgg gtgaa 25

<210> SEQ ID NO 109
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 109
aactgtgaaa gacttgccac tcaat 25

<210> SEQ ID NO 110
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 110
gccactcaat atcttaggtg actga 25

<210> SEQ ID NO 111
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 111
gggttgtttt aggagcatgc cacgg 25

<210> SEQ ID NO 112
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 112
agtccggaca gacattgtgg gggtc 25

<210> SEQ ID NO 113

<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 113
attaaggttt actctgctgc cttgg 25

<210> SEQ ID NO 114
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 114
gccttggcag acttacgatc tcaac 25

<210> SEQ ID NO 115
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 115
cgatctcaac agttcatacg agcag 25

<210> SEQ ID NO 116
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 116
gagggcatgc tcactagtgg ttagt 25

<210> SEQ ID NO 117
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 117
gtggttagta agctgtcgac tttgt 25

<210> SEQ ID NO 118
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 118
gaacatgtac aatttgccac tggga 25

<210> SEQ ID NO 119
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 119
aatgccagct gcgtgtctag ttttg 25

<210> SEQ ID NO 120
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 120
agcaaatcac tcttattttt catcc 25

<210> SEQ ID NO 121
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 121
gtgggagcag tgtacaccaa ctctt 25

<210> SEQ ID NO 122
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 122
aactcttcct gtatattgcc ttttt 25

<210> SEQ ID NO 123
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 123
taacagtaac tgactggccc actga 25

<210> SEQ ID NO 124
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 124
ccacctggga gagaaccacc cgagg 25

<210> SEQ ID NO 125
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 125
gtacccggct ctgacgggtg gtcat 25

<210> SEQ ID NO 126
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 126
ttgctgctgg acttttcgaa gggaa 25

<210> SEQ ID NO 127
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 127
gagcttgctg atgggcgagt tggtc 25

<210> SEQ ID NO 128
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 128
ggtccatcgc ctttagggta tgtcc 25

<210> SEQ ID NO 129
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 129
ctttagggta tgtccacctc tgttc 25

<210> SEQ ID NO 130
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 130
ctctgttcac ttcctccaag gaaaa 25

<210> SEQ ID NO 131
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 131
caccctcagg cagccagaga ttcat 25

<210> SEQ ID NO 132
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 132
aacttcccct cggagggtgg agcat 25

<210> SEQ ID NO 133
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 133
gattattctg tatcctgtgt ttgta 25

<210> SEQ ID NO 134
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 134
ggtgatcacg aaactcgctg gcatg 25

<210> SEQ ID NO 135
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 135
ggaggaagac ttggcgtttt cgaca 25

<210> SEQ ID NO 136
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 136
ggctggggaa tttggctcca gatcc 25

<210> SEQ ID NO 137
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 137
gcgctttggc accatgagtt ctatg 25

<210> SEQ ID NO 138
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 138
ttctatgtct ggggccgacg acact 25

<210> SEQ ID NO 139
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 139
taccactcat cgcggagcaa ggcgc 25

<210> SEQ ID NO 140
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 140
acccgctctt caagcgcttt aggaa 25

<210> SEQ ID NO 141
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 141
gcagggtact tcgttcaaga ccggc 25

<210> SEQ ID NO 142
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 142
cctccagcgt tggccaaatt gtgct 25

<210> SEQ ID NO 143
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 143
ggctgtgcct tcataggtca tctag 25

<210> SEQ ID NO 144
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 144
ggggagtggg gtcatttctg tatat 25

<210> SEQ ID NO 145
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 145
gaaaccagtg tcgccctgga gaagt 25

<210> SEQ ID NO 146
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 146
aggaggcctg cgagaatggc cgcgg 25

<210> SEQ ID NO 147
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 147
tgctgtcagt ggcccggggc aaagt 25

<210> SEQ ID NO 148
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 148
gagggaatcg actttgtgca ccact 25

<210> SEQ ID NO 149
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 149
tctacacaca gagccgcatt ctcaa 25

<210> SEQ ID NO 150
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 150
gcattctcaa ggcgcggctg gaata 25

<210> SEQ ID NO 151
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 151
gggaccagtt ccagattcgt gagaa 25

<210> SEQ ID NO 152
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 152
agaatgactt tcttaccttc gatgc 25

<210> SEQ ID NO 153
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 153
gtcgggccat caggggcaag acgga 25

<210> SEQ ID NO 154
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 154
ggtctttgcc gacaagcggt ttgcc 25

<210> SEQ ID NO 155
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 155
tcagcagctc tgagtggggc gggtg 25

<210> SEQ ID NO 156
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 156
ttagttccaa actcactctt cttac 25

<210> SEQ ID NO 157
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 157
cgacagcact ggccattaca gcaga 25

<210> SEQ ID NO 158
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 158
ttacagcaga ttccgaaacc cttcc 25

<210> SEQ ID NO 159
<211> LENGTH: 25

<212> TYPE: DNA
<213> ORGANISM: Artificial Sequence
<220> FEATURE:
<223> OTHER INFORMATION: Synthetic polynucleotide

<400> SEQUENCE: 159
gagaagtata atcctggtcc ccaag 25

<210> SEQ ID NO 160
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 160
ggtgaatgcc aaaaactgcc gctcc 25

<210> SEQ ID NO 161
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 161
gctccttgat gcaccacgtt aagaa 25

<210> SEQ ID NO 162
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 162
tagcagccct gtcacaagac gagct 25

<210> SEQ ID NO 163
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 163
tatgatttca ttcacacctc ttttg 25

<210> SEQ ID NO 164
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 164
tgatggctgt tttcttatcc catgc 25

<210> SEQ ID NO 165
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 165
tcccatgcct gtacttttca gcggc 25

<210> SEQ ID NO 166
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 166
gctccttgcc agacatcata ggtca 25

<210> SEQ ID NO 167
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 167
gaagcagcag ccagcgaaat agaag 25

<210> SEQ ID NO 168
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 168
aagaggcttt cagattctaa acgaa 25

<210> SEQ ID NO 169
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 169
atacatgcgg tggatttttg gggga 25

<210> SEQ ID NO 170
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 170
tcatctgatg gatcttcaag tgaac 25

<210> SEQ ID NO 171
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 171
gccaaaaacc agtgcttcag attcg 25

<210> SEQ ID NO 172
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 172
gcttcagatt cgcagaactc agtga 25

<210> SEQ ID NO 173
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 173
gaatggaggt gcgaccacca gcagc 25

<210> SEQ ID NO 174
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 174
accagcagct ctagtgatag tgatg 25

<210> SEQ ID NO 175
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 175
agagaagatg gtcctcgtga ccgcc 25

<210> SEQ ID NO 176
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 176
gtgaccgcca gatctgtgtt tggga 25

<210> SEQ ID NO 177
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 177
gaaggaaact aagacgtgcg agggg 25

<210> SEQ ID NO 178
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 178
taagacttgt actatgtgtg gccat 25

<210> SEQ ID NO 179
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 179
gtgtggccat gaactgacat atgaa 25

<210> SEQ ID NO 180
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 180
tcagtgaagg tcacctggcc tggtt 25

<210> SEQ ID NO 181
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 181
gttgtgtgca caatgtcatg tctgt 25

<210> SEQ ID NO 182
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 182
atgtctgtga ttgccttctt acaac 25

<210> SEQ ID NO 183
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 183
aggtgcagaa gtggtaggtc agcta 25

<210> SEQ ID NO 184
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 184
ggacaagata ccaaggcaaa cccta 25

<210> SEQ ID NO 185
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 185
ggctgaactg gattcttaac caaga 25

<210> SEQ ID NO 186
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 186
gcaatggtgg tgcaccactg taccc 25

<210> SEQ ID NO 187
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 187
actgtacccc aggttctagt catgt 25

<210> SEQ ID NO 188
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 188
ttaggacgat ttctgtctcc acgat 25

<210> SEQ ID NO 189
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 189
cccttccaaa gactgtctcc gttga 25

<210> SEQ ID NO 190
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 190
tccaaagact gtctccgttg acctt 25

<210> SEQ ID NO 191
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 191
tgaccttgtc tttttggtat gcctt 25

<210> SEQ ID NO 192

<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 192
ccttgtcttt ttggtatgcc ttggg 25

<210> SEQ ID NO 193
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 193
ttttggtatg ccttggggtt tctga 25

<210> SEQ ID NO 194
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 194
ggtatgcctt ggggtttctg ataat 25

<210> SEQ ID NO 195
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 195
gccttggggt ttctgataat gtgtg 25

<210> SEQ ID NO 196
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 196
aggtaagtga gcatgtcaaa caaaa 25

<210> SEQ ID NO 197
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 197
gtcaaacaaa ataggagctc acatg 25

<210> SEQ ID NO 198
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 198
aggagctcac atggatatat ttatg 25

<210> SEQ ID NO 199
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 199
atggatatat ttatgtcact gagtt 25

<210> SEQ ID NO 200
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 200
gagcctttgt ctggtgaaca gttgg 25

<210> SEQ ID NO 201
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 201
tctccccagg ataaggcggc agagg 25

<210> SEQ ID NO 202
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 202
ggcggcagag gctacaaatg actat 25

<210> SEQ ID NO 203
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 203
aatccaggag gccctaaact gctta 25

<210> SEQ ID NO 204
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 204
gcagatcctg aagttatgct cttga 25

<210> SEQ ID NO 205
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 205
gttatgctct tgactttaag tttgt 25

<210> SEQ ID NO 206
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 206 ggaattttg ttcccataat tggat 25

<210> SEQ ID NO 207
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 207
tcaaaaagca acttctgccc tgcaa 25

<210> SEQ ID NO 208
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 208
ccccactcca tagtctggta ttctg 25

<210> SEQ ID NO 209
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 209
gtctggtatt ctgagcacta gctta 25

<210> SEQ ID NO 210
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 210
gagcactagc ttaatatttc ttcac 25

<210> SEQ ID NO 211
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 211
tatttagaag cctttactca gcccc 25

<210> SEQ ID NO 212
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 212
ggagcttgag ctctacaggt aaggc 25

<210> SEQ ID NO 213
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 213
taaggcagag ctaccggtga atgaa 25

<210> SEQ ID NO 214
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 214
cccctggcat cacatgtgca tgctg 25

<210> SEQ ID NO 215
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 215
gcatgctgta ggcaggacct gagct 25

<210> SEQ ID NO 216
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 216
tccgctgcag gttcagatgc accgc 25

<210> SEQ ID NO 217
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 217
tgcagctgtc cttcagttag ttcac 25

<210> SEQ ID NO 218
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 218
agcctgagcc gggaactggc tgtgc 25

<210> SEQ ID NO 219
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 219
agggcttccg tgtactcagg atgta 25

<210> SEQ ID NO 220
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 220
gtcttctcaa gggactgatc ggcca 25

<210> SEQ ID NO 221
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 221
gatcggccaa gtatgctttt cttta 25

<210> SEQ ID NO 222
<211> LENGTH: 4518
<212> TYPE: DNA
<213> ORGANISM: Homo sapiens

<400> SEQUENCE: 222
ggagtttatt cataacgcgc tctccaagta tacgtggcaa tgcgttgctg ggttatttta 60
atcattctag gcatcgtttt cctccttatg cctctatcat tcctccctat ctacactaac 120
atcccacgct ctgaacgcgc gcccattaat acccttcttt cctccactct ccctgggact 180
cttgatcaaa gcgcggccct ttccccagcc ttagcgaggc gccctgcagc ctggtacgcg 240
cgtggcgtgg cggtgggcgc gcagtgcgtt ctcggtgtgg agggcagctg ttccgcctgc 300
gatgatttat actcacagga caaggatgcg gtttgtcaaa cagtactgct acggaggagc 360
agcagagaaa gggagagggt ttgagaggga gcaaaagaaa atggtaggcg cgcgtagtta 420
attcatgcgg ctctcttact ctgtttacat cctagagcta gagtgctcgg ctgcccggct 480
gagtctcctc cccaccttcc ccaccctccc caccctcccc ataagcgccc ctcccgggtt 540
cccaaagcag agggcgtggg ggaaaagaaa aaagatcctc tctcgctaat ctccgcccac 600
cggcccttta taatgcgagg gtctggacgg ctgaggaccc ccgagctgtg ctgctcgcgg 660
ccgccaccgc cgggccccgg ccgtccctgg ctcccctcct gcctcgagaa gggcagggct 720
tctcagaggc ttggcgggaa aaagaacgga gggagggatc gcgctgagta taaaagccgg 780
ttttcggggc tttatctaac tcgctgtagt aattccagcg agaggcagag ggagcgagcg 840
ggcggccggc tagggtggaa gagccgggcg agcagagctg cgctgcgggc gtcctgggaa 900

```
gggagatccg gagcgaatag ggggcttcgc ctctggccca gccctcccgc tgatccccca    960
gccagcggtc cgcaaccctt gccgcatcca cgaaactttg cccatagcag cgggcgggca   1020
ctttgcactg gaacttacaa cacccgagca aggacgcgac tctcccgacg cggggaggct   1080
attctgccca tttggggaca cttccccgcc gctgccagga cccgcttctc tgaaaggctc   1140
tccttgcagc tgcttagacg ctggattttt ttcgggtagt ggaaaaccag cagcctcccg   1200
cgacgatgcc cctcaacgtt agcttcacca acaggaacta tgacctcgac tacgactcgg   1260
tgcagccgta tttctactgc gacgaggagg agaacttcta ccagcagcag cagcagagcg   1320
agctgcagcc cccggcgccc agcgaggata tctggaagaa attcgagctg ctgcccaccc   1380
cgcccctgtc ccctagccgc cgctccgggc tctgctcgcc ctcctacgtt gcggtcacac   1440
ccttctccct tcggggagac aacgacggcg gtggcgggag cttctccacg gccgaccagc   1500
tggagatggt gaccgagctg ctgggaggag acatggtgaa ccagagtttc atctgcgacc   1560
cggacgacga gaccttcatc aaaaacatca tcatccagga ctgtatgtgg agcggcttct   1620
cggccgccgc caagctcgtc tcagagaagc tggcctccta ccaggctgcg cgcaaagaca   1680
gcggcagccc gaaccccgcc cgcggccaca gcgtctgctc cacctccagc ttgtacctgc   1740
aggatctgag cgccgccgcc tcagagtgca tcgacccctc ggtggtcttc ccctaccctc   1800
tcaacgacag cagctcgccc aagtcctgcg cctcgcaaga ctccagcgcc ttctctccgt   1860
cctcggattc tctgctctcc tcgacggagt cctccccgca gggcagcccc gagcccctgg   1920
tgctccatga ggagacaccg cccaccacca gcagcgactc tgaggaggaa caagaagatg   1980
aggaagaaat cgatgttgtt tctgtggaaa agaggcaggc tcctggcaaa aggtcagagt   2040
ctggatcacc ttctgctgga ggccacagca aacctcctca cagcccactg gtcctcaaga   2100
ggtgccacgt ctccacacat cagcacaact acgcagcgcc tccctccact cggaaggact   2160
atcctgctgc caagagggtc aagttggaca gtgtcagagt cctgagacag atcagcaaca   2220
accgaaaatg caccagcccc aggtcctcgg acaccgagga gaatgtcaag aggcgaacac   2280
acaacgtctt ggagcgccag aggaggaacg agctaaaacg gagctttttt gccctgcgtg   2340
accagatccc ggagttggaa aacaatgaaa aggcccccaa ggtagttatc cttaaaaaag   2400
ccacagcata catcctgtcc gtccaagcag aggagcaaaa gctcatttct gaagaggact   2460
tgttgcggaa acgacgagaa cagttgaaac acaaacttga acagctacgg aactcttgtg   2520
cgtaaggaaa agtaaggaaa acgattcctt ctaacagaaa tgtcctgagc aatcacctat   2580
gaacttgttt caaatgcatg atcaaatgca acctcacaac cttggctgag tcttgagact   2640
gaaagattta gccataatgt aaactgcctc aaattggact ttgggcataa aagaactttt   2700
ttatgcttac catctttttt ttttctttaa cagatttgta tttaagaatt gtttttaaaa   2760
aattttaaga tttacacaat gtttctctgt aaatattgcc attaaatgta aataacttta   2820
ataaaacgtt tatagcagtt acacagaatt tcaatcctag tatatagtac ctagtattat   2880
aggtactata aaccctaatt tttttattt aagtacattt tgctttttaa agttgatttt   2940
tttctattgt ttttagaaaa aataaaataa ctggcaaata tatcattgag ccaaatctta   3000
agttgtgaat gttttgtttc gtttcttccc cctcccaacc accaccatcc ctgtttgttt   3060
tcatcaattg ccccttcaga gggtggtctt aagaaaggca agagttttcc tctgttgaaa   3120
tgggtctggg ggccttaagg tctttaagtt cttggaggtt ctaagatgct tcctggagac   3180
tatgataaca gccagagttg acagttagaa ggaatggcag aaggcaggtg agaaggtgag   3240
```

aggtaggcaa aggagataca agaggtcaaa ggtagcagtt aagtacacaa agaggcataa 3300
ggactgggga gttgggagga aggtgaggaa gaaactcctg ttactttagt taaccagtgc 3360
cagtcccctg ctcactccaa acccaggaat tctgcccagt tgatggggac acggtgggaa 3420
ccagcttctg ctgccttcac aaccaggcgc cagtcctgtc catgggttat ctcgcaaacc 3480
ccagaggatc tctgggagga atgctactat taaccctatt tcacaaacaa ggaaatagaa 3540
gagctcaaag aggttatgta acttatctgt agccacgcag ataatacaaa gcagcaatct 3600
ggacccattc tgttcaaaac acttaaccct tcgctatcat gccttggttc atctgggtct 3660
aatgtgctga gatcaagaag gtttaggacc taatggacag actcaagtca taacaatgct 3720
aagctctatt tgtgtcccaa gcactcctaa gcattttatc cctaactcta catcaacccc 3780
atgaaggaga tactgttgat ttccccatat tagaagtaga gagggaagct gaggcacaca 3840
aagactcatc cacatgccca agattcactg atagggaaaa gtggaagcga gatttgaacc 3900
caggctgttt actcctaacc tgtccaagcc acctctcaga cgacggtagg aatcagctgg 3960
ctgcttgtga gtacaggagt tacagtccag tgggttatgt tttttaagtc tcaacatcta 4020
agcctggtca ggcatcagtt ccccttttt tgtgatttat tttgttttta ttttgttgtt 4080
cattgtttaa tttttccttt tacaatgaga aggtcaccat cttgactcct accttagcca 4140
tttgttgaat cagactcatg acggctcctg ggaagaagcc agttcagatc ataaaataaa 4200
acatatttat tctttgtcat gggagtcatt attttagaaa ctacaaactc tccttgcttc 4260
catccttttt tacatactca tgacacatgc tcatcctgag tccttgaaaa ggtatttttg 4320
aacatgtgta ttaattataa gcctctgaaa acctatggcc caaaccagaa atgatgttga 4380
ttatataggt aaatgaagga tgctattgct gttctaatta cctcattgtc tcagtctcaa 4440
agtaggtctt cagctccctg tactttggga ttttaatcta ccaccaccca taaatcaata 4500
aataattact ttctttga 4518

<210> SEQ ID NO 223
<211> LENGTH: 454
<212> TYPE: PRT
<213> ORGANISM: Homo sapiens

<400> SEQUENCE: 223

Met Asp Phe Phe Arg Val Val Glu Asn Gln Gln Pro Pro Ala Thr Met
1 5 10 15

Pro Leu Asn Val Ser Phe Thr Asn Arg Asn Tyr Asp Leu Asp Tyr Asp
20 25 30

Ser Val Gln Pro Tyr Phe Tyr Cys Asp Glu Glu Glu Asn Phe Tyr Gln
35 40 45

Gln Gln Gln Gln Ser Glu Leu Gln Pro Pro Ala Pro Ser Glu Asp Ile
50 55 60

Trp Lys Lys Phe Glu Leu Leu Pro Thr Pro Pro Leu Ser Pro Ser Arg
65 70 75 80

Arg Ser Gly Leu Cys Ser Pro Ser Tyr Val Ala Val Thr Pro Phe Ser
85 90 95

Leu Arg Gly Asp Asn Asp Gly Gly Gly Gly Ser Phe Ser Thr Ala Asp
100 105 110

Gln Leu Glu Met Val Thr Glu Leu Leu Gly Gly Asp Met Val Asn Gln
115 120 125

Ser Phe Ile Cys Asp Pro Asp Asp Glu Thr Phe Ile Lys Asn Ile Ile
130 135 140

```
Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450
```

<210> SEQ ID NO 224
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 224
gcaacaaccg aaaatgcacc agccc 25

<210> SEQ ID NO 225
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 225
ccccaggtcc tcggacaccg aggag 25

<210> SEQ ID NO 226
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 226
cgaacacaca acgtcttgga gcgcc 25

<210> SEQ ID NO 227
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 227
ggagcgccag aggaggaacg agcta 25

<210> SEQ ID NO 228
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 228
gctaaaacgg agcttttttg ccctg 25

<210> SEQ ID NO 229
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 229
aaaagccaca gcatacatcc tgtcc 25

<210> SEQ ID NO 230
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 230
catcctgtcc gtccaagcag aggag 25

<210> SEQ ID NO 231
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 231
catcctgtcc gtccaagcag aggag 25

<210> SEQ ID NO 232

<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 232
gaggacttgt tgcggaaacg acgag 25

<210> SEQ ID NO 233
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 233
gaacagctac ggaactcttg tgcgt 25

<210> SEQ ID NO 234
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 234
gaaatgtcct gagcaatcac ctatg 25

<210> SEQ ID NO 235
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 235
gcaacctcac aaccttggct gagtc 25

<210> SEQ ID NO 236
<211> LENGTH: 1291
<212> TYPE: DNA
<213> ORGANISM: Homo sapiens

<400> SEQUENCE: 236
gagccgaagg tggaggtcaa aggggcgtgg cgttacagag cctctagcgc tgggtgttgg 60
ggacctgacg ctatggagct ctcggagttt tgtgggggac ggctgtgagt ggggggttcc 120
tgctgcggga tgagaacgta gacgccagtg gctcactcgc tcctggcacc ttccctttca 180
ggctccagat ggaccctggg aaggacaaag agggggtgcc ccagccctca gggccgccag 240
caaggaagaa atttgtgata cccctcgacg aggatgaggt ccctcctgga gtggccaagc 300
ccttattccg atctacacag agccttccca ctgtggacac ctcggcccag gcggcccctc 360
agacctacgc cgaatatgcc atctcacagc ctctggaagg ggctggggcc acgtgcccca 420
cagggtcaga gcccctggca ggagagacgc ccaaccaggc cctgaaaccc ggggcaaaat 480
ccaacagcat cattgtgagc cctcggcaga ggggcaatcc cgtactgaag ttcgtgcgca 540
atgtgccctg ggaatttggc gacgtaattc ccgactatgt gctgggccag agcacctgtg 600
ccctgttcct cagcctccgc taccacaacc tgcacccaga ctacatccat gggcggctgc 660
agagcctggg gaagaacttc gccttgcggg tcctgcttgt ccaggtggat gtgaaagatc 720
cccagcaggc cctcaaggag ctggctaaga tgtgtatcct ggccgactgc acattgatcc 780

```
tcgcctggag ccccgaggaa gctgggcggt acctggagac ctacaaggcc tatgagcaga    840

aaccagcgga cctcctgatg gagaagctag agcaggactt cgtctcccgg gtgactgaat    900

gtctgaccac cgtgaagtca gtcaacaaaa cggacagtca gaccctcctg accacatttg    960

gatctctgga acagctcatc gccgcatcaa gagaagatct ggccttatgc ccaggcctgg   1020

gccctcagaa agtaagagct ctgggaaaga acccaaggag ttgggggaag gagagagccc   1080

caaataaaca caacctgaga ccccaaagtt ttaaggtgaa aaaagaacca aagaccagac   1140

acagtggctt ccgcctgtaa tcccaacatt ttgggaggcc aaggcgggag gactgcttga   1200

ggccagaagt tggagaccag cctgggcaag tggacacctc atttttacta aaaataaaaa   1260

aaactagctg ggcaaaaaaa aaaaaaaaaa a                                  1291


<210> SEQ ID NO 237
<211> LENGTH: 323
<212> TYPE: PRT
<213> ORGANISM: Homo sapiens

<400> SEQUENCE: 237

Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
    50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
    130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
    210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255

Phe Gly Ser Leu Glu Gln Leu Ile Ala Ala Ser Arg Glu Asp Leu Ala
            260                 265                 270

Leu Cys Pro Gly Leu Gly Pro Gln Lys Val Arg Ala Leu Gly Lys Asn
```

-continued 275 280 285

Pro Arg Ser Trp Gly Lys Glu Arg Ala Pro Asn Lys His Asn Leu Arg
290 295 300

Pro Gln Ser Phe Lys Val Lys Lys Glu Pro Lys Thr Arg His Ser Gly
305 310 315 320

Phe Arg Leu

<210> SEQ ID NO 238
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 238
aagatctggc cttatgccca ggcct 25

<210> SEQ ID NO 239
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 239
ccctcagaaa gcccggaggc tgttt 25

<210> SEQ ID NO 240
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 240
ctcagaaagc ccggaggctg tttga 25

<210> SEQ ID NO 241
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 241
gaaagcccgg aggctgtttg atgtc 25

<210> SEQ ID NO 242
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 242
aagcccggag gctgtttgat gtcct 25

<210> SEQ ID NO 243
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 243
ggctgtttga tgtcctgcac gagcc 25

<210> SEQ ID NO 244
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 244
tgcacgagcc cttcttgaaa gtacc 25

<210> SEQ ID NO 245
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 245
gcccttcttg aaagtaccct gatga 25

<210> SEQ ID NO 246
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 246
ccttcttgaa agtaccctga tgacc 25

<210> SEQ ID NO 247
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 247
ttcttgaaag taccctgatg acccc 25

<210> SEQ ID NO 248
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 248
tcttgaaagt accctgatga cccca 25

<210> SEQ ID NO 249
<211> LENGTH: 1220
<212> TYPE: DNA
<213> ORGANISM: Homo sapiens

<400> SEQUENCE: 249
atgcacacat acgcgcgcgc acatgcacat aggcacacag agatacgcgc acacacacac 60
acaaacgcac tcagatttcc cggaccctgg ttttcctcct gtgacccttt cggggccggg 120
ctctcaccct aaagaagcag ccccgccctg gggtggcccc accctctctt gggacctgtc 180
ataagtcgga ccccgggcgc ccggctgcgc agtcccagcc gccttcccca ggcagtggaa 240
ccttcgggct cctgagcttc aggatggttc gtactaagac atggaccctg aagaagcact 300
ttgttggcta tcctactaat agtgactttg agttgaagac agctgagctc ccacccttaa 360
aaaatggaga ggtcctgctt gaagctttgt tcctcaccgt ggatccctac atgagagtgg 420
cagccaaaag attgaaggaa ggtgatacaa tgatggggca gcaagtggcc aaagttgtgg 480
aaagtaaaaa tgtagcccta ccaaaaggaa ctattgtact ggcttctcca ggctggacaa 540
cgcactccat ttctgatggg aaagatctgg aaaagctgct gacagagtgg ccagacacaa 600
taccactgtc tttggctctg ggacagttg gcatgccagg cctgactgcc tactttggcc 660
tacttgaaat ctgtggtgtg aagggtggag aaacagtgat ggttaatgca gcagctggag 720
ctgtgggctc agtcgtgggg cagattgcaa agctcaaggg ctgcaaagtt gttggagcag 780
tagggtctga tgaaaaggtt gcctaccttc aaaagcttgg atttgatgtc gtctttaact 840
acaagacggt agagtctttg gaagaaacct tgaagaaagc gtctcctgat ggttatgatt 900
gttattttga taatgtaggt ggagagtttt caaacactgt tatcggccag atgaagaaat 960
ttggaaggat tgccatatgt ggagccatct ctacatataa cagaaccggc ccacttcccc 1020
caggcccacc cccagagatt gttatctatc aggagcttcg catggaagct tttgtcgtct 1080
accgctggca aggagatgcc cgccaaaaag ctctgaagga cttgctgaaa tgggtcttag 1140
agatcaaaag agaaaatgaa gaagattgaa gcttcaaagc agaaaaatga agggaatatg 1200
tatcattcac cattacctta 1220

<210> SEQ ID NO 250
<211> LENGTH: 301
<212> TYPE: PRT
<213> ORGANISM: Homo sapiens

<400> SEQUENCE: 250

Met Val Arg Thr Lys Thr Trp Thr Leu Lys Lys His Phe Val Gly Tyr
1 5 10 15

Pro Thr Asn Ser Asp Phe Glu Leu Lys Thr Ala Glu Leu Pro Pro Leu
20 25 30

Lys Asn Gly Glu Val Leu Leu Glu Ala Leu Phe Leu Thr Val Asp Pro
35 40 45

Tyr Met Arg Val Ala Ala Lys Arg Leu Lys Glu Gly Asp Thr Met Met
50 55 60

Gly Gln Gln Val Ala Lys Val Val Glu Ser Lys Asn Val Ala Leu Pro
65 70 75 80

Lys Gly Thr Ile Val Leu Ala Ser Pro Gly Trp Thr Thr His Ser Ile
85 90 95

Ser Asp Gly Lys Asp Leu Glu Lys Leu Leu Thr Glu Trp Pro Asp Thr
100 105 110

Ile Pro Leu Ser Leu Ala Leu Gly Thr Val Gly Met Pro Gly Leu Thr
115 120 125

Ala Tyr Phe Gly Leu Leu Glu Ile Cys Gly Val Lys Gly Gly Glu Thr
130 135 140

Val Met Val Asn Ala Ala Ala Gly Ala Val Gly Ser Val Val Gly Gln
145 150 155 160

Ile Ala Lys Leu Lys Gly Cys Lys Val Val Gly Ala Val Gly Ser Asp
165 170 175

Glu Lys Val Ala Tyr Leu Gln Lys Leu Gly Phe Asp Val Val Phe Asn
180 185 190

Tyr Lys Thr Val Glu Ser Leu Glu Glu Thr Leu Lys Lys Ala Ser Pro

```
        195                 200                 205

Asp Gly Tyr Asp Cys Tyr Phe Asp Asn Val Gly Gly Glu Phe Ser Asn
    210                 215                 220

Thr Val Ile Gly Gln Met Lys Lys Phe Gly Arg Ile Ala Ile Cys Gly
225                 230                 235                 240

Ala Ile Ser Thr Tyr Asn Arg Thr Gly Pro Leu Pro Pro Gly Pro Pro
                245                 250                 255

Pro Glu Ile Val Ile Tyr Gln Glu Leu Arg Met Glu Ala Phe Val Val
            260                 265                 270

Tyr Arg Trp Gln Gly Asp Ala Arg Gln Lys Ala Leu Lys Asp Leu Leu
        275                 280                 285

Lys Trp Val Leu Glu Ile Lys Arg Glu Asn Glu Glu Asp
    290                 295                 300


<210> SEQ ID NO 251
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 251

gcttggattt gatgtcgtct ttaac                                           25


<210> SEQ ID NO 252
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 252

gaaagcgtct cctgatggtt atgat                                           25


<210> SEQ ID NO 253
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 253

ttcaaacact gttatcggcc agatg                                           25


<210> SEQ ID NO 254
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 254

atgtggagcc atctctacat ataac                                           25


<210> SEQ ID NO 255
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 255

tacatataac agaaccggcc cactt                                           25
```

<210> SEQ ID NO 256
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 256
cccaccccca gagattgtta tctat 25

<210> SEQ ID NO 257
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 257
gttatctatc aggagcttcg catgg 25

<210> SEQ ID NO 258
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 258
catggaagct tttgtcgtct accgc 25

<210> SEQ ID NO 259
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 259
taccgctggc aaggagatgc ccgcc 25

<210> SEQ ID NO 260
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 260
aggatttgaa aacatgccag ctgca 25

<210> SEQ ID NO 261
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 261
gaggacacat ggaatctgga ggcca 25

<210> SEQ ID NO 262
<211> LENGTH: 2520
<212> TYPE: DNA
<213> ORGANISM: Homo sapiens

<400> SEQUENCE: 262
gcgcgcctgc gtactgcggt cagagggccg aggcctgggg gcgagctggg gtcgtgcagt 60
acagcctctt tccggcaaat cacgcgagat ttcgttcacc cgggctccac agggagtatt 120
ttatacagaa atcttgtgaa accactgccc aaccagagca atgattgttc aaagagtggt 180
attgaattct cgacctggaa aaaatggtaa tccagtggca gagaatttcc gaatggaaga 240
agtctattta ccagataata ttaatgaagg acaagtacaa gttagaactc tttatctttc 300
tgtggatcct tacatgcgtt gtagaatgaa tgaagacact ggcactgatt atataacacc 360
ttggcagcta tctcaagtcg ttgatggagg aggtattgga attatagaag aaagcaaaca 420
cacaaatttg actaaaggcg attttgtgac ttctttctat tggccctggc aaaccaaggt 480
tattctggat ggaaatagcc ttgaaaaggt agacccacaa cttgtggatg gacacctttc 540
atattttctt ggagctatag gtatgcctgg tttgacttcc ttgattggga tacaggaaaa 600
aggtcatata actgctggat ctaataagac aatggttgtc agtggggccg caggtgcctg 660
tggatctgtg gctgggcaga ttggccattt cttaggttgt tccagagtgg tgggaatttg 720
tggaacacat gagaaatgca tcctcttgac ctcagaactg ggctttgatg ctgcaattaa 780
ttataaaaaa gacaatgtgg cagaacagct ccgtgaatca tgcccagctg gagtggatgt 840
ttattttgac aatgttggtg gtaacatcag tgatacagtg ataagtcaga tgaatgagaa 900
cagccacatc atcctgtgtg gtcaaatttc tcagtacaac aaagatgtgc cttatcctcc 960
cccgctatcc cctgctatag aggcaatcca gaaagaaaga aacatcacaa gggaaagatt 1020
tctggtatta aattataaag acaaatttga gcctggcatt ctacagctga gtcagtggtt 1080
taaagaagga aagctaaaga ttaaagagac ggtaataaat gggttggaaa acatgggagc 1140
tgcattccag tccatgatga caggaggtaa cattggaaag cagatagttt gcatttcaga 1200
agaaatctct ttgtaattgc tgtaaatgtc atcaaggcaa tcatagattt cttttccatt 1260
ttgcatattt tcaaagatat gttaaaaaat ccttagacta tacatagctc ttgatttaaa 1320
tgtgatcata ggtgttattt ttagttgcat agggtatttg atacaatcat taatggatca 1380
tacacaatag gtttttaaaa attaataact tttagtaatt acttttatta atttaaaata 1440
gaacgcttga gaggcacttt gtaaagattt gttaaactgg aaacgtttta catgatctga 1500
tacaaccatt aatgaatcat acacaatagg ttttttaaaa ttaatattaa taacttttat 1560
taatttaaaa tagaatgctt aaaataaaat agaatgcttg agaggcactg agtaaagatt 1620
tgttgaactg gaaatgtttt acatgattct taaactgaaa cttggtgtaa aaatagaatt 1680
gagatggcct ttttttcaca ttgtagactg aaaagagact taatggtatg atgtgtacat 1740
agggactggg ggcaggattg ggggtttcgg agcttgtgta acagtttttg ggataggaga 1800
ccagcggttt tgggttggga ttagtatggg aagataaata acttaggttg gttaagttga 1860
caagatttac tccagaggat catctctttg tatttgccaa ataatttact gtatagccta 1920
aaaactccat atatattgag aaaagcatat gtttatttta ggttagcagg cacatactgt 1980
caagttgtaa agattgagag ggcaaacaga tgtaaacatc acttgtaggt gattaaaaag 2040
attgacagcc gggcctgatg tctcaagcct gtaatcctag cactttggga ggcagaggcg 2100
ggcagatcac ttgaggtcag gagttcaaga ccagcctggc caacacggtg aaaccccatc 2160
tctctaaaaa tacaaaaatt agctgggcgt ggtggcacac gcctgtaatc ccagctactc 2220
aggaggctga ggctggagaa tcatttgaac ctgggagggg gaggttgccg tgagctgagc 2280
ttgcaccatt gcactccagc ctgggcgaca agagtgaaat tccatctcaa aaaacaaaaa 2340
cagattgaca acaaagacag tttcagaaaa tgacaggact gggcaaatta acaaatgttt 2400
gtaaacatga atgttcagga actactgatg tacctcaaaa gtttgtttta ttaattgtac 2460
tcaaccctcg cagaacagta aaactgaaga ttattgtttc tgaaaaaaaa aaaaaaaaaa 2520

<210> SEQ ID NO 263
<211> LENGTH: 351
<212> TYPE: PRT
<213> ORGANISM: Homo sapiens

<400> SEQUENCE: 263

Met Ile Val Gln Arg Val Val Leu Asn Ser Arg Pro Gly Lys Asn Gly
1 5 10 15

Asn Pro Val Ala Glu Asn Phe Arg Met Glu Glu Val Tyr Leu Pro Asp
20 25 30

Asn Ile Asn Glu Gly Gln Val Gln Val Arg Thr Leu Tyr Leu Ser Val
35 40 45

Asp Pro Tyr Met Arg Cys Arg Met Asn Glu Asp Thr Gly Thr Asp Tyr
50 55 60

Ile Thr Pro Trp Gln Leu Ser Gln Val Val Asp Gly Gly Gly Ile Gly
65 70 75 80

Ile Ile Glu Glu Ser Lys His Thr Asn Leu Thr Lys Gly Asp Phe Val
85 90 95

Thr Ser Phe Tyr Trp Pro Trp Gln Thr Lys Val Ile Leu Asp Gly Asn
100 105 110

Ser Leu Glu Lys Val Asp Pro Gln Leu Val Asp Gly His Leu Ser Tyr
115 120 125

Phe Leu Gly Ala Ile Gly Met Pro Gly Leu Thr Ser Leu Ile Gly Ile
130 135 140

Gln Glu Lys Gly His Ile Thr Ala Gly Ser Asn Lys Thr Met Val Val
145 150 155 160

Ser Gly Ala Ala Gly Ala Cys Gly Ser Val Ala Gly Gln Ile Gly His
165 170 175

Phe Leu Gly Cys Ser Arg Val Val Gly Ile Cys Gly Thr His Glu Lys
180 185 190

Cys Ile Leu Leu Thr Ser Glu Leu Gly Phe Asp Ala Ala Ile Asn Tyr
195 200 205

Lys Lys Asp Asn Val Ala Glu Gln Leu Arg Glu Ser Cys Pro Ala Gly
210 215 220

Val Asp Val Tyr Phe Asp Asn Val Gly Gly Asn Ile Ser Asp Thr Val
225 230 235 240

Ile Ser Gln Met Asn Glu Asn Ser His Ile Ile Leu Cys Gly Gln Ile
245 250 255

Ser Gln Tyr Asn Lys Asp Val Pro Tyr Pro Pro Pro Leu Ser Pro Ala
260 265 270

Ile Glu Ala Ile Gln Lys Glu Arg Asn Ile Thr Arg Glu Arg Phe Leu
275 280 285

Val Leu Asn Tyr Lys Asp Lys Phe Glu Pro Gly Ile Leu Gln Leu Ser
290 295 300

Gln Trp Phe Lys Glu Gly Lys Leu Lys Ile Lys Glu Thr Val Ile Asn
305 310 315 320

Gly Leu Glu Asn Met Gly Ala Ala Phe Gln Ser Met Met Thr Gly Gly
325 330 335

Asn Ile Gly Lys Gln Ile Val Cys Ile Ser Glu Glu Ile Ser Leu 340 345 350

<210> SEQ ID NO 264
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 264
ggaaagcaga tagtttgcat ttcag 25

<210> SEQ ID NO 265
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 265
aaaatcctta gactatacat agctc 25

<210> SEQ ID NO 266
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 266
agactataca tagctcttga tttaa 25

<210> SEQ ID NO 267
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 267
gatcataggt gttattttta gttgc 25

<210> SEQ ID NO 268
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 268
ttagttgcat agggtatttg ataca 25

<210> SEQ ID NO 269
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 269
gatacaatca ttaatggatc ataca 25

<210> SEQ ID NO 270
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 270
ggatcataca caataggttt ttaaa 25

<210> SEQ ID NO 271
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 271
agaacgcttg agaggcactt tgtaa 25

<210> SEQ ID NO 272
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 272
ggaaacgttt tacatgatct gatac 25

<210> SEQ ID NO 273
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 273
tgatctgata caaccattaa tgaat 25

<210> SEQ ID NO 274
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 274
gaatcataca caataggttt tttaa 25

<210> SEQ ID NO 275
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 275
gcagtctttc ccttgaggct 20

<210> SEQ ID NO 276
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 276
tcgggaatta cgtcgccaaa 20

<210> SEQ ID NO 277
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 277
taccccgagc agttctccta cat 23

<210> SEQ ID NO 278
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 278
gccagttcct tggacaccag gtctg 25

<210> SEQ ID NO 279
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 279
gcatccacct ggagtaccct 20

<210> SEQ ID NO 280
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 280
tcccaggacc ttttggtggt 20

<210> SEQ ID NO 281
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 281
tgaggcagaa aataaggaga gtgaa 25

<210> SEQ ID NO 282
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 282
tggggaagtg aagtgtaaga agagt 25

<210> SEQ ID NO 283
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 283
aggcagaaaa taaggagagt g 21

<210> SEQ ID NO 284
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 284
aagcggatgg atgatagtga g 21

<210> SEQ ID NO 285
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 285
gcgaggtaga gtcaaggaga gtggtct 27

<210> SEQ ID NO 286
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 286
gcgcaaagtt cgttctgctg ctcaag 26

<210> SEQ ID NO 287
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 287
gccgagatga tggagatgaa gatta 25

<210> SEQ ID NO 288
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 288
gcgcagtagg tatggattta tgtga 25

<210> SEQ ID NO 289
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 289
gtagtcattg atgatctgcc caaagag 27

<210> SEQ ID NO 290

<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 290
gagccacaca agctattttc tttctca 27

<210> SEQ ID NO 291
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 291
gcagttcaag gatctaaaga gcatcaa 27

<210> SEQ ID NO 292
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 292
aacatctgta tgctgaggat gaacaca 27

<210> SEQ ID NO 293
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 293
tgatgatgag actaaaacaa aat 23

<210> SEQ ID NO 294
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 294
tgaagaagaa agaataaaat aat 23

<210> SEQ ID NO 295
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 295
ttttccagtc ccattatttt cacag 25

<210> SEQ ID NO 296
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 296
agtcccttct ttcctttcag tctcc 25

<210> SEQ ID NO 297
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 297
tcaaggcaaa gagaaaaaga gtatt 25

<210> SEQ ID NO 298
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 298
agacaccaaa gtaagaccac agatt 25

<210> SEQ ID NO 299
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 299
agacttggag acttcttcgg agacc 25

<210> SEQ ID NO 300
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 300
taaaacacag gcatcaatca aaata 25

<210> SEQ ID NO 301
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 301
gaactgggtg atgcggatgc t 21

<210> SEQ ID NO 302
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 302
gctggaagag gaaggagaga a 21

<210> SEQ ID NO 303
<211> LENGTH: 27
<212> TYPE: DNA

<213> ORGANISM: Artificial Sequence
<220> FEATURE:
<223> OTHER INFORMATION: Synthetic polynucleotide

<400> SEQUENCE: 303
acaaggtgaa accccgtctc tactaaa 27

<210> SEQ ID NO 304
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 304
ttcttccacc taagctttgc cataaat 27

<210> SEQ ID NO 305
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 305
atcaaaaaca tcatcatcca ggactgt 27

<210> SEQ ID NO 306
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 306
tctcaggact ctgacactgt ccaactt 27

<210> SEQ ID NO 307
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 307
caggatggtt cgtactaaga catggac 27

<210> SEQ ID NO 308
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 308
gctttcttca aggtttcttc caaagac 27

<210> SEQ ID NO 309
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 309
catgcgttgt agaatgaatg aagacac 27

<210> SEQ ID NO 310
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 310
tgtactgaga aatttgacca cacagga 27

<210> SEQ ID NO 311
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 311
agcaggttaa tggataattt cttgat 26

<210> SEQ ID NO 312
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 312
ggtcctttgt aaaaaccatt acactt 26

<210> SEQ ID NO 313
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 313
cgtttccttt tattttggag ctaatgc 27

<210> SEQ ID NO 314
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 314
aaggaagtca ctccaaggta cacactg 27

<210> SEQ ID NO 315
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 315
atgcaagaaa tgtctggaga aattgaa 27

<210> SEQ ID NO 316
<211> LENGTH: 27
<212> TYPE: DNA
<213> ORGANISM: Artificial Sequence
<220> FEATURE:

<223> OTHER INFORMATION: Synthetic polynucleotide

<400> SEQUENCE: 316
ccttgtattt tctcagtacg agctcca 27

<210> SEQ ID NO 317
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 317
gcgacggcgg ctgcggctac tggag 25

<210> SEQ ID NO 318
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 318
ttcttctaat gcttcttgac taccc 25

<210> SEQ ID NO 319
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 319
tgaaaggaag gagaaggaga aaaag 25

<210> SEQ ID NO 320
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 320
agaggcagtg agggcagcat tagta 25

<210> SEQ ID NO 321
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 321
taaatggaga ggaggtagaa gaaac 25

<210> SEQ ID NO 322
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 322
ggtggtagaa agagaacgaa aagtc 25

<210> SEQ ID NO 323
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 323
gcgtgacatt aaggagaagc tgt 23

<210> SEQ ID NO 324
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 324
cttgttttct gcgcaagtta ggt 23

<210> SEQ ID NO 325
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 325
aggagccagg agaggact 18

<210> SEQ ID NO 326
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 326
gcagggacga aaggtatc 18

<210> SEQ ID NO 327
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 327
gtatcgtgga aggactcatg acc 23

<210> SEQ ID NO 328
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 328
tctcttcctc ttgtgctctt gct 23

<210> SEQ ID NO 329
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 329
gcacacagaa gcgctcagta agggctttga aacttaacag tttgggagcc agatcctcag 60
gccacatctc tctcctccca cgacctccgc ggtcctccag aaccatagag agttgtacag 120

<210> SEQ ID NO 330
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 330
agatcgccct gctctatgct ctactctcct ggggagcggg gccagagagg ccggaagtgc 60
tgcgagccct gggccacgct ggccgtgctg gcagtgggcc gcctcgatcc ctctgcagtc 120

<210> SEQ ID NO 331
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 331
tttcccttga ggctccaaga ccagcaggtg aggcctcgcg gcgctgaaac cgtgaggccc 60
ggaccacagg tgcgggaggc ggagactgcg ggtggagatt ggcgccgcgg aagccaatca 120

<210> SEQ ID NO 332
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 332
gcgatgggac ttgtggacct gtaaggggcg gggcgagccg aaggtggagg tcaaaggggc 60
gtggcgttac agagcctcta gcgctgggtg ttggggacct gacgctatgg agctctcgga 120

<210> SEQ ID NO 333
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 333
gttttgtggg ggacggctgt gagtgggggg ttcctgctgc gggatgagaa cgtagacgcc 60
agtggctcac tcgctcctgg caccttccct ttcaggctcc agatggaccc tgggaaggac 120

<210> SEQ ID NO 334
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 334
aaagaggggg tgccccagcc ctcagggccg ccagcaagga agaaatttgt gatacccctc 60
gacgaggatg aggtccctcc tggagtggta ggacaaggag atgcggggcc cctgggaggc 120

<210> SEQ ID NO 335
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 335
ttctccccac aggccaagcc cttattccga tctacacaga gccttcccac tgtggacacc 60
tcggcccagg cggcccctca gacctacgcc gaatatgcca tctcacagcc tctggaaggg 120

<210> SEQ ID NO 336
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 336
gctggggcca cgtgccccac agggtcagag cccctggcag gagagacgcc caaccaggcc 60
ctgaaacccg gggcaaaatc caacagcatc attgtgagcc ctcggcaggt gaggagggag 120

<210> SEQ ID NO 337
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 337
ctccccagag gggcaatccc gtactgaagt tcgtgcgcaa tgtgccctgg gaatttggcg 60
acgtaattcc cgactatgtg ctgggccaga gcacctgtgc cctgttcctc aggtgagctc 120

<210> SEQ ID NO 338
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 338
cccccaccag cctccgctac cacaacctgc acccagacta catccatggg cggctgcaga 60
gcctggggaa gaacttcgcc ttgcgggtcc tgcttgtcca ggtggatgtg gtaagcaggg 120

<210> SEQ ID NO 339
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 339
aattctgatt ttctcctcca gaaagatccc cagcaggccc tcaaggagct ggctaagatg 60
tgtatcctgg ccgactgcac attgatcctc gcctggaggt gagatgaggg cttccctgcc 120

<210> SEQ ID NO 340
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 340
gttatcccag ccccgaggaa gctgggcggt acctggagac ctacaaggcc tatgagcaga 60
aaccagcgga cctcctgatg gagaagctag agcaggactt cgtctcccgg gtgaggccac 120

<210> SEQ ID NO 341
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 341
cactcctgcc tccacccttt ccaggtgact gaatgtctga ccaccgtgaa gtcagtcaac 60
aaaacggaca gtcagaccct cctgaccaca tttggagtaa ggaatggctc ccctgcccca 120

<210> SEQ ID NO 342
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 342
ggaggctttt gtgctcaact gccctgaccc ctcgctttca cctttcagtc tctggaacag 60
ctcatcgccg catcaagaga agatctggcc ttatgcccag gcctgggccc tcagaaagta 120

<210> SEQ ID NO 343
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 343
agagctctgg gaaagaaccc aaggagttgg gggaaggaga gagccccaaa taaacacaac 60
ctgagacccc aaagttttaa ggtgaaaaaa gaaccaaaga ccagacacag tggcttccg 119

<210> SEQ ID NO 344
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 344
ggcgggtcga ccccgctgca cagtccggcc ggcgccatga agtgagaagg gggctggggg 60
tcgcgctcgc tagcgggcgc ggggggtctt gaagatgggg tcatcggtgg gcgcgcctgg 120

<210> SEQ ID NO 345
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 345
gtccccaagg gggcgagggg agggtgaagg ggtgggacgg gggcagccgc agggagcagc 60
agtgatagcg aggagacact gagggggccc cgaggctcct gaggacctga gggttaccgg 120

<210> SEQ ID NO 346
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 346
gggcgccggg cccgtcaccc ttctctgggc tcgacgaccg ggcactgtgg aggcgggaga 60
ggggctgagg ggacgggaac tgacccagca gcccctgccg ccaggctcaa cgtggacggg 120

<210> SEQ ID NO 347
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 347
ctcctggtct acttcccgta cgactacatc taccccgagc agttctccta catgcgggag 60
ctcaaacgca cgctggacgc caaggtgggt ggccggtggg cccgacccgc ccactcgacc 120

<210> SEQ ID NO 348
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 348
cctctggtcc ccaacatgca gggtcatgga gtcctggaga tgccctcagg caccgggaag 60
acagtatccc tgttggccct gatcatggca taccagagag tgagtgatgc gctgaacccg 120

<210> SEQ ID NO 349
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 349
agggactgag tccgcttgtt atcggcaggc atatccgctg gaggtgacca aactcatcta 60
ctgctcaaga actgtgccag agattgagaa ggtaagctgg gactcatcct ggtgctccag 120

<210> SEQ ID NO 350
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 350
agtaggtgat tgaagagctt cgaaagttgc tcaacttcta tgagaagcag gagggcgaga 60
agctgccgtt tctgggactg gctctgagct cccgcaaaaa cttgtgtatt caccctgagg 120

<210> SEQ ID NO 351
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 351
aggtgacacc cctgcgcttt gggaaggacg tcgatgggaa atgccacagc ctcacagcct 60
cctatgtgcg ggcgcagtac cagcatgaca ccagcctgcc ccactgccga ttctatgagg 120

<210> SEQ ID NO 352

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 352
aggaatttga tgcccatggg cgtgaggtgc ccctccccgc tggcatctac aacctggatg 60
acctgaaggc cctggggcgg cgccagggct ggtgcccata cttccttgct cgatactcag 120

<210> SEQ ID NO 353
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 353
ggtaggggta ggggttgggg tggcagggcc ctggtaaccc tgctccccgg ccccccagat 60
cctgcatgcc aatgtggtgg tttatagcta ccactacctc ctggacccca agattgcaga 120

<210> SEQ ID NO 354
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 354
cctggtgtcc aaggaactgg cccgcaaggc cgtcgtggtc ttcgacgagg cccacaacat 60
tggtgagggg ggcgccaggg gccaaaggga tgccagcccc tctgagtgag gcccctgcag 120

<210> SEQ ID NO 355
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 355
ccccttctcc agacaacgtc tgcatcgact ccatgagcgt caacctcacc cgccggaccc 60
ttgaccggtg ccagggcaac ctggagaccc tgcagaagac ggtgctcagg tggggccggg 120

<210> SEQ ID NO 356
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 356
acttgtcccc agggttgcca gccccctccc agccccagct catctctccg caggatcaaa 60
gagacagacg agcagcgcct gcgggacgag taccggcgtc tggtggaggg gctgcgggag 120

<210> SEQ ID NO 357
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 357
gccagcgccg cccgggagac ggacgcccac ctggccaacc ccgtgctgcc cgacgaagtg 60
ctgcagggtg agccccgacc ccccgctgcc ccccagtccc tttcccgcct ccccgtcgcc 120

<210> SEQ ID NO 358
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 358
cgcctccccg tcgccgctga tagcgtctcc tcgcagaggc agtgcctggc tccatccgca 60
cggccgagca tttcctgggc ttcctgaggc ggctgctgga gtacgtgaag tggcggctgc 120

<210> SEQ ID NO 359
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 359
gtgtgcagca tgtggtgcag gagagcccgc ccgccttcct gagcggcctg gcccagcgcg 60
tgtgcatcca gcgcaagccc ctcaggtgcg gccccagaca gcgcgcgggg tgggggcccg 120

<210> SEQ ID NO 360
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 360
attctgtgct gaacgcctcc ggtccctgct gcatactctg gagatcaccg accttgctga 60
cttctccccg ctcaccctcc ttgctaactt tgccaccctt gtcagcacct acgccaaagg 120

<210> SEQ ID NO 361
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 361
acccctcctt gcctgccctc tgcaggcttc accatcatca tcgagccctt tgacgacaga 60
accccgacca ttgccaaccc catcctgcac ttcaggtggg accctgcccg gtgagggtgt 120

<210> SEQ ID NO 362
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 362
cctcactgcc ctcatctctc tccagctgca tggacgcctc gctggccatc aaacccgtat 60
ttgagcgttt ccagtctgtc atcatcacat ctggggtaag gacccttccc cgtcccctcc 120

<210> SEQ ID NO 363
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 363
ccgccacaga cactgtcccc gctggacatc taccccaaga tcctggactt ccaccccgtc 60
accatggcaa ccttcaccat gacgctggca cgggtctgcc tctgccctat ggtgagtggg 120

<210> SEQ ID NO 364
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 364
gcttatcgtg acctctgttg ctctccagat catcggccgt ggcaatgacc aggtggccat 60
cagctccaaa tttgagaccc gggaggatat tggtatgctg ccagtggggc tggtttctgt 120

<210> SEQ ID NO 365
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 365
agacagagaa gggaggagga cctgggccag gagagggccc aacctctgac cccttgcagc 60
tgtgatccgg aactatggga acctcctgct ggagatgtcc gctgtggtcc ctgatggcat 120

<210> SEQ ID NO 366
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 366
cgtggccttc ttcaccagct accagtacat ggagagcacc gtggcctcct ggtatgagca 60
ggtacgcctg gccacccccct ccctgcacct gctctcctca gtccctggca ctgcaccgct 120

<210> SEQ ID NO 367
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 367
gggtccttcc ccaggggatc cttgagaaca tccagaggaa caagctgctc tttattgaga 60
cccaggatgg tgccgaaacc agtgtcgccc tggagaagta ccaggaggtg ggtgtgcgag 120

<210> SEQ ID NO 368
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 368
tgcgtctcgg tctccccacc tcaggcctgc gagaatggcc gcggggccat cctgctgtca 60
gtggcccggg gcaaagtgtc cgagggaatc gactttggtg agtggactgg gctcttcctc 120

<210> SEQ ID NO 369
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 369
cgccccctct cctctgccca ccagtgcacc actacgggcg ggccgtcatc atgtttggcg 60
tcccctacgt ctacacacag agccgcattc tcaaggtgag tagctctgtc tcccagggag 120

<210> SEQ ID NO 370
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 370
aggagtggct cccccacctc cccagcttct catcctccgt atctgcaggc gcggctggaa 60
tacctgcggg accagttcca gattcgtgag aatgactttc ttaccttcga tgccatgcgc 120

<210> SEQ ID NO 371
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 371
cacgcggccc agtgtgtggg tcgggccatc aggggcaaga cggactacgg cctcatggtc 60
tttgccgaca aggtgcagct tcaggggtgc ccctgtgctc ccatcccagg ctccaagaac 120

<210> SEQ ID NO 372
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 372
aggctccccg aatgaccttc tgtccctggc ctgcgcttct gcccacagcg gtttgcccgt 60
ggggacaagc gggggaagct gccccgctgg atccaggagc acctcacaga tgccaacctc 120

<210> SEQ ID NO 373
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 373
aacctgaccg tggacgaggg tgtccaggtg gccaagtact tcctgcggca gatggcacag 60
cccttccacc gggtgaggcc tgcgtccccc tcccggcacc ctcccaggct gagcttctcc 120

<210> SEQ ID NO 374
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 374
tctgttctct gcaggaggat cagctgggcc tgtccctgct cagcctggag cagctagaat 60
cagaggagac gctgaagagg atagagcaga ttgctcagca gctctgagtg gggcgggtgg 120

<210> SEQ ID NO 375
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 375
gagcggggtc atcttctctc tgctgctgta gctgccatgg gcaaaagaga ccgagcggac 60
cgcggtgaga cgttgcgcgg gcacgctcag ccacgactgc ccttgccggc cctgcccccc 120

<210> SEQ ID NO 376
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 376
gctctgcctc ggagctgctc cgggcctctg cgccggccga ccctgctggc cctcccgcgc 60
gcaccccgtt gggacaggcc tttgggcggg agagatgctg gacctgggcg cagcccagcg 120

<210> SEQ ID NO 377
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 377
aactcggcct aggggagacg ggtgaggggc gcaacgcctg cgggatgcag gtggctctta 60
gctaggagtt tgcggcggcg caggtgaaat gctgccaagc ggtgcggagg gaaccctgaa 120

<210> SEQ ID NO 378
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 378
gtgttggtat cttgcagaca agaagaaatc caggaagcgg cactatgagg atgaagagga 60
tgatgaagag gacgccccgg ggaacgaccc tcaggaagcg gttccctcgg cggcggggaa 120

<210> SEQ ID NO 379
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 379
gcaggtggat gagtcaggca ccaaagtgga tgaatatgga gccaaggact acaggctgca 60
aatgccgctg aaggacgacc acacctccag gcccctctgg gtggtaagca tgcccttagc 120

<210> SEQ ID NO 380
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 380
aggctcccga tggccatatc ttcttggaag ccttctctcc agtttacaaa tatgcccaag 60
acttcttggt ggctattgca gagccagtgt gccgaccaac ccatgtgcat gagtacaaac 120

<210> SEQ ID NO 381
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 381
taactgccta ctccttgtat gcagctgtca gcgttgggct gcaaaccagt gacatcaccg 60
agtacctcag gaagctcagc aagactggag tccctgatgg aattatgcag tttattaagg 120

<210> SEQ ID NO 382
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 382
cacatttacc tgttggatgt tatctgtatt tgcagttgtg tactgtcagc tatggaaaag 60
tcaagctggt cttgaagcac aacaggtaag agattccatg acaggcctgt cccaaggcac 120

<210> SEQ ID NO 383
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 383
tccaggaggt acctgctggt cagtagaccc cttcttcctc ccctgcttgc agatacttcg 60
ttgaaagttg ccaccctgat gtaatccagc atcttctcca ggaccccgtg atccgagaat 120

<210> SEQ ID NO 384
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 384
gccgcttaag aaactctgaa ggggaggcca ctgagctcat cacagagact ttcacaagca 60
aatctgccgt atgtggactc ctgggccacc cttgggtggg ggcaggcatt taggatttca 120

<210> SEQ ID NO 385
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 385
aatgttgtgt gcacgttcag cacctacctc tctcacagat ttctaagact gctgaaagca 60
gtggtgggcc ctccacttcc cgagtgacag atccacaggg taaatctgac atccccatgg 120

<210> SEQ ID NO 386
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 386
acctgtttga cttctatgag caaatggaca aggatgaaga agaagaagaa gagacacaga 60
cagtgtcttt tgaagtcaag caggttagtg aatgtacctt cctcctggtt ccttcactga 120

<210> SEQ ID NO 387
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 387
tttgtgccct ctttccagga aatgattgag gaactccaga aacgttgcat ccacctggag 60
taccctctgt tggcagaata tgacttccgg aatgattctg tcaaccctga tatcaacatt 120

<210> SEQ ID NO 388
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 388
gacctaaagc ccacagctgt cctcagaccc tatcaggaga agagcttgcg aaagatgttt 60
ggaaacgggc gtgcacgttc gggggtcatt gttcttccct gcggtaagtg gtaccagagt 120

<210> SEQ ID NO 389
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 389
attgcactct tgtttcttgt aggtgctgga aagtccctgg ttggtgtgac tgctgcatgc 60
actgtcagaa aacgctgtct ggtgctgggc aactcagctg tttctgtgga gcagtggaaa 120

<210> SEQ ID NO 390
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 390
gcccagttca agatgtggtc caccattgac gacagccaga tctgccggtt cacctccgat 60
gccaaggaca agcccatcgg ctgctccgtt gccattagca cctactccat gctgggccac 120

<210> SEQ ID NO 391
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 391
accaccaaaa ggtcctggga ggccgagcga gtcatggagt ggctcaagac ccaggagtgg 60
ggcctcatga tcctggatga agtgcacacc ataccaggta agcaggctgg agctgagctg 120

<210> SEQ ID NO 392
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 392
agtgtgaatg ctcccattgt ttcctcagcc aagatgttcc gaagggtgct caccatcgtg 60
caggcccact gtaagctggg tttgactgcg accctcgtcc gcgaagatga caaaattgtg 120

<210> SEQ ID NO 393
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 393
gatttaaatt ttctgattgg gcctaagctc tacgaagcca actggatgga gctgcagaat 60
aatggctaca tcgccaaagt ccagtgtgct gaggtagctg ggcctgggct gggggcgtct 120

<210> SEQ ID NO 394
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 394
gttcttactg tattacaggt ctggtgccct atgtctcctg aattttaccg ggaatatgtg 60
gcaatcaaaa ccaagaaacg aatcttgctg tacaccatga accccaacaa atttagagct 120

<210> SEQ ID NO 395
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 395
tgccagtttc tgatcaagtt tcatgaaagg aggaatgaca agattattgt ctttgctgac 60
aatgtgtttg ccctaaagga atatgccatt cgactgaaca agtaagaatt gaaaacttgg 120

<210> SEQ ID NO 396
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 396
attcttctct agaccctata tctacggacc tacgtctcag ggggaaagga tgcaaattct 60
ccagaatttc aagcacaacc ccaaaattaa caccatcttc atatccaagg tttgtgtggc 120

<210> SEQ ID NO 397
<211> LENGTH: 120
<212> TYPE: DNA

<213> ORGANISM: Artificial Sequence
<220> FEATURE:
<223> OTHER INFORMATION: Synthetic polynucleotide

<400> SEQUENCE: 397
ggtaggtgac acttcgtttg atctgccgga agcaaatgtc ctcattcaga tctcatccca 60
tggtggctcc aggcgtcagg aagcccaaag gctagggcgg gtgcttcgag ctaaaaaagg 120

<210> SEQ ID NO 398
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 398
ggatggttgc agaagagtac aatgcctttt tctactcact ggtatcccag gacacacagg 60
aaatggctta ctcaaccaag cggcagagat tcttggtaga tcaaggttat agcttcaagg 120

<210> SEQ ID NO 399
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 399
agagagagca gaaaggggca tgtctgctgg cttgggcttt gcaggtgatc acgaaactcg 60
ctggcatgga ggaggaagac ttggcgtttt cgacaaaaga agagcaacag cagctcttac 120

<210> SEQ ID NO 400
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 400
agaaagtcct ggcagccact gacctggatg ccgaggagga ggtggtggct ggggaatttg 60
gctccagatc cagccaggtg agtaaatggg tgaggaggtt ccaggtgtca gtgctctcac 120

<210> SEQ ID NO 401
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 401
aggagtatct tttcttctgg agactaacat gggctggttc cccttcccg gcaggcatct 60 cggcgctttg gcaccatgag ttctatgtct ggggccgacg acactgtgta catggagtac 120

<210> SEQ ID NO 402
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 402
cactcatcgc ggagcaaggc gcccagcaaa catgtacacc cgctcttcaa gcgctttagg 60
aaatgatgct taggcagggt acttcgttca agaccggcgc ttggcaccct tgttggaaag 120

<210> SEQ ID NO 403
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 403
acccggaaga gcttccatgg agtcagggca gccggctcga cggattgcca tggcgccgct 60
gctggagtac gagcgacagc tggtgctgga actgctcgac actgacgggc tagtagtgtg 120

<210> SEQ ID NO 404
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 404
cgcccgcggg ctcggcgcgg accggctcct ctaccacttt ctccagctgc actgccaccc 60
agcctgcctg gtgctggtgc tcaacacgca gccggccgag gaggtgcggc cgcgctggcg 120

<210> SEQ ID NO 405
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 405
agcctactaa tcaagtttga tttgatttag gagtatttta tcaatcagct gaagatagaa 60
ggagttgaac acctccctcg ccgtgtaaca aatgaaatca caagcaacag tcgctatgaa 120

<210> SEQ ID NO 406
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 406
gtttacacac aaggtggtgt tatatttgcg acaagtagga tacttgtggt tgacttcttg 60
actgatagaa taccttcaga tttaattact ggtaagaatt tgaaatctta ttattagtat 120

<210> SEQ ID NO 407
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 407
aaattatgtt tctccccctc aggcatcttg gtgtatagag cccacagaat aatcgagtct 60
tgtcaagaag cattcatctt gcgcctcttt cgccagaaaa acaaacgtgg ttttattaaa 120

<210> SEQ ID NO 408
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 408
gctttcacag acaatgctgt tgcctttgat actggttttt gtcatgtgga aagagtgatg 60
agaaatcttt ttgtgaggaa actgtatctg tggccaaggt aaagaacatt atgtgacaaa 120

<210> SEQ ID NO 409
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 409
atatttgtct ctttaggttc catgtagcag taaactcatt tttagaacag cacaaacctg 60
aagttgtaga aatccatgtt tctatgacac ctaccatgct tgctatacag actgctatac 120

<210> SEQ ID NO 410
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 410
tggacatttt aaatgcatgt ctaaaggaac taaaatgcca taacccatcg cttgaagtgg 60
aagatttatc tttagaaaat gctattggaa aacctttga caaggtactc tttttccttt 120

<210> SEQ ID NO 411
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 411
tagcaatacc aaattttatt cttgttttag acaatccgcc attatctgga tcctttgtgg 60
caccagcttg gagccaagac taaatcctta gttcaggatt tgaagatatt acgaactttg 120

<210> SEQ ID NO 412
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 412
ctgcagtatc tctctcagta tgattgtgtc acatttctta atcttctgga atctctgaga 60
gcaacggaaa aagcttttgg tcagaattca ggtgggagat taaaatacta ataatattct 120

<210> SEQ ID NO 413
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 413
ctgttttaaa ttaaccataa attgatggca ctttttcttt taacttttcg tattaggttg 60
gctgtttctt gactccagca cctcgatgtt tataaatgct cgagcaaggg tttatcatct 120

<210> SEQ ID NO 414
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 414
tccagatgcc aaaatgagta aaaaagaaaa aatatctgaa aaaatggaaa ttaaagaagg 60
ggaaggtatc ttgtggggtt aagtctttaa atgtgttttt tatttcggta tttggtatgg 120

<210> SEQ ID NO 415
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 415
acagaaacaa aaaaggaact ggtcctagaa agcaacccaa agtgggaggc actgactgaa 60
gtattaaaag aaattgaggc agaaaataag gagagtgaag ctcttggtgg tccaggtagg 120

<210> SEQ ID NO 416
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 416
ggtcaagtac tgatttgtgc aagtgatgac cgaacatgtt cccagctgag agactatatc 60
actcttggag cggaggcctt cttattgagg ctctacagga aaacctttga gaaggatagc 120

<210> SEQ ID NO 417
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 417
aaagctgaag aagtctggat gaaatttagg aaggaagaca gttcaaagag aattaggaaa 60
tctcacaaaa gacctaaaga cccccaaaac aaagaacggg cttctaccaa agaaagaacc 120

<210> SEQ ID NO 418
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 418
ctcaaaaaga aaaaacggaa gttgacctta actcaaatgg taggaaaacc tgaagaactg 60
gaagaggaag gagatgtcga ggaaggatat cgtcgagaaa taagcagtag cccagaaagc 120

<210> SEQ ID NO 419
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 419
tgcccggaag aaattaagca tgaagaattt gatgtaaatt tgtcatcgga tgctgctttc 60
ggaatcctga aagaacccct cactatcatc catccgcttc tgggttgcag cgacccctat 120

<210> SEQ ID NO 420
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 420
gctctgacaa gggtactaca tgaagtggag ccaagatacg tggttcttta tgacgcagag 60
ctaacctttg ttcggcagct tgaaatttac agggcgagta ggcctgggaa acctctgagg 120

<210> SEQ ID NO 421
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 421
gtcttaacat gcagggttta ctttcttata tacggaggtt caactgagga acaacgctat 60
ctcactgctt tgcggaaaga aaaggaagct tttgaaaaac tcataaggta atacatagaa 120

<210> SEQ ID NO 422
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 422
acagggaaaa agcaagcatg gttgtccctg aagaaagaga aggcagagat gaaacaaact 60
tagacctagt aagaggcaca gcatctgcag atgtttccac tgacactcgg aaagccggtg 120

<210> SEQ ID NO 423
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 423
attccttctt tgagagttct tccccagtga cattacttac tttttctctg taggtggcca 60
ggaacagaat ggtacacagc aaagcatagt tgtggatatg cgtgaatttc gaagtgagct 120

<210> SEQ ID NO 424
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 424
tccatctctg atccatcgtc ggggcattga cattgaaccc gtgactttag aggttggaga 60
ttacatcctc actccagaaa tgtgcgtgga gcgcaagagt atcagtgatt taatcggctc 120

<210> SEQ ID NO 425
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 425
tttaaataac ggccgcctct acagccagtg catctccatg tcccgctact acaagcgtcc 60
cgtgcttctg attgagtttg accctagcaa gcctttctct ctcacttccc gaggtgcctt 120

<210> SEQ ID NO 426
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 426
gtttcaggag atctccagca atgacattag ttccaaactc actcttctta cacttcactt 60
ccccagacta cggattctct ggtgcccctc tcctcatgca acggcggagt tgtttgagga 120

<210> SEQ ID NO 427
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 427
gctgaaacaa agcaagccac agcctgatgc ggcgacagca ctggccatta cagcagattc 60
tgaaaccctt cccgagtcag agaagtataa tcctggtccc caagacttct tgttaaaaat 120

<210> SEQ ID NO 428
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 428
gccaggggtg aatgccaaaa actgccgctc cttgatgcac cacgttaaga acatcgcaga 60
attagcagcc ctgtcacaag acgagctcac gagtattctg ggaatgctg caaatgccaa 120

<210> SEQ ID NO 429
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 429
acagctttat gatttcattc acacctcttt tgcagaagtc gtatcaaaag gaaaagggaa 60
aaagtgaaca gtgatggctg ttttcttatc ccatgcctgt acttttcagc ggctccttgc 120

<210> SEQ ID NO 430
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 430
aggacgcagc cgcctcatgg gggtccaggg gctctggaag ctgctggagt gctccgggcg 60
gcaggtcagc cccgaagcgc tggaagggaa gatcctggct gttggtatcc ttaacgccgc 120

<210> SEQ ID NO 431

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 431
cccggagttt tttccattaa caattctccc agatattagc atttggttaa accaagcact 60
taaaggagtc cgggatcgcc atgggaactc aatagaaaat cctcatcttc tcactttgtt 120

<210> SEQ ID NO 432
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 432
tcatcggctc tgcaaactct tattttttcg aattcgtcct atttttgtgt ttgatgggga 60
tgctccacta ttgaagaaac agactttggt aagtgtcgta tagtttttag taagtgtcaa 120

<210> SEQ ID NO 433
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 433
aggtgaagag aaggcagaga aaggacttag cgtccagtga ctccaggaaa acgacagaga 60
agcttctgaa aacattttg aaaagacaag ccatcaaaac tgccttcaga agcaaaaggc 120

<210> SEQ ID NO 434
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 434
tttgtgtact ttccagagat gaagcactac ccagtcttac ccaagttcga agagaaaacg 60
acctctatgt tttgcctcct ttacaagagg aagaaaaaca caggtaaatg tttaactatt 120

<210> SEQ ID NO 435
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 435
agatatcgta aaagtatgtt tgactttcag ttcagaagag gaagatgaaa aagaatggca 60
agaaagaatg aatcaaaaac aagcattaca ggtatttaga tcatttttga attcagaatg 120

<210> SEQ ID NO 436
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 436
aagtgtatga aatgtaaatt tcatggtgct gtgattttat ctttacagga agagttcttt 60
cataatcctc aagcgataga tattgagtct gaggacttca gcagcctgcc ccctgaagta 120

<210> SEQ ID NO 437
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 437
aagcatgaaa tcttgactga tatgaaagag ttcaccaagc gcagaagaac attatttgaa 60
gcaatgccag aggtgaaata tgcaacagta cattcatgct tagaattaag aacttcagca 120

<210> SEQ ID NO 438
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 438
tttattttgc ctttaggagt ctgatgactt ttcacagtac caactcaaag gcttgcttaa 60
aaagaactat ctgaaccagc atatagaaca tgtccaaaag gaaatgaatc agcaacattc 120

<210> SEQ ID NO 439
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 439
aggacacatc cgaaggcagt atgaagatga agggggcttt ctgaaggagg tagagtcaag 60
gagagtggtc tctgaagaca cttcacatta catcttgata aaaggtatca ggcaccatca 120

<210> SEQ ID NO 440
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 440
aaggtattca agctaagaca gttgcagaag tggattcaga gtctcttcct tcttccagca 60
aaatgcacgg catgtctttt gacgtgaagt catctccatg tgaaaaactg aagacagaga 120

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 451
aagagcctga tgctacccct ccttctccaa gaactttact agctatgcaa gctgccctgc 60
tgggaagtag ctcagaagag gagctggaga gtgaaaatcg aaggcaggcc cgtgggagga 120

<210> SEQ ID NO 452
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 452
acgcacctgc tgctgtagac gaaggctcca tatcaccccg gactctttca gccattaaga 60
gagctcttga cgatgacgaa gatgtaaaag tgtgtgctgg ggatgatgtg cagacgggag 120

<210> SEQ ID NO 453
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 453
ggccaggagc agaagaaatg cgtataaaca gctccaccga gaacagtgat gaaggactta 60
aagtgagaga tggaaaagga ataccgttta ctgcaacact tgcgtcatct agtgtgaact 120

<210> SEQ ID NO 454
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 454
ctgcagagga gcacgtagcc agcactaatg aggggagaga gcccacagac tcagttccaa 60
aagaacaaat gtcacttgtt cacgtgggga ctgaagcctt tccgataagt gatgagtcta 120

<210> SEQ ID NO 455
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 455
tgattaagga cagaaaagat cggctgcctc tggagagtgc agtggttaga catagtgacg 60
cacctgggct cccgaatgga agggaactga caccggcatc tccaacttgt acaaattctg 120

<210> SEQ ID NO 456
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 456
tgtcaaagaa tgaaacacat gctgaagtgc ttgagcagca gaacgaactt tgcccatatg 60
agagtaaatt cgattcttct cttctttcaa gtgatgatga aacaaaatgt aaaccgaatt 120

<210> SEQ ID NO 457
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 457
ctgcttctga agtcattggc cctgtcagtt tgcaagaaac aagtagcata gtaagtgtcc 60
cttcagaggc agtagataat gtggaaaatg tggtgtcatt taatgctaaa gagcatgaga 120

<210> SEQ ID NO 458
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 458

```
attttctgga aaccatccaa gaacagcaga ccactgaatc tgcaggccag gatttaattt      60

ccattccaaa ggccgtggaa ccaatggaaa ttgactcgga agaaagtgaa tctgatggta     120
```

<210> SEQ ID NO 459
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 459

```
tgcaggatca ttttaatgtt ttgattgtag atgaagtgac cttttaattt tggtacagga      60

agtttcattg aagtgcaaag tgtgattagt gatgaggaac ttcaagcaga attccctgaa     120
```

<210> SEQ ID NO 460
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 460

```
acttccaaac ctccctcaga acaaggcgaa gaggaactgg taggaactag ggagggagaa      60

gcccctgctg agtccgagag cctcctgagg gacaactctg agagggacga cgtggatggt     120
```

<210> SEQ ID NO 461
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 461

```
gagccacagg aagctgagaa agatgcggaa gattcgctcc atgaatggca agatattaat      60

ttggtaatac cgtaacattg tgtttcgact tcttgctgag gaagccaggt taagtaggtt     120
```

<210> SEQ ID NO 462
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 462

```
tgtaaacaaa actcatttgg attattaata taaatctata aatgaaaaaa cattttatag      60

gaggagttgg aaactctgga gagcaacctc ttagcacagc agaattcact gaaagctcaa     120
```

<210> SEQ ID NO 463
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 463

```
aaacagcagc aagaacggat cgctgctact gtcaccggac agatgttcct ggaaagccag      60

gtgggtgcag gcagcttggg tttcctttac caccttcttc agacccctgg gggaatgcac     120
```

<210> SEQ ID NO 464
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 464
cctcactctg caggaactcc tgcgcctgtt cggcattccc tacatccagg ctcccatgga 60
agcagaggcg cagtgcgcca tcctggacct gactgatcag acttccggaa ccatcactga 120

<210> SEQ ID NO 465
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 465
tgacagtgat atctggctgt ttggagcgcg gcatgtctat agaaactttt ttaataaaaa 60
caagtttgta gaatattatc aatatgtgga ctttcacaat caattgggta agacttcaga 120

<210> SEQ ID NO 466
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 466
tcatataaga aatcttgata aaaattaaaa aatattgtta ctctttagga ttggaccgga 60
ataagttaat aaatttggct tatttgcttg gaagtgatta taccgaagga ataccaactg 120

<210> SEQ ID NO 467
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 467
tgggttgtgt aaccgccatg gaaattctca atgaattccc tgggcatggc ctggaacctc 60
tcctaaaatt ctcgtaaggt cttttatttc tttaatttgg ataattgtgt aaatacccaa 120

<210> SEQ ID NO 468
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 468
ttgtttcctt tattttacag agaatggtgg catgaagctc aaaaaaatcc aaagataaga 60
cctaatcctc atgacaccaa agtgaaaaaa aaattacgga cattgcaact cacccctggc 120

<210> SEQ ID NO 469
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 469
tttcctaacc cagctgttgc cgaggcctac ctcaaacccg tggtggatga ctcgaaggga 60
tcctttctgt gggggaaacc tgatctcgac aaaattagag aatatccttt gcttcttaaa 120

<210> SEQ ID NO 470
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 470
agtcttaact gcatgcatat tttgtcagcg gtatttcggc tggaacagaa cgaagacaga 60
tgaatctctg tttcctgtat taaagcaact cgatgcccag caggtaatca tggtggaccc 120

<210> SEQ ID NO 471
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 471
agacacagct ccgaattgat tccttcttta gattagcaca acaggagaaa gaagatgcta 60
aacgtattaa gagccagaga ctaaacagag ctgtgacatg tatgctaagg aaagagaaag 120

<210> SEQ ID NO 472
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 472
aagcagcagc cagcgaaata gaagcagttt ctgttgccat ggagaaagaa tttgagctac 60
ttgataaggc aaaaggaaaa acccagaaga gaggcataac aaatacctta gaagagtcat 120

<210> SEQ ID NO 473
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 473
caagcctgaa aagaaagagg ctttcagatt ctaaaggaaa gaatacatgc ggtggatttt 60
tgggggagac ctgcctctca gaatcatctg atggatcttc aagtgaagat gctgaaagtt 120

<210> SEQ ID NO 474
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 474
catctttaat gaatgtacaa aggagaacag ctgcgaaaga gccaaaaacc agtgcttcag 60
attcgcagaa ctcagtgaag gaagctcccg tgaagaatgg aggtgcgacc accagcagct 120

<210> SEQ ID NO 475
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 475
ctagtgatag tgatgacgat ggagggaaag agaagatggt cctcgtgacc gccagatctg 60
tgtttgggaa gaaaagaagg aaactaagac gtgcgagggg aagaaaaagg aaaacctaat 120

<210> SEQ ID NO 476
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 476 ttttttcct tttaggtagt ctgtagagaa tgccaaatga gggaatcccc cactcaagtc 60
aaactcagga gcaagactgt ttacagagtc aacctgtcag taataatgaa gaaatggcaa 120

<210> SEQ ID NO 477
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 477
tcaagcaaga aagtggtggt gatggggagg tggaggagta cctctccttt cgttctgtgg 60
gtgacgggct gtccacctct gctgtggggt gcgcatcagc agctccgagg agagggccag 120

<210> SEQ ID NO 478
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 478
ccctgctgca catcgaccga catcagatcc aggcagtaga gcctagcgcc caggcccttg 60
agctgcaggg tttgggtgtg gacgtctatg accaggacgt gctggaacag ggagtgcttc 120

<210> SEQ ID NO 479
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 479
agcaggtgga caatgccatc catgaggcca gccgtgcctc ccagctcgtt gacgtggaga 60
aggagtatcg gtcggtcctg gatgacctca cgtgagtgca gcccatcttc ttcctttcaa 120

<210> SEQ ID NO 480
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 480
tatattatgc tataaaaatg ttatcagagt gcaaaataga caatttatct tatttttcag 60
gtcatgtacg acatccctaa ggcaaatcaa taaaattatt gaacagctta gccctcaagc 120

<210> SEQ ID NO 481
<211> LENGTH: 120
<212> TYPE: DNA

<213> ORGANISM: Artificial Sequence
<220> FEATURE:
<223> OTHER INFORMATION: Synthetic polynucleotide

<400> SEQUENCE: 481
tgccaccagc agagacatca acaggaaact agattctgta aaacgacaga agtataataa 60
ggtgattcag aataacattc agtattgcat ttttgaaaaa gtcatcattt aggggcactt 120

<210> SEQ ID NO 482
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 482
ttcaaggaac aacagctaaa aaagatcact gcaaaacaaa agcatctcca ggccatcctt 60
ggaggagcag aggtgaaaat tgaactagat cacgccagtc tggaggagga tgcaggtgag 120

<210> SEQ ID NO 483
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 483
ggtggagggg gcagaggcgg acctgtctgg agatggtact gactatgagc tgaagcctct 60
gcccaagggc gggaaacggc agaagaaagt gccagtgcag gagattgatg atgacttttt 120

<210> SEQ ID NO 484
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 484
cccaagttct ggggaagaag ctgaagctgc ttctgtagga gaaggaggag gaggaggtcg 60
gaaagtggga agataccgag atgatggaga tgaagattat tataagcagc ggttaaggtc 120

<210> SEQ ID NO 485
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 485
atttgtagct gcctaatatt tcttgaaaga gtgagcattt cttttgtacc ctcggaaagt 60
ttcatgctag tgcgaaacgc attgctattg ttctttcaga gccggggcca tccagtcttg 120

<210> SEQ ID NO 486
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 486
gcagcatgct catgcctgtc caggagactg cctgggaaga gctcatccgc actggccaga 60
tgacaccttt tggtacccag atccctcaga aacaggagaa aaagcccaga aaaatcatgc 120

<210> SEQ ID NO 487
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 487
ttaatgaagc atcaggcttc gaaaagtatt tggcagatca agcaaaactg tcttttgaaa 60
ggaagaagca aggttgtaat aaaagagcag ctagaaaagc tccagcccca gtcacgcctc 120

<210> SEQ ID NO 488
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 488
cagccccagt gcaaaataaa aacaaaccaa acaagaaagc cagagttctg tccaaaaaag 60
aggagcgttt gaaaaagcac atcaagaaac tccagaagag ggctttgcag ttccagggga 120

<210> SEQ ID NO 489
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 489
aagtgggatt gccaaaggca aggagacctt gggagtcaga catgaggcca gaggcagagg 60
gagactctga gggtgaagag tctgagtatt tccccacaga ggaggaggaa gaggaggaa 119

<210> SEQ ID NO 490
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 490
tggaacacta ggcaaaacca ctaccactag gactaataat acctttttc cgttttagtc 60 ccaagatgcc tcgaacacta agtttacatg aaataactga ccttttagag acagatgaca 120

<210> SEQ ID NO 491
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 491
ttacagaggc acaccctgga caataccatt ttgtattcaa taactttttc accagtattg 60
cacttcttga taagctcagt tcaatgggac atcaggcaac aggtacagtg agaaaggatc 120

<210> SEQ ID NO 492
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 492
acattgacag agttccactg gaatcagatg tagctttaaa gaaaaaagaa agaggcacat 60
ttgattatcg aattgatggc aaaggcaata ttgtctgcag atggaatgat aacagtgttg 120

<210> SEQ ID NO 493
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 493
tcactgttgc ctcatctggt gctggtatcc atcccctgtg tcttgtcagt cgttactccc 60
agaaactgaa aaagaagata caagttcagc agccaaacat gatcaaagtg tataaccagt 120

<210> SEQ ID NO 494
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 494
tcatgggagg cgtagacaga gctgatgaaa acattgataa gtatcgggca tcaatccgtg 60
gaaagaaatg gtattcaagc cctcttttgt tctgtttcga actggtctta caaaatgctt 120

<210> SEQ ID NO 495
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 495
ggcaattgca taaaacatat gatgagaaac cagtggattt tctggagttt cgtcgacgtg 60
tggtatgcca ttatctggag acccatggtc atcctccaga acctggccaa aaaggaagac 120

<210> SEQ ID NO 496
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 496
ctcagaagcg taacattgac tcacgttatg atggcataaa tcatgtgata gtcaaacagg 60
gaaagcaaac gcgatgcgct gaatgtcata agaacacaac ttttcgatgt gaaaaatgtg 120

<210> SEQ ID NO 497
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 497
atgttgcctt acatgtgaag tgttccgttg aatatcacac tgaatagcag gtgtcaccac 60
ctcctgagat aagaaacata gttttataca ttatgtacag tgtagcagtg gttttgccta 120

<210> SEQ ID NO 498
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 498
gtgttccaat tttggaacgt cacataacaa tggaacataa taaatttttt tttctcttca 60
aatttttgtt ccttgaattt ttctaggtaa catatatgaa tttcatgcaa aaattcaaaa 120

<210> SEQ ID NO 499
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 499
gcatagaagc aagtgctata gtgatacaac cacctgaaaa tgctacagca cctgtttctg 60
atgaggaatc aggagatgaa gaaggtggaa caataaataa tctgccaggt tctttgttgc 120

<210> SEQ ID NO 500
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 500
acacagctgc gtatcttatt caagatggct ctgatgctga gtctgactca gatgatccct 60
catacgcacc taaagatgac tctcctgatg aagttccatc tacgtttact gtgcagcaac 120

<210> SEQ ID NO 501
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 501
ctccaccatc aaggaggagg aaaatgacaa aaattctttg caaatggaaa aaagccgacc 60
taactgtaca acccgtagca ggtagagtta cagcaccacc aaacgatttc ttcaccgtaa 120

<210> SEQ ID NO 502
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 502
tgagaactcc cacagaaatt cttgaacttt ttcttgatga cgaggtcatt gaactcattg 60
tcaagtactc caacttatat gcttgcagta aaggtgtaca tcttggcttg actagctctg 120

<210> SEQ ID NO 503
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 503
aattcaaatg ttttctggga attatttttc tgagtggtta tgtctcagtt cctagaaggc 60
gtatgttttg ggaacaaaga acagatgtgc ataatgtact ggttagtgct gccatgagac 120

<210> SEQ ID NO 504
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 504
gtgaccggtt tgaaactata ttttctaatt tgcatgttgc tgacaatgca aatttggatc 60
cagtggacaa attttccaaa ttgcgacctc tcataagcaa acttaatgag agatgcatga 120

<210> SEQ ID NO 505
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 505
aatttgttcc aaatgaaaca tatttcagct ttgatgaatt catggttcct tattttggtc 60
gtcacgggtg caaacaattt attcggggaa agcccattcg gtttggctat aagttttggt 120

<210> SEQ ID NO 506
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 506
gtggtgccac ctgtctgggc tacatttgct ggtttcagcc gtatcagggt aaaaacccaa 60
atactaaaca tgaggaatat ggtgtcggtg cgtcacttgt ccttcagttt agtgaggcac 120

<210> SEQ ID NO 507
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 507
tttaaatctg tcttgtgatc aaaataatgg aaatgtgatt tttattttca tggtaggaga 60
tggaataaac tgagactgca ggacaaagag aaacgtctga agctggagga cgattctgag 120

<210> SEQ ID NO 508
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 508
gaaagtgatg ctgaatttga cgaaggtttt aaagtgccag gttttctgtt caaaaagctt 60
tttaagtatg taccatatgt tctttccttt ctatttgcta tcaagccatt atgtacaaat 120

<210> SEQ ID NO 509
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 509
ttgccatttt ctcttttctt gttggtgttt gttgtcatag gtaccagcag acaggtgtta 60
ggtggctgtg ggaattgcac tgccagcagg caggaggaat tctgggagat gaaatgggat 120

<210> SEQ ID NO 510
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 510
tgggcaagac catccagata attgccttct tggcaggtct gagctacagc aagatcagga 60
ctcgtggttc aaattacagg caagtgctcc tctgcagact gtcagtctgt ggagctcaat 120

<210> SEQ ID NO 511
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 511
tgactgtata tgctctttca tggttgtttt cttcttggac gtttggatgc aggtttgagg 60
ggttgggtcc aactgtaatt gtctgtccaa caacagtgat gcatcagtgg gtgaaggaat 120

<210> SEQ ID NO 512
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 512
ttcacacgtg gtggcctccg ttcagagtgg caattctaca tgaaaccggt tcctataccc 60
acaaaaaggt aacacaatat ttcagtacct ttttgttttg ttttaatgcc ctccatttta 120

<210> SEQ ID NO 513
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 513
taaaactgac tttaccattt tattgtggtc tcaggagaaa ctaattcgag atgttgctca 60
ttgtcatgga attttgatca catcttactc ctacattcga ttgatgcagg atgacattag 120

<210> SEQ ID NO 514
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 514
caggtatgac tggcactatg tgatcttgga cgaaggacac aaaattcgaa atccaaatgc 60
tgctgtcacc cttgcttgca aacaggtatg acctctttta acaagggaga tttccaagtg 120

<210> SEQ ID NO 515

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 515
ttaataaaaa ggtgcttcct ttcctcaaat agtttcgcac ccctcatcgg atcattctgt 60
ctggctcacc gatgcaaaat aacctccgag agctgtggtc gctctttgac ttcatcttcc 120

<210> SEQ ID NO 516
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 516
cgggaaagtt aggcacgttg cctgtgttta tggagcagtt ctccgtcccc atcaccatgg 60
ggggatattc aaatgcttcc ccagtacagg taaaatatta ggatgataat acttttggca 120

<210> SEQ ID NO 517
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 517
aggtcaaaac tgcttacaag tgtgcatgtg tcttacgaga taccataaat ccatacctac 60
tgcggagaat gaagtcagat gtcaagatga gcctttcttt gccagataaa aatgaacagg 120

<210> SEQ ID NO 518
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 518
tcccgtccgt aggtcttatt ttgccgtctt acagatgagc agcataaagt ctaccaaaat 60
ttcgttgatt ccaaagaagt ttacaggatt ctcaatggag agatgcaggt cagctaaaaa 120

<210> SEQ ID NO 519
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 519
ttcttaccac agattttctc cggacttata gccctaagaa aaatttgcaa ccaccctgat 60
ctcttttctg gaggtcccaa gaatctcaaa ggtcttcctg atgatgaact agaagaagat 120

<210> SEQ ID NO 520
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 520
cagtttgggt actggaaacg ttctgggaaa atgattgttg ttgagtcttt gttgaaaata 60
tggcacaagc agggtcagcg agtattgctg ttttctcagt caaggcaggt gagtgcacag 120

<210> SEQ ID NO 521
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 521
acagatgctg gacatacttg aagtattcct tagagcccaa aagtatacct atctcaagat 60
ggatggtacc actacaatag cttcaagaca gccactgatt acgagataca atgaggtaac 120

<210> SEQ ID NO 522
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 522
ggctgagaac tgtaactggt cttaagtgtg tgtgctcagt gttgtgtgtc ttacctctag 60
gacacatcca tatttgtgtt tcttctgacc acgcgggtgg gcggcttagg tgtcaacctg 120

<210> SEQ ID NO 523
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 523
acgggggcaa acagagttgt catctatgac ccagactgga acccaagcac ggacacgcag 60
gtttgttttt attttttttt taaaagaatg tattagtaga aatatagttt catggttagc 120

<210> SEQ ID NO 524
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 524
tctctgttgc aggcccggga gcgagcatgg agaataggcc agaagaagca agtgactgtg 60
tacaggctcc tgactgcggg caccattgaa gaaaagatct accaccggtc agtgcacaca 120

<210> SEQ ID NO 525
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 525
gtagagctac acattgtttt ataccagctt atcttttatt tttttagaca aatcttcaag 60
cagtttttga caaatagagt gctaaaagac ccaaaacaaa ggcggttttt caaatccaat 120

<210> SEQ ID NO 526
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 526
gatctctatg agctatttac tctgactagt cctgatgcat cccagagcac tgaaacaagt 60
gcaatttttg caggtattac ataaaatcat ttaatttaaa gtaatcaatt gcacaagatg 120

<210> SEQ ID NO 527
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 527
ttacaggaac tggatcagat gttcagacac ccaaatgcca tctaaaaaga aggattcaac 60
cagcctttgg agcagaccat gatgttccaa aacgcaagaa gttccctgct tctaacatat 120

<210> SEQ ID NO 528
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 528
ctgtaaatga tgccacatca tctgaagaga aatctgaggc taaaggagct gaagtaaatg 60
cagtaacttc taatcgaagt gatcctttga aagatgaccc tcacatgagt agtaatgtaa 120

<210> SEQ ID NO 529
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 529
ctagcaatga taggcttgga gaagagacaa atgcagtatc tggaccagaa gagttgtcag 60
tgattagtgg aaatggggaa tgttcaaatt cttcaggaac aggcaaaact tctatgccat 120

<210> SEQ ID NO 530
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 530
ctggtgatga aagcattgat gaaaagttag gtctttctta caaaagagaa agacccagcc 60
aggctcaaac agaagctttt tgggagaata aacaaatgga aaataatttt tataagcaca 120

<210> SEQ ID NO 531
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 531
agtcaaaaac aaaacatcat agtgtggcag aagaagagac cctggagaaa catctgagac 60
caaagcaaaa gcctaagaac tctaagcatt gcagagacgc caagtttgaa ggaactcgaa 120

<210> SEQ ID NO 532
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 532
ttccacacct ggtgaagaaa aggcgttacc agaagcaaga cagtgaaaac aagagtgagg 60
ccaaggaaca gagcaatgac gattatgttt tggaaaagct tttcaaaaaa tcaggtaatc 120

<210> SEQ ID NO 533
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 533
tatttctttt cttgctagtt ggcgtgcaca gtgtcatgaa gcacgatgcc atcatggatg 60
gagccagccc agattatgta ctggtggagg cagaagccaa ccgagtggcc caggatgccc 120

<210> SEQ ID NO 534
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 534
tgaaagcact gaggctctct cgtcagcggt gtctgggagc agtgtctggt gttcccacct 60
ggactggcca cagggggatt tctggtgcac cagcaggaaa aaagtaagag attgctgcat 120

<210> SEQ ID NO 535
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 535
tgatgctttt cctttttag gagtagattt ggtaagaaaa ggaattctaa cttctctgtg 60
cagcatcctt catcaacatc tccaacagag aagtgccagg taatatagat aaccttttg 120

<210> SEQ ID NO 536
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 536
tatatcagta tagtggtctt ctttttatag gatggcatca tgaaaaagga gggaaaagat 60
aatgtccctg agcattttag tggaagagca gaagatgcag actcttcatc cgggcccctc 120

<210> SEQ ID NO 537
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 537
gcttcctcct cactcttggc taaaatgaga gctagaaacc acctgattct gccagagcgt 60
ttagaaagtg aaagcgggca cctgcaggaa gcttctgccc tgctgcccac cacagaacac 120

<210> SEQ ID NO 538
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 538
gatgaccttc tggtggagat gagaaacttc atcgctttcc aggcccacac tgatggccag 60
gccagcacca gggagatact gcaggagttt gaatccaagt tatctgcatc acagtcttgt 120

<210> SEQ ID NO 539
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 539
gtcttccgag aactattgag aaatctgtgc actttccata gaacttctgg tggtgaagga 60
atttggaaac tcaagccaga atactgctaa acaacattgc ttcctaaact ttcaagtccc 120

<210> SEQ ID NO 540
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 540
ggtaactgga acccaatccg agggtcatgg aggcatcccg aaggtttccg gaagccgagg 60
ccttgagccc agagcaggct gctcattacc taaggtatgt ctggaccgct gggcgggtct 120

<210> SEQ ID NO 541
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 541 tcttttttt tctatagata tgtgaaagag gccaaagaag caactaagaa tggagacctg 60
gaagaagcat ttaaactttt caatttggca aaggacattt ttcccaatga aaaagtgctg 120

<210> SEQ ID NO 542
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 542
gaagaaatat acaggaaatt tgtgtcttta gatcatatca aggagttgct aatggagacg 60
cgctcacctt tggctgagct aggtgtctta aagaagctgt gtgatcatcc taggctgctg 120

<210> SEQ ID NO 543
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 543
tctgcacggg cttgttgttt gctaaatctt gggacattct ctgctcaaga tggaaatgag 60
ggggaagatt ccccagatgt ggaccatatt gatcaagtaa ctgatgacac attgatggaa 120

<210> SEQ ID NO 544
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 544
gaatctggaa aaatgatatt cctaatggac ctacttaaga ggctgcgaga tgagggacat 60
caaactctgg tgttttctca atcgaggcaa attctaaaca tcattgaacg cctcttaaag 120

<210> SEQ ID NO 545
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 545
aataggcact ttaagacatt gcgaatcgat gggacagtta ctcatctttt ggaacgagaa 60
aaaagaatta acttattcca gcaaaataaa gattactctg tttttctgct taccactcaa 120

<210> SEQ ID NO 546
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 546
gtaggtggtg tcggtttaac attaactgca gcaactagag tggtcatttt tgaccctagc 60
tggaatcctg caactgatgc tcaagctgtg gatagagttt accgaattgg acaaaaagag 120

<210> SEQ ID NO 547
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 547
aatgttgtgg tttataggct aatcacttgt gggactgtag aggaaaaaat atacagaaga 60
caggttttca aggactcatt aataagacaa actactggtg aaaaaaagaa ccctttccga 120

<210> SEQ ID NO 548
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 548
tattttagta aacaagaatt aagagagctc tttacaatcg aggatcttca gaactctgta 60
acccagctgc agcttcagtc tttgcatgct gctcagagga aatctgatat aaaactagat 120

<210> SEQ ID NO 549
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 549
gaacatattg cctacctgca gtctttgggg atagctggaa tctcagacca tgatttgatg 60
tacacatgtg atctgtctgt taaagaagag cttgatgtgg tagaagaatc tcactatatt 120

<210> SEQ ID NO 550
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 550
caacaaaggg ttcagaaagc tcaattcctc gttgaattcg agtctcaaaa taaagagttc 60
ctgatggaac aacaaagaac tagaaatgag gggcctggc taagagaacc tgtatttcct 120

<210> SEQ ID NO 551
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 551
tcttcaacaa agaagaaatg ccctaaattg aataaaccac agcctcagcc ttcacctctt 60
ctaagtactc atcatactca ggaagaagat atcagttcca aaatggcaag tgtagtcatt 120

<210> SEQ ID NO 552
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 552
agcagaatcc aaaaaataca ggaagccttg gaggagttgg cagaacaggg agatgatgaa 60
tttacagatg tgtgcaactc tggcttgcta ctttatcgag aactgcacaa ccaactcttt 120

<210> SEQ ID NO 553
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 553
gatgatctgc ccaaagaggg tgagaaacaa gatctctcca gtataaaggt gaatgttacc 60
accttgcaag atggtaaagg tacaggtagt gctgactcta tagctacttt accaaagggg 120

<210> SEQ ID NO 554
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 554
tttggaagtg tagaagaact ttgtactaac tcttcattgg gaatggaaaa aagctttgca 60
actaaaaatg aagctgtaca aaaagagaca ttacaagagg ggcctaagca agaggcactg 120

<210> SEQ ID NO 555
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 555
caagaggatc ctctggaaag ttttaattat gtacttagca aatcaaccaa agctgatatt 60
gggccaaatt tagatcaact aaaggatgat gagattttac gtcattgcaa tccttggccc 120

<210> SEQ ID NO 556
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 556
attatttcca taacaaatga aagtcaaaat gcagaatcaa atgtatccat tattgaaata 60
gctgatgacc tttcagcatc ccatagtgca ctgcaggatg ctcaagcaag tgaggccaag 120

<210> SEQ ID NO 557
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 557
ttggaagagg aaccttcagc atcttcacca cagtatgcat gtgatttcaa tcttttcttg 60
gaagactcag cagacaacag acaaaatttt tccagtcagt ctttagagca tgttgagaaa 120

<210> SEQ ID NO 558
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 558
gaaaatagct tgtgtggctc tgcacctaat tccagagcag ggtttgtgca tagcaaaaca 60
tgtctcagtt gggagttttc tgagaaagac gatgaaccag aagaagtagt agttaaagca 120

<210> SEQ ID NO 559
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 559
aaaatcagaa gtaaagctag aaggattgtt tcagatggcg aagatgaaga tgattctttt 60
aaagatacct caagcataaa tccattcaac acatctctct ttcaattctc atctgtgaaa 120

<210> SEQ ID NO 560
<211> LENGTH: 120
<212> TYPE: DNA

<213> ORGANISM: Artificial Sequence
<220> FEATURE:
<223> OTHER INFORMATION: Synthetic polynucleotide

<400> SEQUENCE: 560
caatttgatg cttcaactcc caaaaatgac atcagtccac caggaaggtt cttttcatct 60
caaataccca gtagtgtaaa taagtctatg aactctagaa gatctctggc ttctaggagg 120

<210> SEQ ID NO 561
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 561
tctcttatta atatggtttt agaccacgtg gaggacatgg aggaaagact tgacgacagc 60
agtgaagcaa agggtcctga agattatcca gaagaagggg tggaggaaag cagtggcgaa 120

<210> SEQ ID NO 562
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 562
gcctccaagt atacagaaga ggatccttcc ggagaaacac tgtcttcaga aaacaagtcc 60
agctggttaa tgacgtctaa gcctagtgct ctagctcaag agacctctct tggtgcccct 120

<210> SEQ ID NO 563
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 563
gagcaccaga aggaaggcat agctttcctc tatagcctgt atagggatgg aagaaaaggt 60
ggtatattgg ctgatgatat gggattaggg aagactgttc aaatcattgc tttcctttcc 120

<210> SEQ ID NO 564
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 564
gagcctttgt ctggtgaaca gttggttggt tctccccagg ataaggcggc agaggctaca 60
aatgactatg agactcttgt aaagcgtgga aaagaactaa aagagtgtgg aaaaatccag 120

<210> SEQ ID NO 565
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 565
gaggccctaa actgcttagt taaagcgctt gacataaaaa gtgcagatcc tgaagttatg 60
ctcttgactt taagtttgta taagcaactt aataacaatt gagaatgtaa cctgtttatt 120

<210> SEQ ID NO 566
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 566
ggtatgtttg atgcatcact tgtgaatcat gtgctgctga tcatgccaac caatcttatt 60
aacacatggg taaaagaatt catcaagtgg actccaggaa tgagagtcaa aacctttcat 120

<210> SEQ ID NO 567
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 567
ggtcctagca aggatgaacg gaccagaaac ctcaatcgga ttcagcaaag gaatggtgtt 60
attatcacta cataccaaat gttaatcaat aactggcagc aactttcaag ctttaggggc 120

<210> SEQ ID NO 568
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 568
caagagtttg tgtgggacta tgtcatcctc gatgaagcac ataaaataaa aacctcatct 60
actaagtcag caatatgtgc tcgtgctatt cctgcaagta atcgcctcct cctcacagga 120

<210> SEQ ID NO 569
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 569
accccaatcc agaataattt acaagaacta tggtccctat ttgattttgc ttgtcaaggg 60
tccctgctgg gaacattaaa aacttttaag atggagtatg aaaatcctat tactagagca 120

<210> SEQ ID NO 570
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 570
agagagaagg atgctacccc aggagaaaaa gccttgggat ttaaaatatc tgaaaactta 60
atggcaatca taaaacccta ttttctcagg aggactaaag aagacgtaca gaagaaaaag 120

<210> SEQ ID NO 571
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 571
tcaagcaacc cagaggccag acttaatgaa aagaatccag atgttgatgc catttgtgaa 60
atgccttccc tttccaggaa aaatgattta attatttgga tacgacttgt gcctttacaa 120

<210> SEQ ID NO 572
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 572
cgccgccttc cgggtgttac atgcagccgg gctcggcccc tccccctggc cggatggatc 60
cgtcggcgcc acagccccgc gcggaaacct caggcaaagg taccagctcc gcgctcgccc 120

<210> SEQ ID NO 573
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 573
ggaaacttta ttttctttat tcttgcagac atatggcatc caggagaaag atgtcttgcc 60
ccttctccag ataatggaaa actttgtgaa gcaagcataa aatctatcac agtggatgaa 120

<210> SEQ ID NO 574
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 574
aatggcaagt catttgcagt cgtcttatat gcagattttc aagaaaggaa aatacctctt 60
aaacagcttc aagaagtgaa atttgttaaa gattgcccta ggaatcttat atttgatgat 120

<210> SEQ ID NO 575
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 575
gaagatttag aaaaacctta tttcccaaac cgaaaatttc catcatcttc tgttgctttt 60
aaattatctg acaatggaga ctctattcct tataccatca ataggtattt gagagactac 120

<210> SEQ ID NO 576
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 576
caaagagaag gaacccggtt tctttatgga cactacatcc atggaggagg gtgcattctg 60
ggtgatgaca tgggacttgg aaaaacagta caggtattta attatgttat aacagtaaag 120

<210> SEQ ID NO 577
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 577
aaattttgta cgtcatgata cattatacac agtgattgaa aaagtctttt ttccccaggt 60
tatttcattt ctggctgcag ttttgcataa aaagggaact cgtgaggata ttgaaaataa 120

<210> SEQ ID NO 578
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 578
catgccagag tttttactaa gaagtatgaa aaaggaaccc ctttcttcta cagcaaaaaa 60
ggtaaaatct ctagacaatg tatattctac tcatgatgct ggtattacaa aagcatatag 120

<210> SEQ ID NO 579
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 579
aaattttttt attcttgttt tagatgttct taatagttgc tcctctttct gtcctctaca 60
actggaagga tgaattggac acctggggat atttcagagt cactgtttta catggaaaca 120

<210> SEQ ID NO 580
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 580
gaaaagataa tgaattaatt cgtgtaaagc agaggaaatg tgaaattgct ctaacaactt 60
atgaaacact acgcttatgc ctggatgaac ttaacaggta atgggaataa taggaatagg 120

<210> SEQ ID NO 581
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 581
gttttctcaa cctcaccctt ctttttttctt actttatagt ttggaatggt cagctgtcat 60
tgtggatgaa gctcatagaa tcaagaatcc aaaagctaga gtaacagaag ttatgaaagc 120

<210> SEQ ID NO 582
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 582
tttgaaatgt aatgtccgca ttggcctcac tggaaccatc cttcagaaca acatgaagga 60

-continued actgtggtgt gttatggact ggtgagagaa aacacttttt aaaaaattgt ttaatagttc 120

<210> SEQ ID NO 583
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 583
tattgtcttt ataaagggct gtgccaggcc ttttagggag tgggacctac ttcaagaagc 60
agttttctga cccagtagaa catggtcaga gacacacggc aacaaagaga gaactagcca 120

<210> SEQ ID NO 584
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 584
ctggccgaaa ggccatgcaa agacttgcca aaaagatgtc tggctggttt ctcaggcgca 60
ccaagactct tatcaaggat cagttgccta agaaggaaga ccgggtaaga accgcatttg 120

<210> SEQ ID NO 585
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 585
tattgttata aacaaaatac taataactac cttgtatttt atcttggcag atggtgtatt 60
gttctttgac agatttccag aaagctgtct atcaaacagt gttagaaaca gaggacgtga 120

<210> SEQ ID NO 586
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 586
ctttgatact tcaatcttct gagccttgta cctgtaggag tggccaaaaa aggagaaatt 60
gttgttataa ggcaagcatt tcaatatatc tttataatca tgcttttgat tacatagtac 120

<210> SEQ ID NO 587
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 587
cagaccaatt ctcatggtga aacagtgaaa accttgtatc tcagttacct tacagtcctt 60
cagaaggtag ctaaccatgt cgcgctactg caagctgcta gtacttccaa acaacaggtt 120

<210> SEQ ID NO 588
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 588
attatttcaa tttatacagg tttgaatgtg ttaagtggaa atatcttttc ttctgccttt 60
tcccttcaag gaaacactta tcaaaaggat atgtgatcag gtattttcca gattcccaga 120

<210> SEQ ID NO 589
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 589
ttttgtgcag aaaagcaaag atgcagcctt tgaaacactt tctgacccta aatacagtgg 60
aaaaatgaag gtaagtgctc ctctttcagg ttgcatacag acatgataca caaaatatt 119

<210> SEQ ID NO 590
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 590
tgattttctg tggttcattt tcaggtcctt cagcagcttt taaatcattg caggaaaaac 60
agagataaag ttcttctctt ttctttttcc accaaggtga gttcatctaa agtatatcct 120

<210> SEQ ID NO 591
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 591
tacttaacca agattcatgt ttgcccatct tcatacctct cgtctagttg cttgacgtgc 60
tacagcagta ctgtatggcg tctgggcttg attaccgacg acttgatgga agtacaaaat 120

<210> SEQ ID NO 592
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 592
cagaggaaag actcaagatt gtaaaagagt tcaacagtac acaagatgtt aacatttgcc 60
ttgtctctac aatgtaagaa aattaaattt aataactaga tttttatcca attgtttttg 120

<210> SEQ ID NO 593
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 593
tctttcctcc agggctggtg gactaggcct caattttgtc ggtgccaatg ttgttgtatt 60
atttgatcct acttggaatc cagccaatga tcttcaagcc attgacaggt ataatactga 120

<210> SEQ ID NO 594

```
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 594

ccttttacag agcatatagg attggacaat gtagagatgt caaagtgctt aggctgatat      60

ccttgggaac tgtggaggaa atcatgtatt tacgacagat atacaagcag gtaaatatgt     120

<210> SEQ ID NO 595
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 595

gcaaacactt caaaaatgtc ttgtgttttt tctgttttag caacttcact gtgtggtggt      60

tggaagtgaa aatgccaaac gatatttga agcagttcaa ggatctaaag agcatcaagg     120

<210> SEQ ID NO 596
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 596

agagcttttt gggatccata acctcttcaa atttaggtcc caagggtctt gtcttacgaa      60

ggacatcctg gaggtgtgaa cttcttctct gaccttttca ataatatttt aaatacagtt     120

<210> SEQ ID NO 597
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 597

ttttcttcat cttttttttc tctcttagca ccttctagcc accatggcaa cctcatctga      60

agaagttttg ctgattgtaa agaaagtgcg tcaaaagaag caggatggag ctctgtacct     120

<210> SEQ ID NO 598
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 598

catggcagaa agaattgctt gggcacctga aggcaaagat agatttacaa tcagccatat      60

gtatgcagat attaaatgta agtcagctat actaagttct gatgtatttg tatgtcatag     120

<210> SEQ ID NO 599
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 599

aactgccctc atgcttcttt ttaggccaga aaattagtcc agaaggaaaa gctaaaattc      60
```

agcttcagct ggtcctacat gcaggggaca caactaactt ccatttttcc aatgaaagca 120

<210> SEQ ID NO 600
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 600
cagcagtgaa agagcgagat gcagtaaaag accttcttca gcagctgctg cccaaattca 60
agaggaaagc aaataaagaa ctggaagaga agaacaggtg ggaggaaaag aatagccttt 120

<210> SEQ ID NO 601
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 601
agaagttcag ttatattcag tatattctgc tttacagaat gctgcaagaa gatcctgttt 60
tgtttcagct ttataaagac cttgttgtga gtcaagtgat cagtgctgag gaattctggg 120

<210> SEQ ID NO 602
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 602
ccaatcgttt aaatgtgaat gcaacagata gttcttccac atccaatcat aagcaggatg 60
ttggcatttc tgctgcattt ctggtatgtg agccttctag atttctgaag aaaataaaaa 120

<210> SEQ ID NO 603
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 603
ggctttgttt taggctgatg tccggcccca aactgatggc tgtaacggtc taagatataa 60
tttaacttct gatatcattg agtccatatt taggacctat ccagcaggta agaagaatca 120

<210> SEQ ID NO 604
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 604
aaaatggaaa ttcagtatat aatatttgtg ggtttttttc cacagtaaaa atgaaatatg 60
cagaaaatgt tccccacaac atgacagaga aggaattctg gacacgtttt ttccagtccc 120

<210> SEQ ID NO 605
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 605
attattttca cagggatcgg ctgaatacag ggtcaaagga tctctttgca gaatgtgcca 60
aaatagatga aaaaggtaac tgtttatctc tgatagacac tggtatttaa cttgccaccc 120

<210> SEQ ID NO 606
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 606
ttattttgtt gattttctag gcctaaaaac aatggtttca ttaggagtga aaaacccact 60
actagattta acagctttgg aagataaacc attagatgag gtaagaagca ataaaagaag 120

<210> SEQ ID NO 607
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 607
tataataaga aaagcagaac ctttttaaaa aatttttaat ctattatttc tcacagggct 60
atggcatttc ctctgtgcca tctgcttcca attctaaatc cataaaagag aatagtaatg 120

<210> SEQ ID NO 608
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 608
ctgccatcat caagagattt aaccatcaca gtgccatggt cctggcagct ggactcagaa 60
aacagttaag tataaatgca gaggtgcagt aactgggctt ttcaggatat ccagatggag 120

<210> SEQ ID NO 609
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 609
tcccctttat tttaagagaa gcacaaaatg aacaaactag tgagcccagc aacatggatg 60
gaaattccgg agatgcagac tgctttcagc cagcagtcaa aagggtatgg gcaaaaaaat 120

<210> SEQ ID NO 610
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 610
gtgttaataa ttataggcga aattacaaga gtccattgaa tatgaagact tggggaaaaa 60
taattctgta aaaacgattg cactaaacct caagaagtca gataggtaag tttggtcaat 120

<210> SEQ ID NO 611
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 611
ggtattatca tggtccaact ccaatccagt cactacagta tgcaacaagt caggacatta 60
ttaattcttt tcaaagtatt agacaagaaa tggaagctta tacacccaag ttaactcagg 120

<210> SEQ ID NO 612
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 612
ttcatttttt tcaggttctc tcaagtagtg ctgccagtag taccatcaca gcactgtcac 60
ctggaggggc acttatgcag ggaggaacac agcaagccat aaaccgtatg tgccgggcca 120

<210> SEQ ID NO 613
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 613
agagatggtg ccaaatgata ttcaatctga attgaaacac ttatatgtag ctgttggaga 60
acttctacga catttctggt cctgctttcc tgttaatacg ccattcctag aagaaaaggt 120

<210> SEQ ID NO 614
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 614
ctcatctttt ttaggtagtg aaaatgaaaa gtaatttgga acgattccaa gttacgaagc 60
tctgtccatt ccaagaaaag attcggagac agtatttaag cacaaatgta aggcagcaat 120

<210> SEQ ID NO 615
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 615
ttgctgtgtt tttcagttgg taagtcacat agaagagatg ctccagacag cctacaacaa 60
gctccacaca tggcagtcac ggcgtctgat gaagaaaacg tgaggtggcc atgatgctta 120

<210> SEQ ID NO 616
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 616
ttttacagat tattgaataa taaaatacag ttttgaaaaa aatggatgaa gaacctgaaa 60
gaactaagcg atgggaagga ggctatgaaa gaacatggta aggagagctt tattgccctg 120

<210> SEQ ID NO 617
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 617
aacaaataat tatgacttat agggagattc ttaaagaaga tgaatctgga tcacttaaag 60
ctacaataga agacattcta ttcaaggcaa agagaaaaag gtatgtaacc ttcctatgta 120

<210> SEQ ID NO 618
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 618
agtatatgga attacattaa aatgtttgta taattttaac agagtatttg agcaccatgg 60
acaagttcga cttggaatgg tatgtcatta ttttttcttt tactagtaca gaactagttt 120

<210> SEQ ID NO 619
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 619 ttctttttc cgatagatgc gccaccttta tgtggtagta gatggatcaa gaacaatgga 60
agaccaagat ttaaagccta atagactgac gtgtacttta aaggtaaaat ttaagtttat 120

<210> SEQ ID NO 620
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 620
cctttatcta gtatgtcttt ttttgtttaa acagttgttg gaatactttg tagaggaata 60
ttttgatcaa aatcctatta gtcaggtacg tatctaagtg atagaattca gaattagatt 120

<210> SEQ ID NO 621
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 621
atattaataa taatttttgt ttttatttca agattggaat aattgtaact aagagtaaaa 60
gagctgaaaa attgactgaa ctttcaggta tgcataaaat tacctttaca tgactcaagg 120

<210> SEQ ID NO 622
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 622
attttaggaa acccaagaaa acatataacg tctttgaaga aagctgtgga tatgacctgc 60
catggagagc catctcttta taattcccta agcatagcta tgcagactct aaagttagta 120

<210> SEQ ID NO 623
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 623
atctttcttt taagacacat gcctggacat acaagtcgag aagtactaat catctttagc 60
agccttacaa cttgcgatcc atctaatatt tatgatctaa tcaaggtaga ccaaaaaatc 120

<210> SEQ ID NO 624
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 624
cttggatttt atgaagaccc taaaggcagc taaaattaga gtatctgtta ttggattgtc 60
tgcagaagtt cgcgtttgca ctgtacttgc tcgtgaaact ggtggtatat atataattta 120

<210> SEQ ID NO 625
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 625
tgttaggcac gtaccatgtt attttagatg aaagccatta caaagagttg ctcacacatc 60
atgttagtcc tcctcctgct agctcaagtt ctgaatgctc acttattcgt atgggtaagt 120

<210> SEQ ID NO 626
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 626
agaaagtaat acattttctt ctatgaagga tttcctcagc acaccattgc ttctttatct 60
gaccaggatg caaaaccctc tttcagcatg gcgtaagtaa agaccttgaa aatatcagtg 120

<210> SEQ ID NO 627
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 627
ccctacaggc atttggatgg caatactgag ccagggctta cattaggagg ctatttctgc 60
ccacagtgtc gggcaaagta ctgtgagcta cctgttgagt gtaaaatctg tggtaagaaa 120

<210> SEQ ID NO 628
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 628
tgtgttaggt cttactttgg tgtctgctcc ccacttggca cggtcttacc atcatttgtt      60
tcctttggat gcttttcaag aaattcccct agaagaatat aatggagaaa ggtatttcag     120

<210> SEQ ID NO 629
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 629
gtaaattcta agaaaaaaca ttgttaaact tttttttcag attttgttat ggatgtcagg      60
gggaattgaa agaccaacat gtaagttctt tggctttcta aatattaagt aatgtacaag     120

<210> SEQ ID NO 630
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 630
tagctgtgct gtaattaact tttggaaact agtttatcac ttttcttctt ttcactacag      60
gtttatgttt gtgctgtgtg ccaaaatgtt ttctgtgtgg actgtgatgt ttttgttcat     120

<210> SEQ ID NO 631
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 631
gattctctac actgttgccc tggctgtatt cataagattc cagctccttc aggtgtttga      60
ttccagcatg tagtatacat tgtatgtgtt aaaaagaaat ttgcaactgt gaataaaagg     120

<210> SEQ ID NO 632
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 632
tttgagacgc tcccctgacc accacttgct ctgcgctgag gtgctgggac agccatggtt      60
tcagacggtg aggaccctgc agggcgggac ttcgactccg gggctcggct gtctcggtcc     120

<210> SEQ ID NO 633
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 633
tttcttgtta atattttcag aagatgaatt gaatcttctg gttattgtag ttgatgccaa 60
cccaatttgg tggggaaagc aagcattaaa ggaatctcag gtaagactgc ttgaggaggc 120

<210> SEQ ID NO 634
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 634
caacagttca ctttatccaa atgcatagat gccgtgatgg tgctgggaaa ttcgcattta 60
ttcatgaatc gttccaacaa acttgctgtg atagcaagtc acattcaaga aaggtatgac 120

<210> SEQ ID NO 635
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 635
ggcctggtgt aaccaggttt tttcccctgc tgtttcagcc gattcttata tcctggaaag 60
aatggcagac ttggagactt cttcggagac cctggcaacc ctcctgaatt taatccctct 120

<210> SEQ ID NO 636
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 636
gggagtaaag atggaaaata cgaactttta acctcagcaa atgaagttat tgttgaagag 60
attaaagatc taatgaccaa aagtaacaac ttttaaacat tgttattttg caaatagtgt 120

<210> SEQ ID NO 637
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 637
cccttttaat gttttctgtt atttgcaggt gacataaagg gtcaacatac agaaactttg 60
ctggcaggat ccctggccaa agccctttgc tgtatccttg gtgtctgaat catttagaag 120

<210> SEQ ID NO 638
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 638
ttatgaagca aaataatatt tttgtattcc ttaatgttaa gaaattaaga cattcataga 60
atgaacaagg aagttaaagg taagagccta cgttttccta tgagaactgt aatcctactt 120

<210> SEQ ID NO 639
<211> LENGTH: 120
<212> TYPE: DNA

<213> ORGANISM: Artificial Sequence
<220> FEATURE:
<223> OTHER INFORMATION: Synthetic polynucleotide

<400> SEQUENCE: 639
ttagtaagat ttagttaaat ttttttctgc ttttttctct ttgtagacaa tcaggaaatg 60
aaatcaagga tattggtaag ataaaaaaat cattactttt ttatatgaca actataatta 120

<210> SEQ ID NO 640
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 640
ttaacatgac tgtgattttt aggtgattaa ggctgcagaa gacagtgcgt tgcagtatat 60
gaacttcatg aatgtcatct ttgcagcaca gaaacaggtg aactgagagc ctgccgttta 120

<210> SEQ ID NO 641
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 641
attcctgtaa tattttcaaa atgtttcttt tagaatattt tgattgatgc ctgtgtttta 60
gactccgact cagggctcct ccaacaggta tgttttaaaa ccatgctttg tgtcggtggt 120

<210> SEQ ID NO 642
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 642
ggcagcaagc cgcctgtgtc ttgcaggctt gtgacatcac gggaggactg tacctgaagg 60
tgcctcagat gccttctctt ctgcagtatt tgctggtaag gagacagcag cggcgaccct 120

<210> SEQ ID NO 643
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 643
atttttttcc catgttttaa ataaaagttt cttttgtttg tttgttttac agtgggtgtt 60
tcttcccgat caagatcaga gatctcagtt aatcctccca cccccagttc atgttgacta 120

<210> SEQ ID NO 644
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 644
cagggctgct tgcttctgtc atcgaaatct cattgaaatt ggttatgtct gttctgtgtg 60
tttgtcaagt aagttaatgt acctagtttt tcttttttttt ctatgttggg gggcaggaaa 120

<210> SEQ ID NO 645
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 645
ttttcagcca ccctattgtt tcttttttt tttaatttac agtattctgc aatttcagcc 60
ccatttgtac tacgtgcgag taagtatctt tgagattgtg tgggtggcta atacttcaca 120

<210> SEQ ID NO 646
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 646
aatgttttcc tctctgtaat ttcaggacag cctttaaaat ttctctgcct ccagtgctga 60
aagccaagaa aaagaaactg aaagtgtctg cctgaggata aaatattttc cccatctttt 120

<210> SEQ ID NO 647
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 647
acactggcat ggatggtgag gttgcacttc tgacgtttgc attcctcagg tgatggagag 60
caccccttca aggggactga accgagtaca cctacaatgc aggaatctgc aggaattctt 120

<210> SEQ ID NO 648
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 648
agggggcctg agccctgggg tattggaccg attgtatggg caccctgcca catgtctggc 60
tgtcttcagg tgagaagccc cttcatggca gggaaatgta atggggtctg cggagtggaa 120

<210> SEQ ID NO 649
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 649
ctgtacaggg agctcccatc cttggctaag aactgggtga tgcggatgct ctttctggag 60
cagcctttgc cacaggctgc tgtagctctg tgggtaaaga aggaattcag caagtaagtc 120

<210> SEQ ID NO 650
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 650
gggcctcctt tttgttttcc aaatacccta ctcacctctc tgcttctgtt ccagggctca 60
ggaggaaagt acagggctgc tgagcggcct ccggatctgg cacacacagc tgctcccagg 120

<210> SEQ ID NO 651
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 651
cgggctccag ggcctcatcc tcaaccccat tttccgccag aacctccgca ttgcccttct 60
gggtgggtat gtcacttctc tctcttccta agctagggca ggggaactgc tgcttattaa 120

<210> SEQ ID NO 652
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 652
cctggccgta gggggaaggc ctggtctgat gacacaagtc agctgggacc agacaagcat 60
gcccgggacg ttccctccct tgacaagtac gccgaggagc gatgggaggt aagcacttgg 120

<210> SEQ ID NO 653
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 653
ctcttctgtt cttcaggtgg tcttgcactt catggtgggc tcccccagtg cagctgtcag 60
ccaggacttg gctcagctcc tcagccaggc tgggctcatg aagaggtgag gaagccggag 120

<210> SEQ ID NO 654
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 654
ctagtactga acctggagag ccgccctgca ttacttccgc tggcttccag ttcctgttgc 60
tggacacccc ggctcagctc tggtacttta tgttgcagta tttgcagaca gcccaggtga 120

<210> SEQ ID NO 655
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 655
tttgtctctg cctctttctc cctagagccg gggcatggac ctggtagaga ttctctcctt 60
cctcttccag ctcagcttct ctactctggg caaggtaagc agggggctga aaggtataga 120

<210> SEQ ID NO 656
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 656
gaaacctctg ttcctcagga ttactctgtg gaaggtatga gtgattctct gttgaacttc 60
ctgcaacatc tgcgtgagtt tgggcttgtt ttccagagga aggtatgagc gcctagataa 120

<210> SEQ ID NO 657
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 657
agatgtaagg cagtgacttc tgagacaagg catctgcctt tctattcttt tcagaggaaa 60
tctcggcgtt actaccccac acgcctggcc atcaatctct catcaggtgt ctctggagct 120

<210> SEQ ID NO 658
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 658
gggggcactg tgcatcagcc aggtttcatt gtcgtggaaa ccaattaccg actgtatgcc 60
tacacgggtg aggcgggaca gagggcccct ggaagaggag gttgggggtg agggaatgcc 120

<210> SEQ ID NO 659
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 659
agggagtctg ggtgtggggg tggcctcctc atcctctttc tatccctggc tcagagtcgg 60
agctgcagat tgccctcatt gccctcttct ctgagatgct ctatcggttc cccaacatgg 120

<210> SEQ ID NO 660
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 660
tggtggcgca ggtgacccgg gagagtgtgc agcaggcaat cgccagtggc atcacagccc 60
agcaggtatt cccacttggg agaggtggag caggaagaca ggctgcactt gggctgcggg 120

<210> SEQ ID NO 661
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 661
tcttgctgga gccctcatgc cattcttgtc tgttttccta gataatccat ttcctaagga 60
caagagccca cccagtgatg ctcaaacagg tatagacagg ctccaagatg tcagaggctg 120

<210> SEQ ID NO 662
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 662
gcagctggtg atgacatgat ggaaaagaaa aaggggcatc caaatctggg gaagaaacag 60
agggccgggt tgtctggggc agtattctga gtccctacag tcaacccttg ctccttgcag 120

<210> SEQ ID NO 663
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 663
acacctgtgc tgccccccac catcaccgac cagatccggc tctgggagct ggaaagggac 60
agactccggt tcactgaggg tgagtagctt ctggtggcca agtcttggtc attggccaga 120

<210> SEQ ID NO 664
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 664
tctccccgcg cccctcccgt cctgccgacc ccaggtgtcc tgtataacca gttcctgtcg 60
caagtggact ttgagctgct gctggcccac gcgcgggagc tgggcgtgct cgtgttcgag 120

<210> SEQ ID NO 665
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 665
aactcggcca agcggctcat ggtggtgacc ccggccgggc acagcgacgt caagcgcttt 60
tggaagcggc agaaacatag ctcctgagag cgcgggactt ggacacggac ctcggcgggc 120

<210> SEQ ID NO 666
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 666
tttattagca ttcttcaggt catctgaacc ttctgagaaa acatggtcaa cgtcttgaaa 60
ggagtgctta tagaatggtt agtagttttg atactgcatg agttttaagt ttaaatattg 120

<210> SEQ ID NO 667
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 667
tgtcttacaa tcatgtgttt gtctttacag tgatcctgcc atgaagcagt ttctgctgta 60
cttggatgag tccaatgccc tggggaagaa gttcatcatt caagacattg atgacactca 120

<210> SEQ ID NO 668
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 668
cgtctttgta atagcagaat tggttaatgt cctccaggag cgagtgggtg aattaatgga 60
ccaaaatgct ttttccctta cccagaaatg aaaatactca atatggacca tttaggaatt 120

<210> SEQ ID NO 669
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 669
caggacccgc ttctctgaaa ggctctcctt gcagctgctt agacgctgga ttttttttcgg 60 gtagtggaaa accaggtaag caccgaagtc cacttgcctt ttaatttatt tttttatcac 120

<210> SEQ ID NO 670
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 670
aagactgcct cccgctttgt gtgccccgct ccagcagcct cccgcgacga tgcccctcaa 60
cgttagcttc accaacagga actatgacct cgactacgac tcggtgcagc cgtatttcta 120

<210> SEQ ID NO 671
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 671
ctgcgacgag gaggagaact tctaccagca gcagcagcag agcgagctgc agcccccggc 60
gcccagcgag gatatctgga agaaattcga gctgctgccc accccgcccc tgtcccctag 120

<210> SEQ ID NO 672
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 672
ccgccgctcc gggctctgct cgccctccta cgttgcggtc acacccttct cccttcgggg 60
agacaacgac ggcggtggcg ggagcttctc cacggccgac cagctggaga tggtgaccga 120

<210> SEQ ID NO 673

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 673
gctgctggga ggagacatgg tgaaccagag tttcatctgc gacccggacg acgagacctt 60
catcaaaaac atcatcatcc aggactgtat gtggagcggc ttctcggccg ccgccaagct 120

<210> SEQ ID NO 674
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 674
cgtctcagag aagctggcct cctaccaggc tgcgcgcaaa gacagcggca gcccgaaccc 60
cgcccgcggc cacagcgtct gctccacctc cagcttgtac ctgcaggatc tgagcgccgc 120

<210> SEQ ID NO 675
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 675
cgcctcagag tgcatcgacc cctcggtggt cttcccctac cctctcaacg acagcagctc 60
gcccaagtcc tgcgcctcgc aagactccag cgccttctct ccgtcctcgg attctctgct 120

<210> SEQ ID NO 676
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 676
ctcctcgacg gagtcctccc cgcagggcag ccccgagccc ctggtgctcc atgaggagac 60
accgcccacc accagcagcg actctggtaa gcgaagcccg cccaggcctg tcaaaagtgg 120

<210> SEQ ID NO 677
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 677
ctatttcctt tcttaaagag gaggaacaag aagatgagga agaaatcgat gttgtttctg 60
tggaaaagag gcaggctcct ggcaaaaggt cagagtctgg atcaccttct gctggaggcc 120

<210> SEQ ID NO 678
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 678
acagcaaacc tcctcacagc ccactggtcc tcaagaggtg ccacgtctcc acacatcagc 60
acaactacgc agcgcctccc tccactcgga aggactatcc tgctgccaag agggtcaagt 120

<210> SEQ ID NO 679
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 679
tggacagtgt cagagtcctg agacagatca gcaacaaccg aaaatgcacc agccccaggt 60
cctcggacac cgaggagaat gtcaagaggc gaacacacaa cgtcttggag cgccagagga 120

<210> SEQ ID NO 680
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 680
ggaacgagct aaaacggagc ttttttgccc tgcgtgacca gatcccggag ttggaaaaca 60
atgaaaaggc ccccaaggta gttatcctta aaaaagccac agcatacatc ctgtccgtcc 120

<210> SEQ ID NO 681
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 681
aagcagagga gcaaaagctc atttctgaag aggacttgtt gcggaaacga cgagaacagt 60
tgaaacacaa acttgaacag ctacggaact cttgtgcgta aggaaaagta aggaaaacga 120

<210> SEQ ID NO 682
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 682
cttcaggatg gttcgtacta agacatggac cctgaagaag cactttgttg gctatcctac 60
taatagtgac tttgagttga agacagctga gctcccaccc ttaaaaaatg gaggtaagtc 120

<210> SEQ ID NO 683
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 683
gagtttctaa ttgcctatgg aatgctttat tttgtagagg tcctgcttga agctttgttc 60
ctcaccgtgg atccctacat gaggtattat ttatttcgcc cctcaaaatg ctaatgctgt 120

<210> SEQ ID NO 684
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 684
tttttttttt tttttttttt tgcagagtgg cagccaaaag attgaaggaa ggtgatacaa 60
tgatggggca gcaagtggcc aagtaattat ttccatttgt cccagtgctt ggaaaatatg 120

<210> SEQ ID NO 685
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 685
tctcttaaaa aaaccaaaca tctcattctt tattttttta aattttgtgt ctcaatgact 60
agccagttat tataatacca ttggtagaaa tcgtctatgg atctttactg gaatttcag 119

<210> SEQ ID NO 686
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 686
acatgcctta atgccttaat gtgctttatc tttcagagtt gtggaaagta aaaatgtagc 60
cctaccaaaa ggaactattg tactggcttc tccaggctgg acaacgcact ccatttctga 120

<210> SEQ ID NO 687
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 687
tgggaaagat ctggaaaagc tgctgacaga gtggccagac acaataccac tgtctttggc 60
tctggggaca gttggcatgc cagggtgagt ttcatggata tattccattt gtttgaatgt 120

<210> SEQ ID NO 688
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 688
gcctgactgc ctactttggc ctacttgaaa tctgtggtgt gaagggtgga gaaacagtga 60
tggttaatgc agcagctgga gctgtgggct cagtcgtggg gcagattgca aagctcaagg 120

<210> SEQ ID NO 689
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 689
tgacttattc atggtttcct tttttttttt ttttctactt agggctgcaa agttgttgga 60
gcagtagggt ctgatgaaaa ggttgcctac cttcaaaagc ttggatttga tgtcgtcttt 120

<210> SEQ ID NO 690
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 690
aactacaaga cggtagagtc tttggaagaa accttgaaga aagcgtctcc tgatggttat 60
gattgttatt ttgataatgt aagtacaaac tggacttaat atctaattta ttatggaagt 120

<210> SEQ ID NO 691
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 691
gtttaggtag gtggagagtt ttcaaacact gttatcggcc agatgaagaa atttggaagg 60
attgccatat gtggagccat ctctacatat aacagaaccg gcccacttcc cccaggtaat 120

<210> SEQ ID NO 692
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 692
gcccaccccc agagattgtt atctatcagg agcttcgcat ggaagctttt gtcgtctacc 60
gctggcaagg agatgcccgc caaaaagctc tgaaggactt gctgaaatgg gtcttagagg 120

<210> SEQ ID NO 693
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 693
ttgagaatat taaattaagt tttaaaattt gttgttgctt tgatacaggg taaaatccag 60
tacaaggaat atatcattga aggatttgaa aacatgccag ctgcatttat gggaatgctg 120

<210> SEQ ID NO 694
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 694
aaaggagata atttggggaa gacaatagtg aaagcatgaa aaagaggaca catggaatct 60
ggaggccatt tagatgatta gttaatttgt ttttcaccat ttagcaaaaa tgtatactac 120

<210> SEQ ID NO 695
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 695
cttaaatgtc ttaagaaata gtactcataa tgagtttgag ctacttaata aaatacattt 60
aagtggtatg taattagtga tggaggatgg aagtttcaaa gtcaacaaca accagtcacc 120

<210> SEQ ID NO 696
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 696
gatcaaaaga gaaaatgaag aagattgaag cttcaaagca gaaaaatgaa gggaatatgt 60
atcattcacc attaccttag aaggcaaggg tccactttac aaaaggacta caaacattta 120

<210> SEQ ID NO 697
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 697
gggtggctga cccccagcat cctcgggagc gaccatggac tccctggccg agtctcggtg 60
gcctccgggc ctggcagtca tgaaggtgag tgcttcgggg agtttgggag ctcccgggtg 120

<210> SEQ ID NO 698
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 698
atgcatattt gcatttcaga caatagatga tttgctgcgg tgtggaattt gcttcgagta 60
tttcaacatt gcaatgataa tacctcagtg ttcacataac tgtaagtatg ttttgttcct 120

<210> SEQ ID NO 699
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 699
aacattatgt tgcactttgt gttttgcaga ctgctctctc tgtataagaa aatttctgtc 60
ctataaaact cagtgtccaa cttgctgtgt ggtgagtttt tgtttccttt ttttaaaact 120

<210> SEQ ID NO 700
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 700
ccatctgttg tttgtttttt ctagactgtc acagagccgg atctgaaaaa taaccgcata 60
ttagatgaac tggtaaaaag cttgaatttt gcacggtatg atttaatttt gtgactaacc 120

<210> SEQ ID NO 701
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 701
tgtgcttcaa ggaatcatct gctgcagttt gctttagagt caccagccaa atctcctgct 60
tcttcctctt caaagaatct tgctgtcaaa gtatatactc ctgtagcctc cagacagtct 120

<210> SEQ ID NO 702
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 702
ttaaagcagg ggagcaggtt aatggataat ttcttgatca gagaaatgag tggttctaca 60
tcagagttgt tgataaaaga aaataaaagc aaattcagcc ctcaaaaaga ggcgagccct 120

<210> SEQ ID NO 703
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 703
gctgcaaaga ccaaagagac acgttctgta gaagagatcg ctccagatcc ctcagaggct 60
aagcgtcctg agccaccctc gacatccact ttgaaacaag ttactaaagg taggaagtta 120

<210> SEQ ID NO 704
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 704
aaaaatacag tggattgtcc tgtttgcggg gttaacattc cagaaagtca cattaataag 60
catttagaca gctgtttatc acgcgaagag aagaaggaaa gcctcagaag gtaaggaagt 120

<210> SEQ ID NO 705
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 705
atcatcaggt atcttccccc cttttcagtt ctgttcacaa aaggaagccg ctgcccaaaa 60
ctgtatataa tttgctctct gatcgtgatt taaagaaaaa gctaaaagag catggattat 120

<210> SEQ ID NO 706
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 706
ctattcaagg aaataaacaa cagctcatta aaaggcacca agaatttgta cacatgtaca 60
atgcccaatg cgatgctttg catcctaaat caggtaaagt aataaaacag tgagttatgc 120

<210> SEQ ID NO 707
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 707
gttattttct tattttaaca gctgctgaaa tagttcgaga aatcgaaaat atagagaaga 60
ctaggatgcg tcttgaagct agtaaactca atgaaagtgt atgttaatgg gctatttcag 120

<210> SEQ ID NO 708
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 708
tttattaagg tcttttttg attattttag gtaatggttt ttacaaagga ccaaacagaa 60
aaggaaatag atgaaatcca cagtaaatat cgtaagttgc acgactttat ttaatttgta 120

<210> SEQ ID NO 709
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 709
ggttaacttt catagtccta gctttactga gaagatcttt tgaatttcag gtaaaaaaca 60
taagagtgaa tttcagcttc tggtggatca ggctagaaaa ggatacaaga aaattgctgg 120

<210> SEQ ID NO 710
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 710
aatgtcacaa aaaacagtaa caataacaaa agaagatgaa tctacagaaa agctatcttc 60
tgtatgcatg ggtaagagac tataattaaa aacagacata tgtcgaattt cattatttac 120

<210> SEQ ID NO 711
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 711
aagttgtaga ttttaaggta ctcttaaatt tattttttcc taggacagga agataatatg 60
acctcagtaa caaaccactt ttctcaatca aagctggact ccccagagga attggaacct 120

<210> SEQ ID NO 712
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 712

```
gacagagaag aggattcttc tagctgtatt gatattcaag aagttctttc ttcatcagaa     60

tcagattcat gcaataggta agaaacatgc agtagttgat tattttaaat atctacttca    120


<210> SEQ ID NO 713
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 713

tgtcaatact gatgtacata tccttttagt tccagttcag acatcataag agatctttta     60

gaagaagagg aagcctggga agcatcacat aagtgagttc tcataatcat gaaataagca    120


<210> SEQ ID NO 714
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 714

gtcttcagaa acgatcttca agacacagaa ataagtccaa gacagaatcg ccgcacaaga     60

gccgctgaaa gtgctgagat tgaaccaaga aacaagcgta ataggaatta atgtgggctt    120


<210> SEQ ID NO 715
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 715

ttttatacag aaatcttgtg aaaccactgc ccaaccagag caatgattgt tcaaagagtg     60

gtattgaatt ctcgacctgg tatgtatttg cgatgaatga acaactctga tctttgataa    120


<210> SEQ ID NO 716
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 716

gaaaaaatgg taatccagtg gcagagaatt tccgaatgga agaagtctat ttaccagata     60

atattaatga aggacaagta caagttagaa ctctttatct ttctgtggat ccttacatgg    120


<210> SEQ ID NO 717
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 717

tatcttaatg ttttcttttt tcagcgttgt agaatgaatg aagacactgg cactgattat     60

ataacacctt ggcagctatc tcaagtcgtt gatggaggag gtattggaat tatagaagaa    120


<210> SEQ ID NO 718
<211> LENGTH: 120
<212> TYPE: DNA
```

<213> ORGANISM: Artificial Sequence
<220> FEATURE:
<223> OTHER INFORMATION: Synthetic polynucleotide

<400> SEQUENCE: 718
agcaaacaca caaatttgac taaaggcgat tttgtgactt ctttctattg gccctggcaa 60
accaaggtta ttctggatgg aaatagcctt gaaaaggtga tatatatatg aacatatctg 120

<210> SEQ ID NO 719
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 719
cctagtattt ttaaagggta tatattttat tttaggtaga cccacaactt gtggatggac 60
acctttcata ttttcttgga gctataggta tgcctggttt gacttccttg attgggatac 120

<210> SEQ ID NO 720
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 720
aggaaaaagg tcatataact gctggatcta ataagacaat ggttgtcagt ggggccgcag 60
gtgcctgtgg atctgtggct gggcaggtaa actttctgag aattatttga ttttctgatt 120

<210> SEQ ID NO 721
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 721
aaatttcccc cctagattgg ccatttctta ggttgttcca gagtggtggg aatttgtgga 60
acacatgaga aatgcatcct cttgacctca gaactgggct ttgatgctgc aattaattat 120

<210> SEQ ID NO 722
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 722
aaaaaagaca atgtggcaga acagctccgt gaatcatgcc cagctggagt ggatgtttat 60
tttgacaatg ttggtggtaa catcagtgat acagtgataa gtcaggttgt ttgctgattt 120

<210> SEQ ID NO 723
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 723
agccataaaa tcagtaaaca taggaaaggg atattttatc attatttttc tctgtgcaga 60
tgaatgagaa cagccacatc atcctgtgtg gtcaaatttc tcagtacaac aaagatgtgc 120

<210> SEQ ID NO 724
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 724
cttatcctcc cccgctatcc cctgctatag aggcaatcca gaaagaaaga aacatcacaa 60
ggtgtgttct tcctctttgc ccttattacc aggttcatgg ggttttaaat atcatagatg 120

<210> SEQ ID NO 725
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 725
ttcttcctca ctgcagggaa agatttctgg tattaaatta taaagacaaa tttgagcctg 60
gcattctaca gctgagtcag tggtttaaag aaggaaagct aaaggtagaa cttctattct 120

<210> SEQ ID NO 726
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 726
aagtttaaag actattaaat ctagctattt tgatttacag attaaagaga cggtaataaa 60
tgggttggaa aacatgggag gtaagatgaa tgtagactta ttatatacac atgctcagca 120

<210> SEQ ID NO 727
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 727
aacctacttt ctctttttcc agctgcattc cagtccatga tgacaggagg taacattgga 60
aagcagatag tttgcatttc agaagaaatc tctttgtaat tgctgtaaat gtcatcaagg 120

<210> SEQ ID NO 728
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 728
gagctgggag ctaggtcctc ggagtgggcc agagatggcg gcggccgacg gggctttgcc 60
ggaggcggcg gctttagagc aacccgcgga gctgcctgcc tcggtgcggg cgagtatcga 120

<210> SEQ ID NO 729
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 729
gcggaagcgg cagcgggcac tgatgctgcg ccaggcccgg ctggctgccc ggccctactc 60
ggcgacggcg gctgcggcta ctggaggttt gggccgcgtc cgcgctttcc ccttccctct 120

<210> SEQ ID NO 730
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 730
gtaggcatgg ctaatgtaaa agcagcccca aagataattg acacaggagg aggcttcatt 60
ttagaagagg aagaagaaga agaacagaaa attggaaaag ttgttcatca accaggtaaa 120

<210> SEQ ID NO 731
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 731
ttcttaggac ctgttatgga atttgattat gtaatatgcg aagaatgtgg gaaagaattt 60
atggattctt atcttatgaa ccactttgat ttgccaactt gtgataactg caggtactta 120

<210> SEQ ID NO 732
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 732
ataactaatt tatataatgg acttaatctg ttttcagaga tgctgatgat aaacacaagc 60
ttataaccaa aacagaggca aaacaagaat atcttctgaa agactgtgat ttagaaaaaa 120

<210> SEQ ID NO 733
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 733
gagagccacc tcttaaattt attgtgaaga agaatccaca tcattcacaa tggggtgata 60
tgaaactcta cttaaagtta caggtctcta ataagttgta tttattattt ttcactctgg 120

<210> SEQ ID NO 734
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 734
gattgtgaag aggtctcttg aagtttgggg tagtcaagaa gcattagaag aagcaaagga 60
agtccgacag gaaaaccgag aaaaaatgaa acagaagaaa tttgataaaa aagtaaaagg 120

<210> SEQ ID NO 735
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 735
cctgaatagc accactgaaa agatgacttt aaaatttttt tttcagaatt gcggcgagca 60
gtaagaagca gcgtgtggaa aagggagacg attgttcatc aacatgagta tggaccagaa 120

<210> SEQ ID NO 736
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 736
gaaaacctag aagatgacat gtaccgtaag acttgtacta tgtgtggcca tgaactgaca 60
tatgaaaaaa tgtgattttt tagttcagtg acctgtttta tagaatttta tatttaaata 120

<210> SEQ ID NO 737
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 737
caagcaacat ggctcggaaa cgcgcggccg gcggggagcc gcggggacgc gaactgcgca 60
gccagaaatc caaggccaag agcaaggccc ggcgtgagga ggaggaggag ggtgagagcg 120

<210> SEQ ID NO 738
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 738
tatgttctgt gttgtcacct agatgccttt gaagatgaga aacccccaaa gaagagcctt 60
ctctccaaag tttcacaagg aaagaggaaa agaggctgca gtcatcctgg gggttcagca 120

<210> SEQ ID NO 739
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 739
gatggtccag caaaaaagaa agtggccaag gtgactgtta aatctgaaaa cctcaaggtt 60
ataaaggatg aagccctcag cgatggggat gacctcaggt gagatgtctg caaagctttg 120

<210> SEQ ID NO 740
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 740
acagggactt tccaagtgac ctcaagaagg cacaccatct gaagagaggg gctaccatga 60
atgaagacag caatgaagaa gaggaagaaa gtgaaaatga ttgggaagag gttgaaggtg 120

<210> SEQ ID NO 741
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 741
acagtagcta ttattattgt tattactatt actgattttt aaaaatgctt gttgatagaa 60
cttagtgagc ctgtgctggg tgacgtgaga gaaagtacag ccttctctcg atctcttctg 120

<210> SEQ ID NO 742
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 742
cctgtgaagc cagtggagat agagattgaa acgccagagc aggcgaagac aagagaaaga 60
aggtaagctt aggcccttgc ttctaggctc ctgtcacatg cagtaggcaa cagctgctgc 120

<210> SEQ ID NO 743
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 743
tttcactatt tgttgcagtg aaaagataaa actggagttt gagacatatc ttcggagggc 60
gatgaaacgt ttcaataaag ggtccatgga ggacacacac aaggtaaggg caaggaatga 120

<210> SEQ ID NO 744
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 744
ccttccttcc atgctgcccc ttcctccttt cctcttcaca ggttcacctt ctctgcctgc 60
tagcaaatgg cttctatcga aataacatct gcagccagcc agatctgcat gctattggcc 120

<210> SEQ ID NO 745
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 745
tgtccatcat cccagcccgc tttaccagag tgctgcctcg agatgtggac acctactacc 60
tctcaaacct ggtgaagtgg taaggccctc cgcttgtcct gcagagctgg ggagtgtagg 120

<210> SEQ ID NO 746
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 746
gaaatgaaaa ttcccctttg ccctgacctc tgacacaagg aatgcctgct ttctccccag 60
gttcattgga acatttacag ttaatgcaga actttcagcc agtgaacaag ataacctgca 120

<210> SEQ ID NO 747
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 747
gactacattg gaaaggagat ttgctattta ctctgctcga gatgatgagg aattggtcca 60
tgtaagtgat cctcccggat cactgttttt tatcagtact gttaactaat gataatggca 120

<210> SEQ ID NO 748
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 748
tccttttcat catagatatt cttactgatt ctccgggctc tgcagctctt gacccggctg 60
gtattgtctc tacagccaat tcctctgaag tcagcaacag caaaggtgag gtgcgcaggg 120

<210> SEQ ID NO 749
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 749
gggggagaaa aaaaagcaaa atttcttatt ctgtttaagg gaaagaaacc ttccaaggaa 60
agattgactg cggatccagg aggctcctca gaaacttcca gccaagttct agaaaaccac 120

<210> SEQ ID NO 750
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 750
accaaaccaa agaccagcaa aggaaccaaa caagaggaaa cctttgctaa gggcacctgc 60
aggccaagtg ccaaagggaa gaggaacaag ggaggcagaa agaaacggag caagccctcc 120

<210> SEQ ID NO 751
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 751
tccagcgagg aagatgaggg cccaggagac aagcaggaga aggcaaccca gcgacgtccg 60
catggccggg agcggcgggt ggcctccagg gtgtcttata aagaggagag tgggagtgat 120

<210> SEQ ID NO 752

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 752
gaggctggca gcggctctga ttttgagctc tccagtggag aagcctctga tccctctgat 60
gaggattccg aacctggccc tccaaagcag aggaaagccc ccgctcctca gaggacaaag 120

<210> SEQ ID NO 753
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 753
gctgggtcca agagtgcctc caggacccat cgtgggagcc atcgtaagga cccaagcttg 60
ccagcggcat cctcaagctc ttcaagcagt aaaagaggca agaaaatgtg cagcgatggt 120

<210> SEQ ID NO 754
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 754
gagaaggcag aaaaaagaag catagctggt atagaccagt ggctagaggt gttctgtgag 60
caggaggaaa agtgggtatg tgtagactgt gtgcacggtg tggtgggcca gcctctgacc 120

<210> SEQ ID NO 755
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 755
tgttacaagt acgccaccaa gcccatgacc tatgtggtgg gcattgacag tgacggctgg 60
gtccgagatg tcacacagag gtacgaccca gtctggatga cagtgacccg caagtgccgg 120

<210> SEQ ID NO 756
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 756
gttgatgctg agtggtgggc cgagaccttg agaccatacc agagcccatt tatggacagg 60
gagaagaaag aagacttgga ggtaaggcct tggctgccag gggctccaag acacagtcag 120

<210> SEQ ID NO 757
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 757
ctaaataaca tgctcaacct tgtctgtctg gcctttgcag tttcaggcta aacacatgga 60
ccagcctttg cccactgcca ttggcttata taagaaccac cctctgtatg ccctgaagcg 120

<210> SEQ ID NO 758
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 758
gcatctcctg aaatatgagg ccatctatcc cgagacagct gccatccttg ggtattgtcg 60
tggagaagcg gtctactcca ggtgcgtgag gcagcctggt tggcctcagg ggcttcctga 120

<210> SEQ ID NO 759
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 759
tcctgtgttg gttccacagg gattgtgtgc acactctgca ttccagggac acgtggctga 60
agaaagcaag agtggtgagg cttggagaag taccctacaa ggtaactgga gctgggggt 120

<210> SEQ ID NO 760
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 760
ctgaggaact ggatgccttt gttgtaaacg gtggccgtgt cctctggtgc agatggtgaa 60
aggcttttct aaccgtgctc ggaaagcccg acttgctgag ccccagctgc gggaagaaaa 120

<210> SEQ ID NO 761
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 761
tgacctgggc ctgtttggct actggcagac agaggagtat cagcccccag tggccgtgga 60
cgggaaggta agggcagcat cagaagggct caggaccagg ccgccttgtt cccctgctgg 120

<210> SEQ ID NO 762
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 762
tgctggccaa atgctgactt gctcacccga cacaggtgcc ccggaacgag tttgggaatg 60
tgtacctctt cctgcccagc atgatgccta ttggctgtgt ccagctgaac ctgcccaatc 120

<210> SEQ ID NO 763
<211> LENGTH: 120
<212> TYPE: DNA
<213> ORGANISM: Artificial Sequence
<220> FEATURE:

<223> OTHER INFORMATION: Synthetic polynucleotide

<400> SEQUENCE: 763
tacaccgcgt ggcccgcaag ctggacatcg actgtgtcca ggccatcact ggctttgatt 60
tccatggcgg ctactcccat cccgtgtgcg tgaggggcct tcgatggagg ctaaacacag 120

<210> SEQ ID NO 764
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 764
tgtgtcccca caggactgat ggatacatcg tctgcgagga attcaaagac gtgctcctga 60
ctgcctggga aaatgagcag gcagtcattg aaaggaagga gaaggaggta agcgcatatg 120

<210> SEQ ID NO 765
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 765
catttttgcc tgcagaaaaa ggagaagcgg gctctaggga actggaagtt gctggccaaa 60
ggtctgctca tcagggagag gctgaagcgt cgctacgggc ccaaggtcag tgcaggttct 120

<210> SEQ ID NO 766
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 766
acctgtccag agtgaggcag cagctcccca cacagatgca ggaggtggac tctcttctga 60
tgaagaggag gggaccagct ctcaagcaga agcggccagg atactggctg cctcctggcc 120

<210> SEQ ID NO 767
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 767
tcaaaaccga gaagatgaag aaaagcagaa gctgaagggt gggcccaaga agaccaaaag 60
ggaaaagaaa gcagcagctt cccacctgtt cccatttgag cagctgtgag ctgagcgccc 120

<210> SEQ ID NO 768
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 768
cagaaagcgg gcgagcagca gttgagcgag cccgaggaca tggagatgga aggtgaggcc 60
cgagggccgg ccgcggcggg gccgggggc gcctttcatt gtggccgggg gagccgcggg 120

<210> SEQ ID NO 769
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 769
tgaatgtttc tggtcctaaa gacaaggctt ctgtgggatg ctttaaaaaa taaaaaagaa 60
tgctgaggta gagctcctag agattctatg cagtcactct gatgtgggtg agagaacctc 120

<210> SEQ ID NO 770
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 770
ccccatcccc cagcagaggc cactgcagag ccatgcagag atggctggga accacaggct 60
tgggctggaa ggtgagtcag gttttcaggt tgagctcctt atgctggtga tggatggaga 120

<210> SEQ ID NO 771
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 771
ctttaaagcg ggagatacag atgacccacc aagaattact cagaaccctg tgatcaatgg 60
gaatgtggcc ctgagtgatg gacacaacac cgcggaggag gacatggagg atggtaagtg 120

<210> SEQ ID NO 772
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 772
atgatgtgtt ttttttgcag acaccagttg gcgctccgag gcaacctttc agttcactgt 60
ggagcgcttc agcagactga gtgagtcggt ccttagccct ccgtgttttg tgcgaaatct 120

<210> SEQ ID NO 773
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 773
gccatggaag attatggtga tgccacgctt ttatccagac agaccacacc aaaaaagcgt 60
aggattcttt ctccagtgca atgctgaatc tgattccacg taagacagta tttcattact 120

<210> SEQ ID NO 774
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 774
aacatctggt aaataatgtc aactaaggct cagattattc ttttaaacag gtcatggtct 60
tgccatgcac aagcagtgct gaagataata aattacagag atgatgaaaa gtcgttcagt 120

<210> SEQ ID NO 775
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 775
cgtcgtatta gtcatttgtt cttccataaa gaaaatgatt ggggattttc caattttatg 60
gcctggagtg taagtaacag tgtatttagt ctgaacaatt ggtgcattac tgcttgttgt 120

<210> SEQ ID NO 776
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 776
tatttatgtt ttataggaag tgaccgatcc tgagaaagga tttatagatg atgacaaagt 60
tacctttgaa gtctttgtac aggcggatgc tccccatgga gttgcgtaag tttttcttta 120

<210> SEQ ID NO 777
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 777
tttcaggtgg gattcaaaga agcacacagg ctacgtcggc ttaaagaatc agggagcgac 60
ttgttacatg aacagcctgc tacagacgtt atttttcacg aatcagctac gaaaggtaaa 120

<210> SEQ ID NO 778
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 778
taaattcccc tgcatcttct cagagtaaaa attcttattt cttaattgtt tcaggctgtg 60
tacatgatgc caaccgaggg ggatgattcg tctaaaagcg tccctttagc attacaaaga 120

<210> SEQ ID NO 779
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 779
gtgttctatg aattacagca tagtgataaa cctgtaggaa caaaaaagtt aacaaagtca 60
tttgggtatg tattagacat ctgcctttgc cattctgctt cctctttttt tttttttttt 120

<210> SEQ ID NO 780
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 780
ttaaatggag ttgtttgttt tatctttgaa aggtgggaaa ctttagatag cttcatgcaa 60
catgatgttc aggagctttg tcgagtggta agtttcaagc aatacttgta tatttcttac 120

<210> SEQ ID NO 781
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 781
gccaaaacat tctttttcag ttgctcgata atgtggaaaa taagatgaaa ggcacctgtg 60
tagagggcac catacccaaa ttattccgcg gcaaaatggt ggtatgtggc taccagttct 120

<210> SEQ ID NO 782
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 782
ttccttattt gcagtcctat atccagtgta aagaagtaga ctatcggtct gatagaagag 60
aagattatta tgatatccag ctaagtatca aaggaaagaa aaatagtaag tgttgtgtgt 120

<210> SEQ ID NO 783
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 783
ctctctctct ctttaaagta tttgaatcat ttgtggatta tgtggcagta gaacagctcg 60
atggggacaa taaatacgac gctggggaac atggcttaca ggtaaattga gtgttttgtg 120

<210> SEQ ID NO 784
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 784
tttaggaagc agagaaaggt gtgaaattcc taacattgcc accagtgtta catctacaac 60
tgatgagatt tatgtatgac cctcagacgg accaaaatat caagatcaat gataggtaat 120

<210> SEQ ID NO 785
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 785
tgtaaattaa tactgaattt cttttaaaat gttttctaat aggtttgaat tcccagagca 60
gttaccactt gatgaatttt tgcaaaaaac agatcctaag gaccctgcaa attatattct 120

<210> SEQ ID NO 786
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 786
tcatgcagtc ctggttcata gtggagataa tcatggtgga cattatgtgg tttatctaaa 60
ccccaaaggg gatggcaaag taagtggtgg gacccagggc tgaatgcaag ctcatcagaa 120

<210> SEQ ID NO 787
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 787
cttgtcacag tgcttgatcg ctgctggtgt gtgttgtttt ccttgcagtg gtgtaaattt 60
gatgacgacg tggtgtcaag gtgtactaaa gaggaagcaa ttgagcacaa ttatgggggt 120

<210> SEQ ID NO 788
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 788
cacgatgacg acctgtctgt tcgacactgc actaatgctt acatgttagt ctacatcagg 60
gaatcaaaac tgagtgagta gtgttcactt ttgttctgtt ctttactgtg gtggacttgg 120

<210> SEQ ID NO 789
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 789
ctaagagggg aaagtccatc tgcaggggtc aaagaggatg cctttgtcct gcaggtgaag 60
ttttacaggc ggtcaccgac catgatattc ctcagcagtt ggtggagcga ttacaagaag 120

<210> SEQ ID NO 790
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 790
agaaaaggat cgaggctcag aagcggaagg agcggcagga agcccatctc tatatgcaag 60
tgcaggtcag cccccgccct tctgggactc cgggtcacca tgcagccggg cacccatctc 120

<210> SEQ ID NO 791
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 791 tcatttttg tcagttgtca agtcttttct gtgctttcat acatattttc agatagtcgc 60
agaggaccag ttttgtggcc accaagggaa tgacatgtac gatgaagaaa aagtgaaata 120

<210> SEQ ID NO 792
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 792
cactgtgttc aaagtattga agaactcctc gcttgctgag tttgttcaga gcctctctca 60
gaccatggtg cgtaccggtc ccgtggatat accccaccgt ggctcccaac gtccaccttc 120

<210> SEQ ID NO 793
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 793
ttttttcagg gatttccaca agatcaaatt cgattgtggc ccatgcaagc aaggagtaat 60
ggaacaaaac gaccagcaat gttagataat gaagccgacg gcaataaaac agtaaatatt 120

<210> SEQ ID NO 794
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 794
gaaatagatg attgagctca gtgataatga aaacccttgg acaatattcc tggaaacagt 60
tgatcccgag ctggctgcta gtggagcgac cttacccaag tttgataaag atcgtaagtg 120

<210> SEQ ID NO 795
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 795
tattaacctt gtagatgatg taatgttatt tttgaagatg tatgatccca aaacgcggag 60
cttgaattac tgtgggcata tctacacacc aatatcctgt aaaatacgta agtccttcgt 120

<210> SEQ ID NO 796
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 796
catttaaaat atcttctttc tcctaggtga cttgctccca gttatgtgtg acagagcagg 60
atttattcaa gatactagcc ttatcctcta tgaggtttgg atggtttatt tttccataat 120

<210> SEQ ID NO 797
<211> LENGTH: 120
<212> TYPE: DNA

<213> ORGANISM: Artificial Sequence
<220> FEATURE:
<223> OTHER INFORMATION: Synthetic polynucleotide

<400> SEQUENCE: 797
ttcactgtag gaagttaaac cgaatttaac agagagaatt caggactatg acgtgtctct 60
tgataaagcc cttgatgaac taatggatgg tgacatcata gtatttcaga agtatgtact 120

<210> SEQ ID NO 798
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 798
ccatggactt tgattcagac tgcaaacttt ctccctccac cagggatgac cctgaaaatg 60
ataacagtga attacccacc gcaaaggagt atttccgaga tctctaccac cgcgttgatg 120

<210> SEQ ID NO 799
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 799
tcattttctg tgataaaaca atccctaatg atcctggatt tgtggttacg ttatcaaata 60
gaatgaatta ttttcaggta tttaataaat gctcctttcc tcttcagatc ccactccaga 120

<210> SEQ ID NO 800
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 800
tgtgaacctt cctttctgtg tcttaggttg caaagacagt tgcacagagg ctcaacacag 60
atccaatgtt gctgcagttt ttcaagtctc aagggtaggt cacatgtgtg gacacttgct 120

<210> SEQ ID NO 801
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 801
gtgtagttat agggatggcc caggtaatcc tcttagacat aattatgaag gtactttaag 60
agatcttcta cagttcttca agcctagaca acctaagaaa ctttactatc agcaggtatg 120

<210> SEQ ID NO 802
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 802
gaatctttct tttcttaata gcttaagatg aaaatcacag actttgagaa caggcgaagt 60
tttaaatgta tatggttaaa cagccaattt agggaagagg taagtttttt taatactatg 120

<210> SEQ ID NO 803
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 803
cattacttag gaaataacac tatatccaga caagcatggg tgtgtccggg acctgttaga 60
agaatgtaaa aaggccgtgg agcttgggga gaaagcatca gggaaactta ggcaagtatt 120

<210> SEQ ID NO 804
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 804
ctctgttcag gctgctagaa attgtaagct acaaaatcat tggtgttcat caagaagatg 60
aactattaga atgtttatct cctgcaacga gccggacgtt tcgaatagag gtatctgtcc 120

<210> SEQ ID NO 805
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 805
tggacacttt gaccacatca cttgcactta cagaactgtg tctgttgtcc gtgtccccag 60
gaaatccctt tggaccaggt ggacatagac aaagagaatg agatgcttgt cacagtggcg 120

<210> SEQ ID NO 806
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 806
catttccaca aagaggtctt cggaacgttc ggaatcccgt ttttgctgag gatacaccag 60
gtatgctgtt gtggttggcc gagtggctca cgtcaaaacc tggagccttt gagtggccgc 120

<210> SEQ ID NO 807
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 807
agcacatgtc ctttgccatt ctagggcgag cattttcgag aagtgatgaa gcgaatccag 60
agcctgctgg acatccagga gaaggagttt gagaaggtgt gcagctgggg cctcctgggg 120

<210> SEQ ID NO 808
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 808
gtttaaattt gcaattgtaa tgatgggccg acaccagtac ataaatgaag acgagtatga 60
agtaaatttg aaagactttg agccacagcc cggtaagggt tctccccccc ccgggggctg 120

<210> SEQ ID NO 809
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 809
caccaggtaa tatgtctcat cctcggcctt ggctagggct cgaccacttc aacaaagccc 60
caaagaggag tcgctacact taccttgaaa aggccattaa aatccataac tgatttccaa 120

<210> SEQ ID NO 810
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 810
tatttctaga tatggatcag aaactttcga agttggtaga agagctcaca acttcaggag 60
aaccccgact aaatcctgag aaaatgaagg aactgaagaa aatttgcaag tatgtcttag 120

<210> SEQ ID NO 811
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 811
gctcgcatcc ccaggtcttc agaggagcag ctgagccgcg cctaccgcct gctgatagca 60
cagctgaccc aggagcacgc cgagatccgt ctctcagcct tccagattgt ggaggaactc 120

<210> SEQ ID NO 812
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 812
ttcgtcaggt ctcaccagtt ccggatgctg gttgtttcca acttccagga gttcctggag 60
ctcacgctgg gcacagaccc cgcacagcct ctgccgcccc ccagggaggc ggcacagagg 120

<210> SEQ ID NO 813
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 813
ctgaggcagg cgaccacccg ggccgtggaa gggtggaatg agaagtttgg ggaggcctac 60
aagaagcttg ccttgggcta ccacttctta agacacaaca aaaaggtagg tgggcctggc 120

<210> SEQ ID NO 814
<211> LENGTH: 120

<212> TYPE: DNA
<213> ORGANISM: Artificial Sequence
<220> FEATURE:
<223> OTHER INFORMATION: Synthetic polynucleotide

<400> SEQUENCE: 814
gtgagccacc gcgcctgtcc cctagtcttt attttcaatt gctcaggtgg attttcaaga 60
cacgaatgct cggagtctgg cagaaaggaa gagagaagag gagaagcaga agcacttgga 120

<210> SEQ ID NO 815
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 815
taaaatttat caagaaagag ccagccaggc ggagagggag atgcaaggca agtgtccagg 60
acggagggag gggcccacgc ctctgagggt tgcccgtggt ccagcagttc atcctcctgg 120

<210> SEQ ID NO 816
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 816
cttttgctcc acatagcgca gcaaacaggt gtcttgatct tccggcagaa atgtctggag 60
aaattgaatc ctgcttgacg gaggtagaga gctgctttag gctgctggtg ccttttgact 120

<210> SEQ ID NO 817
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 817
ttgacccgaa cccggagacg gaatcccttg gcatggcttc tggcatgtcc gatgcccttc 60
gctcctcctg cgcgggccag gtgggcccct gccggtctgg cacccctgac ccccgggacg 120

<210> SEQ ID NO 818
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 818
gggagcagcc ctgctgcagt agagacctgc ctgcctctgc aggccacccc agagcgggcg 60
gcggggcaca gccatcccag acagccacag gtgacccctc agatgaggac gaggacagcg 120

<210> SEQ ID NO 819
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 819
acctcgagga gtttgtgcgg agccacgggc tgggctcgca caagtacacg ctggatgtgg 60
agctctgctc aggtaactgc cttcgcgggg tctctgtggc gccaccctgc cccggctccc 120

<210> SEQ ID NO 820
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 820
ccagagggcc tgaaggtgca ggagaacgag gacaaccttg ctctcatcca cgccgcccgc 60
gacacactca agctcatccg gaacaagttc ctgccggctg tgtgctcgtg gatccaggtg 120

<210> SEQ ID NO 821
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 821
gtgtgccagg gaccccccgg gccagtggac ctggcatgtg cctcccagca ggacagcttc 60
ccaggtcctg cccggccggc ccctgagctg ttcgcacccc cgtttcgcag cgcttcaccc 120

<210> SEQ ID NO 822
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 822
gcgtcgggac ccacggtgga tgtttaaagc gtgccattga cctgaaggct gaattggagc 60
tcgtactgag aaaatacaag gagctggaca tcgagcctga gggaggggaa aggcgcaggg 120

<210> SEQ ID NO 823
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 823
acagacagaa gccctggggg atgcggagga agatgaggac gatgaggact ttgtggaggt 60
ccctgagaag gaggggtatg agccacacat ccccgaccac ttgcggcctg agtatggtga 120

<210> SEQ ID NO 824
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 824
ggcgggttgt gggagtggtg gcagggagtg gacacgtgtc tgtttcaggg ctggaggcag 60
caccagagaa agacacagtt gtgcggtgct tgcggacgag gacgaggatg gacgaggagg 120

<210> SEQ ID NO 825
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 825
tgtcggaccc cacctctgcg gctgctcagc tgcggcagct ccgggaccac ttgcctccac 60
cctcatctgc caggtgactc ccagtgtcct gtgtgctgag ccccctgccc ggcgctgcca 120

<210> SEQ ID NO 826
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 826
gctgtgggtg gcaccagcag caccgtcagg ctgtcccact ctgctcctgt agcccctcca 60
gagcgttgcc agagccacag gaggcccaga agctggcagc agagcgggcc cgggcgcctg 120

<210> SEQ ID NO 827
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 827
tggtgcccta cggcgtggac ctgcactact ggggccagga gctccccaca gccgggaaga 60
ttgtcaagtg agtccccatg tgtctgaagt cggccagggc acacaaccag ggtcccagcc 120

<210> SEQ ID NO 828
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 828
ctatgagggc ctctggctgt gtctgcaggt ctgactccca gcaccgcttc tggaagccca 60
gcgaggtgga ggaggaagtg gtcaatgccg acatctccga gatgctccgg agccgccaca 120

<210> SEQ ID NO 829
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 829
tcacttttgc cgggaagttt gagcctgtgc agcactggtg ccgtgccccg aggccagacg 60
gccggctctg tgagcgccaa gaccggctga aggtgaggcc gtggcccgag ggcgggggtg 120

<210> SEQ ID NO 830
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 830
gactttccac agctgcccaa gaccttccgg ctccagagga gggacggagc catccccacg 60
tccctgtggc tctcaggacg ccctcctctg aggggcgcgt gattccaggt tgtgtacact 120

<210> SEQ ID NO 831

<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 831
ttggctctgt gataccaccc accctggtcg ctgtttgtgc ccaagtcgtg gtggtggggg 60
gaggtggtca aggcaagcgg acccctcccc gccatcagcc accgtgtcct cgctgtgcag 120

<210> SEQ ID NO 832
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 832
tgccctttcc atgggaagat tgttccacgg gacgacgaag gacggccgct cgacccggaa 60
gacagggctc gtgagcagcg gcggcagctg cagaagcagg agcgcccggg taggtctggg 120

<210> SEQ ID NO 833
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 833
cgtctcctga agtgcttgag ttttgtttgc agaatggcag gaccctgagt tgatgagaga 60
cgtggaagca gccacagggc aggatctcgg ctcatccagg tacagcggga aaggcagggg 120

<210> SEQ ID NO 834
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 834
gaagaagagg aggtacccca gcctcaccaa cctgaaggct caggctgata ccgcccgcgc 60
tcgcattggg agaaaagtct tcgccaagta agagtggctg ctgggtcacc tcccaccgcg 120

<210> SEQ ID NO 835
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 835
tgtttcccca cagggcagct gtgcggaggg tagtggcagc catgaaccgg atggaccaga 60
agaagcacga gaagttttca aaccagttta actacgcact gaactagaga gcggggccca 120

<210> SEQ ID NO 836
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 836
tttttcttta tcttttttt ttttagacta caacaaaatc acaattaaat ccggcctttg 60
aagatgcctg gagcagcagt gatgaagaag gatgaatatc atctttagta ccttttttgtc 120

<210> SEQ ID NO 837
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 837
ctttgccttc tatgttatag gaactttata gtggtagcag agactgcaac attctggctt 60
gggttccatc cttatatgaa ccagttcctg atgatgatga ggtaaatatt attttcacaa 120

<210> SEQ ID NO 838
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 838
accattgctg tttatacagt ttactcagga gaacagataa ctatgcttaa gggacattat 60
aaaactgttg actgctgtgt atttcagtca aatttccagg taagagtgat acaggaattt 120

<210> SEQ ID NO 839
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 839
cttattattt taatcctaca ggtgaactat ggaaaagttt gtaataacag taaaaaagga 60
ttgaaattca ctgtctcctg tggctgcagt tcagaatttg tttttgtacc atatggtagc 120

<210> SEQ ID NO 840
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 840
ctcactgttg gtacagataa tcgaatgagg ctctggaata gttccaatgg agaaaacaca 60
cttgtaagag atttttaagt atatatttgg gtataaatta agaaatggat ctgtgacata 120

<210> SEQ ID NO 841
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 841
acattaaata tgtcctgaat acaagaacag ataaactgaa ctatgttttt cattgcagca 60
aacactgctc ataatgggaa agttaatggc ttatgtttta caagtgatgg acttcacctc 120

<210> SEQ ID NO 842
<211> LENGTH: 120
<212> TYPE: DNA
<213> ORGANISM: Artificial Sequence
<220> FEATURE:

-continued

<223> OTHER INFORMATION: Synthetic polynucleotide

<400> SEQUENCE: 842
ttcttctcag tgctgacagt agagtaaaat tatgggatgt gagaagagca tcaggatgtt 60
tgattactct tgatcaacat aatgggaaaa agtcacaagc tgttgaatca ggtaaggaag 120

<210> SEQ ID NO 843
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 843
gacttttcat atagttgtat ttgcaggtca cagacaagaa atattagcag tttcctggtc 60
tccacgttat gactatatct tggcaacagc aaggtaaaat ttaacttatt tgcttttgaa 120

<210> SEQ ID NO 844
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 844
aatgtctttt gattaccaga ctgcagatgt atttaatttt gaggaaacag tttatagtca 60
tcatatgtct ccagtctcca ccaagcactg tttggtagca ggtttgtaag tgtattcttt 120

<210> SEQ ID NO 845
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 845
tttattttta agagttttgg gactggaatt aaataaagac agagatgttg aaagaatcca 60
cggcggtgga attaacaccc ttgacattga acctgttgaa gggagatagt aagtttatta 120

<210> SEQ ID NO 846
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 846
ccagccggtg tgaggacacg atatgctggg gtttttgtcc gcacgccaaa cgggtttgga 60
ggaccctctt cgccttcgga gagcagagtc aacacggagg taaagaaaac cttacttttt 120

<210> SEQ ID NO 847
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 847
gcatgttcac atcaagctca tttgataaaa ctctgaaagt atgggataca aatacattac 60
aagtaagtac attaaaacat ttgcagattg ctttgtagga taaaggagaa tttaatccta 120

<210> SEQ ID NO 848
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 848
taccagtttt gaaactcaca taagtcagtt aatgtaaatt ttgattgctg ttttgtagag 60
atcatcctga tgttcacaga tacagtgtgg agactgtaca gtggtatcct catgacactg 120

<210> SEQ ID NO 849
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 849
tattatcagc atgttatcag gtggttcaga tggtgtgatt gtactttatg accttgagaa 60
ctccagcaga caatcttatt acacatgtaa agcagtgtgt tccattggca ggtatgtatt 120

<210> SEQ ID NO 850
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 850
ggtattttta ttttatttca aacggcaact actttgagta aacgattcaa taaaaagaaa 60
cgttactaac agtgtattct ttgtaagtga catgactaat gtactttgtg ctggttgttg 120

<210> SEQ ID NO 851
<211> LENGTH: 120
<212> TYPE: DNA
<213> ORGANISM: Artificial Sequence
<220> FEATURE:
<223> OTHER INFORMATION: Synthetic polynucleotide

<400> SEQUENCE: 851
ttttgatgat gacttatgat aaaattatct taaaccggtt ctgtttttac agttggtact 60
agaggaccca aagtacaact ttgtgacttg aagtctggat cctgttctca cattctacag 120

<210> SEQ ID NO 852
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 852
aatttgtgat acccctcgac g 21

<210> SEQ ID NO 853
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 853
tgggaaggct ctgtgtagat cgga 24

<210> SEQ ID NO 854
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 854
tgtgagatgg catattcggc 20

<210> SEQ ID NO 855
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 855
tccttgctaa ctttgccacc 20

<210> SEQ ID NO 856
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 856
tgcttccaca gtgctgagcc t 21

<210> SEQ ID NO 857
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 857
catctttgct actggttttc cc 22

<210> SEQ ID NO 858
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 858
gtccgcgaag atgacaaaat tg 22

<210> SEQ ID NO 859
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 859
agcacactgg actttggcga tgta 24

<210> SEQ ID NO 860
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 860
aattcaggag acatagggca c 21

<210> SEQ ID NO 861
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 861
tctttatgac gcagagctaa cc 22

<210> SEQ ID NO 862
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 862
ttcggcagct tgaaatttac agggc 25

<210> SEQ ID NO 863
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 863
tccgcaaagc agtgagatag 20

<210> SEQ ID NO 864
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 864
gactccagga aaacgacaga g 21

<210> SEQ ID NO 865
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 865
agcaaaagag atgaagcact acccagtc 28

<210> SEQ ID NO 866
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 866
ggaggcaaaa catagaggtc g 21

<210> SEQ ID NO 867

<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 867
ggaaagtggg aagataccga g 21

<210> SEQ ID NO 868
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 868
tgcaggacaa agagaaacgt ctgaagc 27

<210> SEQ ID NO 869
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 869
ccttcgtcaa attcagcatc ac 22

<210> SEQ ID NO 870
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 870
agtagaaata cggctgcacc 20

<210> SEQ ID NO 871
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 871
tccggaaggc cgaggccttg 20

<210> SEQ ID NO 872
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 872
ccaggtctcc attcttagtt gc 22

<210> SEQ ID NO 873
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 873
agccattgac agagcatata gg 22

<210> SEQ ID NO 874
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 874
cctccacagt tcccaaggat atcagc 26

<210> SEQ ID NO 875
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 875
ggcattttca cttccaacca c 21

<210> SEQ ID NO 876
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 876
gtgaggacac gatatgctgg 20

<210> SEQ ID NO 877
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 877
aacacggaga gttttgggac tggaat 26

<210> SEQ ID NO 878
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 878
gccgtggatt ctttcaacat c 21

<210> SEQ ID NO 879
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 879
tccacatcca atcataagca gg 22

<210> SEQ ID NO 880
<211> LENGTH: 23
<212> TYPE: DNA

<213> ORGANISM: Artificial Sequence
<220> FEATURE:
<223> OTHER INFORMATION: Synthetic polynucleotide

<400> SEQUENCE: 880
cggacatcag ccagaaatgc agc 23

<210> SEQ ID NO 881
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 881
cttagaccgt tacagccatc ag 22

<210> SEQ ID NO 882
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 882
caaaaccctc tttcagcatg g 21

<210> SEQ ID NO 883
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 883
tggctcagtg ttgctatcca gatgc 25

<210> SEQ ID NO 884
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 884
agcagacacc aaagtaagac c 21

<210> SEQ ID NO 885
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 885
agccatggtt tcagacgaag 20

<210> SEQ ID NO 886
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 886
ttcctttaat gcttgctttc cccacc 26

<210> SEQ ID NO 887
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 887
tttcccagca ccatcacg 18

<210> SEQ ID NO 888
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 888
ccatctttcc ctcaatctcc ag 22

<210> SEQ ID NO 889
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 889
cgtcgcttaa tcggagccaa agtct 25

<210> SEQ ID NO 890
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 890
ctgcattgta ggtgtactcg g 21

<210> SEQ ID NO 891
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 891
tggtcaacgt cttgaaagga g 21

<210> SEQ ID NO 892
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 892
tgaatgatga acttcttccc cagggc 26

<210> SEQ ID NO 893
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 893
aaccaattct gctattacaa agacg 25

<210> SEQ ID NO 894
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 894
ttcgggtagt ggaaaaccag 20

<210> SEQ ID NO 895
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 895
cccctcaacg ttagcttcac caaca 25

<210> SEQ ID NO 896
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 896
agtagaaata cggctgcacc 20

<210> SEQ ID NO 897
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 897
atataacaga accggcccac 20

<210> SEQ ID NO 898
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 898
catctccttg ccagcggtag acg 23

<210> SEQ ID NO 899
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 899
ccctctaaga cccatttcag c 21

<210> SEQ ID NO 900
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 900
ccctctaaga cccatttcag c 21

<210> SEQ ID NO 901
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 901
tcttgtgaaa ccactgccca acca 24

<210> SEQ ID NO 902
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 902
attctctgcc actggattac c 21

<210> SEQ ID NO 903
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 903
gcaaagacca aagagacacg 20

<210> SEQ ID NO 904
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 904
tcaaagtgga tgtcgagggt ggc 23

<210> SEQ ID NO 905
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 905
ggaatgttaa ccccgcaaac 20

<210> SEQ ID NO 906
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 906
ccaggagaag gagtttgaga ag 22

<210> SEQ ID NO 907
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 907
tttgaaagac tttgagccac agccc 25

<210> SEQ ID NO 908
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 908
ggccgaggat gagacatatt ac 22

<210> SEQ ID NO 909
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 909
gatgaggacg atgaggactt tg 22

<210> SEQ ID NO 910
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 910
cgaccacttg cggcctgagt atg 23

<210> SEQ ID NO 911
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 911
tgtgtctttc tctggtgctg 20

<210> SEQ ID NO 912
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 912
gagtatcgag cggaagcg 18

<210> SEQ ID NO 913
<211> LENGTH: 23

<212> TYPE: DNA
<213> ORGANISM: Artificial Sequence
<220> FEATURE:
<223> OTHER INFORMATION: Synthetic polynucleotide

<400> SEQUENCE: 913
attagccatg cctccagtag ccg 23

<210> SEQ ID NO 914
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 914
ctcctgtgtc aattatcttt ggg 23

<210> SEQ ID NO 915
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 915
gtctctacag ccaattcctc tg 22

<210> SEQ ID NO 916
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 916
tggatccgca gtcaatcttt ccttgg 26

<210> SEQ ID NO 917
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 917
cctttgctgg tctttggttt g 21

<210> SEQ ID NO 918
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 918
accttctaca atgagctgcg 20

<210> SEQ ID NO 919
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 919
atctgggtca tcttctcgcg gttg 24

<210> SEQ ID NO 920
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 920
cctggatagc aacgtacatg g 21

<210> SEQ ID NO 921
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 921
acttgcccag atgttctcag 20

<210> SEQ ID NO 922
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 922
accaaccgat ccaaagtctc cagc 24

<210> SEQ ID NO 923
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 923
gtatccctct agccattcag tg 22

<210> SEQ ID NO 924
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 924
acatcgctca gacaccatg 19

<210> SEQ ID NO 925
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 925
aaggtcggag tcaacggatt tggtc 25

<210> SEQ ID NO 926
<211> LENGTH: 22
<212> TYPE: DNA
<213> ORGANISM: Artificial Sequence -continued

```
<220> FEATURE:
<223> OTHER INFORMATION: Synthetic polynucleotide

<400> SEQUENCE: 926

tgtagttgag gtcaatgaag gg                                              22
```